(12) United States Patent
Borroni et al.

(10) Patent No.: US 6,586,441 B2
(45) Date of Patent: Jul. 1, 2003

(54) ADENOSINE RECEPTOR LIGANDS AND THEIR USE IN THE TREATMENT OF DISEASE

(75) Inventors: Edilio Maurizio Borroni, Basel (CH); Gerda Huber-Trottmann, Grindel (CH); Gavin John Kilpatrick, Cambridgeshire (GB); Roger David Norcross, Rheinfelden (CH)

(73) Assignee: Hoffman-La Roche Inc., Nutley, NJ (US)

( * ) Notice: Subject to any disclaimer, the term of this patent is extended or adjusted under 35 U.S.C. 154(b) by 35 days.

(21) Appl. No.: 09/788,956

(22) Filed: Feb. 20, 2001

(65) Prior Publication Data

US 2001/0027196 A1 Oct. 4, 2001

(30) Foreign Application Priority Data

Feb. 25, 2000 (EP) .......................................... 00103432

(51) Int. Cl.$^7$ .................... A61K 31/505; A61K 31/445; C07D 239/02; C07D 239/70; C07D 217/00
(52) U.S. Cl. ................. 514/275; 514/258.1; 514/266.1; 514/299; 514/307; 514/311; 514/326; 514/329; 544/253; 544/298; 544/319; 544/320; 544/321; 546/112; 546/139; 546/152; 546/212; 546/215; 546/216; 546/223
(58) Field of Search ........................ 514/258.1, 266.1, 514/275, 299, 307, 311, 326, 329; 544/253, 298, 319–321; 546/112, 139, 152, 212, 215, 216, 223

(56) References Cited

U.S. PATENT DOCUMENTS

| | | | | |
|---|---|---|---|---|
| 3,996,228 A | | 12/1976 | Arcari et al. ............. 260/256.4 |
| 5,514,505 A | * | 5/1996 | Limburg et al. ............... 430/41 |
| 5,863,924 A | * | 1/1999 | Berger et al. .......... 514/217.01 |
| 5,952,331 A | * | 9/1999 | Berger et al. ................ 514/256 |
| 5,958,934 A | * | 9/1999 | Berger et al. ................ 514/272 |

FOREIGN PATENT DOCUMENTS

EP  806 418  11/1997

OTHER PUBLICATIONS

Abstract of Geman Patent DE 2459629, 1975.
Abstract of Japanese Patent 0–8134044, 1996.
Poulsen et al., *Bioorganic & Medical Chemistry*, vol. 6, pp. 619–641 (1998).
Muller et al., *Bioorganic & Medical Chemistry*, vol. 6, pp. 707–719 (1998).
Kim et al., *J. Med. Chem.*, vol. 41, pp. 2835–2845 (1998).
Li et al., *J. Med. Chem.*, vol. 41, pp. 3186–3201 (1998).
Baraldi et al.,*J. Med. Chem.*, vol. 41, pp. 2126–2133 (1998).
Li etal., *J. Med. Chem.*, vol. 41, pp. 706–721 (1999).
Baraldi et al.,*J. Med. Chem.*, vol 41, pp. 1164–1171 (1996).
Colotta et al., *Arch. Pharm. Pharm. Med.Chem.*, vol. 332, pp. 39–41 (1999).
Nichigaki et al.,*Tetrahedron Letters*, pp. 247–250 (1969).
Perez etal., *Synthesi* No. 4, pp. 402–404 (1983).
Schmidt et al., *Journal of Heterocycles Chem.*, vol. 24, pp. 1305–1307 (1987).
Jachak et al., *Heterocycles*, vol. 36, pp. 2281–2290 (1993).
Rudorf et al., *Journal für prakt. Chemie*, vol. 320, pp. 576–584 (1978).

* cited by examiner

*Primary Examiner*—Richard L. Raymond
*Assistant Examiner*—Tamthom N. Truong
(74) *Attorney, Agent, or Firm*—George W. Johnston; Patricia S. Rocha-Tramaloni; Kimberly J. Prior

(57) ABSTRACT

The invention relates to cyclic heteroaromatic compounds, containing at least one nitrogen atom, and to their use in the manufacture of medicaments for the treatment of diseases, related to adenosine receptor modulators, such as Alzheimer's disease, Parkinson's disease, neuroprotection, schizophrenia, anxiety, pain, respiration deficits, depression, asthma, allergic responses, hypoxia, ischaemia, seizure, substance abuse, sedation and they may be active as muscle relaxants, antipsychotics, anti epileptics, anticonvulsants and cardioprotective agents.

23 Claims, No Drawings

ADENOSINE RECEPTOR LIGANDS AND THEIR USE IN THE TREATMENT OF DISEASE

FIELD OF THE INVENTION

The present invention is generally related to compounds useful as adenosine receptor ligand and more particularly to compounds showing activity as modulators of the andenosine receptor system.

BACKGROUND OF THE INVENTION

Several compounds related to general formula I have been reported.

The present invention relates to the use of compounds of the general formula

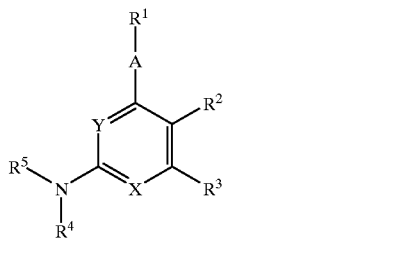

wherein
A is a bond, —S—, —N(R)—, —(CH$_2$)$_2$—, —CH=CH—, —C≡C— or —O—;
X/Y are independently from each other —N= or =N—, —CH= or =CH—, —C(cyano)= or =C(cyano)—, or —C[C(S)—NH$_2$]= or =—C[C(S)—NH$_2$]—, wherein at least one of X or Y is nitrogen;
R$^1$ is hydrogen, lower alkyl, lower alkenyl, lower alkynyl, halogen, cyano, cycloalkyl or the following groups
—(CH$_2$)$_n$—C(O)O-lower alkyl,
—(CH$_2$)$_n$—C(O)O-lower alkyl-phenyl,
—(CH$_2$)$_n$—NH—C(O)O-lower alkyl-phenyl,
—(CH$_2$)$_n$—O-lower alkyl,
—(CH$_2$)$_n$—O-phenyl,
—(CH$_2$)$_n$—NH-phenyl,
—(CH$_2$)$_n$-phenyl, optionally substituted by 1 or 2 substituents, selected from hydroxy, lower alkoxy, lower alkyl, CF$_3$-lower alkenyl, halogen, CF$_3$, OCF$_3$, amino,
—(CH$_2$)$_n$—N-di-lower alkyl, —C(O)NH-lower alkyl or —S(O)$_2$-lower alkyl, or is —(CH$_2$)$_n$-morpholinyl,
—(CH$_2$)$_n$-amino, optionally substituted by lower alkyl or benzyl,
—(CH$_2$)$_n$-piperidin-1-yl or —(CH$_2$)$_n$-piperidin-3-yl, which are optionally substituted by lower alkyl,
—(CH$_2$)$_n$-pyridin-2-yl, —(CH$_2$)$_n$-pyridin-3-yl or —(CH$_2$)$_n$-pyridin-4-yl, which are optionally substituted by 1 or 2 substituents, selected from lower alkyl, hydroxy, nitro, cyano, halogen, CF$_3$ or —OC(O)N(R)$_2$, or is
—(CH$_2$)$_n$—NH-pyridin-2-yl, optionally substituted by lower alkyl or halogen,
—(CH$_2$)$_n$-piperazin-4-yl, optionally substituted by lower alkyl, phenyl or carbonyl-phenyl,
—(CH$_2$)$_n$-phenyl—OC(O)-phenyl, optionally substituted by halogen, or the group

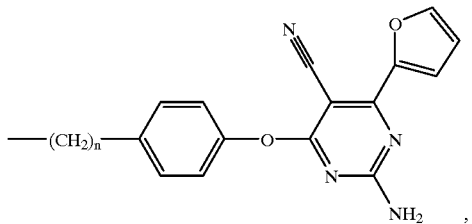

—(CH$_2$)$_n$—S-phenyl or —(CH$_2$)$_n$—S(O)$_2$-phenyl,
—(CH$_2$)$_n$—S-lower alkyl,
—(CH$_2$)$_n$(CH=CH)$_m$-phenyl,
—(CH$_2$)$_n$(CH≡CH)$_m$-phenyl,
—(CH$_2$)$_n$—NH-cycloalkyl,
—(CH$_2$)$_n$—NH-phenyl, optionally substituted by amino or nitro,
—(CH$_2$)$_n$-tetrahydro-pyran-4-yl,
—(CH$_2$)$_n$-quinolin-2-yl,
—(CH$_2$)$_n$-naphthyl or —(CH$_2$)$_n$—NH-naphthyl,
—(CH$_2$)$_n$-3,4-dihydro-1H-isoquinolin-2-yl,
—(CH$_2$)$_n$—benzo[1,3]dioxolyl,
—(CH$_2$)$_n$—NH—S(O)$_2$-phenyl, optionally substituted by halogen,
—(CH$_2$)$_n$-1,2,3,4-tetrahydro-quinolin-2-yl, optionally substituted by lower alkyl or
—(CH$_2$)$_n$-furanyl;
R$^2$ is hydrogen, halogen, cyano, nitro, lower alkyl, lower alkenyl, —C(O)-lower alkyl, —C(O)O-lower alkyl, —C(O)O-lower alkyl-phenyl, lower alkynyl-phenyl, lower alkenyl-C(O)O-lower alkyl, lower alkenyl-cyano or phenyl, optionally substituted by halogen;
R$^3$ is lower alkyl, or
phenyl, which is optionally substituted by lower alkyl, lower alkoxy, or halogen, or is thien-2-yl or fur-2-yl, which is optionally substituted by lower alkyl,
S-lower alkyl, halogen, lower alkoxy, —C(O)O-lower alkyl, —C(=CH$_2$)-O-lower alkyl,
—(CH$_2$)$_n$-halogen, —(CH$_2$).-OH, —(CH$_2$)$_n$-lower alkoxy, cyano, CHF$_2$, or CH$_2$F, or is 2,3-dihydro-benzo[1.4]dioxin-6-yl,
benzo[1.3]dioxol-5-yl,
isoxazol-5-yl, pyridin-2-yl, pyridin-3-yl,
—C(=CH$_2$)O-lower alkyl,
4,5-dihydrofuran-2-yl,
5,6-dihydro-4H-pyran-2-yl,
oxazol-2-yl,
benzofuranyl,
pyrazin-2-yl,
—O—(CH$_2$)$_n$phenyl,
—O—(CH$_2$)$_n$-pyridyl, optionally substituted by lower alkyl,
—S—(CH$_2$)$_n$-pyridyl,
or pyrazol-1-yl, optionally substituted by lower alkyl or halogen;
R$^4$/R$^5$ are independently from each other hydrogen, —CO—(CH$_2$)$_n$-phenyl, optionally substituted by halogen or —CH$_2$N(R)(CH$_2$)$_n$-lower alkyl, or is phenyl, optionally substituted by lower alkoxy, or —C(O)-phenyl;
R is hydrogen or lower alkyl; or A and $R^2$ may be together with the two carbon atoms

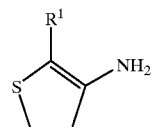

and n is 0, 1, 2, 3, or 4;
m is 1 or 2;

and to their pharmaceutically acceptable salts.

A number of compounds of formula I are known, and are described in the following documents:

Tetrahedron Let., (1969), 247–250, used as intermediates;
Journal fuar prakt. Chemieg 320, (1978), 576–584, synthesis;
Synthesis, (1983), 402–404, used as intermediates;
Journ. of Heterocycl. Chem, 24, (1987), 1305–1307, synthesis;
Heterocycles, 36, (1993), 2281–2290, used for the treatment of AIDS;
EP 806418, used for the treatment of rotaviral diseases and acute gastroentritis;
JP 08134044, uses as antiviral agent; or
DE 24 59 629, used as hypotensive and analgesic agents.

It has now surprisingly been found that the compounds of general formula I are adenosine receptor ligands, and these compounds are therefore useful in the treatment of diseases, based on the modulation of the adenosine system.

Adenosine modulates a wide range of physiological functions by interacting with specific cell surface receptors. The potential of adenosine receptors as drug targets was first reviewed in 1982. Adenosine is related both structurally and metabolically to the bioactive nucleotides adenosine triphosphate (ATP), adenosine diphosphate (ADP), adenosine monophosphate (AMP) and cyclic adenosine monophosphate (cAMP); to the biochemical methylating agent S-adenosyl-L-methione (SAM); and structurally to the coenzymes NAD, FAD and coenzym A; and to RNA. Together adenosine and these related compounds are important in the regulation of many aspects of cellular metabolism and in the modulation of different central nervous system activities.

The receptors for adenosine have been classified as $A_1$, $A_{2A}$, $A_{2B}$ and $A_3$ receptors, belonging to the family of G protein-coupled receptors. Activation of adenosine receptors by adenosine initiates signal transduction mechanism. These mechanisms are dependent on the receptor associated G protein. Each of the adenosine receptor subtypes has been classically characterised by the adenylate cyclase effector system, which utilises cAMP as a second messenger. The $A_1$ and $A_3$ receptors, coupled with G. proteins inhibit adenylate cyclase, leading to a decrease in cellular cAMP levels, while A2A and A2B receptors couple to $G_S$ proteins and activate adenylate cyclase, leading to an increase in cellular cAMP levels. It is known that the $A_1$ receptor system include the activation of phospholipase C and modulation of both potassium and calcium ion channels. The $A_3$ subtype, in addition to its association with adenylate cyclase, also stimulates phospholipase C and so activates calcium ion channels.

The $A_1$ receptor (326–328 amino acids) has been cloned from various species (canine, human, rat, dog, chick, bovine, guinea-pig) with 90–95% sequence identity among the mammalian species. The $A_{2A}$ receptor (409–412 amino acids) has been cloned from canine, rat, human, guinea pig and mouse. The $A_{2B}$ receptor (332 amino acids) has been cloned from human and mouse with 45% homology of human $A_{2B}$ with human $A_1$ and $A_{2A}$ receptors. The $A_3$ receptor (317–320 amino acids) has been cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$) or increase the oxygen supply ($A_{2A}$) and so reinstate the balance of energy supply versus demand within the tissue. The actions of both subtypes is to increase the amount of available oxygen to tissue and to protect cells against damage caused by a short term imbalance of oxygen. One of the important functions of endogenous adenosine is preventing damage during traumas such as hypoxia, ischaemia, hypotension and seizure activity.

Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

Adenosine is also a neuromodulator, possessing global importance in the modulation of molecular mechanisms underlying many aspects of physiological brain function by mediating central inhibitory effects. An increase in neurotransmitter release follows traumas such as hypoxia, ischaemia and seizures. These neurotransmitters are ultimately responsible for neural degeneration and neural death, which causes brain damage or death of the individual. The adenosine $A_1$ agonists which mimic the central inhibitory effects of adenosine may therefore be useful as neuroprotective agents. Adenosine has been proposed as an endogenous anticonvulsant agent, inhibiting glutamate release from excitory neurons and inhibiting neuronal firing. Adenosine agonists therefore may be used as antiepileptic agents. Adenosine antagonists stimulate the activity of the CNS and have proven to be effective as cognition enhancers. Selective $A_{2a}$-antagonists have therapeutic potential in the treatment of various forms of dementia, for example in Alzheimer's disease and are useful as neuroprotective agents. Adenosine $A_2$-receptor antagonists inhibit the release of dopamine from central synaptic terminals and reduce locomotor activity and consequently improve Parkinsonian symptoms. The central activities of adenosine are also implicated in the molecular mechanism underlying sedation, hypnosis, schizophrenia, anxiety, pain, respiration, depression and substance abuse. Drugs acting at adenosine receptors therefore have therapeutic potential as sedatives, muscle relaxants, antipsychotics, anxiolytics, analgesics, respiratory stimulants and antidepressants.

An important role for adenosine in the cardiovascular system is as a cardioprotective agent. Levels of endogenous adenosine increase in response to ischaemia and hypoxia, and protect cardiac tissue during and after trauma (preconditioning). Adenosine agonists thus have potential as cardioprotective agents.

Adenosine modulates many aspects of renal function, including renin release, glomerular filtration rate and renal blood flow. Compounds, which antagonise the renal affects of adenosine, have potential as renal protective agents. Furthermore, adenosine $A_3$ and/or $A_{2B}$ antagonists may be useful in the treatment of asthma and other allergic responses.

Numerous documents describe the current knowledge on adenosine receptors, for example the following publications:

Bioorganic & Medicinal Chemistry, 6, (1998), 619–641,
Bioorganic & Medicinal Chemistry, 6, (1998), 707–719,
J. Med. Chem., (1998), 41, 2835–2845,
J. Med. Chem., (1998), 41, 3186–3201,
J. Med. Chem., (1998), 41, 2126–2133,
J. Med. Chem., (1999), 42, 706–721,
J. Med. Chem., (1996), 39, 1164–1171 or
Arch. Pharm. Med. Chem., (1999), 332, 39–41.

The object of the present invention is the use of compounds of formula I and their pharmaceutically acceptable salts in the control or prevention of illnesses based on the modulation of the adenosine system, such as Alzheimer's disease, Parkinson's disease, neuroprotection, schizophrenia, anxiety, pain, respiration deficits, depression, asthma, allergic responses, hypoxia, ischaemia, seizure and substance abuse. Furthermore, compounds of the present invention may be useful as sedatives, muscle relaxants, antipsychotics, antiepileptics, anticonvulsants and cardioprotective agents. The most preferred indications in accordance with the present invention are those, which base on the $A_{2A}$ receptor antagonistic activity and which include disorders of the central nervous system, for example the treatment or prevention of certain depressive disorders, neuroprotection and Parkinson's disease. The invention relates also to the novel compounds disclosed in the present patent application per se, such as those specifically mentioned below. Furthermore, an object of the present invention are medicaments, based on a compound in accordance with formula I and their production.

As used herein, the term "lower alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1, 2, 3 or 4 carbon atoms.

As used herein, the term "lower alkenyl" and "lower alkynyl" denotes a unsaturated straight- or branched-chain alkyl group containing from 2 to 6 carbon atoms, for example, ethylen, propylen, isopropylen, n-butylen, i-butylen, 2-butylen, t-butylen and the like or ethynylen, propynylen, butyinylen and the like. Preferred lower alkyl groups are groups with 2, 3 or 4 carbon atoms.

The term "cycloalkyl" denotes a saturated carbocyclic group, containing 3, 4, 5 or 6 carbon atoms.

The term "halogen" denotes chlorine, iodine, fluorine and bromine.

The term "lower alkoxy" denotes a group wherein the alkyl residues is as defined above, and which is attached via an oxygen atom.

The term "aryl" denotes preferrably a monocyclic aromatic ring, such as phenyl, optionally substituted by halogen.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Among the compounds of the present invention, preferred compounds include the compounds of Formula I, wherein $R^4$ and $R^5$ are both hydrogen and $R^2$ is cyano, especially the compounds of formulas II, III and IV.

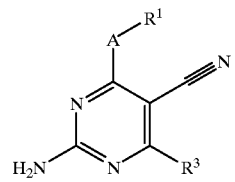

II

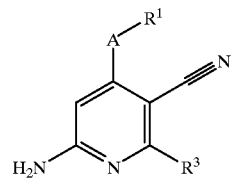

III

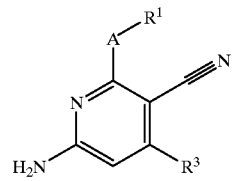

IV

Exemplary preferred compounds, showing selective activity on the $A_{2A}$ receptor, are compounds of formula II, wherein A is —NH—, for example the following compounds:

2-Amino-4-benzylamino-6-furan-2-yl-pyrimidine-5-carbonitrile, 2-amino-4-furan-2-yl-6-(3-phenyl-propylamino)-pyrimidine-5-carbonitrile, 2-amino-4-furan-2-yl-6-[2-(4-hydroxy-phenyl)-ethylamino]-pyrimidine-5-carbonitrile, 2-amino-4-furan-2-yl-6-(2-phenylamino-ethylamino)-pyrimidine-5-carbonitrile, 2-amino-4-furan-2-yl-6-[2-(4-methoxy-phenyl)-ethylamino]-pyrimidine-5-carbonitrile, 2-amino-4-furan-2-yl-6-(2-phenylamino-ethoxy)-pyrimidine-5-carbonitrile, 2-amino-4-furan-2-yl-6-(2-phenoxy-ethylamino)-pyrimidine-5-carbonitrile, 2-amino-4-benzyl amino-6-(5-methyl-furan-2-yl)-pyrimidine-5-carbonitrile, 6-furan-2-yl-5-nitro-N4-(3-phenyl-propyl)-pyrimidine-2,4-diamine, 2-amino-4-furan-2-yl-6-(2-methyl-benzylamino)-pyrimidine-5-carbonitrile, 2-amino-4-furan-2-yl-6-(3-methyl-benzylamino)-pyrimidine-5-carbonitrile, 2-amino-4-furan-2-yl-6-(4-methyl-benzylamino)-pyrimidine-5-carbonitrile, 2-amino-4-furan-2-yl-6-(3-methoxy-benzylamino)-pyrimidine-5-carbonitrile, 2-amino-4-furan-2-yl-6-(2-methoxy-benzylamino)-pyrimidine-5-carbonitrile, 2-amino-4-furan-2-yl-6-[(quinolin-2-yl-methyl)-amino]-pyrimidine-5-carbonitrile, 2-amino-4-furan-2-yl-6-[(naphthalen-2-yl-methyl)-amino]-pyrimidine-5-carbonitrile, (RS)-2-amino-4-furan-2-yl-6-[(1,2,3,4-tetrahydro-quinolin-2-ylmethyl)-amino]-pyrimidine-5-carbonitrile, 2-amino-4-furan-2-yl-6-(2-phenylsulfanyl-ethylamino)-pyrimidine-5-carbonitrile, 2-amino-4-(2-amino-benzylamino)-6-furan-2-yl-pyrimidine-5-carbonitrile, 2-amino-4-(4-dimethylamino-benzylamino)-6-furan-2-yl-pyrimidine-5-carbonitrile, 2-amino-4-[2-(4-chloro-phenylamino)-ethylamino]-6-furan-2-yl-pyrimidine-5-carbonitrile, 2-amino-4-(4-bromo-benzylamino)-6-furan-2-yl-pyrimidine-5-carbonitrile, 2-amino-4-furan-2-yl-6-[2-(pyridin-2-ylamino)-ethylamino]-pyrimidine-5-carbonitrile, 2-amino-4-[(benzo[1,3]dioxol-5a-ylmethyl)-amino]-6-furan-2-yl-pyrimidine-5-carbonitrile, 2-amino-4-furan-2-yl-6-(4-trifluoromethyl-benzylamino)-pyrimidine-5-carbonitrile, 2-amino-4-furan-2-yl-6-(3-trifluoromethyl-benzylamino)-pyrimidine-5-carbonitrile, 2-amino-4-(3,4-dimethyl-benzylamino)-6-furan-2-yl-pyrimidine-5-carbonitrile, 2-amino-4-furan-2-yl-6-[(4-(methyl-pyridin-2-yl-methyl)-amino]-pyrimidine-5-carbonitrile, 2-amino-4-furan-2-yl6(-riloromty-benzylamino)-6-furan-2-yl-pyrimidine-5-carbonitrile, 2-amino-4-(3-dimethyl-benzylamino)-6-furan-2-yl-pyrimidine-5-carbonitrile, 2-amino-4-furan-2-yl-6-[(5-methyl-pyridin-2-ylmethyl)-amino]-pyrimidine-5-carbonitrile, 2-amino-4-furan-2-yl-6-[(isoquinolin-3-yl-methyl)-amino]-pyrimidine-5-carbonitrile, 2-amino-4-furan-2-yl-6-[(3-methyl-pyridin-2-ylmethyl)-amino]-pyrimidine-5-carbonitrile, 2-amino-4-furan-2-yl-6-(4-vinyl-benzylamino)-pyrimidine-5-carbonitrile, 2-amino-4-(4-ethyl-benzylamino)-6-furan-2-yl-pyrimidine-5-carbonitrile, 2-amino-4-[(3-chloro-5-trifluoromethyl-pyridin-2-yl-methyl)-amino]-6-furan-2-yl-pyrimidine-5-carbonitrile, 2-amino-4-[(3,5-dimethyl-pyridin-2-yl-methyl)-amino]-6-furan-2-yl-pyrimidine-5-carbonitrile, 2-amino-4-(4,5-dihydro-furan-2-yl)-6-[(4-methyl-pyridin-2-yl-methyl)-amino]-pyrimidine-5-carbonitrile or 2-amino-4-(2-bromo-benzylamino)-6-(5-bromo-furan-2-yl)-pyrimidine-5-carbonitrile.

Exemplary preferred compounds, showing selective activity on the $A_{2A}$ receptor, are compounds of formula II, wherein A is —S—, for example the following compounds:

2-Amino-4-(2,3-dihydro-benzo[1,4]dioxin-6-yl)-6-methylsulfanyl-pyrimidine-5-carbonitrile, 2-amino-4-benzylsulfanyl-6-furan-2-yl-pyrimidine-5-carbonitrile, 2-amino-4-butylsulfanyl-6-furan-2-yl-pyrimidine-5-carbonitrile, 2-amino-4-ethylsulfanyl-6-furan-2-yl-pyrimidine-5-carbonitrile, 2-amino-4-phenyl-6-(3-phenyl-propylsulfanyl)-pyrimidine-5-carbonitrile, 2-amino-4-furan-2-yl-6-phenethylsulfanyl-pyrimidine-5-carbonitrile, 2-amino-4-furan-2-yl-6-(3-phenyl-propylsulfanyl)-pyrimidine-5-carbonitrile, 2-amino-4-furan-2-yl-6-(pyridin-2-yl-methylsulfanyl)-pyrimidine-5-carbonitrile, 2-amino-4-furan-2-yl-6-(2-pyridin-2-yl-ethylsulfanyl)-pyrimidine-5-carbonitrile, 2-amino-4-(2-pyridin-2-yl-ethylsulfanyl)-6-thiophen-2-yl-pyrimidine-5-carbonitrile, 2-amino-4-(4-methyl-furan-2-yl)-6-(2-pyridin-2-yl-ethylsulfanyl)-pyrimidine-5-carbonitrile, 2-amino-4-(5-chloro-furan-2-yl)-6-(2-pyridin-2-yl-ethylsulfanyl)-pyrimidine-5-carbonitrile, 2-amino-4-(5-bromo-furan-2-yl)-6-(2-pyridin-2-yl-ethylsulfanyl)-pyrimidine-5-carbonitrile, 2-amino-4-(4-bromo-furan-2-yl)-6-(2-pyridin-2-yl-ethylsulfanyl)-pyrimidine-5-carbonitrile, 2-amino-4-(5-cyanomethyl-furan-2-yl)-6-(2-pyridin-2-yl-ethylsulfanyl)-pyrimidine-5-carbonitrile, 2-amino-4-(4-cyano-furan-2-yl)-6-(2-pyridin-2-yl-ethylsulfanyl)-pyrimidine-5-carbonitrile or 2-amino-4-(5-difluoromethyl-furan-2-yl)-6-(2-pyridin-2-yl-ethylsulfanyl)-pryrimidine-5-carbonitrile.

Exemplary preferred compounds, showing selective activity on the $A_{2A}$ receptor, are further compounds of formula II, wherein A is —O—, for example the following compounds:

2-amino-4-ethoxy-6-furan-2-yl-pyrimidine-5-carbonitrile, 2-amino-4-benzyloxy-6-furan-2-yl-pyrimidine-5-carbonitrile, 2-amino-4-furan-2-yl-6-phenethyloxy-pyrimidine-5-carbonitrile, 2-amino-4-furan-2-yl-6-(3-phenyl-propoxy)-pyrimidine-5-carbonitrile, 2-amino-4-cyclohexyloxy-6-furan-2-yl-pyrimidine-5-carbonitrile, 2-amino-4-furan-2-yl-6-isopropoxy-pyrimidine-5-carbonitrile, 2-amino-4-furan-2-yl-6-(pyridin-2-yl-methoxy)-pyrimidine-5-carbonitrile, 2-amino-4-phenethyloxy-6-phenyl-pyrimidine-5-carbonitrile, 2-amino-4-(pyridin-2-yl-6-methoxy)-pyrimidine-5-carbonitrile, 2-amino-4-furan-2-yl-6-(pyridin-2-yl-methoxy)-pyrimidine-5-carbonitrile, 2-amino-4-furan-2-yl-6-(6-methyl-pyridin-2-yl-methoxy)-pyrimidine-5-carbonitrile, 2-amino-4-furan-2-yl-6-(2-pyridin-2-yl-ethoxy)-pyrimidine-5-carbonitrile, 2-amino-4-(5-methyl-furan-2-yl)-6-(6-methyl-pyridin-2-yl-methoxy)-pyrimidine-5-carbonitrile, 2-amino-4-(5-methyl-furan-2-yl)-6-(pyridin-2-yl-methoxy)-pyrimidine-5-carbonitrile, 2-amino-4-furan-2-yl-6-(3-phenyl-allyloxy)-pyrimidine-5-carbonitrile, 2-amino-4-furan-2-yl-6-(naphthalen-2-yl-methoxy)-pyrimidine-5-carbonitrile, 2-amino-4-furan-2-yl-6-(3-methyl-pyridin-2-yl-methoxy)-pyrimidine-5-carbonitrile, 2-amino-4-furan-2-yl-6-(5-methyl-pyridin-2-yl-methoxy)-pyrimidine-5-carbonitrile, 2-amino-4-furan-2-yl-6-(isoquinolin-3-yl-methoxy)-pyrimidine-5-carbonitrile, 2-amino-4-furan--2-yl-6-(4-methyl-pyridin-2-yl-methoxy)-pyrimidine-5-carbonitrile, 2-amino-4-furan-2-yl-6-(6-methyl-pyridin-3-yl-methoxy)-pyrimidine-5-carbonitrile, 2-amino-4-(3,5-dimethyl-pyridin-2-yl-methoxy)-6-furan-2-yl-pyrimidine-5-carbonitrile, 2-amino-4-(3-fluoro-phenyl)-6-(2-pyridin-2-yl-ethoxy)-pyrimidine-5-carbonitrile, 2-amino-4-(4-methyl-furan-2-yl)-6-(2-pyridin-2-yl-ethoxy)-pyrimidine-5-carbonitrile, 2-amino-4-(5-methyl-furan-2-yl)-6-(3-methyl-pyridin-2-yl-methoxy)-pyrimidine-5-carbonitrile, 2-amino-4-(3,5-dimethyl-pyridin-2-yl-methoxy)-6-(5-methyl-furan-2-yl)-pyrimidine-5-carbonitrile, 2-amino-4-(5-bromo-furan-2-yl)-6-(5-methyl-pyridin-2-yl-methoxy)-pyrimidine-5-carbonitrile, 2-amino-4-(5-bromo-furan-2-yl)-6-(5-methyl-pyridin-2-yl-methoxy)-pyrimidine-5-carbonitrile, 2-amino-4-(5-bromo-furan-2-yl)-6-(2-pyridin-2-yl-methoxy)-pyrimidine-5-carbonitrile, 2-amino-4-(5-chloro-furan-2-yl)-6-(2-pyridin-2-yl-ethoxy)-pyrimidine-5-carbonitrile, 2-amino-4-(5-chloro-furan-2-yl)-6-(3,5-dimethyl-pyridin-2-yl-methoxy)-pyrimidine-5-carbonitrile, 2-amino-4-(5-chloro-furan-2-yl)-6-(3-methyl-pyridin-2-yl-methoxy)-pyrimidine-5-carbonitrile, 2-amino-4-(5-chloro-furan-2-yl)-6-(5-methyl-pyridin-2-yl-methoxy)-pyrimidine-5-carbonitrile, 2-amino-4-(4-bromo-furan-2-yl)-6-(5-methyl-pyridin-2-yl-methoxy)-pyrimidine-5-carbonitrile, 2-amino-4-(4-bromo-furan-2-yl)-6-(3,5-dimethyl-pyridin-2-yl-methoxy)-pyrimidine-5-carbonitrile or 2-amino-4-(4-bromo-furan-2-yl)-6-(3-methyl-pyridin-2-yl-methoxy)-pyrimidine-5-carbonitrile.

Preferred are further compounds of formula II, showing selective activity on the $A_{2A}$ receptor, wherein A is a bond, for example the following compounds:

2-Amino-4-furan-2-yl-6-piperidin-1-yl-pyrimidine-5-carbonitrile, 2-amino-6-furan-2-yl-pyrimidine-4,5-dicarbonitrile, 2-amino-4-furan-2-yl-6-phenyl-pyrimidine-5-carbonitrile, (E)-2-amino-4-furan-2-yl-6-styryl-pyrimidine-5-carbonitrile or 2-amino-4-(3,4-dihydro-1H-isoquinolin-2-yl)-6-furan-2-yl-pyrimidine-5-carbonitrile.

Exemplary preferred compounds, showing selective activity on the $A_{2A}$ receptor, are compounds of formula III, wherein A is —NH—, —O— or —S—, for example the following compounds:

6-Amino-2-furan-2-yl-4-(pyridin-2-yl-methoxy)-nicotinonitrile, 6-amino-2-furan-2-yl-4-(2-pyridin-2-yl-ethylsulfanyl)-nicotinonitrile, 6-amino-2-furan-2-yl-4-(4-trifluoromethyl-benzylamino)-nicotinonitrile, 6-amino-2-furan-2-yl-4-[(quinolin-2-yl-methyl)-amino]-nicotinonitrile, 6-amino-2-furan-2-yl-4-[(pyridin-2-yl-methyl)-amino]-nicotinonitrile, 6-amino-2-furan-2-yl-4-[(pyridin-2-yl-methyl)-amino]-nicotinonitrile, 6-amino-2-furan-2-yl-4-[(5-methyl-pyridin-2-yl-methyl)-amino]-nicotinonitrile, 6-amino-2-furan-2-yl-4-(3-methyl-pyridin-2-yl-methoxy)-nicotinonitrile or 6-amino-2-furan-2-yl-4-(2-pyridin-2-yl-ethoxy)-nicotinonitrile.

Preferred are further compounds of formula I, showing selective activity on the $A_{2A}$ receptor, wherein X and Y are nitrogen, A is —O—, —NH—, or —S— and $R^2$ is halogen or nitro, for example the following compounds:

5-Bromo-4-furan-2-yl-6-(pyridin-2-yl-methoxy)-pyrimidin-2-yl-amine, 5-bromo-6-furan-2-yl-N4-(3-phenyl-propyl)-pyrimidine-2,4-diamine, 5-bromo-4-furan-2-yl-6-(3-phenyl-propoxy)-pyrimidin-2-yl-amine, 4-furan-2-yl-5-iodo-6-(3-phenyl-propoxy)-pyrimidin-2-yl-amine, 5-bromo-4-furan-2-yl-6-phenethylsulfanyl-pyrimidin-2-yl-amine, 5-bromo-4-furan-2-yl-6-(3-phenyl-allyloxy)-pyrimidin-2-yl-amine, 4-benzyloxy-6-furan-2-yl-5-nitro-pyrimidin-2-yl-amine, 5-chloro-6-furan-2-yl-N4-(3-phenyl-propyl)-pyrimidine-2,4-diamine, 5-chloro-4-furan-2-yl-6-(3-phenyl-propoxy)-pyrimidin-2-yl-amine, 5-chloro-4-furan-2-yl-6-phenethyloxy-pyrimidin-2-yl-amine, 4-benzylsulfanyl-5-chloro-6-furan-2-yl-pyrimidin-2-yl-amine, 4-furan-2-yl-5-iodo-6-(2-pyridin-2-yl-ethylsulfanyl)-pyrimidin-2-yl-amine, 5-bromo-4-furan-2-yl-6-(2-pyridin-2-yl-ethylsulfanyl)-pyrimidin-2-yl-amine or 5-chloro-4-furan-2-yl-6-(2-pyridin-2-yl-ethylsulfanyl)-pyrimidin-2-yl-amine.

Further preferred are compounds of formula I, showing selective activity on the $A_{2A}$ receptor, wherein X is =C(cyano)—, Y is —N=, A is —S— and $R^2$ is CN, for example the following compound:

2-Amino-6-benzylsulfanyl-4-thiophen-2-yl-pyridine-3,5-dicarbonitrile.

Exemplary preferred compounds, showing selective activity on the $A_{2A}$ receptor, are compounds of formula I, wherein X and Y are nitrogen, A is —S—, $R^2$ is cyano and $R^5$ is —C(O)-phenyl, for example the following compound:

N[5-Cyano-4-furan-2-yl-6-(2-pyridin-2-yl-ethylsulfanyl)-pyrimidin-2-yl]-benzamide.

Additional preferred compounds include compounds having the structure of formula II

II

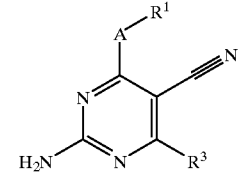

wherein A is —NH and R1 and R3 are as defined above. The more preferred compounds of formula II, include, but are not limited to, compounds wherein $R^1$ is selected from the group consisting of lower alkyl, cycloalkyl, —(CH$_2$)$_n$-phenyl, —(CH$_2$)$_n$-phenyl substituted by 1 or 2 substituents selected from the group consisting of hydroxy, lower alkoxy, lower alkyl, CF$_3$-lower alkenyl, halogen, CF$_3$, OCF$_3$, and amino, —(CH$_2$)$_n$-pyridin-2-yl, —(CH$_2$)$_n$-pyridin-2-yl, substituted by 1 or 2 substituents, selected from lower alkyl and CF$_3$, —(CH$_2$)$_n$(CH=CH)$_m$-phenyl, —(CH$_2$)$_n$-isoquinolin-3-yl, —(CH$_2$)$_n$-quinolin-2-yl, —(CH$_2$)$_n$-naphthyl,
—(CH$_2$)$_n$-3,4-dihydro-1H-isoquinolin-2-yl,
—(CH$_2$)$_n$-benzo[1,3]dioxolyl,
—(CH$_2$)$_n$-isoquinolin-3-yl
—(CH$_2$)$_n$-1,2,3,4-tetrahydro-quinolin-2-yl,
—(CH$_2$)$_n$-1,2,3,4-tetrahydro-quinolin-2-yl, substituted by lower alkyl. In this more preferred series of the structure of formula II, R$^3$ is selected from the group consisting of fur-2yl, fur-2yl, substituted by lower alkyl, and 4,5-dihydrofuran-2-yl; and wherein n is 0, 1, 2, 3 or 4; m is 1 or 2; and pharmaceutically acceptable salts thereof.

Additional more preferred compounds having the structure of formula II include compounds wherein A is —O— and R1 and R3 are as defined above. These compounds include, but are not limited to, R1 being selected from the group consisting of lower alkyl, cycloalkyl, —(CH$_2$)$_n$-phenyl, —(CH$_2$)$_n$-phenyl substituted by 1 or 2 substituents selected from the group consisting of lower alkoxy, lower alkenyl, halogen, —(CH$_2$)$_n$—pyridin-2-yl, —(CH$_2$)$_n$-pyridin-3-yl. —(CH$_2$)$_n$-pyridin-2-yl, and —(CH$_2$)$_n$-pyridin-3-yl substituted by 1 or 2 substituents, selected from lower alkyl, —(CH$_2$)$_n$(CH=CH)$_m$-phenyl, —(CH$_2$)$_n$-isoquinolin-3-yl, and —(CH$_2$)$_n$-naphthyl. R$^3$ is selected from the group consisting of phenyl, phenyl substituted by halogen, thien-2yl, fur-2yl, thien-2yl and fur-2yl substituted by lower alkyl, and halogen; and wherein N is 0, 1, 2, 3 or 4; and m is 1 or 2; and pharmaceutically acceptable salts of the compounds.

Yet additional more preferred compounds related to formula II include, but are not limited to, compounds wherein A is —S—, and R1 and R3 are as defined above. Compounds, and their pharmaceutically acceptable salts in this more preferred series having the structure of formula II include, but are not limited to, RI being selected from the group consisting of lower alkyl, —(CH$_2$)$_n$-phenyl, —(CH$_2$)$_n$-phenyl substituted by lower alkyl, —(CH$_2$)$_n$-pyridin-2-yl substituted by lower alkyl; and wherein R3 is selected from the group consisting of lower alkyl, thiene-2yl, fur-2yl, fur-2yl substituted by halogen, —(CH$_2$)$_n$— cyano, CHF$_2$, and 2,3-dihydro-benzo[1.4]diosin-6-yl; and wherein n is 0, 1, 2, 3 or 4 and m is 1 or 2.

An additional series of more preferred compounds, and the pharmaceutically acceptable salts thereof, having the structure of formula II include, but are not limited to, A is a bond and R1 and R3 are as defined above. These compounds include R1 being selected from the group including cyano, —(CH$_2$)$_n$-phenyl, —(CH$_2$)$_n$(CH=CH)$_m$-phenyl, —(CH$_2$)$_n$-piperidin-1-yl, and —(CH$_2$)$_n$-3,4-dihydro-1H-isoquinolin-2-yl. In this series, R3 is -fur-2yl; and n=0 and m=1.

Yet more preferred compounds include compounds having the structure of formula III

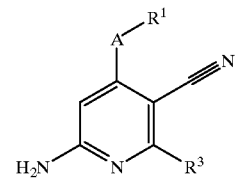

III where A is selected from the group consisting of —NH—, —O—, and —S— and R1 and R3 are as above. These compounds having the structure of formula III and their pharmaceutically salts further include R1 being selected from the group consisting of —(CH$_2$)$_n$-phenyl substituted by CF3, —(CH$_2$)$_n$-pyridin-2-yl, substituted by lower alkyl, and —(CH$_2$)$_n$-quinolin-2-yl substituted by lower alkyl, wherein n=0, 1, 2; R3 is fur-2yl.

The compounds of formula I may be prepared in accordance with the following schemes 1–20:

Preparation of compounds of Formula I wherein A is nitrogen, oxygen or sulfur, X and Y are nitrogen, R$^2$ is hydrogen, alkyl or aryl, and R$^3$ is phenyl (optionally substituted by lower alkyl, lower alkoxy, or halogen), thien-2-yl, fur-2-yl (optionally substituted by lower alkyl, halogen, —(CH$_2$)$_n$-lower alkoxy, cyano, CHF$_2$, or CH$_2$F), 2,3-dihydro-benzo[1.4]dioxin-6-yl, benzo [1.3]dioxol-5-yl, isoxazol-5-yl, pyridin-2yl, pyridin-3-yl, oxazol-2-yl, benzofuranyl, or pyrazin-2-yl.

One method of preparation of compounds of Formula I, wherein A has the above mentioned definition, is from intermediates of formula (5), the preparation of which is shown in Reaction Scheme I below.

REACTION SCHEME I

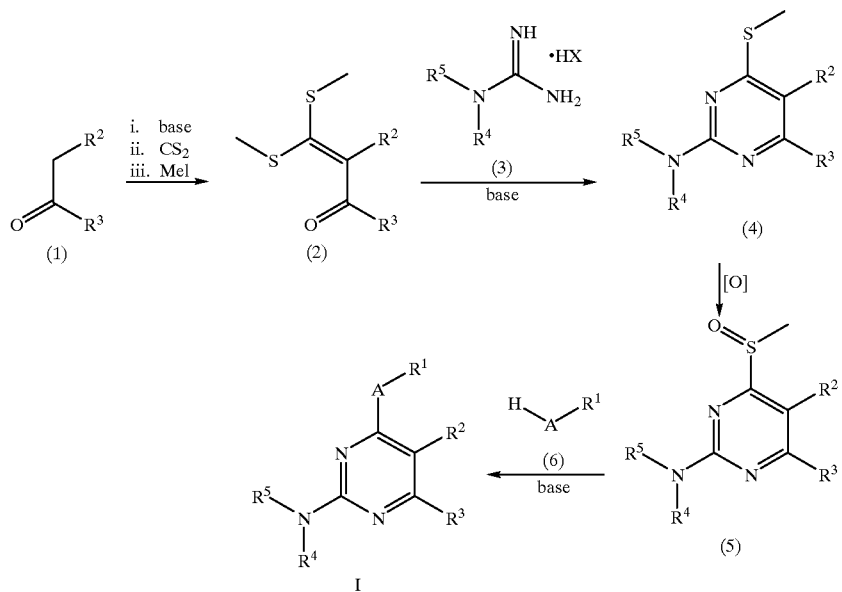

wherein A is nitrogen, oxygen or sulfur, $R^1$ is as defined above, $R^2$ is hydrogen, alkyl or aryl, $R^3$ is phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, and $R^4$ and $R^5$ are hydrogen or lower alkyl.

Preparation of Compounds of Formula (2)

The starting ketone of formula (1) may be obtained commercially, for example from Fluka Chemie AG, or may be prepared according to methods well known in the art.

To prepare compounds of formula (2), a ketone of formula (1) is sequentially treated with a strong non-aqueous base, preferably sodium hydride, and with carbon disulphide, in a polar non-protic solvent, preferably dimethyl sulfoxide, at room temperature for about 1–2 hours, preferably 2 hours, and then treated with methyl iodide at room temperature for about 2–16 hours, preferably 16 hours. The product of formula (2) is isolated by conventional means, and preferably reacted in the next step without further purification. The product of formula (2) may, however, be additionally purified by means of chromatography or recrystallisation.

Preparation of Compounds of Formula (4)

The inorganic acid addition salts of guanidine or of substituted guanidine compounds of formula (3) are commercially available, or may be prepared according to methods well known in the art.

The compounds of formula (4) are prepared by treating compounds of formula (2) with a slight excess of the guanidine compounds of formula (3) in a polar non-protic solvent, preferably dimethylformamide, containing a base, preferably sodium hydride, at reflux for 18–96 hours, preferably 90 hours. The product of formula (4) is isolated by conventional means, and preferably reacted in the next step without further purification. The product of formula (4) may, however, be additionally purified by means of chromatography or recrystallisation.

Preparation of Compounds of Formula (5)

The methylsulfanyl-pyrimidine derivative of formula (4) maybe converted to the corresponding methanesulfinyl-pyrimidine derivative of formula (5) by reacting a compound of formula (4) with an oxidising agent, preferably 3-phenyl-2-(phenylsulfonyl)oxaziridine, in an inert organic solvent, preferably dichloromethane, at room temperature. The product of formula (5) is isolated by conventional means, and preferably reacted in the next step without further purification. The product of formula (5) may, however, be additionally purified by means of chromatography or recrystallisation.

Preparation of compounds of Formula I wherein A is nitrogen, oxygen or sulfur, X and Y are nitrogen, $R^2$ is hydrogen, alkyl or aryl, and $R^3$ is phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-Syl, pyridin-2-yl, pyridin-3-yl, oxazol-2-yl, benzofuranyl, or pyrazin-2-yl.

One method of preparation of compounds of Formula I, wherein A has the above mentioned definition, is by treatment of a compound of formula (5) with an appropriate nucleophilic compound of formula (6), which may be commercially available or may be prepared by methods well known in the art, and which may be chosen from: a primary or secondary aliphatic alcohol or an aromatic alcohol, in each case used together with a non-nucleophilic base, preferably 1,8-diazabicyclo[5.4.0]undec-7-ene (1,5-5); a primary or secondary aliphatic thiol or an aromatic thiol, in each case used together with a non-nucleophilic base, preferably 1,8-diazabicyclo[5.4.0]undec-7-ene (1,5-5) (DBU); a primary or secondary aliphatic amine which is preferably used in excess in the absence of an added base; the inorganic salt of a primary or secondary aliphatic amine, such as a hydrochloride salt, which is used together with a non-nucleophilic base, preferably 1,8-diazabicyclo[5.4.0]undec-7-ene (1,5-5); an alkali metal alcoholate of a primary or secondary aliphatic alcohol or of an aromatic alcohol, preferably a sodium or potassium alcoholate, which is preferably used in excess; or an alkali metal thiolate of a primary or secondary aliphatic thiol or of an aromatic thiol, preferably a sodium or potassium thiolate, which is preferably used in excess. These reactions may be carried out in a non-protic polar solvent such as acetonitrile or in an ethereal solvent such as dioxane, tetrahydrofuran or 1,2-dimethoxyethane, preferably 1,2-dimethoxyethane, at a temperature between room temperature and the reflux temperature of the solvent, preferably about 80° C., for 18–48 hours, preferably 48 hours. The product of Formula I wherein A is nitrogen, oxygen or sulfur, X and Y are nitrogen, $R^2$ is hydrogen, alkyl or aryl, and $R^3$ is phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, is isolated by conventional means, and preferably purified by means of chromatography or recrystallisation.

Alternative preparation of compounds of Formula I, wherein A is nitrogen, oxygen or sulfur, X and Y are nitrogen, $R^2$ is alkyl, and $R^3$ is phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5yl, pyridin-2-yl, pyridin-3-yl, oxazol-2-yl, benzofuranyl, or pyrazin-2-yl.

An alternative method of preparation of compounds of Formula I, wherein A has the above mentioned definition, is from intermediates of formula (11), the preparation of which is shown in Reaction Scheme II below.

REACTION SCHEME II

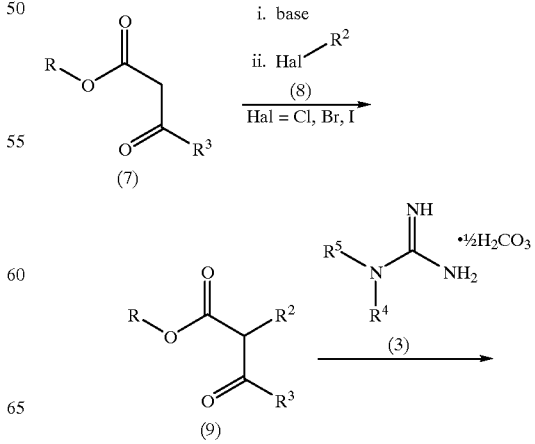

-continued

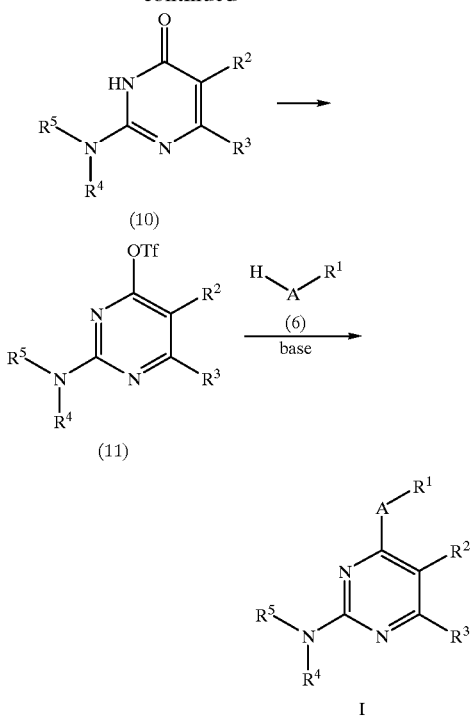

wherein A is nitrogen, oxygen or sulfur, $R^1$ is as defined above, $R^2$ is alkyl, $R^3$i phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, $R^4$ and $R^5$ are hydrogen or lower alkyl and R is lower alkyl.

Preparation of Compounds of Formula (9)

The starting β-ketoester of formula (7) and alkyl halides of formula (8) may be obtained commercially, for example from Fluka Chemie AG, or may be prepared according to methods well known in the art.

To prepare compounds of formula (9), a β-ketoester of formula (7) is reacted with a strong non-aqueous base, preferably lithium hexamethyldisilazide, in an ethereal solvent (for example, tetrahydrofuran, dioxane, diethyl ether, or 1,2-dimethoxyethane, preferably tetrahydrofuran), at a temperature of −78° C. for about 30–60 minutes, preferably 30 minutes, after which time a slight excess of an alkyl halide of formula (8), preferably an alkyl bromide, is added, and the mixture allowed to warm gradually to room temperature over about 12–16 hours. The product of formula (9) is isolated by conventional means, and preferably purified by means of chromatography or recrystallisation.

Preparation of Compounds of Formula (10)

The carbonate salts of guanidine or of substituted guanidine compounds of formula (3) are commercially available, or may be prepared according to methods well known in the art.

The compounds of formula (10) are prepared by treating compounds of formula (9) with a guanidine carbonate compound of formula (3) in a polar solvent, preferably ethanol, at reflux for 1–18 hours, preferably 16 hours. The product of formula (10) is isolated by conventional means, and preferably reacted in the next step without further purification. The product of formula (10) may, however, be additionally purified by means of chromatography or recrystallisation.

Preparation of Compounds of Formula (11)

A compound of formula (10) is reacted with an alkanesulfonic anhydride, preferably trifluoromethanesulfonic anhydride, and an excess of a non-nucleophilic base, preferably 2,6-di-tert-butylpyridine, in an organic solvent, preferably dichloromethane, at a temperature between 0° C. and room temperature for about 16 hours. The product of formula (11) is isolated by conventional means, and is preferably purified by means of chromatography or recrystallisation.

Preparation of compounds of Formula I, wherein A is nitrogen, oxygen or sulfur, X and Y are nitrogen, $R^2$ is alkyl, and $R^3$ is phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl.

The compound of formula (11) is reacted with an appropriate nucleophilic compound of formula (6), which may be commercially available or may be prepared by methods well known in the art, and which may be chosen from: a primary or secondary aliphatic alcohol or an aromatic alcohol, in each case used together with a non-nucleophilic base, preferably 1,8-diazabicyclo[5.4.0]undec-7-ene (1,5-5); a primary or secondary aliphatic thiol or an aromatic thiol, in each case used together with a non-nucleophilic base, preferably 1,8-diazabicyclo[5.4.0]undec-7-ene (1,5-5) (DBU); a primary or secondary aliphatic amine which is preferably used in excess in the absence of an added base; the inorganic salt of a primary or secondary aliphatic amine, such as a hydrochloride salt, which is used together with a non-nucleophilic base, preferably 1,8-diazabicyclo[5.4.0]undec-7-ene (1,5-5); an alkali metal alcoholate of a primary or secondary aliphatic alcohol or of an aromatic alcohol, preferably a sodium or potassium alcoholate, which is preferably used in excess; or an alkali metal thiolate of a primary or secondary aliphatic thiol or of an aromatic thiol, preferably a sodium or potassium thiolate, which is preferably used in excess. These reactions may be carried out in a non-protic polar solvent such as acetonitrile or in an ethereal solvent such as dioxane, tetrahydrofuran or 1,2-dimethoxyethane, preferably 1,2-dimethoxyethane, at room temperature or above, preferably at the reflux temperature of the solvent, for 1–18 hours, preferably 16 hours. The product of Formula I, wherein A has the above mentioned definition, is isolated by conventional means, and preferably purified by means of chromatography or recrystallisation.

Alternative preparation of compounds of Formula I wherein A is nitrogen, oxygen or sulfur, X and Y are nitrogen, $R^2$ is hydrogen, and $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3] dioxol-5-yl, isoxazol-5-yl, pyridin-2-yl, pyridin-3-yl, oxazol-2-yl, benzofuranyl, or pyrazin-2-yl.

An alternative method of preparation of compounds of Formula I, wherein A is as defined above, is from intermediates of formula (12), formula (13), formula (14) or formula (15), the preparation of which is shown in Reaction Scheme III below.

REACTION SCHEME III

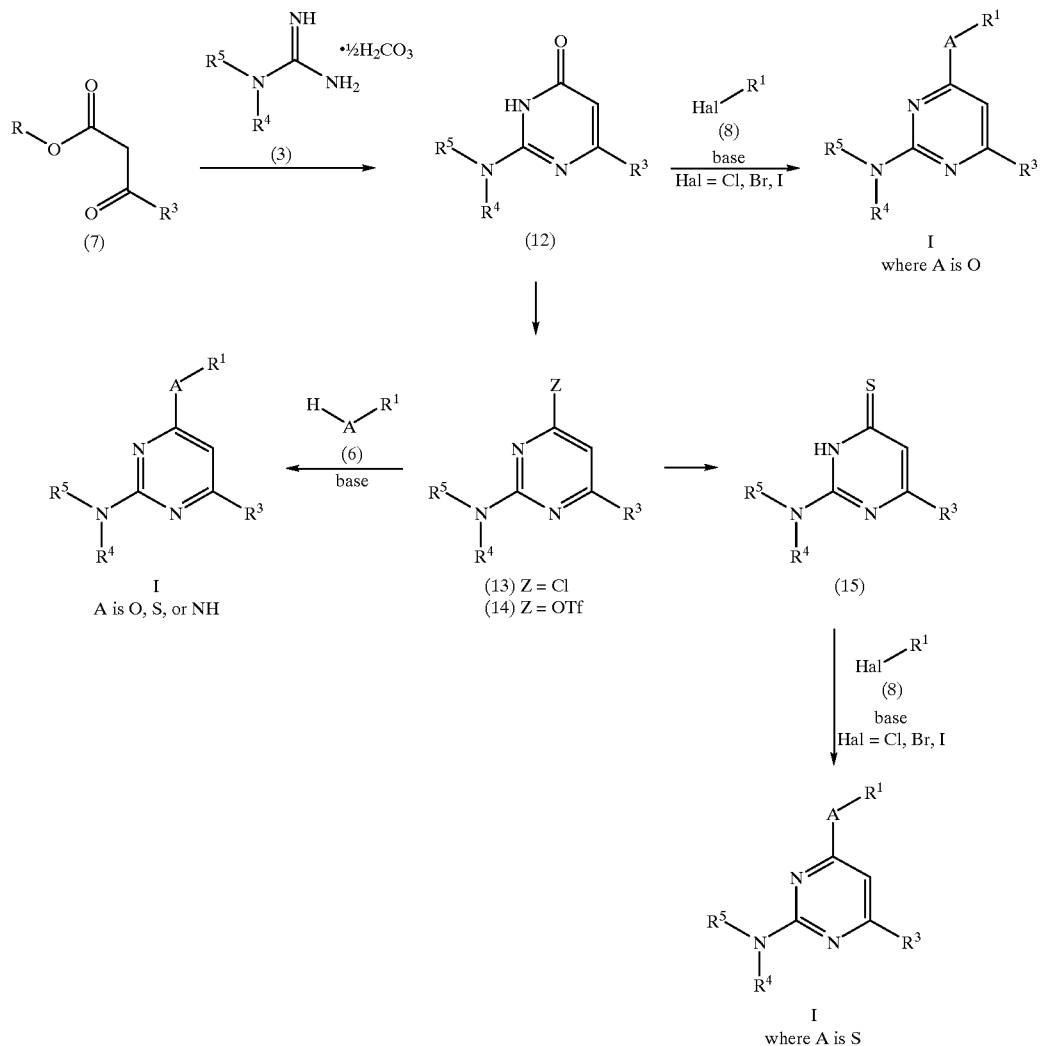

wherein A is nitrogen, oxygen or sulfur, $R^1$ is as defined above, $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, $R^4$ and $R^5$ are hydrogen or lower alkyl and R is lower alkyl.

Preparation of Compounds of Formula (12)

The starting β-ketoester of formula (7) and the carbonate salts of guanidine or of substituted guanidine compounds of formula (3) may be obtained commercially, for example from Fluka Chemie AG, or may be prepared according to methods well known in the art.

The compounds of formula (12) are prepared by treating compounds of formula (7) with a guanidine carbonate compound of formula (3) in a polar solvent, preferably ethanol, at reflux for 1–18 hours, preferably 16 hours. The product of formula (12) is isolated by conventional means, and preferably reacted in the next step without further purification. The product of formula (12) may, however, be additionally purified by means of chromatography or recrystallisation.

Preparation of compounds of Formula I wherein A is oxygen, X and Y are nitrogen, $R^2$ is hydrogen, and $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl.

The compound of formula (12) is reacted with an excess of an appropriate alkyl halide of formula (8), such as a primary or secondary aliphatic halide, preferably an aliphatic bromide or a benzylic bromide, which may be commercially available or may be prepared by methods well known in the art. The reaction is carried out in a polar solvent, preferably dimethylformamide, in the presence of an excess of a base, preferably cesium carbonate, at room temperature or above, preferably at about 100° C. for 1–18 hours, preferably for 16 hours. The product of Formula I where A is oxygen, X and Y are nitrogen, $R^2$ is hydrogen, and $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo

[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, is isolated by conventional means, and preferably purified by means of chromatography or recrystallisation.

Preparation of Compounds of Formula (13)

The compound of formula (12) is reacted with a chlorinating agent, preferably phosphorus oxychloride, preferably in the absence of solvent. The reaction is conducted at the reflux temperature for about 1–3 h, preferably about one and a half hours. The product of formula (13) is isolated by conventional means, and is preferably purified by means of chromatography or recrystallisation.

Preparation of compounds of Formula I, wherein A is nitrogen, oxygen or sulfur, X and Y are nitrogen, $R^2$ is hydrogen, and $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6yl, benzo[1.3]dioxol-5-yl, isoxazol-5-yl, pyridin-2-yl, pyridin-3-yl, oxazol-2-yl, benzofuranyl, or pyrazin-2-yl.

The compound of formula (13) is reacted with an appropriate nucleophilic compound of formula (6), which may be commercially available or may be prepared by methods well known in the art, and which may be chosen from: a primary or secondary aliphatic alcohol or an aromatic alcohol, in each case used together with a non-nucleophilic base, preferably 1,8-diazabicyclo[5.4.0]undec-7-ene (1,5-5); a primary or secondary aliphatic thiol or an aromatic thiol, in each case used together with a non-nucleophilic base, preferably 1,8-diazabicyclo[5.4.0]undec-7-ene (1,5-5) (DBU); a primary or secondary aliphatic amine which is preferably used in excess in the absence of an added base; the inorganic salt of a primary or secondary aliphatic amine, such as a hydrochloride salt, which is used together with a non-nucleophilic base, preferably 1,8-diazabicyclo[5.4.0]undec-7-ene (1,5-5); an alkali metal alcoholate of a primary or secondary aliphatic alcohol or of an aromatic alcohol, preferably a sodium or potassium alcoholate, which is preferably used in excess; or an alkali metal thiolate of a primary or secondary aliphatic thiol or of an aromatic thiol, preferably a sodium or potassium thiolate, which is preferably used in excess. These reactions may be carried out in a non-protic polar solvent such as acetonitrile or in an ethereal solvent such as dioxane, tetrahydrofuran or 1,2-dimethoxyethane, preferably 1,2-dimethoxyethane, at room temperature or above, preferably at the reflux temperature of the solvent, for 1–18 hours, preferably 18 hours. The product of Formula I where A is nitrogen, oxygen, or sulfur, X and Y are nitrogen, $R^2$ is hydrogen, and $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, is isolated by conventional means, and preferably purified by means of chromatography or recrystallisation.

Preparation of Compounds of Formula (14)

A compound of formula (12) is reacted with an alkanesulfonic anhydride, preferably trifluoromethanesulfonic anhydride, and an excess of a non-nucleophilic base, preferably 2,6-di-tert-butylpyridine, in an organic solvent, preferably dichloromethane, at a temperature between 0° C. and room temperature for about 16 hours. The product of formula (14) is isolated by conventional means, and is preferably purified by means of chromatography or recrystallisation.

Preparation of compounds of Formula I, wherein A is nitrogen, oxygen or sulfur, X and Y are nitrogen, $R^2$ is hydrogen, and $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl.

The compound of formula (14) is reacted with an appropriate nucleophilic compound of formula (6), which may be commercially available or may be prepared by methods well known in the art, and which may be chosen from: a primary or secondary aliphatic alcohol or an aromatic alcohol, in each case used together with a non-nucleophilic base, preferably 1,8-diazabicyclo[5.4.0]undec-7-ene (1,5-5); a primary or secondary aliphatic thiol or an aromatic thiol, in each case used together with a non-nucleophilic base, preferably 1,8-diazabicyclo[5.4.0]undec-7-ene (1,5-5) (DBU); a primary or secondary aliphatic amine which is preferably used in excess in the absence of an added base; the inorganic salt of a primary or secondary aliphatic amine, such as a hydrochloride salt, which is used together with a non-nucleophilic base, preferably 1,8-diazabicyclo[5.4.0]undec-7-ene (1,5-5); an alkali metal alcoholate of a primary or secondary aliphatic alcohol or of an aromatic alcohol, preferably a sodium or potassium alcoholate, which is preferably used in excess; or an alkali metal thiolate of a primary or secondary aliphatic thiol or of an aromatic thiol, preferably a sodium or potassium thiolate, which is preferably used in excess. These reactions may be carried out in a non-protic polar solvent such as acetonitrile or in an ethereal solvent such as dioxane, tetrahydrofuran or 1,2-dimethoxyethane, preferably 1,2-dimethoxyethane, at room temperature or above, preferably at the reflux temperature of the solvent, for 1–18 hours, preferably 18 hours. The product of Formula I where A is nitrogen, oxygen, or sulfur, X and Y are nitrogen, $R^2$ is hydrogen, and $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, is isolated by conventional means, and preferably purified by means of chromatography or recrystallisation.

Preparation of Compounds of Formula (15)

A compound of formula (13), or a compound of formula (14), is reacted with an excess of alkali metal thiolate, preferably sodium thiolate, in a polar organic solvent, preferably ethanol. The reaction is preferably carried out at the reflux temperature of the solvent, preferably about 100° C., and preferably for about 16 h. The product of formula (15) is isolated by conventional means, and preferably reacted in the next step without further purification. The product of formula (15) may, however, be additionally purified by means of recrystallisation.

Alternative preparation of compounds of Formula I, wherein A is sulfur, X and Y are nitrogen, $R^2$ is hydrogen, and $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl.

The compound of formula (15) is reacted with an excess of an appropriate organic halide of formula (8), such as a primary or secondary aliphatic halide, preferably an aliphatic bromide or a benzylic bromide, which may be commercially available or may be prepared by methods well known in the art. The reaction is carried out in a polar solvent, preferably methanol or ethanol, in the presence of a base, preferably sodium methylate or sodium, ethylate, at room temperature or above, preferably at the reflux temperature of the solvent, for 1–18 hours, preferably 2 hours. The product of Formula I where A is sulfur, X and Y are nitrogen, $R^2$ is hydrogen, and $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6yl, benzo[1.3]dioxol-5-yl, isoxazol-5-yl, pyridin-2-yl, pyridin-3-yl, oxazol-2-yl, benzofuranyl, or pyrazin-2-yl, is isolated by conventional means, and preferably purified by means of chromatography or recrystallisation.

Preparation of compounds of Formula I, wherein A is nitrogen, oxygen or sulfur, X and Y are nitrogen, $R^2$ is fluoro, and $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-Syl, pyridin-2-yl, pyridin-3-yl, oxazol-2-yl, benzofuranyl, or pyrazin-2-yl.

One method of preparation of compounds of Formula I, wherein A is nitrogen, oxygen or sulfur, X and Y are nitrogen and $R^2$ and $R^3$ are as defined above, is from intermediates of formula (20), the preparation of which is shown in Reaction Scheme IV below.

wherein A is nitrogen, oxygen or sulfur, $R^1$ is as defined above, $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, $R^4$ and $R^5$ are hydrogen or lower alkyl and R is lower alkyl.

Preparation of Compounds of Formula (16)

The starting β-ketoester of formula (7) may be obtained commercially, for example from Fluka Chemie AG, or may be prepared according to methods well known in the art.

To prepare compounds of formula (16), a P-ketoester of formula (7) is reacted with a fluorinating agent, preferably 1-(chloromethyl)-4-fluoro-1,4-diazoniabicyclo [2.2.2] octane bis(tetrafluoroborate), in an organic solvent, preferably acetonitrile, at room temperature for about 1–4 days, preferably 4 days. The product of formula (16) is isolated by conventional means, and preferably purified by means of chromatography or recrystallisation.

Alternative Preparation of Compounds of Formula (16)

The starting a-fluoroester of formula (17) may be obtained commercially, for example from Fluka Chemie AG, or may be prepared according to methods well known in the art.

In an alternative method to prepare compounds of formula (16), a α-fluoroester of formula (17) is reacted with a strong non-aqueous base, preferably lithium diisopropylamide, in an ethereal solvent (for example, tetrahydrofuran, dioxane, diethyl ether, or 1,2-dimethoxyethane, preferably diethyl ether), at a temperature of −78° C. for about 30–60 minutes, preferably 30 minutes, after which time about 1 equivalent of an acyl chloride of formula (18) is added, and the mixture allowed to warm gradually to 0° C. The product of formula

REACTION SCHEME IV

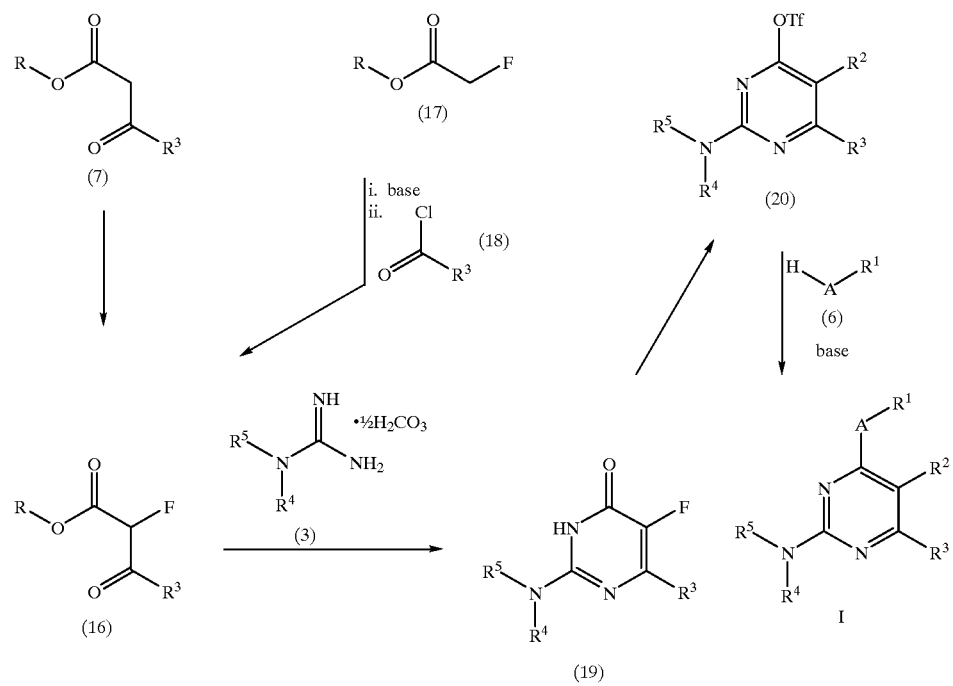

(16) is isolated by conventional means, and preferably purified by means of chromatography or recrystallisation.

Preparation of Compounds of Formula (19)

The carbonate salts of guanidine or of substituted guanidine compounds of formula (3) are commercially available, or may be prepared according to methods well known in the art.

The compounds of formula (19) are prepared by treating compounds of formula (16) with a slight excess of the guanidine carbonate compounds of formula (3) in a polar solvent, preferably ethanol, at reflux for 1–18 hours, preferably 4 hours. The product of formula (19) is isolated by conventional means, and preferably reacted in the next step without further purification. The product of formula (19) may, however, be additionally purified by means of chromatography or recrystallisation.

Preparation of Compounds of Formula (20)

A compound of formula (19) is reacted with an alkanesulfonic anhydride, preferably trifluoromethanesulfonic anhydride, and an excess of a non-nucleophilic base, preferably 2,6-di-tert-butylpyridine, in an inert organic solvent, preferably dichloromethane, at a temperature between 0° C. and room temperature for about 16 hours. The product of formula (20) is isolated by conventional means, and is preferably purified by means of chromatography or recrystallisation.

Preparation of compounds of Formula L wherein A is nitrogen, oxygen or sulfur, X and Y are nitrogen, $R^2$ is fluoro, and $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl.

The compound of formula (20) is reacted with an appropriate nucleophilic compound of formula (6), which may be commercially available or may be prepared by methods well known in the art, and which may be chosen from: a primary or secondary aliphatic alcohol or an aromatic alcohol, in each case used together with a non-nucleophilic base, preferably 1,8-diazabicyclo[5.4.0]undec-7-ene (1,5-5); a primary or secondary aliphatic thiol or an aromatic thiol, in each case used together with a non-nucleophilic base, preferably 1,8-diazabicyclo[5.4.0]undec-7-ene (1,5-5) (DBU); a primary or secondary aliphatic amine which is preferably used in excess in the absence of an added base; the inorganic salt of a primary or secondary aliphatic amine, such as a hydrochloride salt, which is used together with a non-nucleophilic base, preferably 1,8-diazabicyclo[5.4.0]undec-7-ene (1,5-5); an alkali metal alcoholate of a primary or secondary aliphatic alcohol or of an aromatic alcohol, preferably a sodium or potassium alcoholate, which is preferably used in excess; or an alkali metal thiolate of a primary or secondary aliphatic thiol or of an aromatic thiol, preferably a sodium or potassium thiolate, which is preferably used in excess. These reactions may be carried out in a non-protic polar solvent such as acetonitrile or in an ethereal solvent such as dioxane, tetrahydrofuran or 1,2-dimethoxyethane, preferably 1,2-dimethoxyethane, at room temperature or above, preferably at the reflux temperature of the solvent, for 1–18 hours, preferably 18 hours. The product of Formula I wherein A is nitrogen, oxygen or sulfur, X and Y are nitrogen, $R^2$ is fluoro, and $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, is isolated by conventional means, and preferably purified by means of chromatography or recrystallisation.

Preparation of compounds of Formula I, wherein A is nitrogen, oxygen or sulfur, X and Y are nitrogen, $R^2$ is chloro, bromo or iodo, and $R^3$ is phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl.

One method of preparation of compounds of Formula I, wherein A, X, Y, $R^2$ and $R^3$ are defined as above, is from intermediates of formula (23), the preparation of which is shown in Reaction Scheme V below.

REACTION SCHEME V

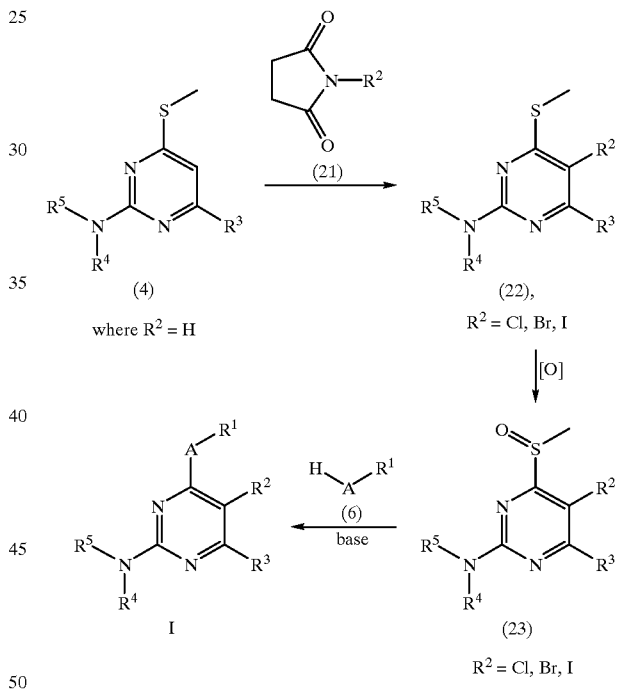

wherein A is nitrogen, oxygen or sulfur, $R^1$ is as defined above, $R^2$ is chloro, bromo or iodo, $R^3$ is phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, and $R^4$ and $R^5$ are hydrogen or lower alkyl.

Preparation of Compounds of Formula (22)

The compounds of formula (4), which may be prepared as depicted in Reaction Scheme I, may be converted to compounds of formula (22) by reacting a compound of formula (4) with a halogenating agent, preferably an N-halosuccinimide of formula (21), where $R^2$ is chloro, bromo or iodo, in an organic solvent, preferably acetic acid, at a temperature between room temperature and 50° C., preferably room temperature in the case of the bromo and iodo derivatives, and preferably 50° C. in the case of the chloro derivatives, for about 16–72 hours. The product of formula (22) is isolated by conventional means, and preferably purified by means of chromatography or recrystallisation.

Preparation of Compounds of Formula (23)

The compounds of formula (22) may be converted to compounds of formula (23) by reacting a compound of formula (22) with an oxidising agent, preferably 3-phenyl-2-(phenylsulfonyl)oxaziridine, in an inert organic solvent, preferably dichloromethane, at room temperature. The product of formula (23) is isolated by conventional means, and preferably reacted in the next step without further purification. The product of formula (23) may, however, be additionally purified by means of chromatography or recrystallisation.

Preparation of compounds of Formula I, wherein A is nitrogen, oxygen or sulfur, X and Y are nitrogen, $R^2$ is chloro, bromo or iodo, and $R^3$ is phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl.

One method of preparation of derivatives of Formula I wherein A, X, Y, $R^2$ and $R^3$ are as defined above, is by treatment of a compound of formula (23) with an appropriate nucleophilic compound of formula (6), which may be commercially available or may be prepared by methods well known in the art, and which may be chosen from: a primary or secondary aliphatic alcohol or an aromatic alcohol, in each case used together with a non-nucleophilic base, preferably 1,8-diazabicyclo[5.4.0]undec-7-ene (1,5-5); a primary or secondary aliphatic thiol or an aromatic thiol, in each case used together with a non-nucleophilic base, preferably 1,8-diazabicyclo[5.4.0]undec-7-ene (1,5-5) (DBU); a primary or secondary aliphatic amine which is preferably used in excess in the absence of an added base; the inorganic salt of a primary or secondary aliphatic amine, such as a hydrochloride salt, which is used together with a non-nucleophilic base, preferably 1,8-diazabicyclo[5.4.0]undec-7-ene (1,5-5); an alkali metal alcoholate of a primary or secondary aliphatic alcohol or of an aromatic alcohol, preferably a sodium or potassium alcoholate, which is preferably used in excess; or an alkali metal thiolate of a primary or secondary aliphatic thiol or of an aromatic thiol, preferably a sodium or potassium thiolate, which is preferably used in excess. These reactions may be carried out in a non-protic polar solvent such as acetonitrile or in an ethereal solvent such as such as dioxane, tetrahydrofuran or 1,2-dimethoxyethane, preferably 1,2-dimethoxyethane, at room temperature or above, preferably at room temperature, for 1–18 hours, preferably 2 hours. The product of Formula I wherein A is nitrogen, oxygen or sulfur, X and Y are nitrogen, K is chloro, bromo or iodo, and $R^3$ is phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, is isolated by conventional means, and preferably purified by means of chromatography or recrystallisation.

Conversion of Compounds of Formula I to Other Compounds of Formula I

Miscellaneous routes to compounds of Formula I from compounds of Formula I where X and Y are nitrogen and $R^2$ is iodo are shown in Reaction Scheme VI:

REACTION SCHEME VI

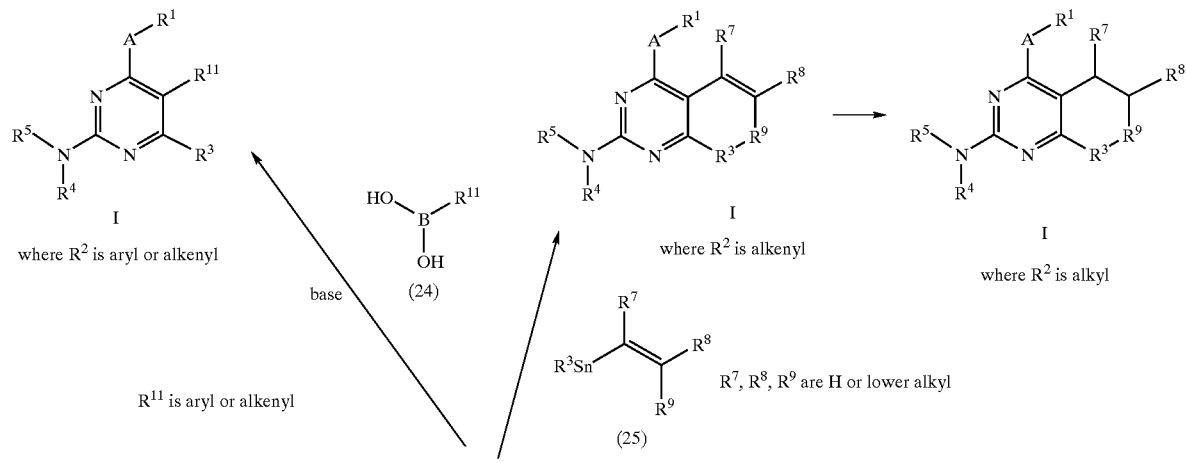

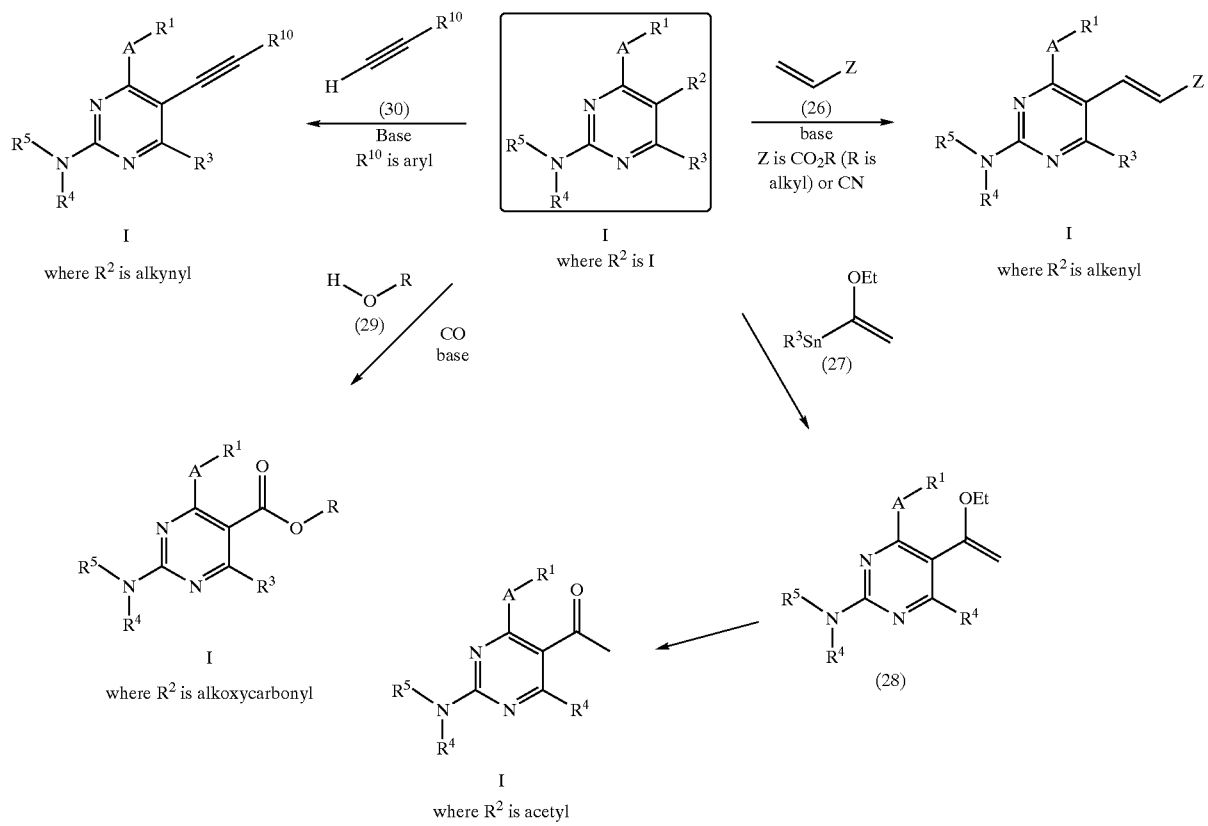

wherein A is nitrogen, oxygen or sulfur, $R^1$ and R3 are as defined above, $R^4$, $R^5$, $R^7$, $R^8$ and $R^9$ are hydrogen or lower alkyl, $R^{10}$ is aryl, $R^{11}$ is aryl or alkenyl R is alkyl or benzyl and Z is an electron-withdrawing group, such as CN or $CO_2R$.

Preparation of Compounds of Formula I, Wherein X and Y are Nitrogen and $R^2$ is Aryl or Alkenyl Boronic acid derivatives of formula (24) where $R^{11}$1 is aryl or alkenyl may be obtained commercially, or may be prepared by methods well known in the art. A compound of Formula I where X and Y are nitrogen and $R^2$ is iodo is reacted with a boronic acid derivative of formula (24) in an aqueous solvent, preferably a mixture of water and dioxane, containing a palladium catalyst, preferably palladium tetrakis(triphenylphosphine), and an inorganic base, preferably sodium carbonate. The reaction is preferably carried out at the reflux temperature of the solvent, preferably about 100° C., for about 6–18 hours, preferably about 16 hours. The product of Formula I where X and Y are nitrogen and $R^2$ is aryl or alkenyl is isolated by conventional means, and preferably purified by chromatography or recrystallisation.

Alternative Preparation of Compounds of Formula I, Wherein X and Y are Nitrogen and $R^2$ is Alkenyl Trialkylstannane derivatives of formula (25), wherein R is methyl or n-butyl and $R^7$, $R^8$ and $R^9$ are independently H or lower alkyl, may be obtained commercially, or may be prepared by methods well known in the art. A compound of Formula I where X and Y are nitrogen and $R^2$ is iodo is reacted with a trialkylstannane derivative of formula (25) in an ethereal solvent (for example 1,2-dimethoxyethane, tetrahydrofuran or dioxane, preferably dioxane), containing a palladium catalyst, preferably palladium tetrakis (triphenylphosphine). The reaction is preferably carried out at the reflux temperature of the solvent, preferably about 100° C., for about 14–36 hours, preferably about 16 hours. The product of Formula I where X and Y are nitrogen and $R^2$ is alkenyl is isolated by conventional means, and preferably purified by chromatography or recrystallisation.

Preparation of Compounds of Formula I, Where X and Y are Nitrogen and $R^2$ is Alkyl A compound of Formula I, wherein X and Y are nitrogen and $R^2$ is alkenyl is reacted with hydrogen gas in an organic solvent (for example 1,2-dimethoxyethane, tetrahydrofuran, dioxane or ethanol, preferably a mixture ethanol) containing a hydrogenation catalyst, preferably 10% palladium on charcoal. The reaction is carried out at room temperature at a pressure of 1 atmosphere or above, preferably at one atmosphere, for about 2–36 hours, preferably about 16 hours. The product of Formula I where X and Y are nitrogen and $R^2$ is alkyl is isolated by conventional means, and preferably purified by chromatography or recrystallisation.

Alternative Preparation of Compounds of Formula I, Wherein X and Y are Nitrogen and $R^2$ is alkenyl Alkene derivatives of formula (26), where in Z is $CO_2R$ or CN and R is alkyl or benzyl, may be obtained commercially, or may be prepared by methods well known in the art. A compound of Formula I where X and Y are nitrogen and $R^2$ is iodo is reacted with an alkene derivative of formula (26) in an ethereal solvent (for example 1,2-dimethoxyethane, tetrahydrofuran or dioxane, preferably dioxane), containing a palladium catalyst, preferably palladium tetrakis(triphenylphosphine), and an inorganic base, preferably cesium carbonate. The reaction is preferably carried out at the reflux temperature of the solvent, preferably about 100° C., for about 8–18 hours, preferably about 12 hours. The product of Formula I where X and Y are nitrogen and $R^2$ is alkenyl is isolated by conventional means, and preferably, purified by chromatography or recrystallisation.

Preparation of Compounds of Formula I, Wherein X and Y are Nitrogen and $R^2$ is Acetyl Compounds of Formula I, wherein X and Y are nitrogen and $R^2$ is acetyl, can be made from intermediates of formula (28), which may themselves be prepared from compounds of Formula I where X and Y are nitrogen and $R^2$ is iodo.

Preparation of Compounds of Formula (28)

Trialkylstannane derivatives of formula (27), wherein R is methyl or n-butyl, may be obtained commercially, or may be prepared by methods well known in the art. A compound of Formula I where X and Y are nitrogen and $R^2$ is iodo is reacted with a trialkylstannane derivative of formula (27) in an ethereal solvent (for example 1,2-dimethoxyethane, tetrahydrofuran or dioxane, preferably dioxane), containing a palladium catalyst, preferably bis(triphenylphosphine) palladium(II) chloride. The reaction is preferably carried out at the reflux temperature of the solvent, preferably about 100° C., for about 10–18 hours, preferably about 16 hours. The product of formula (28) is isolated by conventional means, and preferably reacted in the next step with no further purification.

Preparation of Compounds of Formula I Wherein X and Y are Nitrogen and $R^2$ is Acetyl A compound of formula (28) is reacted with a dilute aqueous solution of a Bronsted acid, preferably hydrochloric acid, in an aqueous solvent, preferably a mixture of tetrahydrofuran and water. The reaction is preferably carried out at room temperature for about 18–48 hours, preferably 44 hours. The product of Formula I where X and Y are nitrogen and $R^2$ is acetyl is isolated by conventional means, and preferably purified by chromatography or recrystallisation.

Preparation of Compounds of Formula I, Wherein X and Y are Nitrogen and $R^2$ is Alkoxycarbonyl A compound of Formula I, wherein X and Y are nitrogen and $R^2$ is iodo, is reacted with carbon monoxide gas in an alcoholic solvent of formula (29) (for example methanol, ethanol, benzyl alcohol, or a solution of one of these alcohols in dimethylformamide), containing a palladium catalyst, preferably tris(dibenzylidineacetone)dipalladium chloroform complex, a catalytic amount of a monodentate ligand, preferably triphenylarsine, and an excess of an organic base, preferably triethylamine. The reaction is carried out at a pressure of 1–20 atmospheres, preferably 1 atmosphere, and at a temperature above room temperature, preferably about 100–110° C., for about 8–18 hours, preferably about 12 hours. The product of Formula I where X and Y are nitrogen and $R^2$ is alkoxycarbonyl is isolated by conventional means, and preferably purified by chromatography or recrystallisation.

Preparation of Compounds of Formula I Where X and Y are Nitrogen and $R^2$ is Alkynyl Alkyne derivatives of formula (30), wherein $R^{10}$ is aryl, may be obtained commercially, or may be prepared by methods well known in the art. A compound of Formula I where X and Y are nitrogen and R2 is iodo is reacted with an alkene derivative of formula (30) in an ethereal solvent (for example 1,2-dimethoxyethane, tetrahydrofuran or dioxane, preferably tetrahydrofuran), containing a palladium catalyst, preferably bis(triphenylphosphine)palladium(II) chloride, a copper co-catalyst, preferably copper(I) iodide, and an excess of an organic base, preferably triethylamine. The reaction is preferably carried out at room temperature for about 16–96 hours, preferably about 18 hours. The product of Formula I where X and Y are nitrogen and $R^2$ is alkynyl is isolated by conventional means, and preferably purified by chromatography or recrystallisation.

Preparation of compounds of Formula I, wherein A is nitrogen, oxygen or sulfur, X and Y are nitrogen, $R^2$ is nitro, $R^3$ is phenyl (optionally substituted by lower alkyl, lower alkoxy, or halogen), thien-2-yl, fur-2-yl (optionally substituted by lower alkyl, —(CH$_2$)$_n$-lower alkoxy), 2,3-dihydro-benzo[1.4]dioxin-6-yl, benzo[1.3]dioxol-5-yl, isoxazol-5-yl, pyridin-2-yl, pyridin-3-yl, —C(=CH$_2$)O-lower alkyl, 4,5-dihydrofuran-2-yl, 5,6-dihydro-4H-pyran-2-yl oxazol-2-yl, benzofuranyl, or pyrazin-2-yl, and $R^4$ and $R^5$ are hydrogen.

One method of preparation of compounds of Formula I, wherein A, X, Y, $R^2$ and $R^3$ is defined above, and $R^4$ and $R^5$ are hydrogen is from intermediates of formula (36), the preparation of which is shown in Reaction Scheme VII below.

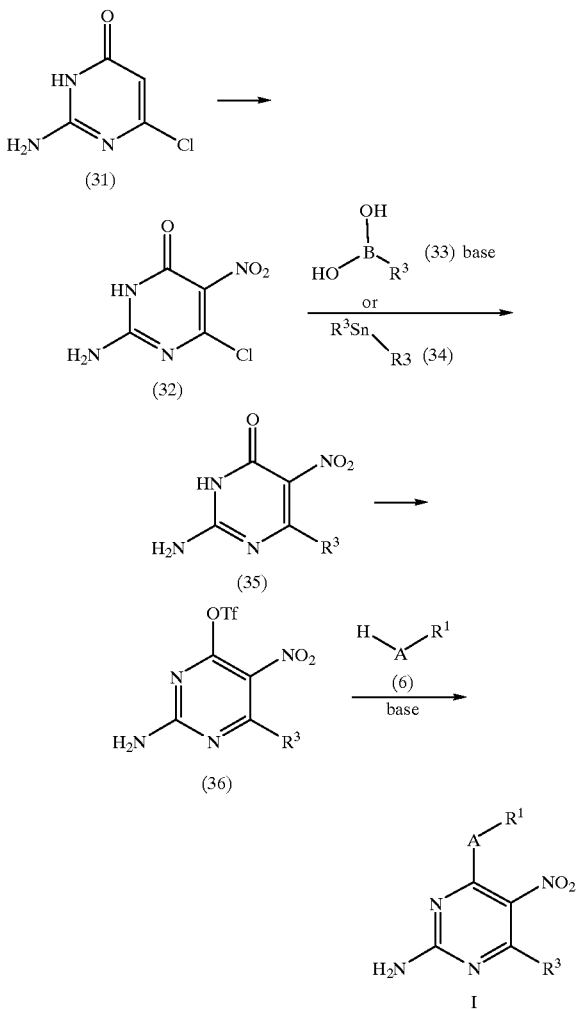

wherein A is nitrogen, oxygen or sulfur, $R^1$ is as defined above, and $R^3$ is phenyl (optionally substituted by lower alkyl, lower alkoxy, or halogen), thien-2-yl, fur-2-yl (optionally substituted by lower alkyl, —(CH$_2$)$_n$-lower alkoxy), 2,3-dihydro-benzo[1.4]dioxin-6-yl, benzo[1.3]dioxol-5-yl, isoxazol-5-yl-pyridin-2-yl, pyridin-3-yl, —C(=CH$_2$)O-lower alkyl, 4,5-dihydrofuran-2-yl, 5,6-dihydro-4H-pyran-2yl oxazol-2-yl, benzofuranyl, or pyrazin-2-yl.

Preparation of Compound of Formula (32)

2-Amino-6-chloro-4-oxo-3,4-dihydro-pyrimidine, a compound of formula (31) wherein R$^4$ and R$^5$ are hydrogen, which may be obtained commercially, for example from Fluka Chemie AG, is reacted with a nitrating mixture, preferably a mixture of concentrated sulphuric and nitric acids, preferably in the absence of added solvent. The reaction is conducted at a temperature of about 20–40° C., for about 30–90 minutes. The product of formula (32), 2-amino-6-chloro-5-nitro-4-oxo-3,4-dihydro-pyrimidine, is isolated by conventional means, and preferably purified by means of recrystallisation.

Preparation of Compounds of Formula (35)

Boronic acid derivatives of formula (33), wherein R$^3$ is phenyl (optionally substituted by lower alkyl, lower alkoxy, or halogen), thien-2-yl, fur-2-yl (optionally substituted by lower alkyl, —(CH$_2$)$_n$-lower alkoxy), 2,3-dihydro-benzo[1.4]dioxin-6-yl, benzo[1.3]dioxol-5-yl, isoxazol-5-yl, pyridin-2-yl, pyridin-3-yl, —C(=CH$_2$)O-lower alkyl, 4,5-dihydrofuran-2-yl, 5,6-dihydro-4H-pyran-2-yl oxazol-2-yl, benzofuranyl, or pyrazin-2-yl, may be obtained commercially, or may be prepared by methods well known in the art. The compound of formula (32), 2-amino-6-chloro-5-nitro-4-oxo-3,4-dihydro-pyrimidine, is reacted with a boronic acid derivative of formula (33) in an aqueous solvent, preferably a mixture of water and dioxane, containing a palladium catalyst, preferably palladium tetrakis (triphenylphosphine), and an inorganic base, preferably sodium carbonate. The reaction is preferably carried out at the reflux temperature of the solvent, preferably about 100° C., for about 2–8 hours, preferably about 4 hours. The product of formula (35) is isolated by conventional means, and preferably purified by chromatography or recrystallisation.

Alternative Preparation of Compounds of Formula (35)

Trialkylstannane derivatives of formula (34), wherein R$^3$ is phenyl (optionally substituted by lower alkyl, lower alkoxy, or halogen), thien-2-yl, fur-2-yl (optionally substituted by lower alkyl, —(CH$_2$)$_n$-lower alkoxy), 2,3-dihydro-benzo[1.4]dioxin-6-yl, benzo[1.3]dioxol-5-yl, isoxazol-5-yl, pyridin-2-yl, pyridin-3-yl, —C(=CH$_2$)O-lower alkyl, 4.5-dihydrofuran-2-yl, 5,6-dihydro-4H-pyran-2-yl oxazol-2-yl, benzofuranyl, or pyrazin-2-yl, and R is methyl or n-butyl, may be obtained commercially, or may be prepared by methods well known in the art. The compound of formula (32), 2-amino-6-chloro-5-nitro-4-oxo-3,4-dihydro-pyrimidine, is reacted with a trialkystannane derivative of formula (34) in an ethereal solvent (for example 1,2-dimethoxyethane, tetrahydrofuran or dioxane, preferably dioxane), containing a palladium catalyst, preferably palladium tetrakis(triphenylphosphine). The reaction is preferably carried out at the reflux temperature of the solvent, preferably about 100° C., for about 10–18 hours, preferably about 16 hours. The product of formula (35) is isolated by conventional means, and preferably purified by chromatography or recrystallisation.

Preparation of Compounds of Formula (36)

A compound of formula (35) is reacted with an alkanesulfonic anhydride, preferably trifluoromethanesulfonic anhydride, and an excess of a non-nucleophilic base, preferably 2,6-di-tert-butylpyridine, in an organic solvent, preferably dichloromethane, at a temperature between 0° C. and room temperature for about 16 hours. The product of formula (36) is isolated by conventional means, and is preferably purified by means of chromatography or recrystallisation.

Preparation of compounds of Formula I, wherein A is nitrogen, oxygen or sulfur, X and Y are nitrogen, R$^2$ is nitro, R$^3$ is phenyl (optionally substituted by lower alkyl, lower alkoxy, or halogen), thien-2-yl, fur-2-yl (optionally substituted by lower alkyl, —(CH$_2$)$_n$-lower alkoxy), 2,3-dihydro-benzo[1.4]dioxin-6-yl, benzo[1.3]dioxol-5-yl, isoxazol-5-yl, pyridin-2-yl, pyridin-3-yl, —C(=CH$_2$)O-lower alkyl, 4,5-dihydrofuran-2-yl, 5,6-dihydro-4H-pyran-2-yl oxazol-2-yl, benzofuranyl, or pyrazin-2-yl, and R$^4$ and R$^5$ are hydrogen.

The compound of formula (36) is reacted with an appropriate nucleophilic compound of formula (6), which may be commercially available or may be prepared by methods well known in the art, and which may be chosen from: a primary or secondary aliphatic alcohol or an aromatic alcohol, in each case used together with a non-nucleophilic base, preferably 1.8-diazabicyclo[5.4.0]undec-7-ene (1,5-5); a primary or secondary aliphatic thiol or an aromatic thiol, in each case used together with a non-nucleophilic base, preferably 1,8-diazabicyclo [5.4.0]undec-7-ene (1,5-5) (DBU); a primary or secondary aliphatic amine which is preferably used in excess in the absence of an added base; the inorganic salt of a primary or secondary aliphatic amine, such as a hydrochloride salt, which is used together with a non-nucleophilic base, preferably 1,8-diazabicyclo[5.4.0]undec-7-ene (1,5-5); an alkali metal alcoholate of a primary or secondary aliphatic alcohol or of an aromatic alcohol, preferably a sodium or potassium alcoholate, which is preferably used in excess; or an alkali metal thiolate of a primary or secondary aliphatic thiol or of an aromatic thiol, preferably a sodium or potassium thiolate, which is preferably used in excess. These reactions may be carried out in a non-protic polar solvent such as acetonitrile or in an ethereal solvent such as dioxane, tetrahydrofuran or 1,2-dimethoxyethane, preferably 1,2-dimethoxyethane, at room temperature or above, preferably at the reflux temperature of the solvent, for 1–18 hours, preferably 16 hours. The product of Formula I wherein A is nitrogen, oxygen or sulfur, X and Y are nitrogen, R$^2$ is nitro, R$^3$ is phenyl (optionally substituted by lower alkyl, lower alkoxy, or halogen), thien-2-yl, fur-2-yl (optionally substituted by lower alkyl, —(CH$_2$)$_n$-lower alkoxy), 2,3-dihydro-benzo[1.4]dioxin-6-yl, benzo[1.3]dioxol-5-yl, isoxazol-5-yl, pyridin-2yl, pyridin-3-yl, —C(=CH$_2$)O-lower alkyl, 4,5-dihydrofuran-2-yl, 5,6-dihydro-4H-pyran-2-yl oxazol-2-yl, benzofuranyl, or pyrazin-2-yl, and R$^4$ and R$^5$ are both hydrogen is isolated by conventional means, and preferably purified by means of chromatography or recrystallisation.

Conversion of compounds of Formula I, wherein A—R$^1$ is methylsulfanyl and R$^3$ is lower alkyl, phenyl (optionally substituted by lower alkyl, lower alkoxy, or halogen), thien-2-yl, fur-2-yl (optionally substituted by lower alkyl, halogen, lower alkoxy, —(CH$_2$)$_n$—OH, —(CH$_2$)$_n$-lower alkoxy, cyano, CHF$_2$, or CH$_2$F), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, pyrazin-2-yl, or pyrazol-1-yl (optionally substituted by lower alkyl or halogen), to other compounds of Formula I wherein A is nitrogen, oxygen or sulfur and R$^3$ is lower alkyl, phenyl (optionally substituted by lower alkyl, lower alkoxy, or halogen), thien-2-yl, fur-2-yl (optionally substituted by lower alkyl, halogen, lower alkoxy, —(CH$_2$)$_n$-OH, —(CH$_2$)$_n$-lower alkoxy, cyano, CHF$_2$, or CH$_2$F), 2,3-dihydro-benzo[1.4]dioxin-6-yl, benzo[1.3]dioxol-5-yl, isoxazol-5yl, pyridin-2-yl, pyridin-3-yl, oxazol-2-yl, benzofuranyl, pyrazin-2-yl, or pyrazol-1-yl (optionally substituted by lower alkyl or halogen).

A method of converting compounds of Formula I as mentioned above, is shown in Reaction Scheme VIII:

REACTION SCHEME VIII

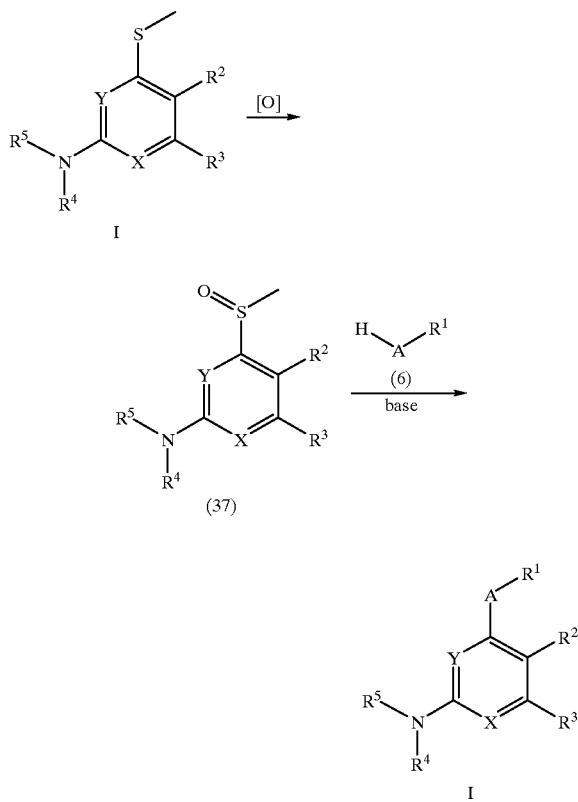

wherein A is nitrogen, oxygen or sulfur, X, Y, $R^1$ and $R^2$ are as defined above, $R^3$ is lower alkyl, phenyl (optionally substituted by lower alkyl, lower alkoxy, or halogen), thien-2-yl, fur-2-yl (optionally substituted by lower alkyl, halogen, lower alkoxy, —$(CH_2)_n$—OH, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, pyrazin-2-yl, or pyrazol-1-yl (optionally substituted by lower alkyl or halogen), and $R^4$ and $R^5$ are hydrogen or lower alkyl.

Preparation of Compounds of Formula (37)

A compound of Formula I, wherein A—$R^1$ is methylsulfanyl and $R^3$ is lower alkyl, phenyl (optionally substituted by lower alkyl, lower alkoxy, or halogen), thien-2-yl, fur-2-yl (optionally substituted by lower alkyl, halogen, lower alkoxy, —$(CH_2)_n$—OH, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, pyrazin-2-yl, or pyrazol-1-yl (optionally substituted by lower alkyl or halogen), is reacted with an oxidising agent, preferably 3-phenyl-2-(phenylsulfonyl)oxaziridine, in an inert organic solvent, preferably dichloromethane, at room temperature. The product of formula (37), a methanesulfinyl-pyrimidine derivative, is isolated by conventional means, and preferably reacted in the next step without further purification. The product of formula (37) may, however, be additionally purified by means of chromatography or recrystallisation.

Preparation of compounds of Formula I, wherein A is nitrogen, oxygen or sulfur, and $R^3$ is lower alkyl, phenyl (optionally substituted by lower alkyl, lower alkoxy, or halogen), thien-2-yl, fur-2-yl (optionally substituted by lower alkyl, halogen, lower alkoxy, —$(CH_2)_n$—OH, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, pyrazin-2-yl, or pyrazol-1-yl (optionally substituted by lower alkyl or halogen).

The methanesulfinyl-pyrimidine derivative of formula (37) is reacted with an appropriate nucleophilic compound of formula (6), which may be commercially available or may be prepared by methods well known in the art, and which may be chosen from: a primary or secondary aliphatic alcohol or an aromatic alcohol, in each case used together with a non-nucleophilic base, preferably 1,8-diazabicyclo[5.4.0]undec-7-ene (1,5-5); a primary or, secondary aliphatic thiol or an aromatic thiol, in each case used together with a non-nucleophilic base, preferably 1,8-diazabicyclo[5.4.0]undec-7-ene (1,5-5) (DBU); a primary or secondary aliphatic amine which is preferably used in excess in the absence of an added base; the inorganic salt of a primary or secondary aliphatic amine, such as a hydrochloride salt, which is used together with a non-nucleophilic base, preferably 1,8-diazabicyclo[5.4.0]undec-7-ene (1,5-5); an alkali metal alcoholate of a primary or secondary aliphatic alcohol or of an aromatic alcohol, preferably a sodium or potassium alcoholate, which is preferably used in excess; or an alkali metal thiolate of a primary or secondary aliphatic thiol or of an aromatic thiol, preferably a sodium or potassium thiolate, which is preferably used in excess. These reactions may be carried out in a non-protic polar solvent such as acetonitrile or in an ethereal solvent such as such as dioxane, tetrahydrofuran or 1,2-dimethoxyethane, preferably 1,2-dimethoxyethane, at room temperature or above, preferably at room temperature, for 1–18 hours, preferably 2 hours. The product of Formula I where A is nitrogen, oxygen or sulfur and $R^3$ is lower alkyl, phenyl (optionally substituted by lower alkyl, lower alkoxy, or halogen), thien-2-yl, fur-2-yl (optionally substituted by lower alkyl, halogen, lower alkoxy, —$(CH_2)_n$—OH, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, pyrazin-2-yl, or pyrazol-1-yl (optionally substituted by lower alkyl or halogen), is isolated by conventional means, and preferably purified by means of chromatography or recrystallisation.

Preparation of compounds of Formula I, wherein A—$R^1$ is hydrogen, X and Y are nitrogen, $R^2$ is cyano or $CO_2R$ (where R is alkyl or benzyl), $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl.

One method of preparation of compounds of Formula I, wherein A—$R^1$, X, Y, $R^2$ and $R^3$ is defined as mentioned above, is from intermediates of formula (39), the preparation of which is shown in Reaction Scheme IX below.

REACTION SCHEME IX

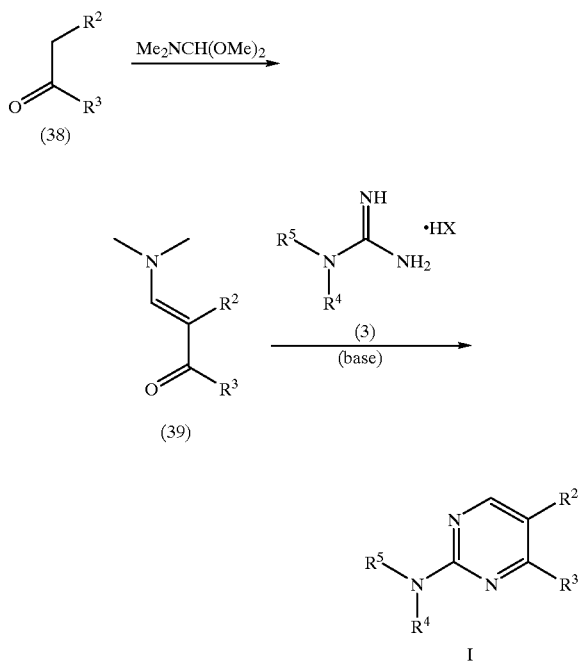

wherein R² is cyano or CO₂R (where R is alkyl or benzyl), R³ is lower alkyl, phenyl (optionally substituted by lower alkyl, lower alkoxy, or halogen), thien-2-yl, fur-2-yl (optionally substituted by lower alkyl, halogen, —(CH₂)ₙ-lower alkoxy, cyano, CHF₂, or CH₂F), 2,3-dihydro-benzo[1.4]dioxin-6-yl, benzo [1.3]dioxol-5-yl, isoxazol-5-yl, pyridin-2-yl, pyridin-3-yl, oxazol-2-yl, benzofuranyl, or pyrazin-2-yl, and R⁴ and R⁵ are hydrogen or lower alkyl.

Preparation of Compounds of Formula (39)

The starting ketones of formula (38) may be obtained commercially, for example from Avocado Research Chemicals Limited, or may be prepared according to methods well known in the art.

To prepare compounds of formula (39), an ketone of formula (38) is reacted with N,N-dimethylformamide dimethyl acetal, preferably in the absence of solvent, at room temperature for about 1–8 hours, preferably 2 hours. The product of formula (39) is isolated by conventional means, and preferably reacted in the next step without further purification. The product of formula (39) may, however, be additionally purified by means of chromatography or recrystallisation.

Preparation of compounds of Formula I, wherein A—R¹ is hydrogen, X and Y are nitrogen, R² is cyano, and R³ is lower alkyl, phenyl (optionally substituted by lower alkyl, lower alkoxy, or halogen), thien-2-yl, fur-2-yl (optionally substituted by lower alkyl, halogen, —(CH₂)ₙ-lower alkoxy, cyano, CHF₂, or CH₂F), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl.

The carbonate salts of guanidine or of substituted guanidine compounds of formula (3) are commercially available, or may be prepared according to methods well known in the art.

The 2-amino-pyrimidine-5-carbonitrile derivative of Formula I where A—R¹ is hydrogen, X and Y are nitrogen, R² is cyano, and R³ is lower alkyl, phenyl (optionally substituted by lower alkyl, lower alkoxy, or halogen), thien-2-yl, fur-2-yl (optionally substituted by lower alkyl, halogen, —(CH₂)ₙ-lower alkoxy, cyano, CHF₂, or CH₂F), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, is prepared by treating compounds of formula (39) with an excess of a guanidine carbonate compound of formula (3) in a polar solvent, preferably methanol, containing an excess of base, preferably sodium methylate, at room temperature for 1–4 hours, preferably about 2 hours. The product of Formula I is isolated by conventional means, and preferably purified by means of chromatography or recrystallisation.

Preparation of compounds of Formula I, where A—R¹ is hydrogen, X and Y are nitrogen, R² is CO₂R (where R is alkyl or benzyl), and R³ is lower alkyl, phenyl (optionally substituted by lower alkyl, lower alkoxy, or halogen), thien-2-yl, fur-2-yl (optionally substituted by lower alkyl, halogen, —(CH₂)ₙ-lower alkoxy, cyano, CHF₂, or CH₂F), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl.

The inorganic acid addition salts, such as the nitrate salts, of guanidine or of substituted guanidine compounds of formula (3) are commercially available, or may be prepared according to methods well known in the art.

The 5-alkoxycarbonyl-2-amino-pyrimidine derivative of Formula I, wherein the definitions are given above, is prepared by treating compounds of formula (39) with a slight excess of a guanidine nitrate compound of formula (3) in a polar solvent, dimethylformamide, containing a slight excess of base, preferably sodium acetate or triethylamine, at 90° C. for 12–36 hours, preferably about 18 hours. The product of Formula I is isolated by conventional means, and preferably purified by means of chromatography or recrystallisation.

Preparation of compounds of Formula I, wherein A—R¹ is hydrogen, X and Y are nitrogen, R² is hydrogen, chloro, bromo or iodo, and R³ is phenyl (optionally substituted by lower alkyl, lower alkoxy, or halogen), thien-2-yl, fur-2-yl (optionally substituted by lower alkyl, halogen, —(CH₂)ₙ-lower alkoxy, cyano, CHF₂, or CH₂F), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl.

One method of preparation of compounds of Formula I, with the above mentioned definitions is from intermediates of formula (41), the preparation of which is shown in Reaction Scheme X below.

REACTION SCHEME X

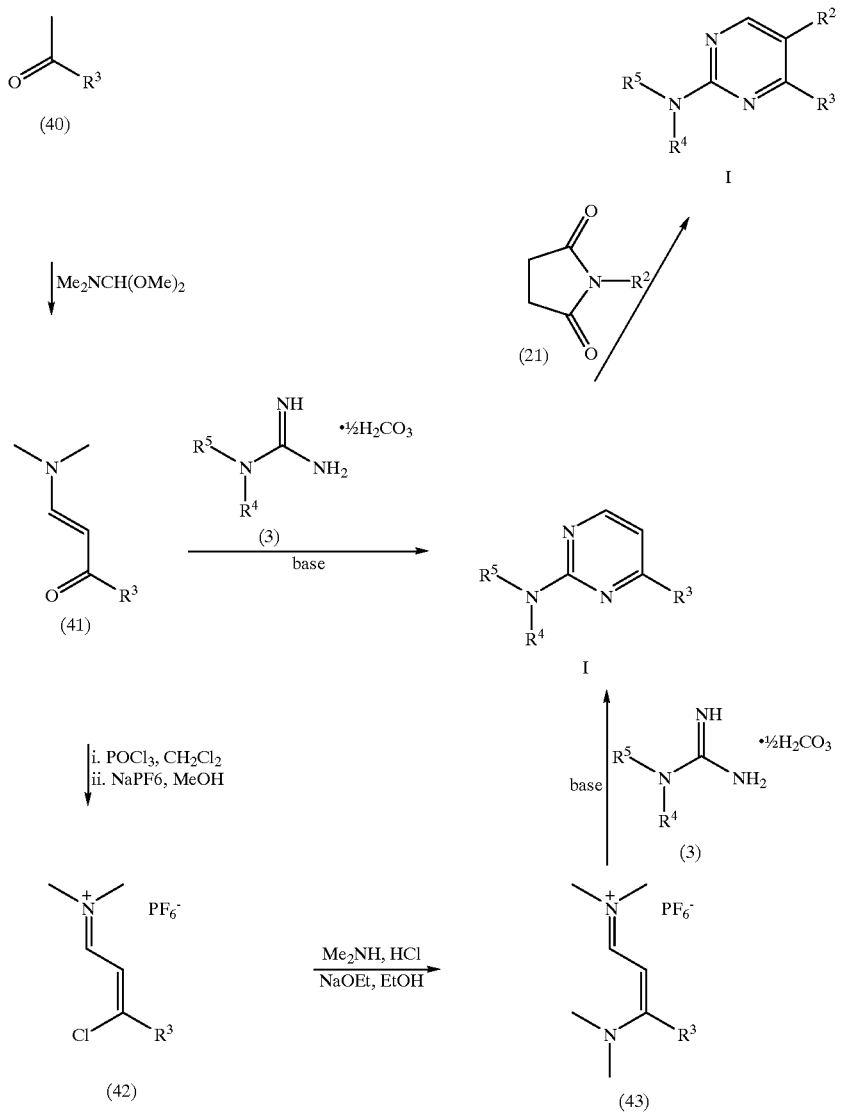

wherein R² is hydrogen, chloro, bromo or iodo, R³ is phenyl (optionally substituted by lower alkyl, lower alkoxy, or halogen), thien-2-yl, fur-2-yl (optionally substituted by lower alkyl, halogen, —(CH₂)ₙ-lower alkoxy, cyano, CHF₂, or CH₂F), 2,3-dihydro-benzo[1.4]dioxin-6-yl, benzo[1.3]]dioxol-5-yl, isoxazol-5-yl, pyridin-2-yl, pyridin-3-yl, oxazol-2-yl, benzofuranyl, or pyrazin-2-yl and R⁴ and R⁵ are hydrogen or lower alkyl.

Preparation of Compounds of Formula (41) The starting methylketone of formula (40) may be obtained commercially, for example from Fluka Chemie AG, or may be prepared according to methods well known in the art.

To prepare compounds of formula (41), a methylketone of formula (40) is reacted with N,N-dimethylformamide dimethyl acetal in N,N-dimethylformamide at reflux for about 16 hours. The product of formula (41) is isolated by conventional means, and preferably purified by means of chromatography or recrystallisation.

Preparation of Compounds of Formula (42)

A compound of formula (41) is reacted with a chlorinating agent, preferably phosphorus oxychloride, in on organic solvent, preferably dichloromethane, at room temperature for 1 hour. The solvent is then removed in vacuo and the residue is reacted with sodium hexafluorophosphate in an alcoholic solvent, preferably methanol, at 0° C. for about 15 minutes. The product of formula (42) is isolated by conventional means, and preferably used in the next reaction without further purification.

Preparation of Compounds of Formula (43)

A compound of formula (42) is reacted with an excess of a salt of a secondary alkyl amine, preferably dimethylamine hydrochloride, in an alcoholic solvent, preferably ethanol, containing a base, preferably sodium ethylate. The reaction is preferably performed at room temperature for 1–18 hours, preferably 16 hours. The product of formula (43) is isolated by conventional means, and preferably used in the next reaction without further purification.

Preparation of compounds of Formula I, wherein A—$R^1$ is hydrogen, X and Y are nitrogen, $R^2$ is hydrogen, and $R^3$ is phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl.

The carbonate salts of guanidine or of substituted guanidine compounds of formula (3) are commercially available, or may be prepared according to methods well known in the art.

The 2-amino-pyrimidine derivative of Formula I, wherein A—$R^1$ is hydrogen, X and Y are nitrogen, $R^2$ is hydrogen, and $R^3$ is phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl is prepared by treating compounds of formula (43) with a slight excess of the guanidine carbonate compounds of formula (3) in a polar non-protic solvent, preferably dimethylformamide, containing an excess of base, preferably sodium hydride. The reaction is carried out at a temperature between room temperature and the reflux temperature of the solvent, preferably about 100° C., for 1–16 hours, preferably about 1 hours. The product of Formula I is isolated by conventional means, and preferably purified by means of chromatography or recrystallisation.

Alternative preparation of compounds of Formula I, wherein A—$R^1$ is hydrogen, X and Y are nitrogen, $R^2$ is hydrogen, and $R^3$ is phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl.

The carbonate salts of guanidine or of substituted guanidine compounds of formula (3) are commercially available, or may be prepared according to methods well known in the art.

The 2-amino-pyrimidine derivative of Formula I, wherein the definitions are given above, is prepared by treating compounds of formula (41) with an excess of the guanidine carbonate compounds of formula (3) in a polar solvent, preferably methanol, containing an excess of base, preferably sodium methylate, at a temperature between room temperature and the reflux temperature of the solvent, preferably about 80° C., for about 2 hours. The product of Formula I where A—$R^1$ is hydrogen, X and Y are nitrogen, $R^2$ is hydrogen, chloro, bromo or iodo, and $R^3$ is phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, is isolated by conventional means, and preferably purified by means of chromatography or recrystallisation.

Preparation of compounds of Formula I, wherein A—$R^1$ is hydrogen, X and Y are nitrogen, $R^2$ is chloro, bromo or iodo, and $R^3$ is phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl.

Compounds of Formula I, wherein A—$R^1$ is hydrogen, X and Y are nitrogen, $R^2$ is hydrogen, and $R^3$ is phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, may be converted to the corresponding 5-halo derivatives of Formula I where $R^2$ is chloro, bromo or iodo, by reacting a compound of Formula I where A—$R^1$ is hydrogen, X and Y are nitrogen, $R^2$ is hydrogen, and $R^3$ is phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6yl, benzo[1.3]dioxol-5-yl, isoxazol-5-yl, pyridin-2-yl, pyridin-3-yl, oxazol-2-yl, benzofuranyl, or pyrazin-2-yl, with a halogenating agent, preferably an N-halosuccinimide of formula (21), where $R^2$ is chloro, bromo or iodo, in an organic solvent, preferably acetic acid, at room temperature for about 16–72 hours. The product of formula I is isolated by conventional means, and preferably purified by means of chromatography or recrystallisation.

Conversion of compounds of Formula I, wherein A—$R^1$ is hydrogen, X and Y are nitrogen, and $R^2$ is iodo, to other compounds of Formula I, where A—$R^1$ is hydrogen and X and Y are nitrogen.

Miscellaneous routes to compounds of Formula I, where in A—$R^1$ is hydrogen and X and Y are nitrogen, from compounds of Formula I, wherein A—$R^1$ is hydrogen, X and Y are nitrogen and $R^2$ is iodo are shown in Reaction Scheme XI:

REACTION SCHEME XI

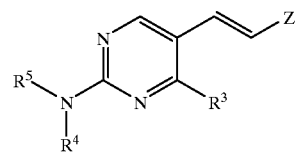

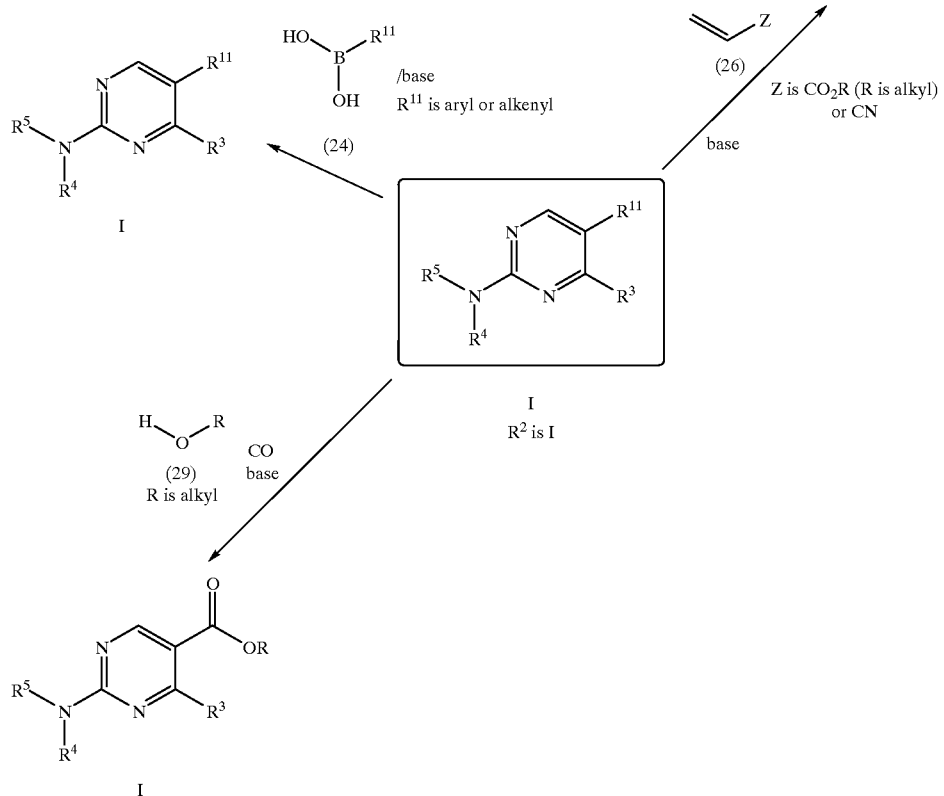

wherein R³ is as defined above, R⁴ and R⁵ are hydrogen or lower alkyl, R is alkyl or benzyl, and Z is an electron-withdrawing group such as CN or $CO_2R$.

Preparation of Compounds of Formula I, Wherein A—R¹ is Hydrogen, X and Y are Nitrogen and R² is aryl or Alkenyl Boronic acid derivatives of formula (24), wherein $R^{11}$ is aryl or alkenyl, may be obtained commercially, or may be prepared by methods well known in the art. A compound of Formula I where A—R¹ is hydrogen, X and Y are nitrogen and R² is iodo is reacted with a boronic acid derivative of formula (24) in an aqueous solvent, preferably a mixture of water and dioxane, containing a palladium catalyst, preferably palladium tetrakis(triphenyl-phosphine), and an inorganic base, preferably sodium carbonate. The reaction is preferably carried out at the reflux temperature of the solvent, preferably about 100° C., for about 6–18 hours, preferably about 16 hours. The product of Formula I where A—R¹ is hydrogen, X and Y are nitrogen and R² is aryl or alkenyl is isolated by conventional means, and preferably purified by chromatography or recrystallisation.

Alternative Preparation of Compounds of Formula I, Wherein A—R¹ is Hydrogen, X and Y are Nitrogen and R² is Alkenyl Alkene derivatives of formula (26), wherein Z is $CO_2R$ or CN and R is alkyl or benzyl, may be obtained commercially, or may be prepared by methods well known in the art. A compound of Formula I where A—R¹ is hydrogen, X and Y are nitrogen and R² is iodo is reacted with an alkene derivative of formula (26) in an ethereal solvent (for example 1,2-dimethoxyethane, tetrahydrofuran or dioxane, preferably dioxane), containing a palladium catalyst, preferably palladium tetrakis(triphenylphosphine), and an inorganic base, preferably cesium carbonate. The reaction is preferably carried out at the reflux temperature of the solvent, preferably about 100° C., for about 8–18 hours, preferably about 12 hours. The product of Formula I where A—R¹ is hydrogen, X and Y are nitrogen and R² is alkenyl is isolated by conventional means, and preferably purified by chromatography or recrystallisation.

Preparation of Compounds of Formula I, Wherein A—R¹ is Hydrogen X and Y are Nitrogen and R² is Alkoxycarbonyl A compound of Formula I, wherein A—R¹ is hydrogen, X and Y are nitrogen and R² is iodo, is reacted with carbon monoxide gas in an alcoholic solvent of formula (29) (for example methanol, ethanol, benzyl alcohol, or a solution of one of these alcohols in dimethylformamide), containing a palladium catalyst, preferably tris(dibenzylidine-acetone) dipalladium chloroform complex, a catalytic amount of a monodentate ligand, preferably triphenylarsine, and an excess of an organic base, preferably triethylamine. The reaction is carried out at a pressure of 1–20 atmospheres, preferably 1 atmosphere, and at a temperature above room temperature, preferably about 100–110° C., for about 8–18 hours, preferably about 12 hours. The product of Formula I where A—R¹ is hydrogen, X and Y are nitrogen and R² is alkoxycarbonyl is isolated by conventional means, and preferably purified by chromatography or recrystallisation.

Preparation of compounds of Formula I, wherein A is nitrogen, oxygen or sulfur, X is C—CN, Y is nitrogen, R² is cyano, R³ is phenyl (optionally substituted by lower alkyl, lower alkoxy, or halogen), thien-2-yl, fur-2-yl (optionally substituted by lower alkyl, halogen, lower alkoxy, —(CH₂)ₙ—OH, —(CH₂)ₙ-lower alkoxy, cyano, CHF₂, or CH₂F), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, and R⁴ and R⁵ are both hydrogen p One method of preparation of compounds of Formula I as mentioned above is from intermediates of formula (47), the preparation of which is shown in Reaction Scheme XII below.

2-cyanothioacetamide of formula (44) and one equivalent of malonitrile. The reaction is carried out in a polar organic

REACTION SCHEME XII

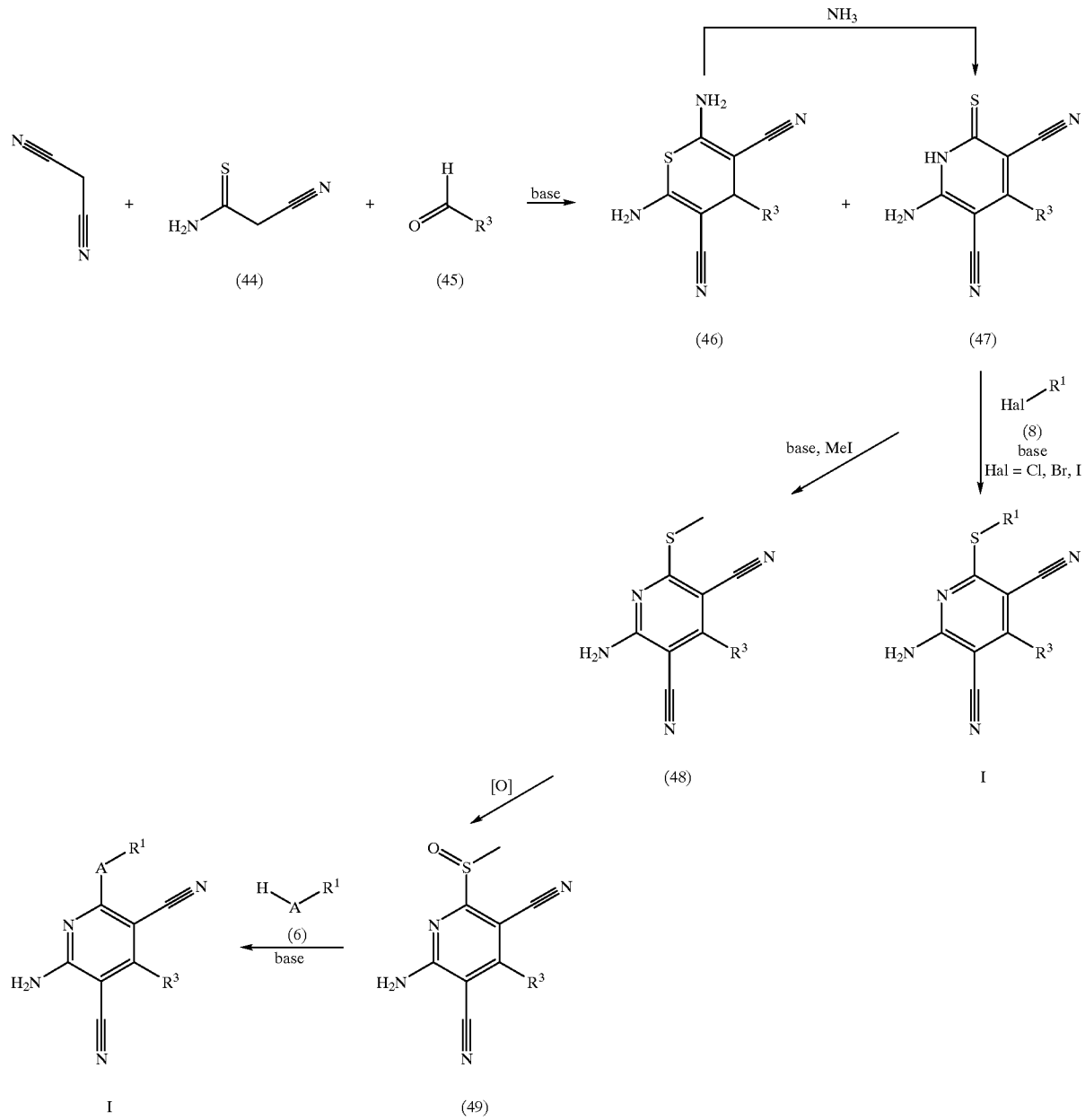

wherein A is nitrogen, oxygen or sulfur, $R^1$ is as defined above, and $R^3$ is phenyl (optionally substituted by lower alkyl, lower alkoxy, or halogen), thien-2-yl, fur-2-yl (optionally substituted by lower alkyl, halogen, lower alkoxy, —$(CH_2)_n$—OH, —$(CH_2)_n$— lower alkoxy, cyano, $CHF_2$, or $CH_2F$), 2,3-dihydro-benzo[1.4]dioxin-6-yl, benzo[1.3]dioxol 5-yl, isoxazol-5-yl, pyridin-2-yl, pyridin-3-yl, oxazol-2-yl, benzofaranyl, or pyrazin-2-yl.

Preparation of Compounds of Formula (46) and Formula (47)

An aldehyde of formula (45), which may be obtained commercially or may be prepared according to methods well known in the art, is reacted with one equivalent of solvent (for example ethanol, dimethylformamide, or a mixture of ethanol and dimethylformamide, preferably a mixture of ethanol and dimethylformamide) containing a catalytic amount of an amine base (for example piperidine, triethylamine or morpholine, preferably piperidine). The reaction is carried out at a temperature between 0° C. and 100° C., preferably about 0° C., for about 30 minutes to 2 hours, preferably about 1 hour. The products of formula (46), a 2,6-diamino-4H-thiopyran-3,5-dicarbonitrile derivative, and of formula (47), a 6-amino-2-thioxo-1,2-dihydro-pyridine-3,5-dicarbonitrile derivative, are isolated by conventional means, and preferably purified by chromaotography or recrystallisation. The ratio between the amount of product of formula (46) which is obtained and the amount of product of formula (47) which is obtained is dependent on the nature of the substituent $R^3$.

Conversion of Compounds of Formula (46) to Compounds of Formula (47)

A 2,6-diamino-4H-thiopyran-3,5-dicarbonitrile derivative of formula (46) may be converted to a 6-amino-2-thioxo-1,2-dihydro-pyridine-3,5-dicarbonitrile derivative of formula (47) by treatment with an excess of concentrated aqueous ammonia. The reaction is carried out in an alcoholic solvent, such as methanol or ethanol, at room temperature for about 2–4 hours. The product of formula (47) is isolated by conventional means, and preferably purified by chromatography or recrystallisation.

Preparation of Compounds of Formula (48)

A compound of formula (47) is reacted with an excess of methyl iodide. The reaction is carried out in a polar solvent, preferably methanol or ethanol, in the presence of about one equivalent of a base, preferably sodium methylate or sodium ethylate, at room temperature or above, preferably room temperature, for 1–18 hours, preferably about 2 hours. The product of formula (48) is isolated by conventional means, and preferably purified by means of chromatography or recrystallisation.

Preparation of Compounds of Formula (49)

A methylsulfanyl-pyridine compound of formula (48) may be converted to the methanesulfinyl-pyridine derivative of formula (49) by reacting a compound of formula (48) with an oxidising agent, preferably 3-phenyl-2-(phenylsulfonyl)oxaziridine, in an organic solvent, preferably dichloromethane, at room temperature. The product of formula (49) is isolated by conventional means, and preferably reacted in the next step without further purification. The product of formula (49) may, however, be additionally purified by means of chromatography or recrystallisation.

Preparation of compounds of Formula I, where in A is nitrogen, oxygen or sulfur, X is C—CN, Y is nitrogen, $R^2$ is cyano, $R^3$ is phenyl (optionally substituted by lower alkyl, lower alkoxy, or halogen), thien-2-yl, fur-2-yl (optionally substituted by lower alkyl, halogen, lower alkoxy, —$(CH_2)_n$—OH, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, and $R^4$ and $R^5$ are both hydrogen.

A compound of formula (49) is reacted with an appropriate nucleophilic compound of formula (6), which may be commercially available or may be prepared by methods well known in the art, and which may be chosen from: a primary or secondary aliphatic alcohol or an aromatic alcohol, in each case used together with a non-nucleophilic base, preferably 1,8-diazabicyclo[5.4.0]undec-7-ene (1,5-5); a primary or secondary aliphatic thiol or an aromatic thiol, in each case used together with a non-nucleophilic base, preferably 1,8-diazabicyclo[5.4.0]undec-7-ene (1,5-5) (DBU); a primary or secondary aliphatic amine which is preferably used in excess in the absence of an added base; the inorganic salt of a primary or secondary aliphatic amine, such as a hydrochloride salt, which is used together with a non-nucleophilic base, preferably 1,8-diazabicyclo[5.4.0]undec-7-ene (1,5-5); an alkali metal alcoholate of a primary or secondary aliphatic alcohol or of an aromatic alcohol, preferably a sodium or potassium alcoholate, which is preferably used in excess; or an alkali metal thiolate of a primary or secondary aliphatic thiol or of an aromatic thiol, preferably a sodium or potassium thiolate, which is preferably used in excess. These reactions may be carried out in a non-protic polar solvent such as acetonitrile or in an ethereal solvent such as dioxane, tetrahydrofuran or 1,2-dimethoxyethane, preferably 1,2-dimethoxyethane, at room temperature or above, preferably at room temperature of the solvent, for 1–18 hours, preferably 1 hour. The product of Formula I where A is nitrogen, oxygen or sulfur, X is C—CN, Y is nitrogen, $R^2$ is cyano, $R^3$ is phenyl (optionally substituted by lower alkyl, lower alkoxy, or halogen), thien-2-yl, fur-2-yl (optionally substituted by lower alkyl, halogen, lower alkoxy, —$(CH_2)_n$—OH, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, and $R^4$ and $R^5$ are both hydrogen is isolated by conventional means, and preferably purified by means of chromatography or recrystallisation.

Alternative preparation of compounds of Formula I, wherein A is sulfur, X is C—CN, Y is Nitrogen, $R^2$ is cyano, $R^3$ is phenyl (optionally substituted by lower alkyl, lower alkoxy, or halogen), thien-2-yl, fur-2-yl (optionally substituted by lower alkyl, halogen, lower alkoxy, —$(CH_2)_n$—OH, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, and $R^4$ and $R^5$ are both hydrogen.

An alternative method of converting a compound of formula (47) to a compound of Formula I as mentioned above is by reaction of the compound of formula (47) with an excess of an appropriate organic halide of formula (8), such as a primary or secondary aliphatic halide, preferably an aliphatic bromide or a benzylic bromide, which may be commercially available or may be prepared by methods well known in the art. The reaction is carried out in a polar solvent, preferably methanol or ethanol, in the presence of an excess of a base, preferably sodium methylate or sodium ethylate, at room temperature or above, preferably at the reflux temperature of the solvent, for 1–18 hours, preferably 1 hour. The product of Formula I where A is sulfur, X is C—CN, Y is nitrogen, $R^2$ is cyano, $R^3$ is phenyl (optionally substituted by lower alkyl, lower alkoxy, or halogen), thien-2-yl, fur-2-yl (optionally substituted by lower alkyl, halogen, lower alkoxy, —$(CH_2)_n$—OH, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, and $R^4$ and $R^5$ are both hydrogen is isolated by conventional means, and preferably purified by means of chromatography or recrystallisation.

Preparation of Compounds of Formula II

Preparation of compounds of Formula II, wherein A is nitrogen, oxygen or sulfur, and $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl.

One method of preparation of compounds of Formula II, wherein the substituents are defined above, is from intermediates of formula (52), of formula (53) or of formula (54), the preparation of which is shown in Reaction Scheme XIII below.

REACTION SCHEME XIII

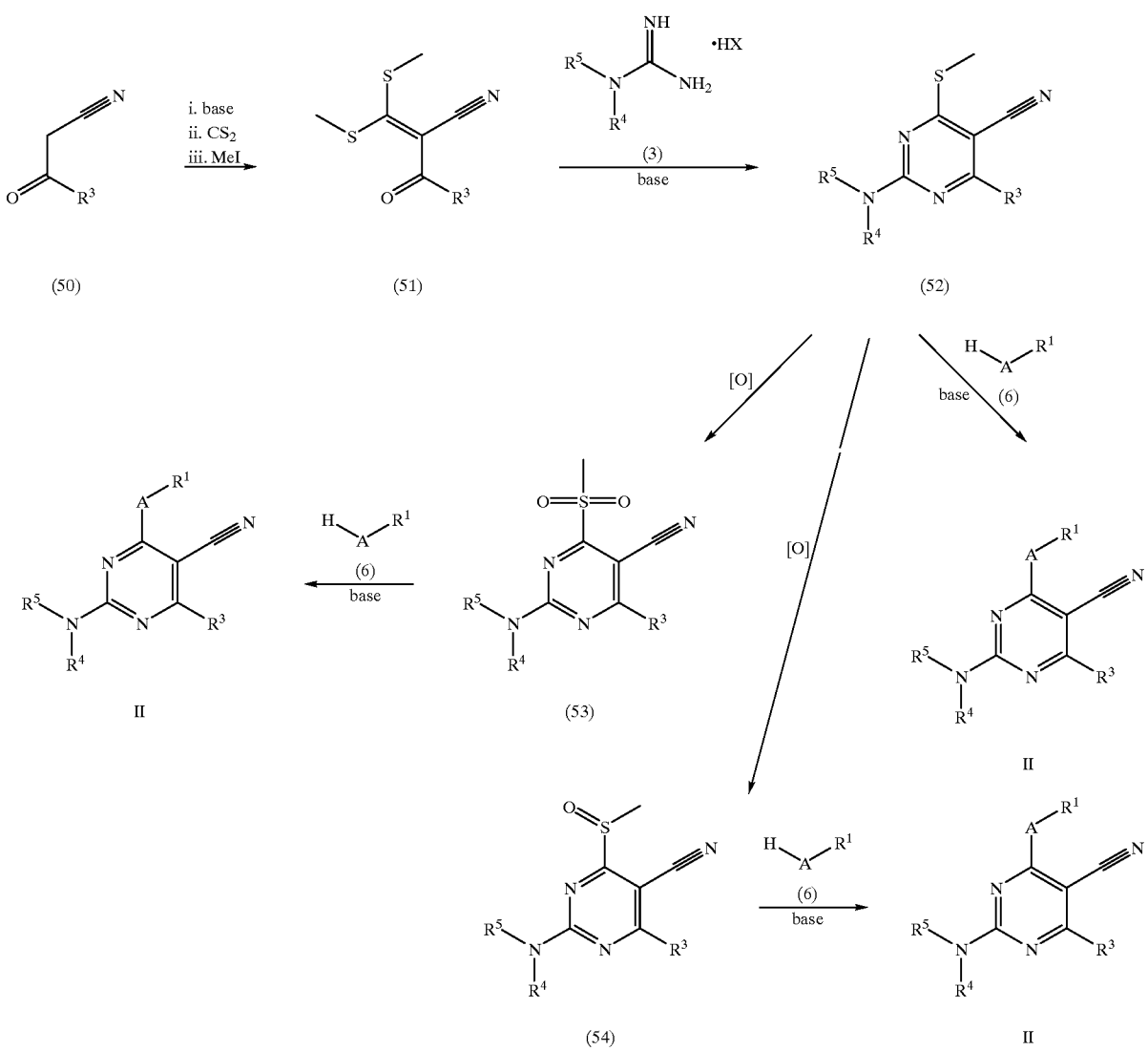

wherein A is nitrogen, oxygen or sulfur, $R^1$ is as defined above, $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5y-1, pyridin-2-yl, pyridin-3-yl, oxazol-2-yl, benzofuranyl, or pyrazin-2-yl, and $R^4$ and $R^5$ are hydrogen or lower alkyl.

Preparation of Compounds of Formula (51)

The starting α-cyanoketone of formula (50) may be obtained commercially, for example from Avocado Research Chemicals Limited, or may be prepared according to methods well known in the art.

Compounds of formula (51) may be prepared by using the method of Rudorf and Augustin in DD 119041 and *Phosphorus and Sulfur*, 1981, 9, 329, in which an α-cyanoketone of formula (50) is sequentially treated with a strong non-aqueous base, preferably sodium hydride, and with carbon disulphide, in a polar non-protic solvent, preferably dimethyl sulfoxide, at room temperature for about 1–2 hours, preferably 2 hours, and then treated with methyl iodide at room temperature for about 2–16 hours, preferably 2 hours.

The product of formula (51) is isolated by conventional means, and preferably reacted in the next step without further purification. The product of formula (51) may, however, be additionally purified by means of chromatography or recrystallisation.

Preparation of Compounds of Formula (52)

The inorganic salts of guanidine or of substituted guanidine compounds of formula (3) are commercially available, or may be prepared according to methods well known in the art.

The compounds of formula (52) are prepared according to the method of Rudorf and Augustin in *J. Prakt. Chem.*, 1978, 320, 576, in which compounds of formula (51) are treated with a slight excess of the guanidine compounds of formula (3) in a polar non-protic solvent, preferably dimethylformamide, containing a base, preferably triethylamine or sodium hydride, at reflux for 1–8 hours, preferably 1 hour in the case where sodium hydride is used, and preferably 6 hours in the case where triethylamine is used. The product of formula (52) is isolated by conventional means, and preferably reacted in the next step without further purification. The product of formula (52) may, however, be additionally purified by means of chromatography or recrystallisation.

Preparation of Compounds of Formula (53) and Formula (54)

The methylsulfanyl-pyrimidine compound of formula (52) is reacted with an oxidising agent, preferably meta-chloroperbenzoic acid or 3-phenyl-2-(phenylsulfonyl) oxaziridine, in an organic solvent, preferably dichloromethane, at room temperature to give a product of formula (53) or formula (54), whereby in the case of using meta-chloroperbenzoic acid the methanesulfonyl-pyrimidine derivative of formula (53) is preferentially formed, and in the case of using 3-phenyl-2-(phenylsulfonyl)oxaziridine the methanesulfinyl-pyrimidine derivative of formula (54) is preferentially formed. The products of formula (53) or of formula (54) are isolated by conventional means, and preferably reacted in the next step without further purification. The products of formula (53) or formula (54) may, however, be additionally purified by means of chromatography or recrystallisation.

Preparation of compounds of Formula II, wherein A is nitrogen, oxygen or sulfur, and $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl.

One method of preparation of compounds of Formula II as mentioned above is by treatment of compounds of formula (53) with an appropriate nucleophilic compound of formula (6), which may be commercially available or may be prepared by methods well known in the art, and which may be chosen from: a primary or secondary aliphatic alcohol or an aromatic alcohol, in each case used together with a non-nucleophilic base, preferably 1,8-diazabicyclo[5.4.0]undec-7-ene (1,5-5); a primary or secondary aliphatic thiol or an aromatic thiol, in each case used together with a non-nucleophilic base, preferably 1,8-diazabicyclo[5.4.0]undec-7-ene (1,5-5) (DBU); a primary or secondary aliphatic amine which is preferably used in excess in the absence of an added base; the inorganic salt of a primary or secondary aliphatic amine, such as a hydrochloride salt, which is used together with a non-nucleophilic base, preferably 1,8-diazabicyclo[5.4.0]undec-7-ene (1,5-5); an alkali metal alcoholate of a primary or secondary aliphatic alcohol or of an aromatic alcohol, preferably a sodium or potassium alcoholate, which is preferably used in excess; or an alkali metal thiolate of a primary or secondary aliphatic thiol or of an aromatic thiol, preferably a sodium or potassium thiolate, which is preferably used in excess. These reactions may be carried out in a non-protic polar solvent such as acetonitrile or in an ethereal solvent such as dioxane, tetrahydrofuran or 1,2-dimethoxyethane, preferably 1,2-dimethoxyethane, at room temperature or above, preferably at the reflux temperature of the solvent, for 1–18 hours, preferably 18 hours. The product of Formula II where A is nitrogen, oxygen or sulfur, and $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6yl, benzo[1.3]dioxol-5-yl, isoxazol-5-yl, pyridin-2-yl, pyridin-3-yl, oxazol-2-yl, benzofuranyl, or pyrazin-2-yl, is isolated by conventional means, and preferably purified by means of chromatography or recrystallisation.

An alternative method of preparation of compounds of Formula II, wherein A is nitrogen, oxygen or sulfur, and $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, is by treatment compounds of formula (54) with an appropriate nucleophilic compound of formula (6), which may be commercially available or may be prepared by methods well known in the art, and which may be chosen from: a primary or secondary aliphatic alcohol or an aromatic alcohol, in each case used together with a non-nucleophilic base, preferably 1,8-diazabicyclo[5.4.0]undec-7-ene (1,5-5); a primary or secondary aliphatic thiol or an aromatic thiol, in each case used together with a non-nucleophilic base, preferably 1,8-diazabicyclo[5.4.0]undec-7-ene (1,5-5) (DBU); a primary or secondary aliphatic amine which is preferably used in excess in the absence of an added base; the inorganic salt of a primary or secondary aliphatic amine, such as a hydrochloride salt, which is used together with a non-nucleophilic base, preferably 1,8-diazabicyclo[5.4.0]undec-7-ene (1,5-5); an alkali metal alcoholate of a primary or secondary aliphatic alcohol or of an aromatic alcohol, preferably a sodium or potassium alcoholate, which is preferably used in excess; or an alkali metal thiolate of a primary or secondary aliphatic thiol or of an aromatic thiol, preferably a sodium or potassium thiolate, which is preferably used in excess. These reactions may be carried out in a non-protic polar solvent such as acetonitrile or in an ethereal solvent such as such as dioxane, tetrahydrofuran or 1,2-dimethoxyethane, preferably 1,2-dimethoxyethane, at room temperature or above, preferably at room temperature, for 1–18 hours, preferably 2 hours. The product of Formula II where A is nitrogen, oxygen or sulfur, and $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, is isolated by conventional means, and preferably purified by means of chromatography or recrystallisation.

Yet another method of preparation of compounds of Formula II, wherein A is nitrogen, oxygen or sulfur, and $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, is by treatment of compounds of formula (52) with an appropriate nucleophilic compound of formula (6), which may be commercially available or may be prepared by methods well known in the art, and which may be chosen from: a primary or secondary amine which is preferably used in excess in the absence of an added base; an alkali metal alcoholate of a primary or secondary aliphatic alcohol or of an aromatic alcohol, preferably a sodium or potassium alcoholate, which is preferably used in excess; or an alkali metal thiolate of a primary or secondary aliphatic thiol or of an aromatic thiol, preferably a sodium or potassium thiolate, which is preferably used in excess. These reactions may be carried out in a non-protic polar solvent such as acetonitrile or in an ethereal solvent such as such as dioxane, tetrahydrofuran or 1,2-dimethoxyethane, preferably 1,2-dimethoxyethane. These reactions are carried out at room temperature or above, preferably at the reflux temperature of the solvent, for 16–48 hours, preferably for 18 hours. The product of Formula II where A is nitrogen, oxygen or sulfur, and $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, is isolated by conventional means, and preferably purified by means of chromatography or recrystallisation. Additionally, if the nucleophile of formula (6) used is a primary or secondary aliphatic amine, and if this nucleophile is used in excess in the absence of an added base, then the reaction may be carried out in an aqueous solvent, preferably a mixture of water and an organic solvent such as ethanol, 1,2-dimethoxyethane or dioxane, preferably ethanol. These reactions are carried out at room temperature or above, preferably at the reflux temperature of the solvent, for 16–48 hours. The product of Formula II is isolated by conventional means, and preferably purified by means of chromatography or recrystallisation.

Alternative preparation of compounds of Formula (52), wherein $R^3$ is phenyl (optionally substituted by lower alkyl, lower alkoxy, or halogen), thien-2-yl, fur-2-yl (optionally substituted by lower alkyl, —$(CH_2)_n$-lower alkoxy), 2,3-dihydro-benzo[1.4]dioxin-6-yl, benzo[1.3]dioxol-5-yl, isoxazol-5-yl, pyridin-2-yl, pyridin-3-yl, —C(=$CH_2$)O-lower alkyl, 4,5-dihydrofuran-2-yl, 5,6-dihydro-4H-pyran-2yl oxazol-2-yl, benzofuranyl, or pyrazin-2-yl, and $R^4$ and $R^5$ are hydrogen.

An alternative method of preparation of compounds of formula (52), wherein $R^3$ is phenyl (optionally substituted by lower alkyl, lower alkoxy, or halogen), thien-2-yl, fur-2-yl (optionally substituted by lower alkyl, —$(CH_2)_n$-lower alkoxy), 2,3-dihydro-benzo[1.4]dioxin-6-yl, benzo[1.3]dioxol-5-yl, isoxazol-5-yl, pyridin-2-yl, pyridin-3-yl, —C(=$CH_2$)O-lower alkyl, 4,5-dihydrofuran-2yl, 5,6-dihydro-4H-pyran-2yl oxazol-2-yl, benzofuranyl, or pyrazin-2-yl, and $R^4$ and $R^5$ are both hydrogen, is from intermediates of formula (57) as shown in Reaction Scheme XIV below.

REACTION SCHEME XIV

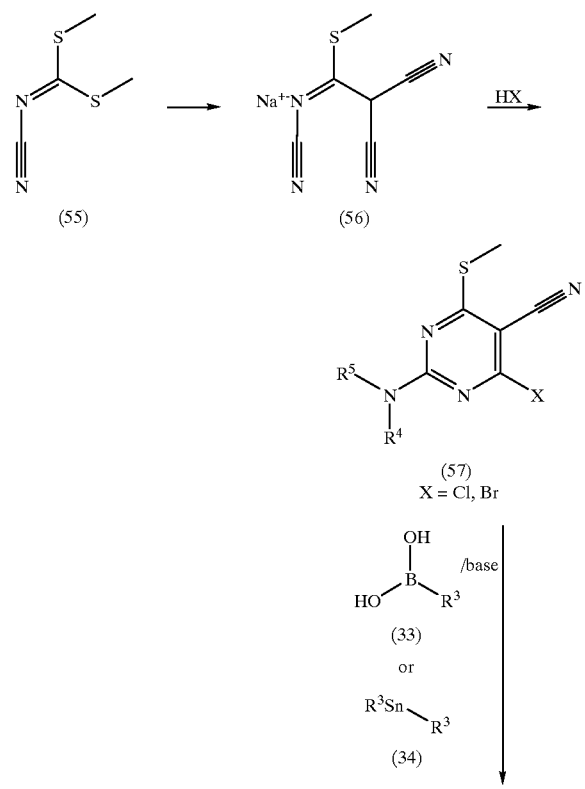

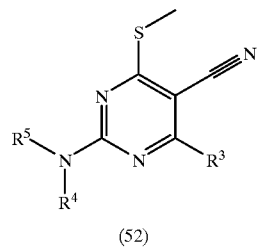

wherein $R^3$ is phenyl (optionally substituted by lower alkyl, lower alkoxy, or halogen), thien-2-yl, fur-2-yl (optionally substituted by lower alkyl, —$(CH_2)_n$-lower alkoxy), 2,3-dihydro-benzo[1.4]dioxin-6-yl, benzo[1.3]dioxol-5-yl, isoxazol-5-yl, pyridin-2-yl, pyridin-3-yl, —C(=$CH_2$)0-lower alkyl, 4,5-dihydrofuran-2-yl, 5,6-dihydro-4H-pyran-2-yl oxazol-2-yl, benzofuranyl, or pyrazin-2-yl, and $R^4$ and $R^5$ are hydrogen.

Preparation of Compound of Formula (56)

N-Cyano-imido-S,S-dimethyl-carbonate, a compound of formula (55) which may be obtained commercially, for example from Fluka Chemie AG, is reacted with malonitrile in a polar solvent, preferably methanol or ethanol, in the presence of a base, preferably sodium methylate or sodium ethylate, at room temperature for 1–18 hours, preferably 14 hours. The product of formula (56), the sodium salt of 2,2-dicyano-1-methylsulfanyl-vinyl-cyanamide, is isolated by conventional means, and preferably purified by means of recrystallisation.

Preparation of Compound of Formula (57)

The compound of formula (56), the sodium salt of 2,2-dicyano-1-methylsulfanyl-vinyl-cyanamide, is reacted by addition to a large excess of anhydrous hydrogen chloride in an ethereal solvent, preferably diethyl ether, at 0° C. and the mixture is allowed to warm slowly to room temperature for over 1–36 hours, preferably 18 hours. The product of formula (57), 2-amino-4-chloro-6-methylsulfanyl-pyrimidine-5-carbonitrile, is isolated by conventional means, and preferably purified by means of recrystallisation or chromatography. Alternatively, the compound of formula (56), the sodium salt of 2,2-dicyano-1-methylsulfanyl-vinyl-cyanamide, is reacted with hydrogen bromide in a protic solvent, preferably acetic acid, at 5° C. and the mixture is allowed to warm slowly to room temperature for over 1–36 hours, preferably 1 hour. The product of formula (57), 2-amino-4-bromo-6-methylsulfanyl-pyrimidine-5-carbonitrile, is isolated by conventional means, and preferably purified by means of recrystallisation or chromatography.

Preparation of Compounds of Formula (52)

Boronic acid derivatives of formula (33), wherein $R^3$ is phenyl (optionally substituted by lower alkyl, lower alkoxy, or halogen), thien-2-yl, fur-2-yl (optionally substituted by lower alkyl, —$(CH_2)_n$-lower alkoxy), 2,3-dihydro-benzo[1.4]dioxin-6-yl, benzo[1.3]dioxol-5-yl, isoxazol-5-yl, pyridin-2-yl, pyridin-3-yl, —C(=$CH_2$)O-lower alkyl, 4,5-dihydrofuran-2-yl, 5,6-dihydro-4H-pyran-2-yl oxazol-2-yl, benzofuranyl, or pyrazin-2-yl, may be obtained commercially, or may be prepared by methods well known in the art. The compound of formula (57), 2-amino-4-bromo-6-methylsulfanyl-pyrimidine-5-carbonitrile or 2-amino-4-chloro-6-methylsulfanyl-pyrimidine-5-carbonitrile, is reacted with a boronic acid derivative of formula (33) in an aqueous solvent, preferably a mixture of water and dioxane, containing a palladium catalyst, preferably palladium tetrakis(triphenylphosphine), and an inorganic base, preferably sodium carbonate. The reaction is preferably carried out at the reflux temperature of the solvent, preferably about 100° C., for about 2–8 hours, preferably about 4 hours. The product of formula (52) is isolated by conventional means, and preferably purified by chromatography or recrystallisation.

Preparation of compounds of Formula II, wherein A is nitrogen, oxygen or sulfur, and $R^3$ is pyrazol-1-yl (optionally substituted by lower alkyl or halogen). One method of preparation of compounds of Formula II, wherein A is nitrogen, oxygen or sulfur, and $R^3$ is pyrazol-1-yl (optionally substituted by lower alkyl or halogen), is from intermediates of formula (84), the preparation of which is shown in Reaction Scheme XV below.

REACTION SCHEME XV

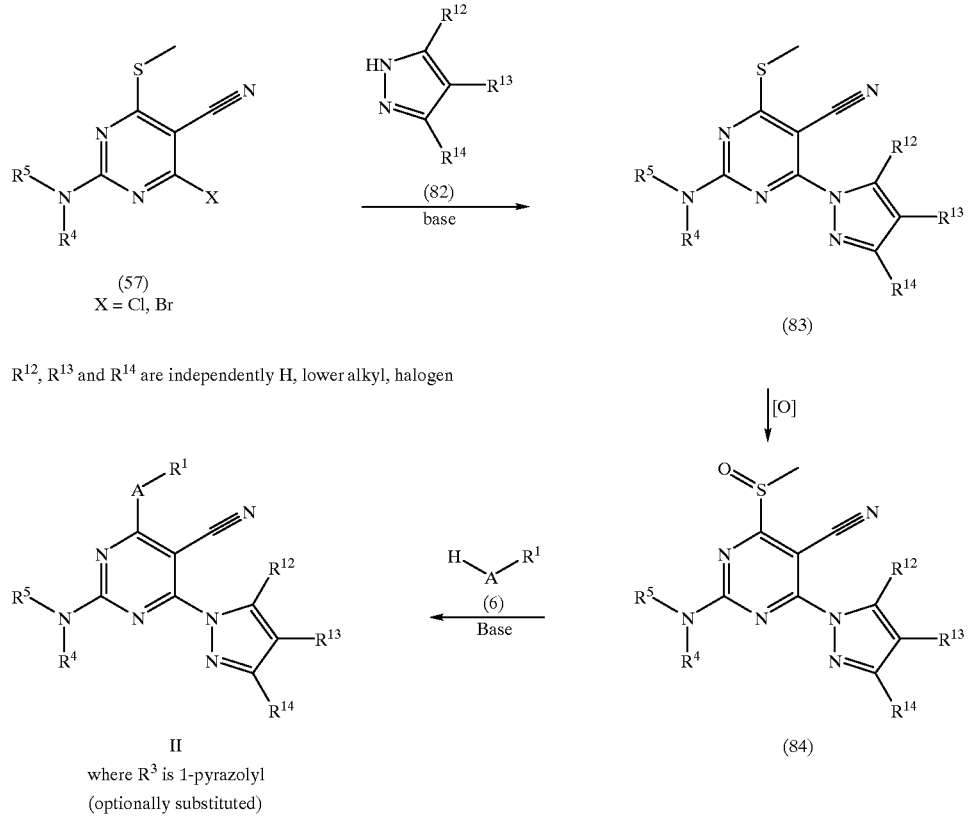

Alternative Preparation of Compounds of Formula (52)

Trialkylstannane derivatives of formula (34), wherein $R^3$ is phenyl (optionally substituted by lower alkyl, lower alkoxy, or halogen), thien-2-yl, fur-2-yl (optionally substituted by lower alkyl, —(CH$_2$)$_n$-lower alkoxy), 2,3-dihydrobenzo[1.4]dioxin-6-yl, benzo[1.3]dioxol-5-yl, isoxazol-5-yl, pyridin-2-yl, pyridin-3-yl, —C(=CH$_2$)O-lower alkyl, 4,5-dihydrofuran-2-yl, 5,6-dihydro-4H-pyran-2-yl oxazol-2-yl, benzofuranyl, or pyrazin-2-yl, and R is methyl or n-butyl, may be obtained commercially, or may be prepared by methods well known in the art. The compound of formula (57), 2-amino-4-bromo-6-methylsulfanyl-pyrimidine-5-carbonitrile or 2-amino-4-chloro-6-methylsulfanyl-pyrimidine-5-carbonitrile, is reacted with a trialkystannane derivative of formula (34) in an ethereal solvent (for example 1,2-dimethoxyethane, tetrahydrofuran or dioxane, preferably dioxane), containing a palladium catalyst, preferably palladium tetrakis(triphenylphosphine). The reaction is preferably carried out at the reflux temperature of the solvent, preferably about 100° C., for about 10–18 hours, preferably about 16 hours. The product of formula (52) is isolated by conventional means, and preferably purified by chromatography or recrystallisation.

wherein A is nitrogen, oxygen or sulfur, $R^1$ is as defined above, $R^4$ and $R^5$ are hydrogen, and $R^{12}$, $R^{13}$ and $R^{14}$ are independently hydrogen, lower alkyl, or halogen.

Preparation of Compounds of Formula (83)

The starting pyrazoles of formula (82) may be obtained commercially, or may be prepared according to methods well known in the art.

Compounds of formula (83) may be prepared by treating a compound of formula (57), either 2-amino-4-bromo-6-methylsulfanyl-pyrimidine-5-carbonitrile or 2-amino-4-chloro-6-methylsulfanyl-pyrimidine-5-carbonitrile, with an excess of the pyrazole compounds of formula (82) in a polar non-protic solvent, such as N-methylpyrrolidone, N,N-dimethyl-formamide or diglyme, preferably N-methylpyrrolidone, in the presence of a base, such as sodium hydride, potassium hydride, or cesium carbonate, preferably cesium carbonate, at an elevated temperature, preferably 60–70° C., for about 2–18 hours, preferably 16 hours. The product of formula (83) is isolated by conventional means, and preferably purified by means of chromatography or recrystallisation.

Preparation of Compounds of Formula (84)

The methylsulfanyl-pyrimidine compound of formula (83) is reacted with an oxidising agent, preferably 3-phenyl- 2-(phenylsulfonyl)oxaziridine, in an organic solvent, preferably dichloromethane, at room temperature. The product of formula (84), a methanesulfinyl-pyrimidine derivative, is isolated by conventional means, and preferably reacted in the next step without further purification. The product of formula (84) may, however, be additionally purified by means of chromatography or recrystallisation.

Preparation of compounds of Formula II, wherein A is nitrogen, oxygen or sulfur, and $R^3$ is pyrazol-1-yl (optionally substituted by lower alkyl or halogen). The methanesulfinyl-pyrimidine derivative of formula (84) is reacted with an appropriate nucleophilic compound of formula (6), which may be commercially available or may be prepared by methods well known in the art, and which may be chosen from: a primary or secondary aliphatic alcohol or an aromatic alcohol, in each case used together with a non-nucleophilic base, preferably 1,8-diazabicyclo[5.4.0]undec-7-ene (1,5-5); a primary or secondary aliphatic thiol or an aromatic thiol, in each case used together with a non-nucleophilic base, preferably 1,8-diazabicyclo [5.4.0]undec-7-ene (1,5-5) (DBU); a primary or secondary aliphatic amine which is preferably used in excess in the absence of an added base; the inorganic salt of a primary or secondary aliphatic amine, such as a hydrochloride salt, which is used together with a non-nucleophilic base, preferably 1,8-diazabicyclo [5.4.0]undec-7-ene (1,5-5); an alkali metal alcoholate of a primary or secondary aliphatic alcohol or of an aromatic alcohol, preferably a sodium or potassium alcoholate, which is preferably used in excess; or an alkali metal thiolate of a primary or secondary aliphatic thiol or of an aromatic thiol, preferably a sodium or potassium thiolate, which is preferably used in excess. These reactions may be carried out in a non-protic polar solvent such as acetonitrile or in an ethereal solvent such as such as dioxane, tetrahydrofuran or 1,2-dimethoxyethane, preferably 1,2-dimethoxyethane, at room temperature or above, preferably at room temperature, for 1–18 hours, preferably 2 hours. The product of Formula II, wherein A is nitrogen, oxygen or sulfur, and $R^3$ is pyrazol-1-yl (optionally substituted by lower alkyl or halogen), is isolated by conventional means, and preferably purified by means of chromatography or recrystallisation.

Alternative preparation of compounds of Formula II where A is oxygen or sulfur and $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl.

An alternative method of converting a compound of formula (52) to a compound of Formula II, wherein A is oxygen or sulfur, and $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, is shown below in Reaction Scheme XVI.

REACTION SCHEME XVI

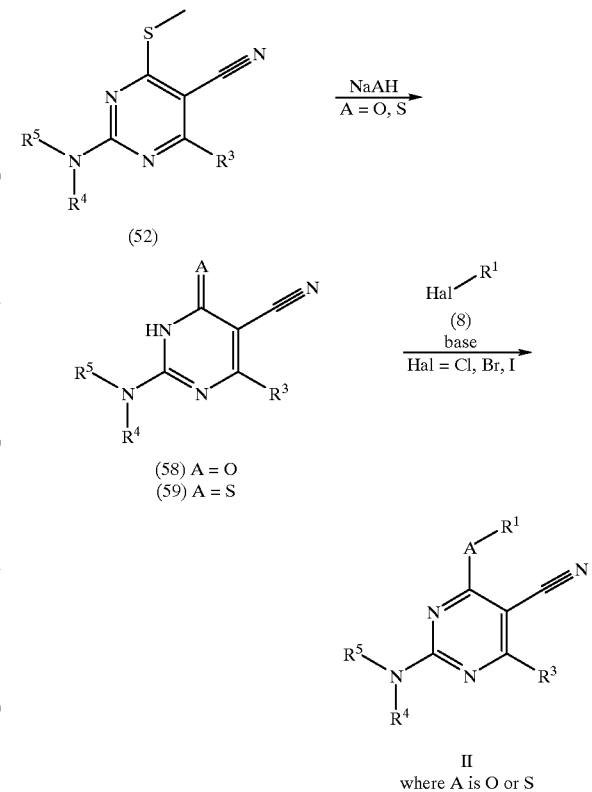

wherein A is oxygen or sulfur, $R^1$ is as defined above, $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, and $R^4$ and $R^5$ are hydrogen or lower alkyl.

Preparation of Compounds of Formula (58)

A compound of formula (52) is reacted with an excess of alkali metal hydroxide, preferably sodium hydroxide, in an aqueous solvent, preferably a mixture of water and an ethereal organic solvent such as 1,2-dimethoxyethane or dioxane, preferably dioxane. The reaction is preferably carried out at the reflux temperature of the solvent, preferably about 100° C., and preferably for about 16 h. The product of formula (58) is isolated by conventional means, and preferably reacted in the next step without further purification. The product of formula (58) may, however, be additionally purified by means of recrystallisation.

Preparation of compounds of Formula II where A is oxygen and $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo [1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl.

The compound of formula (58) is reacted with an excess of an appropriate organic halide of formula (8), such as a primary or secondary aliphatic halide, preferably an aliphatic bromide or a benzylic bromide, which may be commercially available or may be prepared by methods well known in the art. The reaction is carried out in a polar solvent, preferably methanol or ethanol, in the presence of a base, preferably sodium methylate or sodium ethylate, at room temperature or above, preferably at the reflux temperature of the solvent, for 1–18 hours, preferably 2 hours. The product of Formula II, wherein A is oxygen and $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, is isolated by conventional means, and preferably purified by means of chromatography or recrystallisation.

Preparation of Compounds of Formula (59)

A compound of formula (52) is reacted with an excess of alkali metal thiolate, preferably sodium thiolate, in a polar organic solvent, preferably ethanol. The reaction is preferably carried out at the reflux temperature of the solvent, preferably about 100° C., and preferably for about 16 h. The product of formula (59) is isolated by conventional means, and preferably reacted in the next step without further purification. The product of formula (59) may, however, be additionally purified by means of recrystallisation.

Preparation of compounds of Formula II where A is sulfur and $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl.

The compound of formula (59) is reacted with an excess of an appropriate organic halide of formula (8), such as a primary or secondary aliphatic halide, preferably an aliphatic bromide or a benzylic bromide, which may be commercially available or may be prepared by methods well known in the art. The reaction is carried out in a polar solvent, preferably methanol or ethanol, in the presence of a base, preferably sodium methylate or sodium ethylate, at room temperature or above, preferably at the reflux temperature of the solvent, for 1–18 hours, preferably 2 hours. The product of Formula II where A is sulfur and $R^3$ is lower alkyl, phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, is isolated by conventional means, and preferably purified by means of chromatography or recrystallisation.

Alternative preparation of compounds of Formula (52), (58) and (59), wherein $R^3$ is phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, and $R^4$ and $R^5$ are hydrogen.

An alternative method of preparation of compounds of formula (52), (58) and (59), in which $R^3$ is phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, and $R^4$ and $R^5$ are both hydrogen, is from intermediates of formula (61) as shown in Reaction Scheme XVII below.

REACTION SCHEME XVII

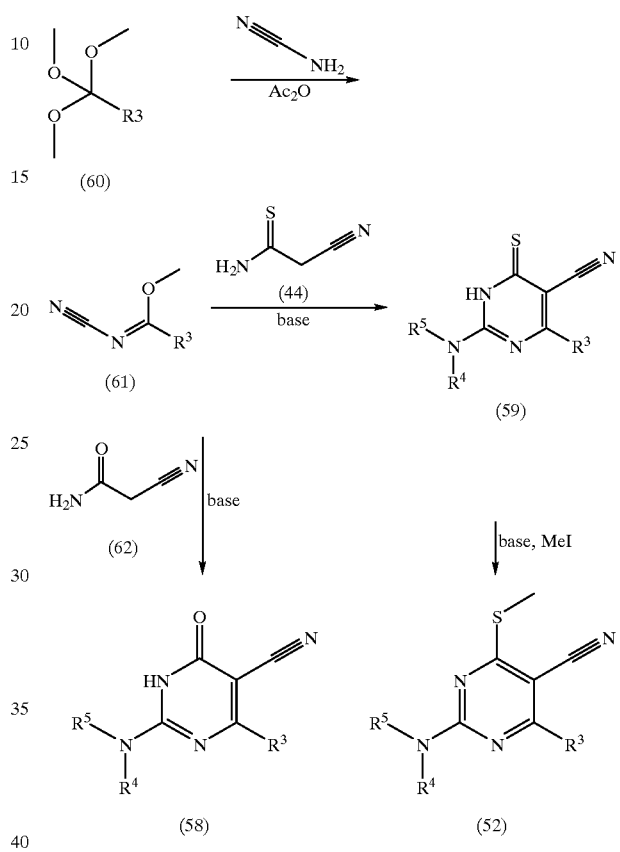

wherein $R^3$ is phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, and $R^4$ and $R^5$ are hydrogen.

The starting orthoester derivatives of formula (60) may be obtained commercially, for example from Fluka Chemie AG, or may be prepared according to methods well known in the art. 2-Cyanoacetamide (formula (62)) and 2-cyanothioacetamide (formula (44)) may both be obtained commercially.

Preparation of Compounds of Formula (61)

An orthoester derivative of formula (60) is reacted with cyanamide and acetic anhydride, preferably in the absence of solvent, at elevated temperature, preferably around 130–150° C. for about 1 hour. The product of formula (61), an N-cyano-imidate ester derivative, is preferably purified by distillation.

Preparation of Compounds of Formula (58)

The N-cyano-imidate ester derivative of formula (61) is reacted with 2-cyanoacetamide of formula (62). The reaction is carried out in a polar solvent, preferably methanol or ethanol, in the presence of a base, preferably sodium methylate or sodium ethylate, at room temperature or above, preferably at the reflux temperature of the solvent, for 1–18 hours, preferably 2 hours. The product of formula (58) is isolated by conventional means, and preferably purified by recrystallisation.

Preparation of Compounds of Formula (59)

The N-cyano-imidate ester derivative of formula (61) is reacted with 2-cyanothio-acetamide of formula (44). The reaction is carried out in a polar solvent, preferably methanol or ethanol, in the presence of a base, preferably sodium methylate or sodium ethylate, at room temperature or above, preferably at the reflux temperature of the solvent, for 1–18 hours, preferably 3 hours. The product of formula (59) is isolated by conventional means, and preferably purified by recrystallisation.

Preparation of Compounds of Formula (52)

The compound of formula (59) is reacted with an excess of methyl iodide. The reaction is carried out in a polar solvent, preferably methanol or ethanol, in the presence of a base, preferably sodium methylate or sodium ethylate, at room temperature or above, preferably room temperature, for 1–18 hours, preferably 2 hours. The product of formula (52) is isolated by conventional means, and preferably purified by means of chromatography or recrystallisation.

Alternative preparation of compounds of Formula (58), wherein $R^3$ is phenyl (optionally substituted by lower alkyl, lower alkoxy, or halogen), thien-2-yl, fur-2-yl (optionally substituted by lower alkyl, —(CH$_2$)$_n$-lower alkoxy), 2,3-dihydro-benzo[1.4]dioxin-6-yl, benzo[1.3]dioxol-5-yl, isoxazol-5-yl, pyridin-2-yl, pyridin-3-yl, —C(=CH$_2$)O-lower alkyl, 4,5-dihydrofuran-2-yl, 5,6-dihydro-4H-pyran-2yl oxazol-2-yl, benzofuranyl, or pyrazin-2-yl, and $R^4$ and $R^5$ are hydrogen.

An alternative method of preparation of compounds of formula (58), in which $R^3$ is phenyl (optionally substituted by lower alkyl, lower alkoxy, or halogen), thien-2-yl, fur-2-yl, (optionally substituted by lower alkyl, —(CH$_2$)$_n$-lower alkoxy), 2,3-dihydro-benzo[1.4]dioxin-6-yl, benzo[1.3]dioxol-5-yl, isoxazol-5-yl, pyridin-2-yl, pyridin-3-yl, —C(=CH$_2$)O-lower alkyl, 4,5-dihydrofuran-2-yl, 5,6-dihydro-4H-pyran-2-yl oxazol-2-yl, benzofuranyl, or pyrazin-2-yl, and $R^4$ and $R^5$ are both hydrogen, is from an intermediate of formula (86) as shown in Reaction Scheme XVIII below.

REACTION SCHEME XVIII

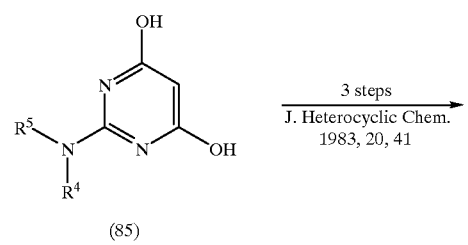

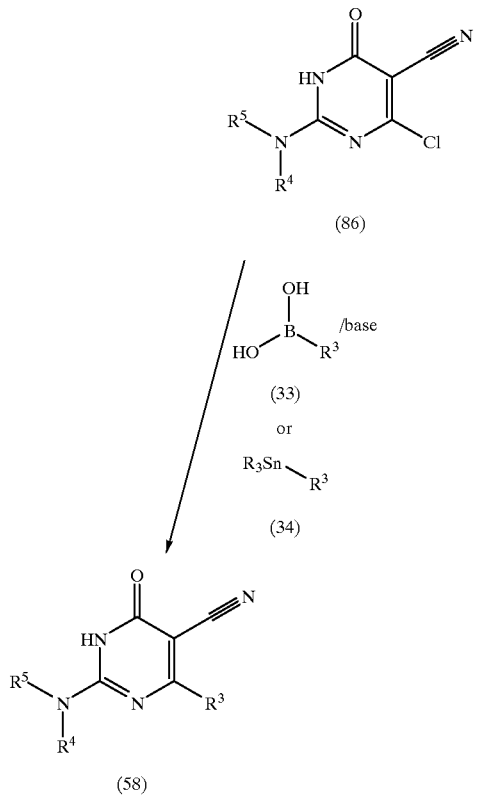

wherein $R^3$ is phenyl (optionally substituted by lower alkyl, lower alkoxy, or halogen), thien-2-yl, fur-2-yl (optionally substituted by lower alkyl, —(CH$_2$)$_n$-lower alkoxy), 2,3-dihydro-benzo[1.4]dioxin-6-yl, benzo[1.3]dioxol-5-yl, isoxazol-5-yl, pyridin-2-yl, pyridin-3-yl, —C(=CH$_2$)O-lower alkyl, 4,5-dihydrofuran-2-yl, 5,6-dihydro-4H-pyran-2-yl oxazol-2-yl, benzofuranyl, or pyrazin-2-yl, and $R^4$ and $R^5$ are hydrogen.

Preparation of compound of Formula (86)

The compound of formula (86), 2-amino-4-chloro-6-oxo-1,6-dihydro-pyrimidine-5-carbonitrile, is known in the literature, and may be prepared in three steps from commercially available 2-amino-4,6-dihydroxy-pyrimdine (85) according to the procedure of Bell et al. (*J. Heterocyclic Chem.* 1983, 20, 41).

Preparation of Compounds of Formula (58)

Boronic acid derivatives of formula (33), wherein $R^3$ is phenyl (optionally substituted by lower alkyl, lower alkoxy, or halogen), thien-2-yl, fur-2-yl (optionally substituted by lower alkyl, —(CH$_2$)$_n$-lower alkoxy), 2,3-dihydro-benzo[1.4]dioxin-6-yl, benzo [1.3]dioxol-5-yl, isoxazol-5-yl, pyridin-2-yl, pyridin-3-yl, —C(=CH$_2$)O-lower alkyl, 4,5-dihydrofuran-2-yl, 5,6-dihydro-4H-pyran-2-yl oxazol-2-yl, benzofuranyl, or pyrazin-2-yl, may be obtained commercially, or may be prepared by methods well known in the art. The compound of formula (86), 2-amino-4-chloro-6-oxo-1,6-dihydro-pyrimidine-5-carbonitrile, is reacted with a boronic acid derivative of formula (33) in an aqueous solvent, preferably a mixture of water and dioxane, containing a palladium catalyst, preferably bis(triphenylphosphine) palladium(II) chloride, and an inorganic base, preferably sodium carbonate. The reaction is preferably carried out at the reflux temperature of the solvent, preferably about 100° C., for about 2–8 hours, preferably about 4 hours. The product of formula (58) is isolated by conventional means, and preferably purified by chromatography or recrystallisation.

Alternative Preparation of Compounds of Formula (58)

Trialkylstannane derivatives of formula (34), wherein R³ is phenyl (optionally substituted by lower alkyl, lower alkoxy, or halogen), thien-2-yl, fur-2-yl (optionally substituted by lower alkyl, —(CH₂)ₙ-lower alkoxy), 2,3-dihydro-benzo[1.4]dioxin-6-yl, benzo[1.3]dioxol-5-yl, isoxazol-5-yl, pyridin-2yl, pyridin-3-yl, —C(=CH₂)O-lower alkyl, 4,5-dihydrofiuran-2-yl, 5,6-dihydro-4H-pyran-2-yl oxazol-2-yl, benzofuranyl, or pyrazin-2-yl, and R is methyl or n-butyl, may be obtained commercially, or may be prepared by methods well known in the art. The compound of formula (86), 2-amino-4-chloro-6-oxo-1,6-dihydro-pyrimidine-5-carbonitrile, is reacted with a trialkystannane derivative of formula (34) in an ethereal solvent (for example 1,2-dimethoxyethane, tetrahydrofuran or dioxane, preferably dioxane), containing a palladium catalyst, preferably bis(triphenylphosphine)palladium(II) chloride. The reaction is preferably carried out at the reflux temperature of the solvent, preferably about 100° C., for about 10–18 hours, preferably about 16 hours. The product of formula (58) is isolated by conventional means, and preferably purified by chromatography or recrystallisation.

Alternative preparation of compounds of Formula II, wherein A is nitrogen, oxygen or sulfur, and R³ is phenyl (optionally substituted by lower alkyl, lower alkoxy, or halogen), thien-2-yl, fur-2-yl (optionally substituted by lower alkyl, halogen, —(CH₂)ₙ-lower alkoxy, cyano, CHF₂, or CH₂F), 2,3-dihydro-benzo[1.4]dioxin-6-yl, benzo[1.3]dioxol-5-yl, isoxazol-5-yl, pyridin-2-yl, pyridin-3-yl, —C(=CH₂)O-lower alkyl, 4,5-dihydrofuran-2-yl, 5,6-dihydro-4H-pyran-2-yl, oxazol-2-yl, benzofuranyl, or pyrazin-2-yl, from chloro or triflate derivatives.

Another method of converting a compound of formula (58) to a compound of Formula II where A is nitrogen, oxygen or sulfur, and R³ is phenyl (optionally substituted by lower alkyl, lower alkoxy, or halogen), thien-2-yl, fur-2-yl (optionally substituted by lower alkyl, halogen, —(CH₂)ₙ-lower alkoxy, cyano, CHF₂, or CH₂F), 2,3-dihydro-benzo[1.4]dioxin-6-yl, benzo[1.3]dioxol-5-yl, isoxazol-5-yl, pyridin-2-yl, pyridin-3-yl, —C(=CH₂)O-lower alkyl, 4,5-dihydrofuran-2-yl, 5,6-dihydro-4H-pyran-2-yl, oxazol-2-yl, benzofuranyl, or pyrazin-2-yl, is via intermediates of formula (63) or formula (64), the preparation of which is shown below in Reaction Scheme XIX.

REACTION SCHEME XIX

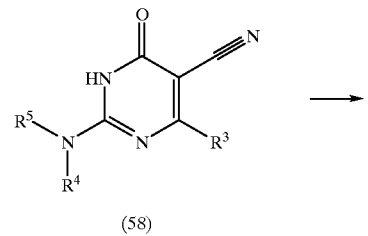

(58)

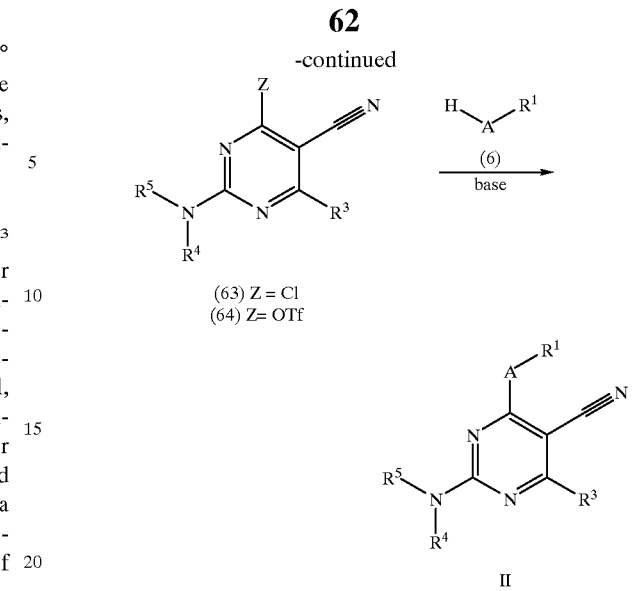

(63) Z = Cl
(64) Z = OTf

II wherein A is nitrogen, oxygen or sulfur, R¹ is as defined above, R³ is phenyl (optionally substituted by lower alkyl, lower alkoxy, or halogen), thien-2-yl, fur-2-yl (optionally substituted by lower alkyl, halogen, —(CH₂)ₙ-lower alkoxy, cyano, CHF₂, or CH₂F), 2,3-dihydro-benzo[1.4]dioxin-6yl, benzo[1.3]dioxol-5-yl, isoxazol-5-yl, pyridin-2-yl, pyridin-3-yl, —C(=CH₂)O-lower alkyl, 4,5-dihydrofuran-2-yl, 5,6-dihydro-4H-pyran-2-yl, oxazol-2-yl, benzofuranyl, or pyrazin-2-yl, and R⁴ and R⁵ are hydrogen or lower alkyl.

Preparation of Compounds of Formula (63)

A compound of formula (58) is reacted with a chlorinating agent, preferably phosphorus oxychloride, preferably in the absence of solvent. The reaction is conducted at the reflux temperature for about 1–3 h, preferably about one and a half hours. The product of formula (63) is isolated by conventional means, and is preferably purified by means of chromatography or recrystallisation.

Preparation of compounds of Formula II, wherein A is nitrogen, oxygen or sulfur, and R³ is phenyl (optionally substituted by lower alkyl, lower alkoxy, or halogen), thien-2-yl, fur-2-yl (optionally substituted by lower alkyl, halogen, —(CH₂)ₙ-lower alkoxy, cyano, CHF₂, or CH₂F), 2,3-dihydro-benzo[1.4]dioxin-6-yl, benzo[1.3]dioxol-5-yl, isoxazol-5-yl, pyridin-2-yl, pyridin-3-yl, —C(=CH₂)O-lower alkyl, 4,5-dihydrofuran-2-yl, 5,6-dihydro-4H-pyran-2-yl, oxazol-2-yl, benzofuranyl, or pyrazin-2-yl.

The compound of formula (63) is reacted with an appropriate nucleophilic compound of formula (6), which may be commercially available or may be prepared by methods well known in the art, and which may be chosen from: a primary or secondary aliphatic alcohol or an aromatic alcohol, in each case used together with a non-nucleophilic base, preferably 1,8-diazabicyclo[5.4.0]undec-7-ene (1,5-5); a primary or secondary aliphatic thiol or an aromatic thiol, in each case used together with a non-nucleophilic base, preferably 1,8-diazabicyclo [5.4.0]undec-7-ene (1,5-5) (DBU); a primary or secondary aliphatic amine which is preferably used in excess in the absence of an added base; the inorganic salt of a primary or secondary aliphatic amine, such as a hydrochloride salt, which is used together with a non-nucleophilic base, preferably 1,8-diazabicyclo[5.4.0]undec-7-ene (1,5-5); an alkali metal alcoholate of a primary or secondary aliphatic alcohol or of an aromatic alcohol, preferably a sodium or potassium alcoholate, which is preferably used in excess; or an alkali metal thiolate of a primary or secondary aliphatic thiol or of an aromatic thiol, preferably a sodium or potassium thiolate, which is preferably used in excess. These reactions may be carried out in a non-protic polar solvent such as acetonitrile or in an ethereal solvent such as dioxane, tetrahydrofuran or 1,2-dimethoxyethane, preferably 1,2-dimethoxyethane, at room temperature or above, preferably at the reflux temperature of the solvent, for 1–18 hours, preferably 18 hours. The product of Formula II, wherein A is nitrogen, oxygen or sulfur, and $R^3$ is phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, —C(=$CH_2$)O-lower alkyl, 4,5-dihydrofuran-2-yl, 5,6-dihydro-4H-pyran-2-yl, oxazol-2-yl, benzofuranyl, or pyrazin-2-yl, is isolated by conventional means, and preferably purified by means of chromatography or recrystallisation.

Preparation of Compounds of Formula (64)

A compound of formula (58) is reacted with an alkanesulfonic anhydride, preferably trifluoromethanesulfonic anhydride, and an excess of a non-nucleophilic base, preferably 2,6-di-tert-butylpyridine, in an organic solvent, preferably dichloromethane, at a temperature between 0° C. and room temperature for about 16 hours. The product of formula (64) is isolated by conventional means, and is preferably purified by means of chromatography or recrystallisation.

Preparation of compounds of Formula II, wherein A is nitrogen, oxygen or sulfur, and $R^3$ is phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, —C(=$CH_2$)O-lower alkyl, 4,5-dihydrofuran-2-yl, 5,6-dihydro-4H-pyran-2-yl, oxazol-2-yl, benzofuranyl, or pyrazin-2-yl.

The compound of formula (64) is reacted with an appropriate nucleophilic compound of formula (6), which may be commercially available or may be prepared by methods well known in the art, and which may be chosen from: a primary or secondary aliphatic alcohol or an aromatic alcohol, in each case used together with a non-nucleophilic base, preferably 1,8-diazabicyclo[5.4.0]undec-7-ene (1,5-5); a primary or secondary aliphatic thiol or an aromatic thiol, in each case used together with a non-nucleophilic base, preferably 1,8-diazabicyclo[5.4.0]undec-7-ene (1,5-5) (DBU); a primary or secondary aliphatic amine which is preferably used in excess in the absence of an added base; the inorganic salt of a primary or secondary aliphatic amine, such as a hydrochloride salt, which is used together with a non-nucleophilic base, preferably 1,8-diazabicyclo[5.4.0]undec-7-ene (1,5-5); an alkali metal alcoholate of a primary or secondary aliphatic alcohol or of an aromatic alcohol, preferably a sodium or potassium alcoholate, which is preferably used in excess; or an alkali metal thiolate of a primary or secondary aliphatic thiol or of an aromatic thiol, preferably a sodium or potassium thiolate, which is preferably used in excess. These reactions may be carried out in a non-protic polar solvent such as acetonitrile or in an ethereal solvent such as dioxane, tetrahydrofuran or 1,2-dimethoxyethane, preferably 1,2-dimethoxyethane, at room temperature or above, preferably at the reflux temperature of the solvent, for 1–18 hours, preferably 18 hours. The product of Formula II where A is nitrogen, oxygen or sulfur, and $R^3$ is phenyl (optionally substituted by lower alkyl, lower alkoxy, or halogen), thien-2-yl, fur-2-yl (optionally substituted by lower alkyl, halogen, —$(CH_2)_n$-lower alkoxy, cyano, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, —C(=$CH_2$)O-lower alkyl, 4,5-dihydrofuran-2-yl, 5,6-dihydro-4H-pyran-2-yl, oxazol-2-yl, benzofuranyl, or pyrazin-2-yl, is isolated by conventional means, and preferably purified by means of chromatography or recrystallisation.

Alternative preparation of compounds of Formula II, wherein A is nitrogen, oxygen or sulfur, and $R^3$ is phenyl (optionally substituted by lower alkyl, lower alkoxy, or halogen), thien-2-yl, fur—l (optionally substituted by lower alkyl, —$(CH_2)_n$-lower alkoxy), 2,3-dihydro-benzo[1.4]dioxin-6-yl, benzo[1.3]dioxol-5-yl, isoxazol-5-yl, pyridin-2-yl, pyridin-3-yl, —C(=$CH_2$)O-lower alkyl, 4,5-dihydrofuran-2-yl, 5,6-dihydro-4H-pyran-2-yl oxazol-2-yl, benzofuranyl, or pyrazin-2-yl, from the compound of Formula (86)

Another method of converting the compound of formula (86) to compounds of Formula II where A is nitrogen, oxygen or sulfur, and $R^3$ is phenyl (optionally substituted by lower alkyl, lower alkoxy, or halogen), thien-2-yl, fur-2-yl (optionally substituted by lower alkyl, —$(CH_2)_n$-lower alkoxy), 2,3-dihydro-benzo[1.4]dioxin-6-yl, benzo[1.3]dioxol-5-yl, isoxazol-5-yl, pyridin-2-yl, pyridin-3-yl, —C(=$CH_2$)O-lower alkyl, 4,5-dihydrofuran-2yl, 5,6-dihydro-4H-pyran-2-yl oxazol-2-yl, benzofuranyl, or pyrazin-2-yl, is via intermediates of formula (88), the preparation of which is shown below in Reaction Scheme XX.

REACTION SCHEME XX

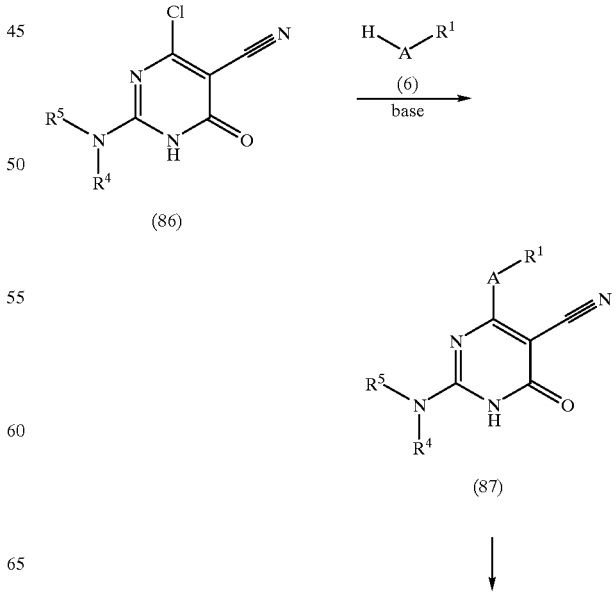

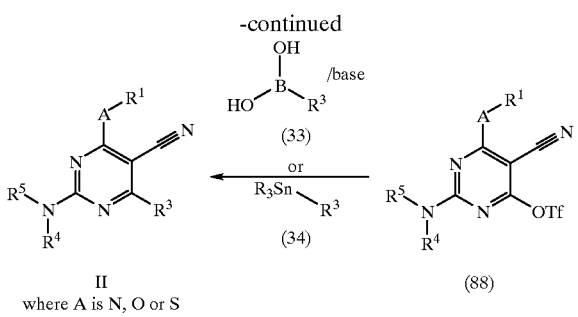

where A is N, O or S wherein A is nitrogen, oxygen or sulfur, $R^1$ is as defined above, $R^3$ is phenyl (optionally substituted by lower alkyl, lower alkoxy, or halogen), thien-2-yl, fur-2-yl (optionally substituted by lower alkyl, —$(CH_2)_n$-lower alkoxy), 2,3-dihydro-benzo[1.4]dioxin-6-yl, benzo[1.3]dioxol-5-yl, isoxazol-5-yl, pyridin-2-yl, pyridin-3-yl, —C(=$CH_2$)O-lower alkyl, 4,5-dihydrofuran-2-yl, 5,6-dihydro-4H-pyran-2-yl oxazol-2-yl, benzofuranyl, or pyrazin-2-yl, and $R^4$ and $R^5$ are hydrogen.

Preparation of Compounds of Formula (87)

The compound of formula (86), 2-amino-4-chloro-6-oxo-1,6-dihydro-pyrimidine-5-carbonitrile, is reacted with an appropriate nucleophilic compound of formula (6), which may be commercially available or may be prepared by methods well known in the art, and which may be chosen from: a primary or secondary aliphatic alcohol or an aromatic alcohol, in each case used together with a non-nucleophilic base, preferably 1,8-diazabicyclo[5.4.0]undec-7-ene (1,5-5); a primary or secondary aliphatic thiol or an aromatic thiol, in each case used together with a non-nucleophilic base, preferably 1,8-diazabicyclo[5.4.0]undec-7-ene (1,5-5) (DBU); a primary or secondary aliphatic amine which is preferably used in excess in the absence of an added base; the inorganic salt of a primary or secondary aliphatic amine, such as a hydrochloride salt, which is used together with a non-nucleophilic base, preferably 1,8-diazabicyclo [5.4.0]undec-7-ene (1,5-5); an alkali metal alcoholate of a primary or secondary aliphatic alcohol or of an aromatic alcohol, preferably a sodium or potassium alcoholate, which is preferably used in excess; or an alkali metal thiolate of a primary or secondary aliphatic thiol or of an aromatic thiol, preferably a sodium or potassium thiolate, which is preferably used in excess. These reactions may be carried out in a non-protic polar solvent such as acetonitrile or in an ethereal solvent such as such as dioxane, tetrahydrofuran or 1,2-dimethoxyethane, preferably 1,2-dimethoxyethane, at room temperature or above, preferably at room temperature, for 1–18 hours, preferably 2 hours. The product of formula (87) is isolated by conventional means, and preferably purified by means of chromatography or recrystallisation.

Preparation of Compounds of Formula (88)

A compound of formula (87) is reacted with an alkanesulfonic anhydride, preferably trifluoromethanesulfonic anhydride, and an excess of a non-nucleophilic base, preferably 2,6-di-tert-butylpyridine, in an organic solvent, preferably dichloromethane, at a temperature between 0° C. and room temperature for about 16 hours. The product of formula (88) is isolated by conventional means, and is preferably purified by means of chromatography or recrystallisation.

Preparation of Compounds of Formula II, wherein A is nitrogen, oxygen or sulfur, and $R^3$ is phenyl (optionally substituted by lower alkyl, lower alkoxy, or halogen), thien-2-yl, fur-2-yl (optionally substituted by lower alkyl, —$(CH_2)_n$-lower alkoxy), 2,3-dihydro-benzo[1.4]dioxin-6-yl, benzo[1.3]dioxol-5-yl, isoxazol-5-yl, pyridin-2-yl, pyridin-3-yl, —C(=$CH_2$)O-lower alkyl, 4,5-dihydrofuran-2-yl, 5,6-dihydro-4H-pyran-2-yl oxazol-2-yl, benzofuranyl, or pyrazin-2-yl.

Boronic acid derivatives of formula (33), wherein $R^3$ is phenyl (optionally substituted by lower alkyl, lower alkoxy, or halogen), thien-2-yl, fur-2-yl (optionally substituted by lower alkyl, —$(CH_2)_n$-lower alkoxy), 2,3-dihydro-benzo [1.4]dioxin-6-yl, benzo[1.3]dioxol-5-yl, isoxazol-5-yl, pyridin-2-yl, pyridin-3-yl, —C(=$CH_2$)O-lower alkyl, 4,5-dihydrofuran-2-yl, 5,6-dihydro-4H-pyran-2-yl oxazol-2-yl, benzofuranyl, or pyrazin-2-yl, may be obtained commercially, or may be prepared by methods well known in the art. A compound of formula (88) is reacted with a boronic acid derivative of formula (33) in an aqueous solvent, preferably a mixture of water and dioxane, containing a palladium catalyst, preferably bis(triphenylphosphine)palladium(II) chloride, and an inorganic base, preferably sodium carbonate. The reaction is preferably carried out at the reflux temperature of the solvent, preferably about 100° C., for about 2–8 hours, preferably about 4 hours. The product of Formula II, wherein A is nitrogen, oxygen or sulfur, and $R^3$ is phenyl (optionally substituted by lower alkyl, lower alkoxy, or halogen), thien-2-yl, fur-2-yl (optionally substituted by lower alkyl, —$(CH_2)_n$-lower alkoxy), 2,3-dihydro-benzo[1.4]dioxin-6-yl, benzo[1.3] dioxol-5-yl, isoxazol-5-yl, pyridin-2-yl, pyridin-3-yl, —C(=$CH_2$)O-lower alkyl, 4,5-dihydrofuran-2-yl, 5,6-dihydro-4H-pyran-2-yl oxazol-2-yl, benzofuranyl, or pyrazin-2-yl, is isolated by conventional means, and preferably purified by chromatography or recrystallisation.

Alternative preparation of compounds of Formula IL wherein A is nitrogen, oxygen or sulfur, and $R^3$ is phenyl (optionally substituted by lower alkyl, lower alkoxy, or halogen), thien-2-yl, fur-2-yl (optionally substituted by lower alkyl, —$(CH_2)_n$-lower alkoxy), 2,3-dihydro-benzo [1.4]dioxin-6-yl, benzo[1.3]dioxol-5-yl, isoxazol-5yl, pyridin-2-yl, pyridin-3-yl, —C(=$CH_2$)O-lower alkyl, 4,5-dihydrofuran-2-yl, 5,6-dihydro-4H-pyran-2-yl oxazol-2-yl, benzofuranyl, or pyrazin-2-yl.

Trialkylstannane derivatives of formula (34), wherein $R^3$ is phenyl (optionally substituted by lower alkyl, lower alkoxy, or halogen), thien-2-yl, fur-2-yl (optionally substituted by lower alkyl, —$(CH_2)_n$-lower alkoxy), 2,3-dihydro-benzo[1.4]dioxin-6-yl, benzo[1.3]dioxol-5-yl, isoxazol-5-yl, pyridin-2-yl, pyridin-3-yl, —C(=$CH_2$)O-lower alkyl, 4,5-dihydrofuran-2-yl, 5,6-dihydro-4H-pyran-2-yl oxazol-2-yl, benzofuranyl, or pyrazin-2-yl, and R is methyl or n-butyl, may be obtained commercially, or may be prepared by methods well known in the art. A compound of formula (88) is reacted with a trialkystannane derivative of formula (34) in an ethereal solvent (for example 1,2-dimethoxyethane, tetrahydrofuran or dioxane, preferably dioxane), containing a palladium catalyst, preferably bis (triphenyl-phosphine)palladium(II) chloride. The reaction is preferably carried out at the reflux temperature of the solvent, preferably about 100° C., for about 10–18 hours, preferably about 16 hours. The product of Formula II, wherein A is nitrogen, oxygen or sulfur, and $R^3$ is phenyl (optionally substituted by lower alkyl, lower alkoxy, or halogen), thien-2-yl, fur-2-yl (optionally substituted by lower alkyl, —$(CH_2)_n$-lower alkoxy), 2,3-dihydro-benzo [1.4]dioxin-6-yl, benzo[1.3]dioxol-5-yl, isoxazol-5-yl, pyridin-2-yl, pyridin-3-yl, —C(=$CH_2$)O-lower alkyl, 4,5-dihydrofuran-2-yl, 5,6-dihydro-4H-pyran-2-yl oxazol-2-yl, benzofuranyl, or pyrazin-2-yl, is isolated by conventional means, and preferably purified by chromatography or recrystallisation.

Alternative preparation of compounds of Formula II, where A is =C<, —C≡C—, —CH=CH— or —CH$_2$CH$_2$—.

One method of preparation of compounds of Formula II, wherein A is a carbon atom having olefinic or aromatic character and varying degrees of substitution, is from intermediates of formula (63) or (64), as shown in Reaction Scheme XXI below.

(for example 1,2-dimethoxyethane, tetrahydrofuran or dioxane, preferably dioxane), containing a palladium catalyst, preferably palladium tetrakis(triphenylphosphine). The reaction is preferably carried out at the reflux temperature of the solvent, preferably about 100° C., for about 14–36 hours, preferably about 16 hours. The product of Formula II where A is =C< is isolated by conventional means, and preferably purified by chromatography or recrystallisation. In the case where a boronic acid derivative

REACTION SCHEME XXI

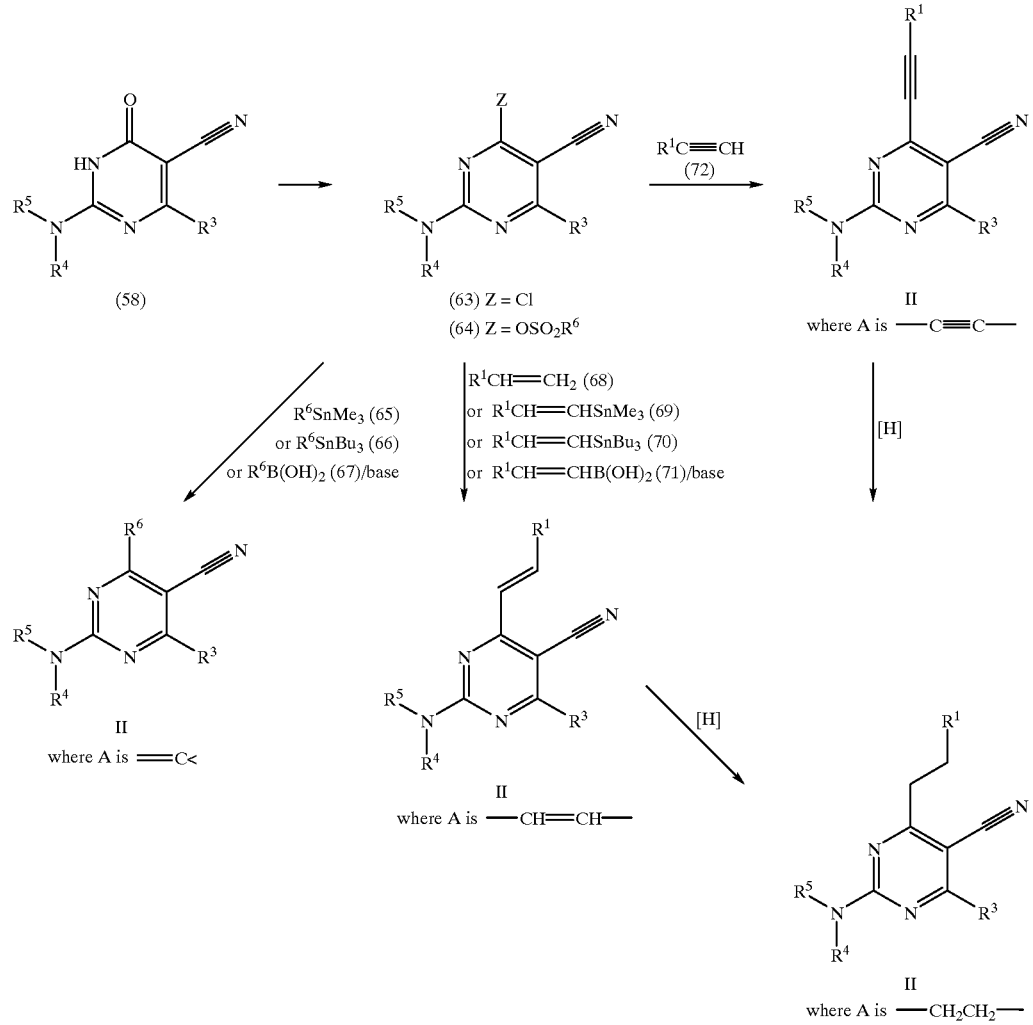

wherein A is a carbon atom having olefinic or aromatic character and varying degrees of substitution, $R^1$, $R^3$, $R^6$ and $R^7$ are as defined above and $R^4$ and $R^5$ are hydrogen or lower alkyl.

Preparation of Compounds of Formula II Where A is =C<

A compound of formula (63), or a compound of formula (64), is reacted with an appropriate organometallic compound, which may be commercially available or may be prepared by methods well known in the art, and which may be chosen from: a trimethyl-stannane derivative of formula (65); or a tributylstannane derivative of formula (66); of a boronic acid derivative of formula (67). In the case where an organostannane derivative of formula (65) or of formula (66) is used, the reaction is carried out in an ethereal solvent of formula (67) is used, the reaction is carried out in an aqueous solvent, preferably a mixture of water and dioxane, containing a palladium catalyst, preferably palladium tetrakis(triphenylphosphine), and an inorganic base, preferably sodium carbonate. The reaction is preferably carried out at the reflux temperature of the solvent, preferably about 100° C., for about 14–36 hours, preferably about 16 hours. The product of Formula II where A is =C< is isolated by conventional means, and preferably purified by chromatography or recrystallisation.

Alternative Preparation of Compounds of Formula II Wherein A is —CH=CH—

A compound of formula (63), or a compound of formula (64), is reacted with an appropriate organometallic compound, which may be commercially available or may be prepared by methods well known in the art, and which may be chosen from: an olefin of formula (68); a trimethylstannane derivative of formula (69); or a tributylstannane derivative of formula (70); or a boronic acid derivative of formula (71). In the case where an olefin derivative of formula (68) is used, the reaction is carried in an ethereal solvent (for example 1,2-dimethoxyethane, tetrahydrofuran or dioxane, preferably dioxane), containing a palladium catalyst, preferably palladium tetrakis(triphenylphosphine), and an inorganic base, preferably cesium carbonate. The reaction is preferably carried out at the reflux temperature of the solvent, preferably about 100° C., for about 14–36 hours, preferably about 16 hours. The product of Formula II where A is —CH=CH— is isolated by conventional means, and preferably purified by chromatography or recrystallisation. In the case where an organostannane derivative of formula (69) or of formula (70) is used, the reaction is carried out in an ethereal solvent (for example 1,2-dimethoxyethane, tetrahydrofuran or dioxane, preferably dioxane), containing a palladium catalyst, preferably palladium tetrakis (triphenylphosphine). The reaction is preferably carried out at the reflux temperature of the solvent, preferably about 100° C., for about 14–36 hours, preferably about 16 hours. The product of Formula II where A is —CH=CH— is isolated by conventional means, and preferably purified by chromatography or recrystallisation. In the case where boronic acid derivative of formula (71) is used, the reaction is carried out in an aqueous solvent, preferably a mixture of water and dioxane, containing a palladium catalyst, preferably palladium tetrakis(triphenylphosphine), and an inorganic base, preferably sodium carbonate. The reaction is preferably carried out at the reflux temperature of the solvent, preferably about 100° C., for about 14–36 hours, preferably about 16 hours. The product of Formula II where A is —CH=CH— is isolated by conventional means, and preferably purified by chromatography or recrystallisation.

Alternative Preparation of Compounds of Formula II, Wherein A is —C≡C—

A compound of formula (63), or a compound of formula (64), is reacted with an appropriate acetylinic compound of formula (72), which may be commercially available or may be prepared by methods well known in the art. The reaction is carried out in an ethereal solvent (for example 1,2-dimethoxyethane, tetrahydrofuran or dioxane, preferably tetrahydrofuran), containing a palladium catalyst, preferably bis(triphenylphosphine) palladium(II) chloride, a base, preferably triethylamine, and a copper co-catalyst, preferably copper(I) iodide. The reaction is preferably carried out at a temperature between room temperature and the reflux temperature of the solvent, preferably about 50° C., for about 1–18 hours, preferably about 3 hours. The product of Formula II where A is —C≡C— is isolated by conventional means, and preferably purified by chromatography or recrystallisation.

Alternative Preparation of Compounds of Formula II Wherein A is —CH₂CH₂—

A compound of Formula II, wherein A is —CH=CH—, or a compound of Formula II, wherein A is —C≡C—, is reacted with hydrogen gas in an organic solvent (for example 1,2-dimethoxyethane, tetrahydrofuran, dioxane or ethanol, preferably a mixture of dioxane and ethanol) containing a hydrogenation catalyst, preferably 10% palladium on charcoal. The reaction is carried out at room temperature at a pressure of 1 atmosphere or above, preferably at one atmosphere, for about 2–36 hours, preferably about 16 hours. The product of Formula II where A is —CH₂CH₂— is isolated by conventional means, and preferably purified by chromatography or recrystallisation.

Preparation of compounds of Formula II, wherein A—R$^1$ is halogen, and R$^3$ is —O— (CH$_2$)$_n$phenyl, —O—(CH$_2$)$_n$-pyridyl (optionally substituted by lower alkyl), or S—(CH$_2$)$_n$-pyridyl.

One method of preparation of compounds of Formula II, wherein A—R$^1$ is halogen, and R$^3$ is —O—(CH$_2$)$_n$phenyl, —O—(CH$_2$)$_n$-pyridyl (optionally substituted by lower alkyl), or S—(CH$_2$)$_n$-pyridyl, is from intermediates of formula (89), the preparation of which is shown in Reaction Scheme XXII below.

REACTION SCHEME XXII

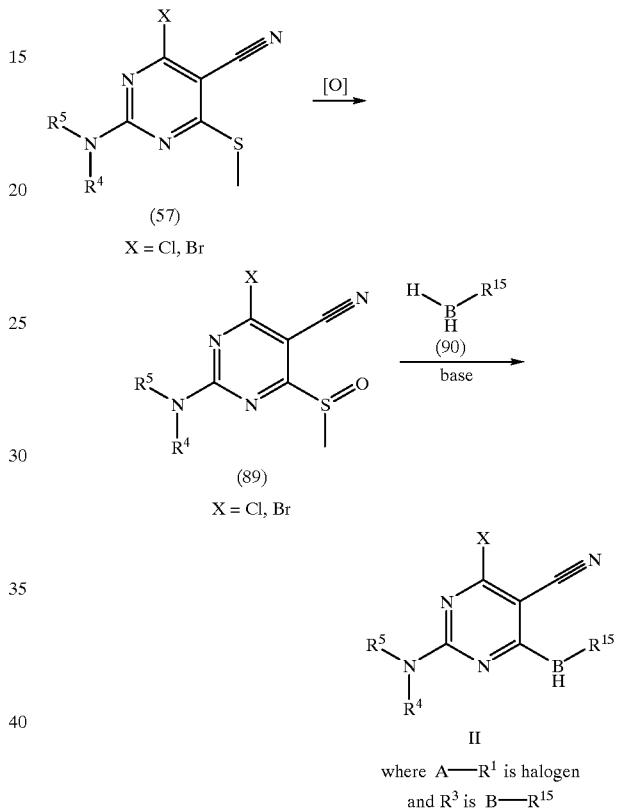

wherein X is bromo or chloro, B is oxygen or sulfur, R$^4$ and R$^5$ are hydrogen, and R$^{15}$ is —(CH$_2$)$_n$phenyl, or —(CH$_2$)$_n$-pyridyl, optionally substituted by lower alkyl.

Preparation of Compounds of Formula (89)

A compound of formula (57) is reacted with an oxidising agent, preferably 3-phenyl-2-(phenylsulfonyl)oxaziridine, in an inert organic solvent, preferably a mixture of dichloromethane and N,N-dimethylformamide, at room temperature. The product of formula (89) is isolated by conventional means, and preferably reacted in the next step without further purification. The product of formula (89) may, however, be additionally purified by means of chromatography or recrystallisation.

Preparation of compounds of Formula II, wherein A—R$^1$ is halogen, and R$^3$ is —O— (CH$_2$)$_n$phenyl, —O—(CH$_2$)$_n$-pyridyl (optionally substituted by lower alkyl), or S—(CH$_2$)$_n$—pyridyl.

A compound of formula (89) is reacted with an appropriate nucleophilic compound of formula (90), which may be commercially available or may be prepared by methods well known in the art, in the presence of a non-nucleophilic base, preferably 1,8-diazabicyclo [5.4.0]undec-7-ene (1,5-5). The reaction is carried out in an ethereal solvent such as such as dioxane, tetrahydrofuran or 1,2-dimethoxyethane, preferably 1,2-dimethoxyethane, at room temperature or above, preferably at room temperature, for 1–18 hours, preferably 2 hours. The product of Formula II, wherein A—$R^1$ is halogen, and $R^3$ is —O—$(CH_2)_n$phenyl, —O—$(CH_2)_n$-pyridyl (optionally substituted by lower alkyl), or S—$(CH_2)_n$-pyridyl, is isolated by conventional means, and preferably purified by means of chromatography or recrystallisation.

Preparation of compounds of Formula II, wherein A is nitrogen, oxygen or sulfur, and $R^3$ is —O—$(CH_2)_n$phenyl, —O—$(CH_2)_n$-pyridyl (optionally substituted by lower alkyl), or S—$(CH_2)_n$-pyridyl.

One method of preparation of compounds of Formula II, wherein A is nitrogen, oxygen or sulfur, and $R^3$ is —O—$(CH_2)_n$phenyl, —O—$(CH_2)_n$-pyridyl (optionally substituted by lower alkyl), or S—$(CH_2)_n$-pyridyl, is from intermediates of formula (92), the preparation of which is shown in Reaction Scheme XXIII below.

REACTION SCHEME XXIII

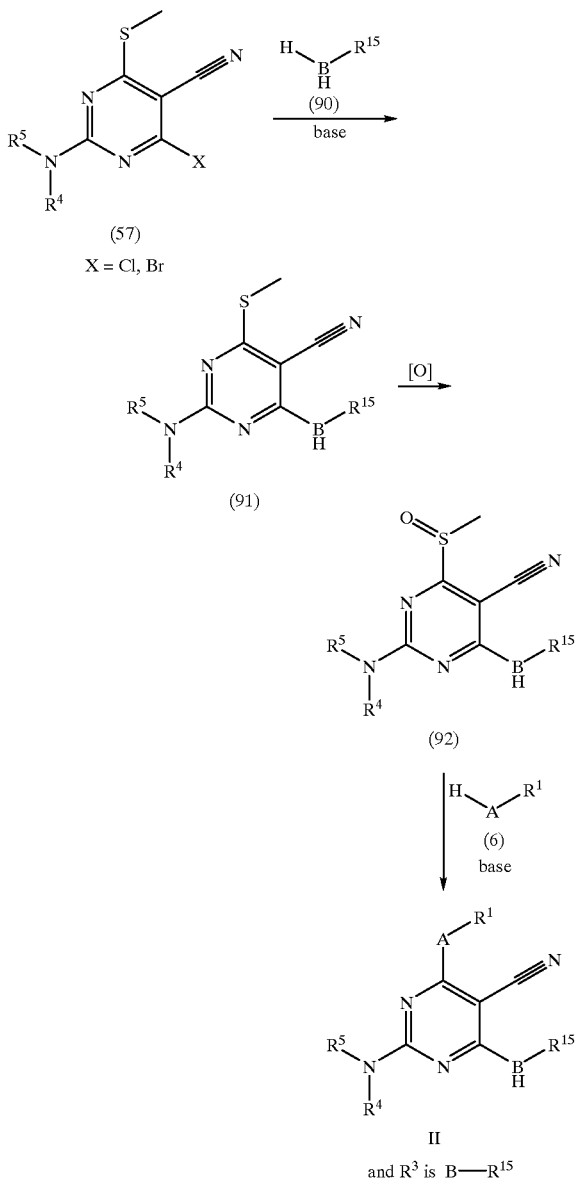

wherein X is bromo or chloro, A is nitrogen, oxygen or sulfur, B is oxygen or sulfur, $R^1$ is as defined above, $R^4$ and $R^5$ are hydrogen, and $R^{15}$ is —$(CH_2)_n$phenyl, or —$(CH_2)_n$-pyridyl (optionally substituted by lower alkyl).

Preparation of Compounds of Formula (91)

A compound of formula (57) is reacted with an appropriate nucleophilic compound of formula (90), which may be commercially available or may be prepared by methods well known in the art, in the presence of a non-nucleophilic base, preferably 1,8-diazabicyclo [5.4.0]undec-7-ene (1,5-5). The reaction is carried out in an ethereal solvent such as such as dioxane, tetrahydrofuran or 1,2-dimethoxyethane, preferably 1,2-dimethoxyethane, at room temperature or above, preferably at room temperature, for 1–18 hours, preferably 16 hours. The product of formula (91) is isolated by conventional means, and preferably purified by means of chromatography or recrystallisation.

Preparation of Compounds of Formula (92)

A compound of formula (91) is reacted with an oxidising agent, preferably 3-phenyl-2-(phenylsulfonyl)oxaziridine, in an inert organic solvent, preferably dichloromethane, at room temperature. The product of formula (92) is isolated by conventional means, and preferably reacted in the next step without further purification. The product of formula (92) may, however, be additionally purified by means of chromatography or recrystallisation.

Preparation of compounds of Formula II, wherein A is nitrogen, oxygen or sulfur, and $R^3$ is —O—$(CH_2)_n$phenyl, —O—$(CH_2)_n$-pyridyl (optionally substituted by lower alkyl), or S—$(CH_2)_n$-pyridyl.

A compound of formula (92) is reacted with an appropriate nucleophilic compound of formula (6), which may be commercially available or may be prepared by methods well known in the art, and which may be chosen from: a primary or secondary aliphatic alcohol or an aromatic alcohol, in each case used together with a non-nucleophilic base, preferably 1,8-diazabicyclo[5.4.0]undec-7-ene (1,5-5); a primary or secondary aliphatic thiol or an aromatic thiol, in each case used together with a non-nucleophilic base, preferably 1,8-diazabicyclo [5.4.0]undec-7-ene (1,5-5) (DBU); a primary or secondary aliphatic amine which is preferably used in excess in the absence of an added base; the inorganic salt of a primary or secondary aliphatic amine, such as a hydrochloride salt, which is used together with a non-nucleophilic base, preferably 1,8-diazabicyclo[5.4.0]undec-7-ene (1,5-5); an alkali metal alcoholate of a primary or secondary aliphatic alcohol or of an aromatic alcohol, preferably a sodium or potassium alcoholate, which is preferably used in excess; or an alkali metal thiolate of a primary or secondary aliphatic thiol or of an aromatic thiol, preferably a sodium or potassium thiolate, which is preferably used in excess. These reactions may be carried out in a non-protic polar solvent such as acetonitrile or in an ethereal solvent such as such as dioxane, tetrahydrofuran or 1,2-dimethoxyethane, preferably 1,2-dimethoxyethane, at room temperature or above, preferably at room temperature, for 1–18 hours, preferably 2 hours. The product of Formula II, wherein A is nitrogen, oxygen or sulfur, and $R^3$ is —O—$(CH_2)_n$phenyl, —O—$(CH_2)_n$-pyridyl (optionally substituted by lower alkyl), or S—$(CH_2)_n$-pyridyl is isolated by conventional means, and preferably purified by means of chromatography or recrystallisation.

Conversion of Compounds of Formula II, wherein A—$R^1$ is halogen, and $R^3$ is —O— $(CH_2)_n$phenyl, —O—$(CH_2)_n$-pyridyl (optionally substituted by lower alkyl), or S—$(CH_2)_n$-pyridyl, to compounds of Formula II, wherein A is nitrogen, oxygen or sulfur, and $R^3$ is —O—$(CH_2)_n$phenyl, —O—$(CH_2)_n$-pyridyl (optionally substituted by lower alkyl), or S—$(CH_2)_n$-pyridyl.

A method of converting compounds of Formula II, wherein A—$R^1$ is halogen, and $R^3$ is —O—$(CH_2)_n$phenyl, —O—$(CH_2)_n$-pyridyl (optionally substituted by lower alkyl), or S—$(CH_2)_n$-pyridyl, to compounds of Formula II, wherein A is nitrogen, oxygen or sulfur, and $R^3$ is —O—$(CH_2)_n$phenyl, —O—$(CH_2)_n$-pyridyl (optionally substituted by lower alkyl), or S—(CH$_2$)$_n$-pyridyl, is shown in Reaction Scheme XXIV below.

REACTION SCHEME XXIV

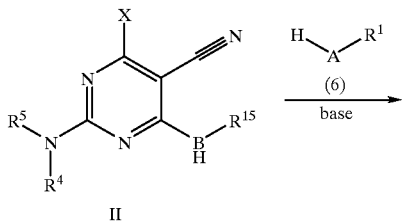

where A—R$^1$ is halogen
and R$^3$ is B—R$^{15}$

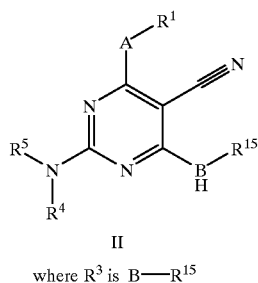

where R$^3$ is B—R$^{15}$ wherein X is bromo or chloro, A is nitrogen, oxygen or sulfur, B is oxygen or sulfur, R$^1$ is as defined above, R$^4$ and R$^5$ are hydrogen, and R$^5$ is. —(CH$_2$)$_n$phenyl, or —(CH$_2$)$_n$-pyridyl (optionally substituted by lower alkyl).

Preparation of compounds of Formula II, wherein A is nitrogen, oxygen or sulfur, and R$^3$ is —O—(CH$_2$)$_n$phenyl, —O—(CH$_2$)$_n$-pyridyl (optionally substituted by lower alkyl), or S—(CH$_2$)$_n$-pyridyl.

A compound of Formula II, wherein A—R$^1$ is halogen, and R$^3$ is —O—(CH$_2$)$_n$phenyl, —O— (CH$_2$)$_n$-pyridyl (optionally substituted by lower alkyl), or S—(CH$_2$)$_n$-pyridyl, is reacted with an appropriate nucleophilic compound of formula (6), which may be commercially available or may be prepared by methods well known in the art, and which may be chosen from: a primary or secondary aliphatic alcohol or an aromatic alcohol, in each case used together with a non-nucleophilic base, preferably 1,8-diazabicyclo [5.4.0]undec-7-ene (1,5-5); a primary or secondary aliphatic thiol or an aromatic thiol, in each case used together with a non-nucleophilic base, preferably 1,8-diazabicyclo[5.4.0] undec-7-ene (1,5-5) (DBU); a primary or secondary aliphatic amine which is preferably used in excess in the absence of an added base; the inorganic salt of a primary or secondary aliphatic amine, such as a hydrochloride salt, which is used together with a non-nucleophilic base, preferably 1,8-diazabicyclo[5.4.0]undec-7-ene (1,5-5); an alkali metal alcoholate of a primary or secondary aliphatic alcohol or of an aromatic alcohol, preferably a sodium or potassium alcoholate, which is preferably used in excess; or an alkali metal thiolate of a primary or secondary aliphatic thiol or of an aromatic thiol, preferably a sodium or potassium thiolate, which is preferably used in excess. These reactions may be carried out in a non-protic polar solvent such as acetonitrile or in an ethereal solvent such as such as dioxane, tetrahydrofuran or 1,2-dimethoxyethane, preferably 1,2-dimethoxyethane, at room temperature or above, preferably at room temperature, for 1–18 hours, preferably 2 hours. The product of Formula II, wherein A is nitrogen, oxygen or sulfur, and R$^3$ is —O—(CH$_2$)$_n$phenyl, —O—(CH$_2$)$_n$-pyridyl (optionally substituted by lower alkyl), or S—(CH$_2$)$_n$-pyridyl is isolated by conventional means, and preferably purified by means of chromatography or recrystallisation.

Conversion of Compounds of Formula II, wherein A is nitrogen, oxygen or sulfur, and R$^3$ is 5-methyl-furan-2-yl to compounds of Formula II, wherein A is nitrogen, oxygen or sulfur, and R$^3$ is 5-bromomethyl-furan-2-yl or 5-hydroxymethyl-furan-2-yl.

A method of converting compounds of Formula II, wherein A is nitrogen, oxygen or sulfur, and R$^3$ is 5-methyl-furan-2-yl to compounds of Formula II, wherein A is nitrogen, oxygen or sulfur, and R$^3$ is 5-bromomethyl-furan-2-yl or 5-hydroxymethyl-furan-2-yl is shown in Reaction Scheme XXV below.

REACTION SCHEME XXV

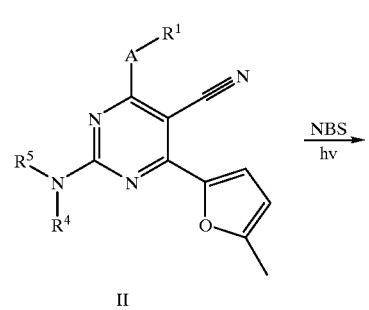

where R$^3$ is
5-methyl-furan-2-yl

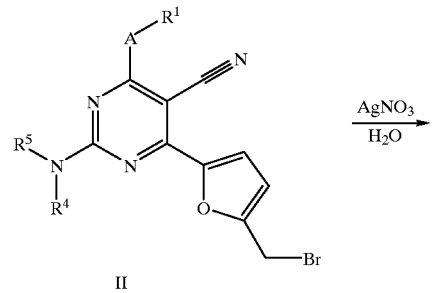

where R$^3$ is
5-bromomethyl-furan-2-yl

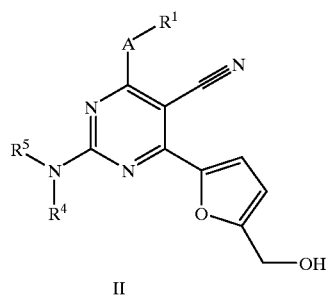

where R$^3$ is
5-hydroxymethyl-furan-2-yl wherein A is nitrogen, oxygen or sulfur, R$^1$ is as defined above, and R$^4$ and R$^5$ are hydrogen.

Preparation of Compounds of Formula II, Wherein A is Nitrogen, Oxygen or Sulfur, and R$^3$ is 5-bromomethyl-furan-2-yl A compound of Formula II, wherein A is nitrogen, oxygen or sulfur, and R$^3$ is 5-methyl-furan-2-yl, is reacted with a slight excess of N-bromosuccinimide in a non-polar organic solvent, preferably carbon tetrachloride, in the presence of a radical initiator, preferably benzoyl peroxide, and with concomitant irradiation from a high intensity light source, preferably a halogen lamp. The reaction is preferably carried out at room temperature for about 8–18 hours, preferably 8 hours. The product of Formula II, wherein A is nitrogen, oxygen or sulfur, and $R^3$ is 5-bromomethyl-furan-2-yl, is isolated by conventional means, and preferably purified by chromatography or recrystallisation.

Preparation of Compounds of Formula II, wherein A is nitrogen, oxygen or sulfur, and $R^3$ is 5-hydroxymethyl-furan-2-yl A compound of Formula II, wherein A is nitrogen, oxygen or sulfur, and $R^3$ is 5-bromomethyl-furan-2-yl, is reacted with an excess of silver nitrate in an aqueous solvent system, such as a mixture of water and a water-miscible polar organic solvent, preferably a mixture of water and acetone. The reaction is preferably carried out at room temperature, and preferably in the dark, for about 8–18 hours, preferably 16 hours. The product of Formula II, wherein A is nitrogen, oxygen or sulfur, and $R^3$ is 5-hydroxymethyl-furan-2-yl, is isolated by conventional means, and preferably purified by chromatography or recrystallisation.

Conversion of Compounds of Formula II, wherein A is nitrogen, oxygen or sulfur, and $R^3$ is furan-2-yl to compounds of Formula II, wherein A is nitrogen, oxygen or sulfur, and $R^3$ is 5-bromo-furan-2-yl, 5-chloro-furan-2-yl, 5-methoxy-furan-2-yl, 5-methylsulfanyl-furan-2-yl, 5-ethoxycarbonyl-furan-2-yl, 5-(1-ethoxy-vinyl)-furan-2-yl, or 5-cyanomethyl-furan-2-yl.

Methods of converting compounds of Formula II, wherein A is nitrogen, oxygen or sulfur, and $R^3$ is furan-2-yl to compounds of Formula II, wherein A is nitrogen, oxygen or sulfur, and $R^3$ is 5-bromo-furan-2-yl, 5-chloro-furan-2-yl, 5-methoxy-furan-2-yl, 5-methylsulfanyl-furan-2-yl, 5-ethoxycarbonyl-furan-2-yl, 5-(1-ethoxy-vinyl)-furan-2-yl, or 5-cyanomethyl-furan-2-yl are shown in Reaction Scheme XXVI below.

REACTION SCHEME XXVI

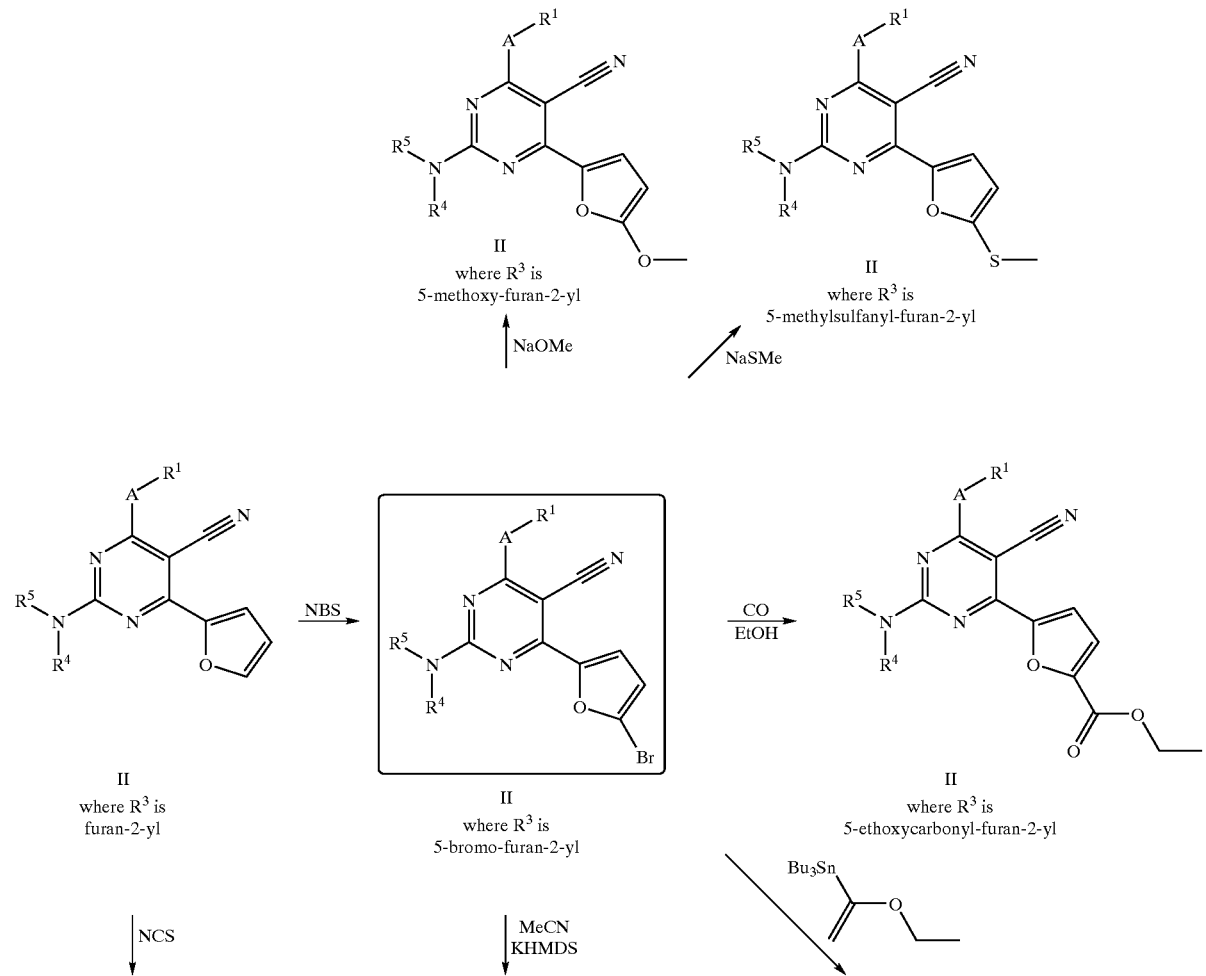

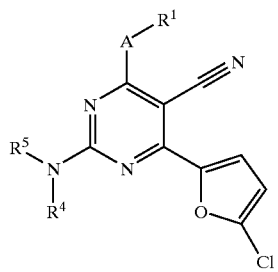

II
where R³ is
5-chloro-furan-2-yl

-continued

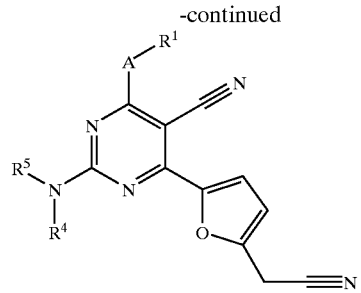

II
where R³ is
5-cyanomethyl-furan-2-yl

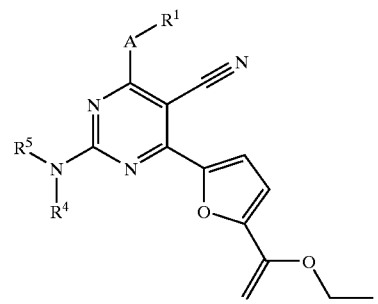

II
where R³ is
5-(1-ethoxy-vinyl)-furan-2-yl wherein A is nitrogen, oxygen or Sulfur, R¹ is as defined above, and R⁴ and R⁵ are hydrogen.

Preparation of Compounds of Formula II, wherein A is nitrogen, oxygen or sulfur, and R³ is 5-bromo-furan-2-yl.

A compound of Formula II, wherein A is nitrogen, oxygen or sulfur, and R³ is furan-2-yl, is reacted with a slight excess of N-bromosuccinimide in a polar organic solvent, preferably N,N-dimethylformamide. The reaction is carried out at a temperature between room temperature and 50° C., preferably 50° C., for about 1–2 hours. The product of Formula II, wherein A is nitrogen, oxygen or sulfur, and R³ is 5-bromo-furan-2-yl, is isolated by conventional means, and preferably purified by chromatography or recrystallisation.

Preparation of Compounds of Formula II, wherein A is nitrogen, oxygen or sulfur, and R³ is 5-chloro-furan-2-yl.

A compound of Formula II, wherein A is nitrogen, oxygen or sulfur, and R³ is furan-2-yl, is reacted with a slight excess of N-chlorosuccinimide in a polar organic solvent, preferably N,N-dimethylformamide. The reaction is carried out at a temperature between room temperature and 50° C., preferably 50° C., for about 1–2 hours. The product of Formula II, wherein A is nitrogen, oxygen or sulfur, and R³ is 5-chloro-furan-2-yl, is isolated by conventional means, and preferably purified by chromatography or recrystallisation.

Preparation of Compounds of Formula II, wherein A is nitrogen, oxygen or sulfur, and R³ is 5-methoxy-furan-2-yl.

A compound of Formula II, wherein A is nitrogen, oxygen or sulfur, and R³ is 5-bromo-furan-2-yl, is reacted with an excess of sodium methylate in a non-protic polar organic solvent, preferably 1,2-dimethoxyethane. The reaction is carried out at a temperature between room temperature and 50° C., preferably 50° C., for about 1–2 hours. The product of Formula II, wherein A is nitrogen, oxygen or sulfur, and R³ is 5-methoxy-furan-2-yl, is isolated by conventional means, and preferably purified by chromatography or recrystallisation.

Preparation of Compounds of Formula II, wherein A is nitrogen, oxygen or sulfur, and R³ is 5-methylsulfanyl-furan-2-yl.

A compound of Formula II, wherein A is nitrogen, oxygen or sulfur, and R³ is 5-bromo-furan-2-yl, is reacted with an excess of sodium methanethiolate in a non-protic polar organic solvent, preferably 1,2-dimethoxyethane. The reaction is carried out at a temperature between room temperature and 50° C., preferably 50° C., for about 1–2 hours. The product of Formula II, wherein A is nitrogen, oxygen or sulfur, and R³ is 5-methylsulfanyl-furan-2-yl, is isolated by conventional means, and preferably purified by chromatography or recrystallisation.

Preparation of Compounds of Formula II wherein A is nitrogen, oxygen or sulfur, and R³ is 5-ethoxycarbonyl-furan-2-yl.

A compound of Formula II, wherein A is nitrogen, oxygen or sulfur, and R³ is 5-bromo-furan-2-yl, is reacted with carbon monoxide gas in a solvent mixture comprising ethanol and N,N-dimethylformamide. The reaction mixture also contains a palladium catalyst, preferably tris(dibenzylidineacetone)dipalladium chloroform complex, a catalytic amount of a monodentate ligand, preferably triphenylarsine, and an excess of an organic base, preferably triethylamine. The reaction is carried out at a pressure of 1–20 atmospheres, preferably 1 atmosphere, and at a temperature above room temperature, preferably about 90–100° C., for about 8–18 hours, preferably about 16 hours. The product of Formula II, wherein A is nitrogen, oxygen or sulfur, and R³ is 5-ethoxycarbonyl-furan-2-yl, is isolated by conventional means, and preferably purified by chromatography or recrystallisation.

Preparation of Compounds of Formula II, wherein A is nitrogen, oxygen or sulfur, and R³ is 5-(1-ethoxy-vinyl)-furan-2-yl.

A compound of Formula II, wherein A is nitrogen, oxygen or sulfur, and R³ is 5-bromo-furan-2-yl, is reacted with a slight excess of (1-ethoxyvinyl)tributylstannane in an ethereal solvent (for example 1,2-dimethoxyethane, tetrahydrofuran or dioxane, preferably dioxane), containing a palladium catalyst, preferably bis(triphenylphosphine)palladium (II) chloride. The reaction is preferably carried out at the reflux temperature of the solvent, preferably about 100° C., for about 10–18 hours, preferably about 16 hours. The product of Formula II, wherein A is nitrogen, oxygen or sulfur, and R³ is 5-(1-ethoxy-vinyl)-furan-2-yl, is isolated by conventional means, and preferably purified by chromatography or recrystallisation.

Preparation of Compounds of Formula II, wherein A is nitrogen, oxygen or sulfur, and R³ is 5-cyanomethyl-furan-2-yl.

To prepare compounds of Formula II, wherein A is nitrogen, oxygen or sulfur, and R³ is 5-cyanomethyl-furan-2-yl, an excess of acetonitrile is reacted with a strong non-aqueous base, preferably potassium bis(trimethylsilyl)amide. The reaction is carried out in an ethereal solvent (for example, tetrahydrofuran, dioxane, diethyl ether, or 1,2-dimethoxyethane, preferably tetrahydrofuran), at a temperature of −78° C. for about 1 hour, after which time a compound of Formula II, wherein A is nitrogen, oxygen or sulfur, and R³ is 5-bromo-furan-2-yl, is added, and the mixture allowed to warm gradually to −40° C. over about 5–6 hours. The product of Formula II, wherein A is nitrogen, oxygen or sulfur, and R³ is 5-cyanomethyl-furan-2-yl, is isolated by conventional means, and preferably purified by chromatography or recrystallisation.

Preparation of Compounds of Formula III
Preparation of compounds of Formula III, wherein A is nitrogen, oxygen or sulfur, and R³ is phenyl (optionally substituted by lower alkyl, lower alkoxy), thien-2.yl, fur-2.yl (optionally substituted by lower alkyl, —(CH₂)ₙ-lower alkoxy, CHF₂, or CH₂F), 2,3-dihydro-benzo[1.4]dioxin-6yl, benzo[1.3]dioxol-5-yl, isoxazol-5-yl, pyridin-2-yl, pyridin-3-yl, —C(=CH₂)O-lower alkyl, 4,5-dihydrofuran-2-yl, 5,6-dihydro-4H-pyran-2-yl oxazol-2-yl, benzofuranyl, or pyrazin-2-yl.

One method of preparation of compounds of Formula III, wherein A is nitrogen, oxygen or sulfur, and R³ is phenyl (optionally substituted by lower alkyl, lower alkoxy), thien-2-yl, fur-2-yl (optionally substituted by lower alkyl, —(CH₂)ₙ-lower alkoxy, CHF₂, or CH₂F), 2,3-dihydro-benzo[1.4]dioxin-6-yl, benzo[1.3]dioxol-5-yl, isoxazol-5-yl, pyridin-2-yl, pyridin-3-yl, —C(=CH₂)O-lower alkyl, 4,5-dihydrofuran-2-yl, 5,6-dihydro-4H-pyran-2-yl oxazol-2-yl, benzofuranyl, or pyrazin-2-yl, is from intermediates of formula (78), the preparation of which is shown in Reaction Scheme XXVII below.

example, tetrahydrofuran, dioxane, diethyl ether, or 1,2-dimethoxyethane, preferably tetrahydrofuran), at a temperature of −78 IC for about 15–30 minutes, preferably 15 minutes, after which time a slight excess of a nitrile of formula (73) is added, and the mixture allowed to warm gradually to 0° C. over about 1–2 hours. The product of formula (74) is isolated by conventional means, and preferably used in the next step without further purification.
Preparation of Compounds of Formula (76)
A compound of formula (74) is reacted with a slight excess of 2-cyanoacetic acid of formula (75) and a slight excess of acetic anhydride in an ethereal solvent (for example dioxane or tetrahydrofuran, preferably dioxane). The reaction is preferably carried out at the reflux temperature of the solvent, preferably about 100° C., for about 1–2 hours, preferably about 90 minutes. The product of formula (76) is isolated by conventional means, and preferably purified by recrystallisation.
Preparation of Compounds of Formula (77)
A compound of formula (76) is reacted in an alcoholic solvent, preferably ethanol, with a base, preferably sodium ethylate. The reaction is preferably performed at the reflux temperature of the solvent, preferably about 100° C., for 1–2 hours, preferably 1 hour. The product of formula (77) is isolated by conventional means, and preferably purified by recrystallisation.

REACTION SCHEME XXVII

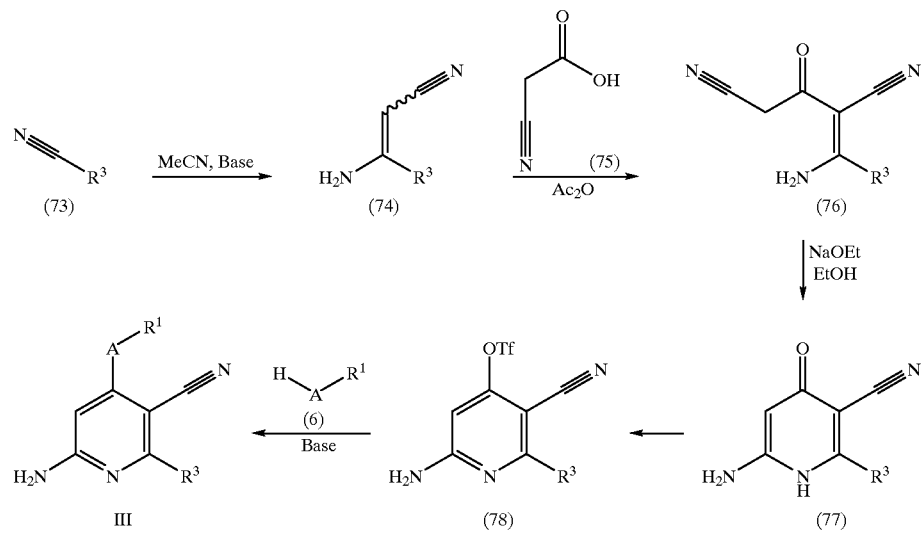

wherein A is nitrogen, oxygen or sulfur, R¹ is as defined above, and R³ is phenyl (optionally substituted by lower alkyl, lower alkoxy), thien-2-yl, fur-2-yl (optionally substituted by lower alkyl, —(CH₂)ₙ-lower alkoxy, CHF₂, or CH₂F), 2,3-dihydro-benzo[1.4]dioxin-6-yl, benzo[1.3]dioxol-5-yl, isoxazol-5-yl, pyridin-2-yl, pyridin-3-yl, —C(=CH₂)O-lower alkyl, 4,5-dihydrofuran-2-yl, 5,6-dihydro-4H-pyran-2-yl oxazol-2-yl, benzofuranyl, or pyrazin-2-yl.
Preparation of Compounds of Formula (74)
The starting nitrites of formula (73) may be obtained commercially, for example from Fluka Chemie AG, or may be prepared according to methods well known in the art.

To prepare compounds of formula (73), acetonitrile is reacted with about one equivalent of a strong non-aqueous base, for example a lower alkyl lithium, preferably n-butyl lithium. The reaction is carried out in an ethereal solvent (for Preparation of Compounds of Formula (78)
A compound of formula (77) is reacted with an alkanesulfonic anhydride, preferably trifluoromethanesulfonic anhydride, and an excess of a non-nucleophilic base, preferably 2,6-di-tert-butylpyridine, in an organic solvent, preferably dichloromethane, at a temperature between 0° C. and room temperature for about 16 hours. The product of formula (78) is isolated by conventional means, and is preferably purified by means of chromatography or recrystallisation.
Preparation of compounds of Formula III wherine A is nitrogen, oxygen or sulfur, and R³ is phenyl (optionally substituted by lower alkyl, lower alkoxy), thien-2-yl, fur-2-yl (optionally substituted by lower alkyl, —(CH₂)ₙ-lower alkoxy, CHF₂, or CH₂F), 2,3-dihydro-benzo[1.4]dioxin-6-yl, benzo[1.3]dioxol-5-yl, isoxazol-5-yl, pyridin-2-yl, pyridin-3-yl, —C(=CH₂)O-lower alkyl, 4,5-dihydrofuran- 2-yl, 5,6-dihydro-4H-pyran-2-yl oxazol-2-yl, benzofuranyl, or pyrazin-2-yl.

The compound of formula (78) is reacted with an appropriate nucleophilic compound of formula (6), which may be commercially available or may be prepared by methods well known in the art, and which may be chosen from: a primary or secondary aliphatic alcohol or an aromatic alcohol, in each case used together with a non-nucleophilic base, preferably 1,8-diazabicyclo[5.4.0]undec-7-ene (1,5-5); a primary or secondary aliphatic thiol or an aromatic thiol, in each case used together with a non-nucleophilic base, preferably 1,8-diazabicyclo[5.4.0]undec-7-ene (1,5-5) (DBU); a primary or secondary aliphatic amine which is preferably used in excess in the absence of an added base; the inorganic salt of a primary or secondary aliphatic amine, such as a hydrochloride salt, which is used together with a non-nucleophilic base, preferably 1,8-diazabicyclo[5.4.0]undec-7-ene (1,5-5); an alkali metal alcoholate of a primary or secondary aliphatic alcohol or of an aromatic alcohol, preferably a sodium or potassium alcoholate, which is preferably used in excess; or an alkali metal thiolate of a primary or secondary aliphatic thiol or of an aromatic thiol, preferably a sodium or potassium thiolate, which is preferably used in excess. These reactions may be carried out in a non-protic polar solvent such as acetonitrile or in an ethereal solvent such as dioxane, tetrahydrofuran or 1,2-dimethoxyethane, preferably 1,2-dimethoxyethane, at room temperature or above, preferably at the reflux temperature of the solvent, for 1–72 hours, preferably 48 hours. The product of Formula III where A is nitrogen, oxygen or sulfur and $R^3$ is phenyl (optionally substituted by lower alkyl, lower alkoxy), thien-2yl, fur-2yl (optionally substituted by lower alkyl, —$(CH_2)_n$-lower alkoxy, $CHF_2$, or $CH_2F$), 2,3-dihydro-benzo[1.4]dioxin-6yl, benzo[1.3]dioxol-5-yl, isoxazol-5-yl, pyridin-2-yl, pyridin-3-yl, —C(=$CH_2$)O-lower alkyl, 4,5-dihydrofuran-2-yl, 5,6-dihydro-4H-pyran-2-yl oxazol-2-yl, benzofuranyl, or pyrazin-2-yl, is isolated by conventional means, and preferably purified by means of chromatography or recrystallisation.

Preparation of Compounds of Formula IV

Preparation of compounds of Formula IV, wherein A is nitrogen, oxygen or sulfur, and $R^3$ is phenyl (optionally substituted by lower alkyl, lower alkoxy, or halogen), thien-2-yl, fur-2-yl (optionally substituted by lower alkyl, halogen, lower alkoxy, —$(CH_2)_n$—OH, —$(CH_2)_n$-lower alkoxy, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl.

One method of preparation of compounds of Formula IV, wherein A is nitrogen, oxygen or sulfur, and $R^3$ is phenyl (optionally substituted by lower alkyl, lower alkoxy, or halogen), thien-2-yl, fur-2-yl (optionally substituted by lower alkyl, halogen, lower alkoxy, —$(CH_2)_n$—OH, —$(CH_2)_n$-lower alkoxy, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, is from intermediates of formula (81), the preparation of which is shown in Reaction Scheme XXVIII below.

REACTION SCHEME XXVIII

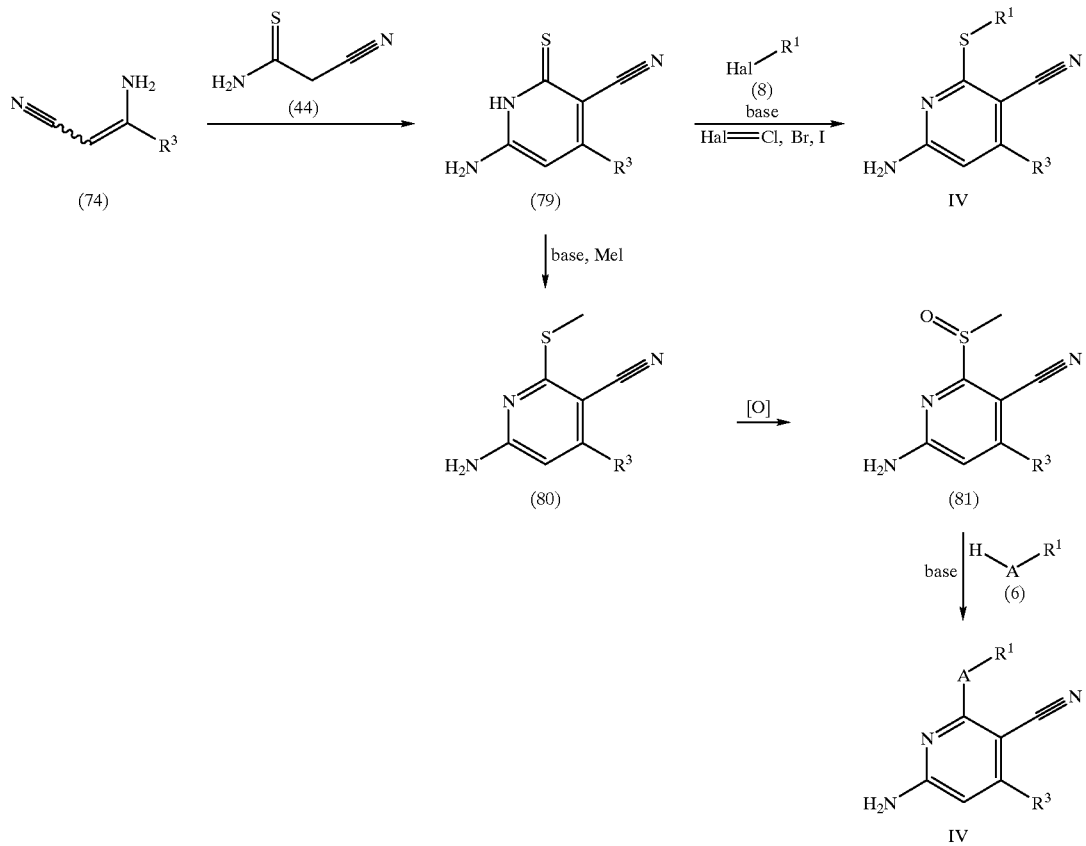

wherein A is nitrogen, oxygen or sulfur, $R^1$ is as defined above, and $R^3$ is phenyl (optionally substituted by lower alkyl, lower alkoxy, or halogen), thien-2-yl, fur-2-yl (optionally substituted by lower alkyl, halogen, lower alkoxy, —$(CH_2)_n$—OH, —$(CH_2)_n$-lower alkoxy, $CHF_2$, or $CH_2F$), 2,3-dihydro-benzo[1.4]dioxin-6-yl, benzo[1.3]dioxol-yl-isoxazol-5-yl, pyridin-2-yl, pyridin-3-yl, oxazol-2-yl, benzofuranyl, or pyrazin-2-yl.

Preparation of Compounds of Formula (79)

A compound of formula (74), is reacted with an excess of 2-cyanothioacetamide of formula (44) in an ethereal solvent (for example dioxane or tetrahydrofuran, preferably dioxane). The reaction is preferably carried out at the reflux temperature of the solvent, preferably about 100° C., for about 12–72 hours, preferably about 60 hours. The product of formula (79) is isolated by conventional means, and preferably purified by chromatography or recrystallisation.

Preparation of Compounds of Formula (80)

A compound of formula (79) is reacted with about one equivalent of methyl iodide. The reaction is carried out in a polar solvent, preferably methanol or ethanol, in the presence of about one equivalent of a base, preferably sodium methylate or sodium ethylate, at room temperature or above, preferably room temperature, for 30–90 minutes, preferably about 30 minutes. The product of formula (80) is isolated by conventional means, and preferably purified by means of chromatography or recrystallisation.

Preparation of Compounds of Formula (81)

The compound of formula (80) may be converted to a compound of formula (81) by reacting a compound of formula (80) with an oxidising agent, preferably 3-phenyl-2-(phenylsulfonyl)oxaziridine, in an organic solvent, preferably dichloromethane, at room temperature. The product of formula (81) is isolated by conventional means, and preferably reacted in the next step without further purification. The product of formula (81) may, however, be additionally purified by means of chromatography or recrystallisation.

Preparation of compounds of Formula IV, wherein A is nitrogen, oxygen or sulfur, and $R^3$ is phenyl (optionally substituted by lower alkyl, lower alkoxy, or halogen), thien-2-yl, fur-2-yl (optionally substituted by lower alkyl, halogen, lower alkoxy, —$(CH_2)_n$—OH, —$(CH_2)_n$-lower alkoxy, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl.

The compound of formula (81) is reacted with an appropriate nucleophilic compound of formula (6), which may be commercially available or may be prepared by methods well known in the art, and which may be chosen from: a primary or secondary aliphatic alcohol or an aromatic alcohol, in each case used together with a non-nucleophilic base, preferably 1,8-diazabicyclo[5.4.0]undec-7-ene (1,5-5); a primary or secondary aliphatic thiol or an aromatic thiol, in each case used together with a non-nucleophilic base, preferably 1,8-diazabicyclo[5.4.0]undec-7-ene (1,5-5) (DBU); a primary or secondary aliphatic amine which is preferably used in excess in the absence of an added base; the inorganic salt of a primary or secondary aliphatic amine, such as a hydrochloride salt, which is used together with a non-nucleophilic base, preferably 1,8-diazabicyclo[5.4.0]undec-7-ene (1,5-5); an alkali metal alcoholate of a primary or secondary aliphatic alcohol or of an aromatic alcohol, preferably a sodium or potassium alcoholate, which is preferably used in excess; or an alkali metal thiolate of a primary or secondary aliphatic thiol or of an aromatic thiol, preferably a sodium or potassium thiolate, which is preferably used in excess. These reactions may be carried out in a non-protic polar solvent such as acetonitrile or in an ethereal solvent such as dioxane, tetrahydrofuran or 1,2-dimethoxyethane, preferably 1,2-dimethoxyethane, at room temperature or above, preferably at the reflux temperature of the solvent, for 1–48 hours, preferably 16 hours. The product of Formula IV where A is nitrogen, oxygen or sulfur, and $R^3$ is phenyl (optionally substituted by lower alkyl, lower alkoxy, or halogen), thien-2-yl, fur-2-yl (optionally substituted by lower alkyl, halogen, lower alkoxy, —$(CH_2)_n$—OH, —$(CH_2)_n$-lower alkoxy, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, is isolated by conventional means, and preferably purified by means of chromatography or recrystallisation.

Alternative preparation of compounds of Formula IV, wherein A is sulfur, and $R^3$ is phenyl (optionally substituted by lower alkyl, lower alkoxy, or halogen), thien-2-yl, fur-2-yl (optionally substituted by lower alkyl, halogen, lower alkoxy, —$(CH_2)_n$—OH, —$(CH_2)_n$-lower alkoxy, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl.

An alternative method of converting a compound of formula (79) to a compound of Formula IV, wherein A is sulfur, and $R^3$ is phenyl (optionally substituted by lower alkyl, lower alkoxy, or halogen), thien-2-yl, fur-2-yl (optionally substituted by lower alkyl, halogen, lower alkoxy, —$(CH_2)_n$—OH, —$(CH_2)_n$-lower alkoxy, $CHF_2$, or $CH_2F$), 2,3-dihydro-benzo[1.4]dioxin-6-yl, benzo[1.3]dioxol-5-yl, isoxazol-5-yl, pyridin-2-yl, pyridin-3-yl, oxazol-2-yl, benzofuranyl, or pyrazin-2-yl, is by reaction of a compound of formula (79) with an excess of an appropriate organic halide of formula (8), such as a primary or secondary aliphatic halide, preferably an aliphatic bromide or a benzylic bromide, which may be commercially available or may be prepared by methods well known in the art. The reaction is carried out in a polar solvent, preferably methanol or ethanol, in the presence of an excess of a base, preferably sodium methylate or sodium ethylate, at room temperature or above, preferably at the reflux temperature of the solvent, for 1–18 hours, preferably 1 hour. The product of Formula IV where A is sulfur, and $R^3$ is phenyl (optionally substituted by lower alkyl, lower alkoxy, or halogen), thien-2-yl, fur-2-yl (optionally substituted by lower alkyl, halogen, lower alkoxy, —$(CH_2)_n$—OH, —$(CH_2)_n$-lower alkoxy, $CHF_2$, or $CH_2F$), 2,3-dihydro-benzo[1.4]dioxin-6-yl, benzo [1.3]dioxol-5-yl, isoxazol-5-yl, pyridin-2-yl, pyridin-3-yl, oxazol-2-yl, benzofuranyl, or pyrazin-2-yl, is isolated by conventional means, and preferably purified by means of chromatography or recrystallisation.

Conversion of Compounds of Formula I to Other Compounds of Formula I

The compounds of Formula I wherein X, Y, A, $R^1$, $R^2$ and $R^3$ are as defined above and $R^4$ and $R^5$ are hydrogen may be converted to other compounds of Formula I by replacing one or both hydrogens of $R^4$ and $R^5$ with other groups:

For example, a compound of Formula I where $R^4$ and $R^5$ are hydrogen is reacted with an acylating agent, for example an acyl chloride or an acyl anhydride, optionally in the presence of a catalyst such as 4-dimethylaminopyridine. The reaction is carried out in an organic solvent such as dichloromethane containing a base such as pyridine. The reaction is performed at a temperature between 0° C. and 100° C., preferably at room temperature, for about 1 to 18 hours. The resulting monoacyl product, a compound of Formula I where $R^4$ is acyl and $R^5$ is hydrogen, is isolated by conventional means, and preferably purified by means of chromatography or recrystallisation.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the Preparations and Examples herein below. However, other equivalent separation or isolation procedues could, of course, also be used.

Salts of Compounds of Formula I

The compounds of Formula I may be basic, for example in cases where the residue $R^1$ contains a basic group such as an aliphatic or aromatic amine moiety, or in cases where X is N and Y is CH, or in cases where X is CH and Y is N. In such cases the compounds of Formula I may be converted to a corresponding acid addition salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of Formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention are adenosine receptor ligands.

The compounds were investigated in accordance with the tests given hereinafter.

Human Adenosine $A_1$ Receptor

The gene encoding human adenosine $A_1$ receptor was recombinantly introduced and expressed in chinese hamster ovary (CHO) cells using the semliki forest virus expression system. Cells were harvested, washed twice by centrifugation, homogenised and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A). The $[^3H]$-DPCPX (([propyl-3H]8-cyclopentyl-1,3-dipropyxanthine); 0.6 nM) binding assay was carried out in 96-well plates in the presence of 2.5 μg of membrane protein, 0.5 mg of Ysi-poly-1-lysine SPA beads and 0.1 U adenosine deaminase in a final volume of 200 μl of buffer A. Non-specific binding was defined using xanthine amine congener (XAC; 2 μM). Compounds were tested at 10 concentrations from 10 μM-0.3 nM. All assays were conducted in duplicate and repeated at least two times. Assay plates were incubated for 1 hour at room temperature before centrifugation and then bound ligand determined using a Packard Topcount scintillation counter. $IC_{50}$ values were calculated using a non-linear curve fitting program and Ki values calculated using the Cheng-Prussoff equation.

Human Adenosine $A_{2A}$ Receptor

The gene encoding human adenosine $A_2A$ receptor was recombinantly introduced and expressed in chinese hamster ovary (CHO) cells using the semliki forest virus expression system. Cells were harvested, washed twice by centrifugation, homogenised and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A). The $[^3H]$-SCH-58261 (Dionisotti et al., 1997, Br. J. Pharmacol. 121, 353; 1 nM) binding assay was carried out in 96-well plates in the presence of 2.5 μg of membrane protein, 0.5 mg of Ysi-poly-1-lysine SPA beads and 0.1 U adenosine deaminase in a final volume of 200 μl of buffer A. Non-specific binding was defined using xanthine amine congener (XAC; 2 EM). Compounds were tested at 10 concentrations from 10 μM-0.3 nM. All assays were conducted in duplicate and repeated at least two times. Assay plates were incubated for 1 hour at room temperature before centrifugation and then bound ligand determined using a Packard Topcount scintillation counter. $IC_{50}$ values were calculated using a non-linear curve fitting program and Ki values calculated using the Cheng-Prussoff equation.

Human Adenosine $A_3$ Receptor

The gene encoding human adenosine $A_3$ receptor was recombinantly introduced and expressed in chinese hamster ovary (CHO) cells using the semliki forest virus expression system. Cells were harvested, washed twice by centrifugation, homogenised and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A). The $[^{125}I]$-AB-MECA ([N(6)-(4-amino-3-iodobenzyl)-5'-N-methylcarbamoyl-adenosine]; 0.05 nM) binding assay was carried out in 96-well plates in the presence of 20 μg of membrane protein and 0.1 U adenosine deaminase in a final volume of 200 μl of buffer A. Non-specific binding was defined using xanthine amine congener (XAC; 2 μM). Compounds were tested at 10 concentrations from 10 μM-0.3 nM. All assays were conducted in duplicate and repeated at least two times. Assay plates were incubated for 1 hour at room temperature before filtration through Whatman Unifilter GF/C 96-well filter plates (preincubated with 0.3% polyethyleneimine). Filters were washed 3 times with 0.3 ml of cold (4° C.) Tris (50 mM)-Nacl (120 mM) buffer (pH 7.4). Microscint 40 scintillation fluid (50 μl) was added to each well and the wells sealed. After gentle shaking for 20 min, plates were counted on a Packard Topcount scintillation counter. $IC_{50}$ values were calculated using a non-linear curve fitting program and Ki values calculated using the Cheng-Prussoff equation.

In the following table the affinity to the human $A_{2a}$ receptor is shown for the preferred compounds, given as pKi.

| Example | pKi | Systematic Name |
|---|---|---|
| 23 | 8.04 | 2-Amino-4-(2,3-dihydro-benzo[1,4]dioxin-6-yl)-6-methylsulfanyl-pyrimidine-5-carbonitrile |
| 38 | 8.00 | 2-Amino-4-ethoxy-6-furan-2-yl-pyrimidine-5-carbonitrile |
| 41 | 8.07 | 2-Amino-4-furan-2-yl-6-piperidin-1-yl-pyrimidine-5-carbonitrile |
| 42 | 8.33 | 2-Amino-4-benzylamino-6-furan-2-yl-pyrimidine-5-carbonitrile |
| 44 | 8.60 | 2-Amino-4-furan-2-yl-6-(3-phenyl-propylamino)-pyrimidine-5-carbonitrile |
| 47 | 8.42 | 2-Amino-4-benzyloxy-6-furan-2-yl-pyrimidine-5-carbonitrile |
| 52 | 8.40 | 2-Amino-4-benzylsulfanyl-6-furan-2-yl-pyrimidine-5-carbonitrile |
| 53 | 8.20 | 2-Amino-4-furan-2-yl-6-phenethyloxy-pyrimidine-5-carbonitrile |
| 54 | 8.13 | 2-Amino-4-furan-2-yl-6-(3-phenyl-propoxy)-pyrimidine-5-carbonitrile |
| 55 | 8.13 | 2-Amino-4-cyclohexyloxy-6-furan-2-yl-pyrimidine-5-carbonitrile |
| 58 | 8.19 | 2-Amino-4-furan-2-yl-6-[2-(4-hydroxy-phenyl)-ethylamino]-pyrimidine-5-carbonitrile |
| 60 | 8.34 | 2-Amino-4-butylsulfanyl-6-furan-2-yl-pyrimidine-5-carbonitrile |
| 61 | 8.16 | 2-Amino-4-furan-2-yl-6-isopropoxy-pyrimidine-5-carbonitrile |
| 75 | 8.00 | 2-Amino-4-ethylsulfanyl-6-furan-2-yl-pyrimidine-5-carbonitrile |
| 76 | 8.68 | 2-Amino-4-furan-2-yl-6-(pyridin-2-ylmethoxy)-pyrimidine-5-carbonitrile |
| 85 | 8.10 | 2-Amino-4-phenyl-6-(3-phenyl-propylsulfanyl)-pyrimidine-5-carbonitrile |
| 94 | 8.01 | 2-Amino-6-furan-2-yl-pyrimidine-4,5-dicarbonitrile |
| 104 | 8.40 | 2-Amino-4-phenethyloxy-6-phenyl-pyrimidine-5-carbonitrile |
| 105 | 8.13 | 2-Amino-4-phenyl-6-(pyridin-2-ylmethoxy)-pyrimidine-5-carbonitrile |
| 132 | 8.33 | 2-Amino-4-furan-2-yl-6-(2-phenylamino-ethylamino)-pyrimidine-5-carbonitrile |
| 144 | 8.55 | 2-Amino-4-furan-2-yl-6-[2-(4-methoxy-phenyl)-ethylamino]-pyrimidine-5-carbonitrile |
| 148 | 8.19 | 2-Amino-4-furan-2-yl-6-phenyl-pyrimidine-5-carbonitrile |
| 149 | 8.34 | (E)-2-Amino-4-furan-2-yl-6-styryl-pyrimidine-5-carbonitrile |
| 168 | 8.03 | 5-Bromo-4-furan-2-yl-6-(pyridin-2-ylmethoxy)-pyrimidin-2-ylamine |
| 206 | 8.02 | 2-Amino-4-(pyridin-2-ylmethoxy)-6-thiophen-2-yl-pyrimidine-5-carbonitrile |
| 208 | 8.04 | 5-Bromo-6-furan-2-yl-N4-(3-phenyl-propyl)-pyrimidine-2,4-diamine hydrochloride |
| 219 | 8.23 | 2-Amino-4-furan-2-yl-6-(pyridin-3-ylmethoxy)-pyrimidine-5-carbonitrile |
| 230 | 8.78 | 5-Bromo-4-furan-2-yl-6-(3-phenyl-propoxy)-pyrimidin-2-ylamine |
| 231 | 8.09 | 2-Amino-4-furan-2-yl-6-(2-phenylamino-ethoxy)-pyrimidine-5-carbonitrile |
| 233 | 8.56 | 2-Amino-4-furan-2-yl-6-phenethylsulfanyl-pyrimidine-5-carbonitrile |
| 234 | 8.26 | 2-Amino-4-furan-2-yl-6-(3-phenyl-propylsulfanyl)-pyrimidine-5-carbonitrile |
| 235 | 8.46 | 2-Amino-4-furan-2-yl-6-(2-phenoxy-ethylamino)-pyrimidine-5-carbonitrile |
| 237 | 8.53 | 2-Amino-4-furan-2-yl-6-(6-methyl-pyridin-2-yl-methoxy)-pyrimidine-5-carbonitrile |
| 241 | 8.66 | 2-Amino-4-furan-2-yl-6-(2-pyridin-2-yl-ethoxy)-pyrimidine-5-carbonitrile |
| 245 | 8.26 | 2-Amino-4-benzylamino-6-(5-methyl-furan-2-yl)-pyrimidine-5-carbonitrile |
| 246 | 8.73 | 2-Amino-4-(5-methyl-furan-2-yl)-6-(6-methyl-pyridin-2-ylmethoxy)-pyrimidine-5-carbonitrile |
| 247 | 8.67 | 2-Amino-4-(5-methyl-furan-2-yl)-6-(pyridin-2-ylmethoxy)-pyrimidine-5-carbonitrile |
| 267 | 8.36 | 4-Furan-2-yl-5-iodo-6-(3-phenyl-propoxy)-pyrimidin-2-ylamine |
| 269 | 8.11 | 5-Bromo-4-furan-2-yl-6-phenethylsulfanyl-pyrimidin-2-ylamine |
| 278 | 8.43 | 2-Amino-4-furan-2-yl-6-(3-phenyl-allyloxy)-pyrimidine-5-carbonitrile |
| 280 | 8.03 | 5-Bromo-4-furan-2-yl-6-(3-phenyl-allyloxy)-pyrimidin-2-ylamine |
| 283 | 8.23 | 2-Amino-4-furan-2-yl-6-[(pyridin-2-ylmethyl)-amino]-pyrimidine-5-carbonitrile |
| 284 | 8.41 | 2-Amino-4-furan-2-yl-6-(pyridin-2-ylmethylsulfanyl)-pyrimidine-5-carbonitrile |
| 286 | 8.02 | 4-Benzyloxy-6-furan-2-yl-5-nitro-pyrimidin-2-ylamine |
| 288 | 8.59 | 2-Amino-4-furan-2-yl-6-(2-methyl-benzylamino)-pyrimidine-5-carbonitrile |
| 289 | 8.43 | 2-Amino-4-furan-2-yl-6-(3-methyl-benzylamino)-pyrimidine-5-carbonitrile |
| 290 | 8.17 | 2-Amino-4-furan-2-yl-6-(4-methyl-benzylamino)-pyrimidine-5-carbonitrile |
| 291 | 8.48 | 2-Amino-4-furan-2-yl-6-(3-methoxy-benzylamino)-pyrimidine-5-carbonitrile |
| 293 | 8.43 | 2-Amino-4-furan-2-yl-6-(2-methoxy-benzylamino)-pyrimidine-5-carbonitrile |
| 297 | 8.86 | 2-Amino-4-furan-2-yl-6-[(quinolin-2-ylmethyl)-amino]-pyrimidine-5-carbonitrile |
| 298 | 8.23 | 2-Amino-4-furan-2-yl-6-[(naphthalen-2-ylmethyl)-amino]-pyrimidine-5-carbonitrile |
| 299 | 8.20 | (RS)-2-Amino-4-furan-2-yl-6-[(1,2,3,4-tetrahydro-quinolin-2-ylmethyl)-amino]-pyrimidine-5-carbonitrile |
| 302 | 8.11 | 2-Amino-4-furan-2-yl-6-(2-phenylsulfanyl-ethylamino)-pyrimidine-5-carbonitrile |
| 303 | 8.60 | 2-Amino-4-furan-2-yl-6-(naphthalen-2-ylmethoxy)-pyrimidine-5-carbonitrile |
| 304 | 8.45 | 2-Amino-4-(2-amino-benzylamino)-6-furan-2-yl-pyrimidine-5-carbonitrile |
| 305 | 8.05 | 2-Amino-4-(4-amino-benzylamino)-6-furan-2-yl-pyrimidine-5-carbonitrile |
| 312 | 8.01 | 2-Amino-4-(4-dimethylamino-benzylamino)-6-furan-2-yl-pyrimidine-5-carbonitrile |
| 313 | 9.08 | 2-Amino-4-furan-2-yl-6-(2-pyridin-2-yl-ethylsulfanyl)-pyrimidine-5-carbonitrile |
| 318 | 8.27 | 2-Amino-4-[2-(4-chloro-phenylamino)-ethylamino[-6-furan-2-yl-pyrimidine-5-carbonitrile |
| 320 | 8.00 | 5-Chloro-6-furan-2-yl-N4-(3-phenyl-propyl)-pyrimidine-2,4-diamine |
| 321 | 8.55 | 5-Chloro-4-furan-2-yl-6-(3-phenyl-propoxy)-pyrimidin-2-ylamine |
| 322 | 8.01 | 5-Chloro-4-furan-2-yl-6-phenethyloxy-pyrimidin-2-ylamine |
| 324 | 8.04 | 4-Benzylsulfanyl-5-chloro-6-furan-2-yl-pyrimidin-2-ylamine |
| 325 | 8.26 | 2-Amino-4-(4-bromo-benzylamino)-6-furan-2-yl-pyrimidine-5-carbonitrile |
| 330 | 8.10 | 2-Amino-4-furan-2-yl-6-[2-(pyridin-2-ylamino)-ethylamino]-pyrimidine-5-carbonitrile |
| 336 | 8.09 | 2-Amino-4-(3,4-dihydro-1H-isoquinolin-2-yl)-6-furan-2-yl-pyrimidine-5-carbonitrile |
| 337 | 8.18 | 2-Amino-4-[(benzo[1,3]dioxol-5-yl-methyl)-amino]-6-furan-2-yl-pyrimidine-5-carbonitrile |
| 345 | 8.38 | 2-Amino-4-furan-2-yl-6-(4-trifluoromethyl-benzylamino)-pyrimidine-5-carbonitrile |
| 346 | 8.62 | 2-Amino-4-furan-2-yl-6-(3-trifluoromethyl-benzylamino)-pyrimidine-5-carbonitrile |
| 347 | 8.78 | 2-Amino-4-(3,4-dimethyl-benzylamino)-6-furan-2-yl-pyrimidine-5-carbonitrile |
| 348 | 8.68 | 2-Amino-4-furan-2-yl-6-[(4-methyl-pyridin-2-yl-methyl)-amino]-pyrimidine-5-carbonitrile |
| 352 | 8.29 | 4-Furan-2-yl-5-iodo-6-(2-pyridin-2-yl-ethylsulfanyl)-pyrimidin-2-ylamine |
| 353 | 8.42 | 5-Bromo-4-furan-2-yl-6-(2-pyridin-2-yl-ethylsulfanyl)-pyrimidin-2-ylamine |
| 354 | 8.31 | 5-Chloro-4-furan-2-yl-6-(2-pyridin-2-yl-ethylsulfanyl)-pyrimidin-2-ylamine |
| 355 | 8.52 | 6-Amino-2-furan-2-yl-4-(pyridin-2-yl-methoxy)-nicotinonitrile |
| 356 | 9.04 | 6-Amino-2-furan-2-yl-4-(2-pyridin-2-yl-ethylsulfanyl)-nicotinonitrile |
| 357 | 8.04 | 6-Amino-2-furan-2-7l-4-(4-trifluoromethyl-benzylamino)-nicotinonitrile |

-continued

| Example | pKi | Systematic Name |
|---|---|---|
| 359 | 9.20 | 2-Amino-4-(2-bromo-benzylamino)-6-furan-2-yl-pyrimidine-5-carbonitrile |
| 360 | 9.23 | 2-Amino-4-(2-chloro-benzylamino)-6-furan-2-yl-pyrimidine-5-carbonitrile |
| 361 | 9.22 | 2-Amino-4-furan-2-yl-6-(3-methyl-pyridin-2-yl-methoxy)-pyrimidine-5-carbonitrile |
| 362 | 8.58 | 2-Amino-4-furan-2-yl-6-(5-methyl-pyridin-2-yl-methoxy)-pyrimidine-5-carbonitrile |
| 363 | 8.49 | 2-Amino-4-furan-2-yl-6-[(5-methyl-pyridin-2-yl-methyl)-amino]-pyrimidine-5-carbonitrile |
| 364 | 8.41 | 6-Amino-2-furan-2-yl-4-[(quinolin-2-yl-methyl)-amino]-nicotinonitrile |
| 366 | 8.74 | 2-Amino-4-furan-2-yl-6-(isoquinolin-3-yl-methoxy)-pyrimidine-5-carbonitrile |
| 367 | 8.64 | 2-Amino-4-furan-2-yl-6-[(isoquinolin-3-yl-methyl)-amino]-pyrimidine-5-carbonitrile |
| 368 | 8.73 | 2-Amino-4-furan-2-yl-6-[(3-methyl-pyridin-2-yl-methyl)-amino]-pyrimidine-5-carbonitrile |
| 370 | 8.05 | 2-Amino-4-(2-pyridin-2-yl-ethylsulfanyl)-6-thiophen-2-yl-pyrimidine-5-carbonitrile |
| 371 | 8.09 | 6-Amino-2-furan-2-yl-4-[(pyridin-2-yl-methyl)-amino]-nicotinonitrile |
| 373 | 8.29 | 2-Amino-4-furan-2-yl-6-(4-methyl-pyridin-2-yl-methoxy)-pyrimidine-5-carbonitrile |
| 374 | 8.03 | 2-Amino-4-furan-2-yl-6-(4-vinyl-benzylamino)-pyrimidine-5-carbonitrile |
| 375 | 8.40 | 2-Amino-4-(4-ethyl-benzylamino)-6-furan-2-yl-pyrimidine-5-carbonitrile |
| 376 | 8.34 | 6-Amino-2-furan-2-yl-4-[(3-methyl-pyridin-2-yl-methyl)-amino]-nicotinonitrile |
| 377 | 8.11 | 6-Amino-2-furan-2-yl-4-[(5-methyl-pyridin-2-yl-methyl)-amino]-nicotinonitrile |
| 381 | 8.46 | 2-Amino-4-furan-2-yl-6-(6-methyl-pyridin-3-yl-methoxy)-pyrimidine-5-carbonitrile |
| 383 | 8.72 | 6-Amino-2-furan-2-yl-4-(3-methyl-pyridin-2-yl-methoxy)-nicotinonitrile |
| 384 | 8.52 | 6-Amino-2-furan-2-yl-4-(2-pyridin-2-yl-ethoxy)-nicotinonitrile |
| 389 | 8.08 | 2-Amino-6-benzylsulfanyl-4-thiophen-2-yl-pyridine-3,5-dicarbonitrile |
| 400 | 8.44 | 2-Amino-4-[(3-chloro-5-trifluoromethyl-pyridin-2-yl-methyl)-amino]-6-furan-2-yl-pyrimidine-5-carbonitrile |
| 401 | 9.16 | 2-Amino-4-(3,5-dimethyl-pyridin-2-yl-methoxy)-6-furan-2-yl-pyrimidine-5-carbonitrile |
| 402 | 8.67 | 2-Amino-4-[(3,5-dimethyl-pyridin-2-yl-methyl)-amino]-6-furan-2-yl-pyrimidine-5-carbonitrile |
| 405 | 8.13 | 2-Amino-4-(3-fluoro-phenyl)-6-(2-pyridin-2-yl-ethoxy)-pyrimidine-5-carbonitrile |
| 422 | 8.87 | 2-Amino-4-(4-methyl-furan-2-yl)-6-(2-pyridin-2-yl-ethylsulfanyl)-pyrimidine-5-carbonitrile |
| 423 | 8.52 | 2-Amino-4-(4-methyl-furan-2-yl)-6-(2-pyridin-2-yl-ethoxy)-pyrimidine-5-carbonitrile |
| 437 | 8.09 | 2-Amino-4-isoxazol-5-yl-6-methylsulfanyl-pyrimidine-5-carbonitrile |
| 464 | 8.12 | 2-Amino-4-[(3-chloro-5-trifluoromethyl-pyridin-2-ylmethyl)-amino]-6-(4-methyl-furan-2-yl)-pyrimidin-5-carbonitrile |
| 465 | 9.18 | 2-Amino-4-(1-ethoxy-vinyl)-6-methylsulfanyl-pyrimidine-5-carbonitrile |
| 466 | 8.97 | 2-Amino-4-methylsulfanyl-6-pyridin-2-yl-pyrimidine-5-carbonitrile |
| 478 | 8.96 | 2-Amino-4-(4,5-dihydro-furan-2-yl)-6-methylsulfanyl-pyrimidine-5-carbonitrile |
| 483 | 8.77 | 2-Amino-4-(5,6-dihydro-4H-pyran-2-yl)-6-methylsulfanyl-pyrimidine-5-carbonitrile |
| 511 | 8.50 | 2-Amino-4-pyridin-2-yl-6-(2-pyridin-2-yl-ethylsulfanyl)-pyrimidine-5-carbonitrile |
| 512 | 8.88 | 2-Amino-4-(2-methoxy-phenyl)-6-methylsulfanyl-pyrimidine-5-carbonitrile |
| 513 | 9.23 | 2-Amino-4-methylsulfanyl-6-pyrazol-1-yl-pyrimidine-5-carbonitrile |
| 516 | 8.90 | 2-Amino-4-(1-ethoxy-vinyl)-6-(2-pyridin-2-yl-ethylsulfanyl)-pyrimidine-5-carbonitrile |
| 521 | 8.93 | 2-Amino-4-(4-bromo-furan-2-yl)-6-(2-pyridin-2-yl-ethylsulfanyl)-pyrimidine-5-carbonitrile |
| 524 | 8.24 | 2-Amino-4-(5-cyanomethyl-furan-2-yl)-6-(2-pyridin-2-yl-ethylsulfanyl)-pyrimidine-5-carbonitrile |
| 525 | 9.06 | 2-Amino-4-(5-chloro-furan-2-yl)-6-(2-pyridin-2-yl-ethoxy)-pyrimidine-5-carbonitrile |
| 526 | 8.37 | 2-Amino-4-(5-chloro-furan-2-yl)-6-(3,5-dimethyl-pyridin-2-ylmethoxy)-pyrimidine-5-carbonitrile |
| 530 | 8.76 | 2-Amino-4-(5-chloro-furan-2-yl)-6-(3-methyl-pyridin-2-ylmethoxy)-pyrimidine-5-carbonitrile |
| 531 | 8.25 | 2-Amino-4-(5-chloro-furan-2-yl)-6-(5-methyl-pyridin-2-ylmethoxy)-pyrimidine-5-carbonitrile |
| 532 | 8.25 | 2-Amino-4-(4-bromo-furan-2-yl)-6-(5-methyl-pyridin-2-ylmethoxy)-pyrimidine-5-carbonitrile |
| 533 | 8.85 | 2-Amino-4-(4-bromo-furan-2-yl)-6-(3,5-dimethyl-pyridin-2-ylmethoxy)-pyrimidine-5-carbonitrile |
| 534 | 9.02 | 2-Amino-4-(4-bromo-furan-2-yl)-6-(3-methyl-pyridin-2-ylmethoxy)-pyrimidine-5-carbonitrile |
| 535 | 8.40 | 2-Amino-4-(4-cyano-furan-2-yl)-6-(2-pyridin-2-yl-ethylsulfanyl)-pyrimidine-5-carbonitrile |
| 538 | 8.71 | 2-Amino-4-(5-difluoromethyl-furan-2-yl)-6-(2-pyridin-2-yl-ethylsulfanyl)-pyrimidine-5-carbonitrile |

Furthermore, it has been shown that compounds of formula I have a high selectivity toward the $A_1$ and $A_3$ receptor, as it is shown in the table below:

| Example No. | hA$_1$ (pKi) | hA$_2$ (pKi) | hA$_3$ (pKi) |
|---|---|---|---|
| 15 | 5.88 | 7.24 | 5.71 |
| 26 | 5.60 | 7.44 | 5.90 |
| 42 | 5.78 | 8.33 | 5.05 |
| 132 | 6.16 | 8.33 | 5.22 |
| 149 | 6.41 | 8.34 | 5.69 |
| 288 | 6.43 | 8.59 | 6.82 |
| 290 | 5.69 | 8.17 | 5.02 |
| 298 | 5.16 | 8.23 | 5.02 |
| 303 | 6.50 | 8.60 | 5.06 |
| 318 | 6.07 | 8.27 | 5.14 |
| 325 | 5.54 | 8.26 | 5.40 |
| 345 | 5.20 | 8.38 | 524 |
| 375 | 6.19 | 8.40 | 5.67 |
| 400 | 5.35 | 8.44 | 5.02 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of supositories, parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the adenosine receptor antagonistic activity, such as Alzheimer's disease, Parkinson's disease, neuroprotection, schizophrenia, anxiety, pain, respiration deficits, depression, asthma, allergic responses, hypoxia, ischaemia, seizure and substance abuse. Furthermore, compounds of the present invention may be useful as sedatives, muscle relaxants, antipsychotics, antiepileptics, anticonvulsants and cardiaprotective agents and for the production of corresponding medicaments.

The most preferred indications in accordance with the present invention are those, which include disorders of the central nervous system, for example the treatment or prevention of certain depressive disorders, neuroprotection and Parkinson's disease.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| Item | Ingredients | mg/tablet | | | |
|---|---|---|---|---|---|
| | | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
 1. Mix items 1, 2, 3 and 4 and granulate with purified water.
 2. Dry the granules at 50° C.
 3. Pass the granules through suitable milling equipment.
 4. Add item 5 and mix for three minutes; compress on a suitable press.

Capsule Formulation

| Item | Ingredients | mg/capsule | | | |
|---|---|---|---|---|---|
| | | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
 1. Mix items 1, 2 and 3 in a suitable mixer for 30 minutes.
 2. Add items 4 and 5 and mix for 3 minutes.
 3. Fill into a suitable capsule.

EXAMPLES

The following examples illustrate the invention but are not intended to limit its scope.

Example 1

2-Amino-4,5-diphenylpyrimidine a) 3-(Dimethylamino)acrylophenone

To a stirred solution of 5.0 ml (42.8 mmol) acetophenone in 40 ml DMF was added 11.4 ml (85.6 mmol) N,N-dimethylformamide dimethyl acetal and the mixture heated at reflux for 16 h. The reaction mixture was then concentrated in vacuo. Trituration in hexane/ethyl acetate (4/1) afforded 6.4 g (85%) 3-(dimethylamino)acrylophenone as a crystalline solid. EI-MS m/e (%): 175 ($M^+$, 45), 158 ([M—OH]$^+$, 100), 98 ([M—$C_6H_5$)$^+$, 63), 42 (72).

b) 2-Amino-4-phenylpyrimidine

To a stirred solution of 3.0 g (17.1 mmol) 3-(dimethylamino)acrylophenone and 10.2 g (56.5 mmol) guanidine carbonate in 50 ml methanol was added 21.2 ml (114 mmol) sodium methylate (5.4M in methanol) and the mixture heated at reflux for 3 hours. The reaction mixture was then concentrated in vacuo. On addition of 50 ml water, a precipitate appeared which was collected by filtration and washed sequentially with water and ether to afford 2.4 g (82%) 2-amino-4-phenylpyrimidine as a crystalline solid. EI-MS m/e (%): 171 ($M^+$, 100), 170 ([M—H]$^+$, 94).

c) 5-Iodo-4-phenyl-pyrimidin-2-ylamine

To a stirred solution of 500 mg (2.9 mmol) 2-amino-4-phenylpyrimidine in 38 ml acetic acid was added 689 mg (3.1 mmol) N-iodosuccinimide and stirring continued in the dark at room temperature for 16 h. The reaction mixture was then concentrated in vacuo and the residue partitioned between ether and water. The organic phase was then dried over sodium sulfate and concentrated in vacuo. Trituration in ether/ethyl acetate then afforded 138 mg (16%) 5-iodo-4-phenyl-pyrimidin-2-ylamine as a yellow crystalline solid. EI-MS m/e (%): 297 ($M^+$, 100), 170 ([M—I]$^+$, 38).

d) 2-Amino-4,5-diphenylpyrimidine

To a stirred solution of 260 mg (0.88 mmol) 5-iodo-4-phenyl-pyrimidin-2-ylamine in 10 ml dioxane under argon at room temperature were added 112 mg (0.92 mmol) phenylboronic acid, 101 mg (0.09 mmol) tetrakis(triphenylphosphine)palladium(O) and 2.0 ml (4.0 mmol) 2M aqueous sodium carbonate solution. The reaction mixture was heated at reflux for 16 h, then cooled to room temperature, 1 g of kieselgel added, and the mixture concentrated in vacuo. Flash chromatography (1/1 ethyl acetate/ hexane) followed by recrystallisation from ethyl acetate/pentane afforded 110 mg (51%) 2-amino-4,5-diphenylpyrimidine as a white crystalline solid. EI-MS m/e (%): 247 (M⁺, 90), 246 ([M—H]⁺, 100).

Example 2
2-Amino-4-(methylthio)-6-phenyl-pyrimidine-5-carbonitrile a) 2-Benzoyl-3,3-bis(methylthio)acrylonitrile Following the method of Rudorf and Augustin (*Phosphorus and Sulfur* 1981, 9, 329), a solution of 15.0 g (103 mmol) benzoylacetonitrile in 200 ml dry DMSO was added dropwise to a stirred suspension of 8.27 g (206 mmol, 60% dispersion in mineral oil) sodium hydride in 200 ml DMSO under argon at room temperature. 6.23 ml (103 mmol) carbon disulfide was then added dropwise, with external water bath cooling, and stirring continued for 2 hours, after which 12.9 ml (206 mmol) methyl iodide was added dropwise, with external water bath cooling, and stirring continued for a further 16 h. The reaction mixture was then poured into 7.5 l ice-cold water, and the precipitate collected by filtration and dried in vacuo to afford 25.6 g (99%) 2-benzoyl-3,3-bis(methylthio)acrylonitrile none as a pale yellow crystalline solid. EI-MS m/e (%): 249 (M⁺, 8), 248 ([M—H]⁺, 17), 234 ([M—CH₃]⁺, 25), 105 ([PhCO]⁺, 100), 77 ([Ph]⁺, 54).

b) 2-Amino-4-(methylthio)-6-phenyl-pyrimidine-5-carbonitrile

Following the method of Rudorf and Augustin (*J. Prakt. Chem.* 1978, 320, 576), a solution of 15.9 g (63.9 mmol) 2-benzoyl-3,3-bis(methylthio)acrylonitrile, 9.36 g (76.7 mmol) guanidine nitrate and 22.3 ml (160 mmol) triethylamine in 200 ml DMF was heated at reflux for 6 h. The reaction mixture was then cooled to room temperature. On addition of 300 ml water, a precipitate appeared which was collected by filtration and washed with water to afford 12.7 g (86%) 2-amino-4-(methylthio)-6-phenyl-pyrimidine-5-carbonitrile as a sand-coloured solid. EI-MS m-e (%): 242 (M⁺, 32), 241 ([M—H]⁺, 100).

In an analogous manner there were obtained:

Example 3
2-Amino-4-(m-methoxyphenyl)-6-(methylthio)-pyrimidine-5-carbonitrile From 3-methoxybenzoylacetonitrile with sodium hydride, carbon disulphide and methyl iodide in DMSO. Then treatment with guanidine nitrate and triethylamine in DMF. EI-MS m/e (%): 272 (M⁺, 96), 271 ([M—H]⁺, 100), 257 ([M—CH₃]⁺, 25).

Example 4
2-Amino-4-(methylthio)-6-m-tolyl-pyrimidine-5-carbonitrile

From 3-methylbenzoylacetonitrile with sodium hydride, carbon disulphide and methyl iodide in DMSO. Then treatment with guanidine nitrate and triethylamine in DMF. EI-MS m/e (%): 256 (M⁺, 74), 255 ([M—H]⁺, 100), 241 ([M—CH₃]⁺, 98).

Example 5
2-Amino-4-(p-chlorophenyl)-6-(methylthio)-pyrimidine-5-carbonitrile From 4-chlorobenzoylacetonitrile with sodium hydride, carbon disulphide and methyl iodide in DMSO. Then treatment with guanidine nitrate and triethylamine in DMF. EI-MS m/e (%): 278 (M{³⁷Cl}⁺, 14), 277 ([M{³⁷Cl}—H]⁺, 42), 276 (M{³⁵Cl} +, 46), 275 ([M{³⁵Cl}—H]+, 100), 241 ([M—Cl]⁺, 30).

Example 6
2-Amino-4-(p-methoxyphenyl)-6-(methylthio)-pyrimidine-5-carbonitrile From 4-methoxybenzoylacetonitrile with sodium hydride, carbon disulphide and methyl iodide in DMSO. Then treatment with guanidine nitrate and triethylamine in DMF. EI-MS m/e (%): 272 (M⁺, 96), 271 ([M—H]⁺, 100), 257 ([M—CH₃]⁺, ²⁵).

Example 7
2-Amino-4-(o-chlorophenl)-6-(methylthio)-pyrimidine-5-carbonitrile From 2-chlorobenzoylacetonitrile with sodium hydride, carbon disulphide and methyl iodide in DMSO. Then treatment with guanidine nitrate and triethylamine in DMF. EI-MS m/e (%): 278 (M{³⁷Cl}⁺, 12), 277 ([M{³⁷Cl}—H]⁺, 20)., 276 (M{³⁵Cl}⁺, 30), 275 ([M{³⁵Cl}—H]⁺, 38), 241 ([M—Cl]⁺, 100).

Example 8
2-Amino-4-(methylthio)-6-(2-thienyl)-pyrimidine-5-carbonitrile

From 2-thenoylacetonitrile with sodium hydride, carbon disulphide and methyl iodide in DMSO. Then treatment with guanidine nitrate and triethylamine in DMF. EI-MS m/e (%): 248 (M⁺, 42), 247 ([M—H]⁺, 100).

Example 9
2-Amino-4-(2-furyl)-6-(methylthio)-pyrimidine-5-carbonitrile

From 2-furoylacetonitrile with sodium hydride, carbon disulphide and methyl iodide in DMSO. Then treatment with guanidine nitrate and triethylamine in DMF. EI-MS m/e (%):232 (M⁺, 40), 231 ([M—H]⁺, 100).

Example 10
2-Amino-5-cyano-6-phenylpyrimidine a) 2-Benzoyl-3-dimethylaminoacrylonitrile Following the method of Toche et al. (*Org. Prep. Proc. Intl.* 1998, 39, 367), a mixture of 5.0 g (34.4 mmol) benzoylacetonitrile and 9.2 ml (69.0 mmol) N,N-dimethylformamide dimethyl acetal was stirred for 1 hour at room temperature. The reaction mixture was then concentrated in vacuo and the residue partitioned between dichloromethane and water. The organic phase was dried with sodium sulfate. Concentration in vacuo afforded 6.9 g (100%) 2-benzoyl-3-dimethylaminoacrylonitrile as a yellow oil which was used in the next step without further purification. ES-MS m/e (%):223 (M+Na⁺, 40), 201 (M+H⁺, 100).

b) 2-Amino-5-cyano-6-phenylpyrimidine

Following the method of Earley et al. (*J. Het. Chem.* 1983, 20, 1195), to a stirred solution of 6.9 g (34.4 mmol) 2-benzoyl-3-dimethylaminoacrylonitrile and 20.6 g (114 mmol) guanidine carbonate in 50 ml methanol was added 43 ml (232 mmol) sodium methylate (5.4 M in methanol) and the mixture stirred at room temperature for 2 h. The reaction mixture was then concentrated in vacuo. The residue was resuspended in ethyl acetate and water, and the aqueous phase acidified to pH 8 by addition of hydrochloric acid. The phases were separated and the aqueous phase extracted twice more with ethyl acetate. The combined organic phases were dried over sodium sulfate and concentrated in vacuo. The residue was triturated in a mixture of ethyl acetate, ether, dichloromethane and ethanol, and the resulting crystals were then additionally recrystallised from ethanol/ether to afford 2.83 g (41%) 2-amino-5-cyano-6-phenylpyrimidine as a light yellow crystalline solid. EI-MS m/e (%): 196 (M⁺, 100), 195 ([M—H]⁺, 40), 170 ([M—CN]⁺, 36).

In an analogous manner there was obtained:

Example 11
2-Amino-5-cyano-4-(3,4,5-trimethoxyphenyl)pyrimidine

From 3,4,5-trimethoxybenzoylacetonitrile and N,N-dimethylformamide dimethyl acetal. Then treatment with guanidine carbonate and sodium methylate in methanol. EI-MS m/e (%): 286 ($M^+$, 100), 271 ($[M-CH_3]^+$, 44), 243 (27), 228 (15), 213 (30), 157 (16).

Example 12
4-(4-Chloro-phenyl)-6-phenyl-pyrimidin-2-ylamine a) (E)-3-(4-Chloro-phenyl)-1-phenyl-propenone Following the method of Davey and Tivey (*J. Chem. Soc.* 1958, 1230), to a solution of 19.5 ml (167 mmol) acetophenone and 23.4 g (167 mmol) 4-chloro-benzaldehyde in 50 ml ethanol was added 6.2 ml (31 mmol) 5M sodium hydroxide solution and the reaction mixture stirred for 30 minutes at room temperature. The resulting crystals were collected by filtration and recrystallised from ethanol to afford 20.5 g (51%) (E)-3-(4-chloro-phenyl)-1-phenyl-propenone as a yellow crystalline solid, m.p. 112.4–114.1° C.

b) 4-(4-Chloro-phenyl)-6-phenyl-pyrimidin-2-ylamine

Following the method of Oluwadiya (*J. Het. Chem.* 1983, 20, 1111), a mixture of 5.0 g (20.6 mmol) (E)-3-(4-chloro-phenyl)-1-phenyl-propenone and 3.7 g (20.6 mmol) guanidine carbonate in 20 ml p-xylene was heated at reflux for 16 hours. The reaction mixture was then partitioned between ethyl acetate and water. The organic phase was dried over sodium carbonate and concentrated in vacuo. Chromatography (3% methanol in dichloromethane) afforded 2.56 g of a solid which was then recrystallised from isopropylether/ethyl acetate to afford 0.94 g (16%) 4-(4-Chloro-phenyl)-6-phenyl-pyrimidin-2-ylamine as a white solid. ES-MS m/e (%): 282 ($[M+H]^+$, 100).

Example 13
N-(5-Cyano-4-furan-2-yl-6-methylsulfanyl-pyrimidin-2-yl)-2-(2-iodo-phenyl)-acetamide To a stirred solution of 338 mg (1.29 mmol) 2-iodophenylacetic acid in 5 ml dichloromethane were added dropwise 0.19 ml (2.58 mmol) thionyl chloride and one drop of N,N-dimethylformamide and the mixtured stirred at 50° C. for 2 hours. The reaction mixture was then concentrated in vacuo, protecting from moisture as much as possible, and the residue redissolved in 5 ml dichloromethane. 65 mg (0.43 mmol) 2-Amino-4-(2-furyl)-6-(methylthio)-5-pyrimidinecarbonitrile and 0.48 ml (6.0 mmol) pyridine were added and the reaction mixture stirred at room temperature for 16 hours. The reaction mixture was then concentrated in vacuo. Chromatography (dichloromethane then 5% methanol in dichloromethane) followed by trituration in ether afforded 32 mg (24%) N-(5-Cyano-4-furan-2-yl-6-methylsulfanyl-pyrimidin-2-yl)-2-(2-iodo-phenyl)-acetamide as a white crystalline solid. EI-MS m/e (%): 476 ($M^+$, 68).

In an analogous manner there was obtained:

Example 14
N-[5-Cyano-4-(3,4,5-trimethoxy-phenyl)-pyrimidin-2-yl]-2-(2-iodo-phenyl)-acetamide From 2-iodophenylacetic acid, thionyl chloride and N,N-in dichloromethane. Then treatment with 2-amino-5-cyano-4-(3,4,5-trimethoxyphenyl)pyrimidine and pyridine in dichloromethane. ES-MS m/e (%): 553 ($M+Na^+$, 15), 531 ($M+H^+$, 100).

Analogously to Example 2 there was obtained:

Example 15
2-Amino-4-methylsulfanyl-6-(3,4,5-trimethoxy-phenyl)-pyrimidine-5-carbonitrile From 3,4,5-trimethoxybenzoylacetonitrile with sodium hydride, carbon disulphide and methyl iodide in DMSO. Then treatment with guanidine nitrate and triethylamine in DMF. EI-MS m/e (%): 332 ($M^+$, 100), 317 ($[M-CH_3]^+$, 36).

Example 16
4-Chloro-6-phenyl-pyrimidin-2-ylamine a) 2-Amino-6-phenyl-3H-pyrimidin-4-one Following the method of Jaeger (*Liebigs. Ann. Chem.* 1891, 262, 365), a mixture of 12.4 ml (72 mmol) ethyl benzoylacetate and 7.79 g (43.2 mmol) guanidine carbonate in 25 ml ethanol was heated at 80° C. for 4 h. The reaction mixture was then cooled to room temperature and the resulting crystals collected by filtration and washed sequentially with ice-cold water and ethanol to afford 7.2 g (53%) 2-amino-6-phenyl-3H-pyrimidin-4-one as a white crystalline solid. EI-MS m/e (%): 187 ($M^+$, 100).

b) 4-Chloro-6-phenyl-pyrimidin-2-ylamine

A stirred suspension of 3.69 g (19.7 mmol) 2-amino-6-phenyl-3H-pyrimidin-4-one in 4.5 ml (49.2 mmol) phosphorus oxychloride was heated at reflux for 2 h. The reaction mixture was then cooled to about 70° C. and poured cautiously onto 20 ml rapidly stirred ice-water. The mixture was briefly warmed to room temperature and then was recooled to 0° C. 100 ml 25% ammonium hydroxide solution was added and the resulting crystals were collected by filtration and washed with ice-cold water and then with a little ether to afford 3.49 g (86%) 4-chloro-6-phenyl-pyrimidin-2-ylamine as a pale yellow crystalline solid. EI-MS m/e (%): 207 ($M\{^{37}Cl\}^+$, 35), 206 ($[M\{^{37}Cl\}-H]^+$, 30)., 205 ($M\{^{35}Cl\}^+$, 100), 204 ($[M\{^{35}Cl\}-H]^+$, 56), 170 ($[M-Cl]^+$, 35), 128 (($[M-C_6H_5]^+$, 85).

Example 17
2-Amino-6-methylsulfanyl-4-phenyl-pyridine-3,5-dicarbonitrile a) 6-Amino-4-phenyl-2-thioxo-1,2-dihydro-pyridine-3,5-dicarbonitrile Following the method of Elghandour et al. (*Ind. J Chem.* 1997, B36, 79), a stirred solution of 0.66 g (10 mmol) malonitrile, 1.0 g (10 mmol) cyanothioacetamide, 1.0 ml (10 mmol) benzaldehyde and 0.1 ml (1.0 mmol) piperidine in 50 ml ethanol was heated at reflux for 1.5 hours. The reaction mixture was then poured onto ice-water and acidified to pH 3 with 1M hydrochloric acid. The resulting crystals were collected by filtration. Chromatography (ethyl acetate) afforded 0.24 g (10%) 6-amino-4-phenyl-2-thioxo-1,2-dihydro-pyridine-3,5-dicarbonitrile as a yellow crystalline solid. EI-MS m/e (%): 252 ($M^+$, 100), 251 ($[M-H]^+$, 92).

b) 2-Amino-6-methylsulfanyl-4-phenyl-pyridine-3,5-dicarbonitrile

To a stirred solution of 0.19 g (0.75 mmol) 6-amino-4-phenyl-2-thioxo-1,2-dihydro-pyridine-3,5-dicarbonitrile in 25 ml methanol were added 0.14 ml (0.76 mmol) sodium methylate solutiuon (5.4M in methanol) and 0.09 ml (1.5 mmol) methyl iodide and stirring continued for 16 hours at room temperature. The reaction mixture was then cooled to 0° C. and the resulting crystals collected by filtration and washed with ether/methanol (3/1) to afford 0.1 g (50%) 2-amino-6-methylsulfanyl-4-phenyl-pyridine-3,5-dicarbonitrile as a white crystalline solid. EI-MS m/e (%): 266 ($M^+$, 40), 265 ($[M-H]^+$, 100).

Analogously to Example 10 there was obtained:

Example 18
2-Amino-4-furan-2-yl-pyrimidine-5-carbonitrile

From 2-furoylacetonitrile and N,N-dimethylformamide dimethyl acetal. Then treatment with guanidine carbonate and sodium methylate in methanol. EI-MS m/e (%): 186 ($M^+$, 100).

Example 19

(2-Amino-5-cyano-6-phenyl-pyrimidin-4-ylsulfanyl)-acetic Acid Methyl Ester a) N-Cyano-benzenecarboximidic Acid Ethyl Ester Following the method of Huffmann and Schaefer (*J. Org. Chem.* 1963, 28, 1816), a stirred mixture of 50 ml (221 mmol) triethylorthobenzoate, 9.3 g (221 mmol) cyanamide and 42 ml (442 mmol) acetic anhydride was heated at 130–150° C. for 1.5 hours with concomitant removal of the ensuing ethyl acetate and acetic anhydride by distillation from the reaction flask. The reaction mixture was then concentrated in vacuo using a rotary evaporater. Kugelrohr distillation (120° C., 3 mbar) afforded 35.8 g (93%) N-cyano-benzenecarboximidic acid ethyl ester as a colourless oil. ES-MS m/e (%): 175 (M+H$^+$, 100).

b) 2-Amino-4-phenyl-6-thioxo-1,6-dihydro-pyrimidine-5-carbonitrile

Following the method of Pérez et al. (Synthesis 1983, 402), a stirred mixture of 14.4 g (82.4 mmol N-cyano-benzenecarboximidic acid ethyl ester, 8.25 g (82.4 mmol) 2-cyanothioacetamide and 31 ml (165 mmol) sodium methylate solution (5.4M in methanol) was heated at 130° C. for 1.5 hours. The reaction mixture was then cooled to 0° C. and 12.4 ml concentrated sulfuric acid added dropwise. The reaction mixture was concentrated in vacuo and the residue partitioned between ethyl acetate and water. The organic phase was dried over sodium sulfate and concentrated in vacuo. Chromatography (1/1 ethyl acetate/hexane) afforded 7.9 g (42%) 2-amino-4-phenyl-6-thioxo-1,6-dihydro-pyrimidine-5-carbonitrile as a yellow crystalline solid. ES-MS m/e (%): 229 (M+H$^+$, 100).

c) (2-Amino-5-cyano-6-phenyl-pyrimidin-4-ylsulfanyl)-acetic Acid Methyl Ester

Following the method of Perez et al. (Synthesis 1983, 402), to a stirred solution of 1.0 g (4.4 mmol) 2-amino-4-phenyl-6-thioxo-1,6-dihydro-pyrimidine-5-carbonitrile in 50 ml methanol were added 1.0 ml (5.4 mmol) sodium methylate solution (5.4M in methanol) and 0.39 ml (4.4 mmol) methyl chloroacetate and stirring continued for 3 hours at reflux. The reaction mixture was then concentrated in vacuo and the residue partitioned between ethyl acetate and water. The organic phase was dried over sodium sulfate and concentrated in vacuo. Chromatography (1/1 ethyl acetate/hexane) followed by trituration in 8/1 ethyl acetate/methanol afforded 0.41 g (32%) (2-Amino-5-cyano-6-phenyl-pyrimidin-4-ylsulfanyl)-acetic acid methyl ester as a light yellow crystalline solid. EI-MS m/e (%): 300 (M$^+$, 38), 299 ([M—H]$^+$, 100), 241 (74), 240 (50).

In an analogous manner there was obtained:

Example 20

(2-Amino-5-cyano-6-phenyl-pyrimidin-4-ylsulfanyl)-acetic Acid Benzyl Ester

From 2-amino-4-phenyl-6-thioxo-1,6-dihydro-pyrimidine-5-carbonitrile, benzyl chloroacetate and sodium methylate in methanol. ES-MS m/e (%): 399 (M+Na$^+$, 40), 377 (M+H$^+$, 100).

Example 21

2,5-Diamino-4-phenyl-thieno[2.3-d]pyrimidine-6-carboxylic Acid Methyl Ester

Following the method of Perez et al. (Synthesis 1983, 402), to a stirred solution of 0.27 g (0.9 mmol) (2-amino-5-cyano-6-phenyl-pyrimidin-4-ylsulfanyl)-acetic acid methyl ester in 25 ml methanol was added 0.17 ml (0.9 mmol) sodium methylate solutiuon (5.4M in methanol) and stirring continued for 16 hours at reflux. The reaction mixture was then concentrated in vacuo to ca 5 ml and the resulting crystals collected by filtration and washed with ether/methanol (10/1) to afford 0.2 g (74%) 2,5-diamino-4-phenyl-thieno[2,3-d]pyrimidine-6-carboxylic acid methyl ester as a yellow crystalline solid. ES-MS m/e (%): 301 (M+H$^+$, 100), 269 ([M+H-MeOH]$^+$, 45).

Analogously to Example 10 there was obtained:

Example 22

2-Amino-4-(2,3-dihydro-benzor[1,4]dioxin-6-yl)-pyrimidine-5-carbonitrile

From 3-(2,3-Dihydro-benzo[1,4]dioxin-6-yl)-3-oxo-propionitrile and N,N-dimethylformamide dimethyl acetal. Then treatment with guanidine carbonate and sodium methylate in methanol. EI-MS m/e (%): 254 (M$^+$, 100).

Analogously to Example 2 there was obtained:

Example 23

2-Amino-4-(2,3-dihydro-benzo[1,4]dioxin-6-yl)-6-methylsulfanyl-pyrimidine-5-carbonitrile From 3-(2,3-dihydro-benzo[1,4]dioxin-6-yl)-3-oxo-propionitrile with sodium hydride, carbon disulphide and methyl iodide in DMSO. Then treatment with guanidine nitrate and triethylamine in DMF. EI-MS m/e (%):300 (M$^+$, 100), 299 ([M—H]$^+$, 92).

Example 24

2-Amino-4-benzo[1,3]dioxol-5-yl-6-methylsulfanyl-pyrimidine-5-carbonitrile

From 3-benzo[1,3]dioxol-5-yl-3-oxo-propionitrile with sodium hydride, carbon disulphide and methyl iodide in DMSO. Then treatment with guanidine nitrate and triethylamine in DMF. EI-MS m/e (%):286 (M$^+$, 96), 285 ([M—H]$^+$, 100).

Analogously to Example 10 there was obtained:

Example 25

2-Amino-4-benzo[1,3]dioxol-5-yl-pyrimidine-5-carbonitrile

From 3-benzo[1,3]dioxol-5-yl-3-oxo-propionitrile and N,N-dimethylformamide dimethyl acetal. Then treatment with guanidine carbonate and sodium methylate in methanol. EI-MS m/e (%): 240 (M$^+$, 100), 239 ([M—H]+, 62).

Example 26

2-Amino-4-thiophen-2-yl-2-pyrimidine-5-carbonitrile

From 2-thienoylacetonitrile and N,N-dimethylformamide dimethyl acetal. Then treatment with guanidine carbonate and sodium methylate in methanol. EI-MS m/e (%): 202 (M$^+$, 100), 201 ([M—H]$^+$, 40), 161 (52).

Analogously to Example 17 there was obtained:

Example 27

2-Amino-6-methylsulfanyl-4-(3,4,5-trimethoxy-phenyl)-pyridine-3,5-dicarbonitrile From 3,4,5-trimethoxybenzaldehyde, malonitrile, cyanothioacetamide and piperidine in EtOH. Then treatment with methyl iodide and sodium methylate in methanol. EI-MS m/e (%): 356 (M$^+$, 100).

Analogously to Example 19 there was obtained:

Example 28

2-Amino-4-ethylsulfanyl-6-phenyl-pyrimidine-5-carbonitrile

From 2-amino-4-phenyl-6-thioxo-1,6-dihydro-pyrimidine-5-carbonitrile, ethyl bromide and sodium ethylate in ethanol. EI-MS m/e (%):256 (M$^+$, 29), 255 ([M—H]$^+$, 100).

Example 29
2-Amino-4-benzylsulfanyl-6-phenyl-pyrimidine-5-carbonitrile

From 2-amino-4-phenyl-6-thioxo-1,6-dihydro-pyrimidine-5-carbonitrile, benzyl bromide and sodium ethylate in ethanol. EI-MS m/e (%):318 ($M^+$, 50), 317 ([M—H]$^+$, 100), 285 (20), 91 (84).

Example 30
2-Amino-4-ethoxy-6-phenyl-pyrimidine-5-carbonitrile

To a stirred solution of 0.2 g (0.86 mmol) 2-amino-4-(methylthio)-6-phenyl-5-pyrimidinecarbonitrile in 10 ml ethanol was added 0.33 ml (0.89 mmol) sodium ethylate solution (2.7M in ethanol) and the mixture heated at reflux for 2 h. The reaction mixture was then concentrated in vacuo. The residue was partitioned between water and dichloromethane and the organic phase dried over sodium sulfate and concentrated in vacuo. Chromatography (ethyl acetate/hexane 1/1) afforded 60 mg (29%) 2-amino-4-ethoxy-6-phenyl-pyrimidine-5-carbonitrile as a white crystalline solid. MS m/e (%):240 ($M^+$, 100), 239 ([M—H]$^+$, 50), 170 (56).

Analogously to Example 19 there was obtained:

Example 31
2-Amino-4-(2-methoxy-ethylsulfanyl)-6-phenyl-pyrimidine-5-carbonitrile From 2-amino-4-phenyl-6-thioxo-1,6-dihydro-pyrimidine-5-carbonitrile, 2-methoxyethyl bromide and sodium ethylate in ethanol. EI-MS m/e (%): 286 ($M^+$, 6), 228 ([M—MeOCH=CH$_2$]$^+$, 100).

Example 32
2-Amino-4-butylsulfanyl-6-phenyl-pyrimidine-5-carbonitrile

From 2-amino-4-phenyl-6-thioxo-1,6-dihydro-pyrimidine-5-carbonitrile, butyl bromide and sodium ethylate in ethanol. EI-MS m/e (%): 284 ($M^+$, 48), 283 ([M—H]$^+$, 100), 241 (([M—C$_3$H$_7$]$^+$, 95), 228 (([M—C$_2$H$_5$CH=CH$_2$]$^+$, 92).

Example 33
2-Amino-4-cyclopentylsulfanyl-6-phenyl-pyrimidine-5-carbonitrile

From 2-amino-4-phenyl-6-thioxo-1,6-dihydro-pyrimidine-5-carbonitrile, cyclopentyl bromide and sodium ethylate in ethanol. EI-MS m/e (%): 296 ($M^+$, 36), 295 ([M—H]$^+$, 100), 228 ([M—C$_5$H$_8$]$^+$, 100).

Example 34
2-Amino-4-isopropylsulfanyl-6-phenyl-pyrimidine-5-carbonitrile

From 2-amino-4-phenyl-6-thioxo-1,6-dihydro-pyrimidine-5-carbonitrile, isopropyl bromide and sodium ethylate in ethanol. EI-MS m/e (%): 270 ($M^+$, 30), 269 ([M—H]$^+$, 100).

Example 35
2-Amino-4-chloro-6-phenyl-pyrimidine-5-carbonitrile
a) 2-Amino-6-oxo-4-phenyl-16-dihydro-pyrimidine-5-carbonitrile Following the method of Pérez et al. (*Synthesis* 1983, 402), a stirred mixture of 19.0 g (109 mmol N-cyano-benzenecarboximidic acid ethyl ester, 9.2 g (109 mmol) 2-cyano-acetamide and 40 ml (216 mmol) sodium methylate solution (5.4M in methanol) was heated at reflux for 2 hours. The reaction mixture was then cooled to 0° C. and 16.4 ml concentrated sulfuric acid added dropwise. The resulting crystals were collected by filtration and washed with water to afford 22.3 g (96%) 2-amino-6-oxo-4-phenyl-1,6-dihydro-pyrimidine-5-carbonitrile as a yellow crystalline solid. EI-MS m/e (%): 212 ($M^+$, 100), 170 ([M—NCO]$^+$, 95).

b) 2-Amino-4-chloro-6-phenyl-1yrimidine-5-carbonitrile

Following the method of Hull (*J. Chem. Soc.* 1957, 4845), a stirred suspension of 25.2 g (119 mmol) 2-amino-6-oxo-4-phenyl-1,6-dihydro-pyrimidine-5-carbonitrile in 27.1 ml (297 mmol) phosphorus oxychloride was heated at reflux for 2 h. The reaction mixture was then cooled to about 70° C. and poured cautiously onto rapidly stirred ice-water such that the temperature remained around 10° C. The resulting crystals were collected by filtration to afford 12.0 g (44%) 2-amino-4-chloro-6-phenyl-pyrimidine-5-carbonitrile as a light beige crystalline solid. This material was pure enough to be used in subsequent steps, however analytically pure material was obtained by chromatography (ethyl acetate/hexane 1/1) which afforded 5.9 g (22%) 2-amino-4-chloro-6-phenyl-pyrimidine-5-carbonitrile as a light yellow crystalline solid. EI-MS m/e (%): 232 (M$\{^{37}$Cl$\}^+$, 26), 230 (M$\{^{35}$Cl$\}^+$, 80), 190 ([M—Cl]$^+$, 100), 153 (38).

Example 36
2-Amino-4-methoxy-6-phenyl-pyrimidine-5-carbonitrile

To a stirred solution of 200 mg (0.87 mmol) 2-amino-4-chloro-6-phenyl-pyrimidine-5-carbonitrile in 5 ml methanol was added 0.4 ml (2.16 mmol) sodium methylate solution (5.4 M in methanol) and the mixture heated at reflux for 16 h. The reaction mixture was then concentrated in vacuo and the residue partitioned between ethyl acetate and water. The organic phase was dried over sodium sulfate and concentrated in vacuo to afford 130 mg (66%) 2-amino-4-methoxy-6-phenyl-pyrimidine-5-carbonitrile as a light yellow crystalline solid. ES-MS m/e (%): 227 (M+H$^+$, 100).

Analogously to Example 30 there were obtained:

Example 37
2-Amino-4-furan-2-yl-6-methoxy-pyrimidine-5-carbonitrile

From 2-amino-4-(2-furyl)-6-(methylthio)-5-pyrimidinecarbonitrile and sodium methylate in methanol. EI-MS m/e (%): 216 ($M^+$, 100), 215 ([M—H]$^+$, 36).

Example 38
2-Amino-4-ethoxy-6-furan-2-yl-pyrimidine-5-carbonitrile

From 2-amino-4-(2-furyl)-6-(methylthio)-5-pyrimidinecarbonitrile and sodium ethylate in ethanol. Anal. found C 57.39%, H 4.38%, N 24.34%. C$_{11}$H$_{10}$N$_4$O$_2$ requires C 57.43%, H 4.47%, N 24.42%.

Example 39
2-Amino-4-furan-2-yl-6-methylamino-pyrimidine-5-carbonitrile

A stirred solution of 200 mg (0.87 mmol) 2-amino-4-(2-furyl)-6-(methylthio)-5-pyrimidinecarbonitrile and 5.0 ml (129 mmol) methylamine in 15 ml ethanol in a pressure tube was heated at 100° C. for 16 h. The reaction mixture was then concentrated in vacuo and the resulting crystals washed with ether and ether/ethanol to afford 130 mg (75%) 2-amino-4-furan-2-yl-6-methylamino-pyrimidine-5-carbonitrile as a white crystalline solid. EI-MS m/e (%): 215 ($M^+$, 100), 214 ([M—H]$^+$, 76), 186 (40).

In an analogous manner there was obtained:

Example 40
2-Amino-4-dimethylamino-6-furan-2-yl-pyrimidine-5-carbonitrile

From 2-amino-4-(2-furyl)-6-(methylthio)-5-pyrimidinecarbonitrile and dimethylamine in ethanol.

EI-MS m/e (%): 229 (M$^+$, 49), 228 ([M—H]$^+$, 100), 214 (3)8), 200 (48), 44 (44).

Example 41
2-Amino-4-furan-2-yl-6-piperidin-1-yl-pyrimidine-5-carbonitrile

From 2-amino-4-(2-furyl)-6-(methylthio)-5-pyrimidinecarbonitrile and piperidine in ethanol. EI-MS m/e (%): 269 (M$^+$, 36), 268 ([M—H]$^+$, 100), 240 (38).

Example 42
2-Amino-4-benzylamino-6-furan-2-yl-pyrimidine-5-carbonitrile

From 2-amino-4-(2-furyl)-6-(methylthio)-5-pyrimidinecarbonitrile and benzylamine in ethanol. EI-MS m/e (%): 291 (M$^+$, 100), 290 ([M—H]$^+$, 36), 106 (64), 91 (48).

Example 43
2-Amino-4-furan-2-yl-6-phenethylamino-pyrimidine-5-carbonitrile

From 2-amino-4-(2-furyl)-6-(methylthio)-5-pyrimidinecarbonitrile and phenylethylamine in ethanol. ES-MS m/e (%): 306 (M+H$^+$, 100).

Example 44
2-Amino-4-furan-2-yl-6-(3-phenyl-propylamino)-pyrimidine-5-carbonitrile From 2-amino-4-(2-furyl)-6-(methylthio)-5-pyrimidinecarbonitrile and phenylpropylamine in ethanol. ES-MS m/e (%): 320 (M+H$^+$, 100).

Example 45
2-Amino-4-furan-2-yl-6-morpholin-4-yl-pyrimidine-5-carbonitrile

From 2-amino-4-(2-furyl)-6-(methylthio)-5-pyrimidinecarbonitrile and morpholine in ethanol. EI-MS m/e (%): 271 (M$^+$, 50), 270 ([M—H]$^+$, 100), 240 (28), 214 (48), 213 (35), 186 (40).

Example 46
2-Amino-4-cyclohexylamino-6-furan-2-yl-pyrimidine-5-carbonitrile

From 2-amino-4-(2-furyl)-6-(methylthio)-5-pyrimidinecarbonitrile and cyclohexylamine in ethanol. EI-MS m/e (%): 283 (M$^+$, 22), 282 ([M—H]$^+$, 20), 240 ([M—C$_2$H$_5$]$^+$, 16), 226 ([M—C$_4$H$_9$]$^+$, 36), 201 ([M—C$_6$H$_{10}$]$^+$, 100).

Example 47
2-Amino-4-benzyloxy-6-furan-2-yl-pyrimidine-5-carbonitrile a) 2-Amino-4-furan-2-yl-6-methanesulfonyl-pyrimidine-5-carbonitrile To a cooled (0° C.) stirred suspension of 1.0 g (4.3 mmol) 2-amino-4-(2-furyl)-6-(methylthio)-5-pyrimidinecarbonitrile in 43 ml dichloromethane was added 4.25 g (17.2 mmol) m-chloroperbenzoic acid (70% purity) and stirring continued for 2 hours at 0° C. and 16 hours at room temperature. The reaction mixture was then concentrated in vacuo and the resulting crystals washed with 21 ml ethanol to afford 0.76 g (67%) 2-amino-4-furan-2-yl-6-methanesulfonyl-pyrimidine-5-carbonitrile as a light yellow crystalline solid. ES-MS m/e (%): 282 (M+NH$_4$$^{+, 100}$), 265 (M+H$^+$, 100).

b) 2-Amino-4-benzyloxy-6-furan-2-yl-pyrimidine-5-carbonitrile

To a stirred suspension of 300 mg (1.14 mmol) 2-amino-4-furan-2-yl-6-methanesulfonyl-pyrimidine-5-carbonitrile in 9 ml dimethoxyethane were added 0.41 ml (4.0 mmol) benzyl alcohol and 0.25 ml (1.7 mmol) DBU and the mixture heated at 100° C. for 1 hour. The reaction mixture was then concentrated in vacuo. Chromatography (ethyl acetate/hexane 2/1) followed by trituration in ether/hexane afforded 185 mg (56%) 2-amino-4-benzyloxy-6-furan-2-yl-pyrimidine-5-carbonitrile as a white crystalline solid. EI-MS m/e (%): 292 (M$^+$, 40), 91 (C$_7$H$_7$$^+$, 100).

In an analogous manner there was obtained:

Example 48
2-Amino-4-furan-2-yl-6-phenylsulfanyl-pyrimidine-5-carbonitrile

From 2-amino-4-furan-2-yl-6-methanesulfonyl-pyrimidine-5-carbonitrile, thiophenol and DBU in DME. ES-MS m/e (%): 295 (M+H$^+$, 100).

Analogously to Example 39 there was obtained:

Example 49
2-Amino-4-furan-2-yl-6-propylamino-pyrimidine-5-carbonitrile

From 2-amino-4-(2-furyl)-6-(methylthio)-5-pyrimidinecarbonitrile and propylamine in ethanol. EI-MS m/e (%). 243 (M$^+$, 44), 242 ([M—H]$^+$, 28), 228 ([M—CH$_3$]$^+$, 16), 214 ([M—C$_2$H$_5$]$^+$, 100), 201 ([M—C$_3$H$_6$]$^+$, 70).

Example 50
2-Amino-4-furan-2-yl-6-(2-morpholin-4-yl-ethylamino)-]yrimidine-5-carbonitrile From 2-amino-4-(2-furyl)-6-(methylthio)-5-pyrimidinecarbonitrile and 4-(2-aminoethyl)morpholine in ethanol. ES-MS m/e (%): 315 (M+H$^+$, 100).

Analogously to Example 47 there were obtained:

Example 51
2-Amino-4-furan-2-yl-6-phenoxy-pyrimidine-5-carbonitrile

From 2-amino-4-furan-2-yl-6-methanesulfonyl-pyrimidine-5-carbonitrile, phenol and DBU in DME. EI-MS m/e (%): 278 (M$^+$, 100), 277 ([M—H]$^+$, 22), 250 (68), 249 (89).

Example 52
2-Amino-4-benzylsulfanyl-6-furan-2-yl-pyrimidine-5-carbonitrile

From 2-amino-4-furan-2-yl-6-methanesulfonyl-pyrimidine-5-carbonitrile, benzyl mercaptan and DBU in DME. EI-MS m/e (%): 308 (M$^+$, 68), 307 ([M—H]$^+$, 48), 275 (24), 91 (100).

Example 53
2-Amino-4-furan-2-yl-6-phenethyloxy-pyrimidine-5-carbonitrile

From 2-amino-4-furan-2-yl-6-methanesulfonyl-pyrimidine-5-carbonitrile, phenethyl alcohol and DBU in DME. EI-MS m/e (%): 306 (M$^+$, 4), 202 ([M—C$_6$H$_5$CH=CH$_2$]$^+$, 48), 104 (21).

Example 54
2-Amino-4-furan-2-yl-6-(3-phenyl-propoxy)-pyrimidine-5-carbonitrile From 2-amino-4-furan-2-yl-6-methanesulfonyl-pyrimidine-5-carbonitrile, 3-phenyl-1-propanol and DBU in DME. ES-MS m/e (%): 359 (M+K$^+$, 20), 343 (M+Na+, 21), 321 (M+H$^+$, 100).

Example 55
2-Amino-4-cyclohexyloxy-6-furan-2-yl-pyrimidine-5-carbonitrile

From 2-amino-4-furan-2-yl-6-methanesulfonyl-pyrimidine-5-carbonitrile, cyclohexanol and DBU in DME. ES-MS m/e (%): 285 (M+H$^+$, 75), 203 ([M—C$_6$H$_{10}$]$^+$, 100).

Example 56
2-Amino-4-furan-2-yl-6-(2-molpholin-4-yl-ethoxy)-pyrimidine-5-carbonitrile From 2-amino-4-furan-2-yl-6-methanesulfonyl-pyrimidine-5-carbonitrile, N-(2-hydroxyethyl)-morpholine and DBU in DME. ES-MS m/e (%): 338 (M+Na$^+$, 16), 316 (M+H$^+$, 100).

Example 57
2-Amino-4-furan-2-yl-6-(2-methoxy-ethoxy)-pyrimidine-5-carbonitrile From 2-amino-4-furan-2-yl-6-methanesulfonyl-pyrimidine-5-carbonitrile, 2-methoxyethanol and DBU in DME. ES-MS m/e (%): 283 (M+Na$^+$, 15), 261 (M+H$^+$, 100).

Example 58
2-Amino-4-furan-2-yl-6-[2-(4-hydroxy-phenyl)-ethylamino]-pyrimidine-5-carbonitrile From 2-amino-4-furan-2-yl-6-methanesulfonyl-pyrimidine-5-carbonitrile and tyramine in DME. ES-MS m/e (%): 322 (M+H$^+$, 100).

Example 59
2-Amino-4-(benzyl-methyl-amino)-6-furan-2-yl-pyrimidine-5-carbonitrile From 2-amino-4-furan-2-yl-6-methanesulfonyl-pyrimidine-5-carbonitrile and N-benzylmethylamine in DME. EI-MS m/e (%): 305 (M$^+$, 44), 304 ([M—H]$^+$, 48), 291 (56), 290 (100), 214 (36), 120 (50), 106 (36), 91 (82), 65 (24).

Example 60
2-Amino-4-butylsulfanyl-6-furan-2-yl-pyrimidine-5-carbonitrile

From 2-amino-4-furan-2-yl-6-methanesulfonyl-pyrimidine-5-carbonitrile, butylmercaptan and DBU in DME. ES-MS m/e (%): 275 (M+H$^+$, 100).

Example 61
2-Amino-4-furan-2-yl-6-isopropoxy-pyrimidine-5-carbonitrile

From 2-amino-4-furan-2-yl-6-methanesulfonyl-pyrimidine-5-carbonitrile, isopropyl alcohol and DBU in DME. EI-MS m/e (%): 244 (M$^+$, 40), 202 ([M—C$_3$H$_6$]$^+$, 100).

Example 62
2-Amino-4-butoxy-6-furan-2-yl-pyrimidine-5-carbonitrile

From 2-amino-4-furan-2-yl-6-methanesulfonyl-pyrimidine-5-carbonitrile, butanol and DBU in DME. EI-MS m/e (%): 258 (M$^+$, 20), 202 ([M—C$_4$H$_8$]$^+$, 100).

Example 63
2-Amino-4-furan-2-yl-6-(4-phenyl-butoxy)-pyrimidine-5-carbonitrile From 2-amino-4-furan-2-yl-6-methanesulfonyl-pyrimidine-5-carbonitrile, 4-phenyl-1-butanol and DBU in DME. ES-MS m/e (%): 357 (M+Na$^+$, 20), 335 (M+H$^+$, 100).

Example 64
2-Amino-4-furan-2-yl-6-(4-phenyl-butylamino)-pyrimidine-5-carbonitrile From 2-amino-4-furan-2-yl-6-methanesulfonyl-pyrimidine-5-carbonitrile and 4-phenylbutylamine in DME. ES-MS m/e (%): 334 (M+H$^+$, 100).

Analogously to Example 39 there was obtained:

Example 65
2-Amino-4-benzylamino-6-phenyl-pyrimidine-5-carbonitrile

From 2-Amino-4-(methylthio)-6-phenyl-pyrimidine-5-carbonitrile and benzylamine in ethanol. ES-MS m/e (%): 302 (M+H$^+$, 100).

Example 66
2-Amino-4-benzo[1,3]dioxol-5-yl-6-benzylamino-pyrimidine-5-carbonitrile From 2-Amino-4-benzo[1,3]dioxol-5-yl-6-methylsulfanyl-pyrimidine-5-carbonitrile and benzylamine in ethanol. ES-MS m/e (%): 346 (M+H$^+$, 100).

Analogously to Example 47 there was obtained:

Example 67
2-Amino-4-furan-2-yl-6-(2-methoxy-ethylamino)-pyrimidine-5-carbonitrile From 2-amino-4-furan-2-yl-6-methanesulfonyl-pyrimidine-5-carbonitrile and 2-methoxyethylamine in DME. EI-MS m/e (%): 259 (M$^+$, 15), 214 ([M—MeOCH$_2$]$^+$, 100), 201 ([M—MeOCH=CH$_2$]$^+$, 78).

Example 68
2-Amino-4-(2-dimethylamino-ethylamino)-6-furan-2-yl-pyrimidine-5-carbonitrile From 2-amino-4-furan-2-yl-6-methanesulfonyl-pyrimidine-5-carbonitrile and 2-dimethylaminoethylamine in DME. ES-MS m/e (%): 273 (M+H$^+$, 100), 228 ([M—Me$_2$NH]$^+$, 80).

Example 69
2-Amino-4-(2-dimethylamino-ethoxy)-6-furan-2-yl-pyrimidine-5-carbonitrile From 2-amino-4-furan-2-yl-6-methanesulfonyl-pyrimidine-5-carbonitrile, 2-dimethylaminoethanol and DBU in DME. ES-MS m/e (%): 274 (M+H$^+$, 100).

Example 70
2-Amino-4-furan-2-yl-6-(2-piperidin-1-yl-ethoxy)-pyrimidine-5-carbonitrile From 2-amino-4-furan-2-yl-6-methanesulfonyl-pyrimidine-5-carbonitrile, hydroxyethylpiperidine and DBU in DME. ES-MS m/e (%:314 (M+H$^+$, 100).

Example 71
2-Amino-4-phenyl-6-(3-phenyl-propylamino)-pyrimidine-5-carbonitrile From 2-amino-4-methanesulfonyl-6-phenyl-pyrimidine-5-carbonitrile and 3-phenylpropylamine in DME. ES-MS m/e (%): 330 (M+H$^+$, 100).

Example 72
2-Amino-4-phenethylamino-6-phenyl-pyrimidine-5-carbonitrile

From 2-amino-4-methanesulfonyl-6-phenyl-pyrimidine-5-carbonitrile and 2-phenylethylamine in DME. ES-MS m/e (%): 316 (M+H$^+$, 100).

Example 73
2-Amino-4-phenyl-6-propylamino-pyrimidine-5-carbonitrile

From 2-amino-4-methanesulfonyl-6-phenyl-pyrimidine-5-carbonitrile and propylamine in DME. ES-MS m/e (%): 254 (M+H$^+$, 100).

Example 74
2-Amino-4-furan-2-yl-6-(2-pyridin-2-yl-ethylamino)-pyrimidine-5-carbonitrile From 2-amino-4-furan-2-yl-6-methanesulfonyl-pyrimidine-5-carbonitrile and 2-(2-aminoethyl)pyridine in DME. EI-MS m/e (%): 306 ($M^+$, 80), 93 (100).

Example 75
2-Amino-4-ethylsulfanyl-6-furan-2-yl-pyrimidine-5-carbonitrile

From 2-amino-4-furan-2-yl-6-methanesulfonyl-pyrimidine-5-carbonitrile, ethanethiol and DBU in DME. EI-MS m/e (%): 246 ($M^+$, 49), 245 ($[M-H]^+$, 100).

Example 76
2-Amino-4-furan-2-yl-6-(pyridin-2-ylmethoxy)-pyrimidine-5-carbonitrile From 2-amino-4-furan-2-yl-6-methanesulfonyl-pyrimidine-5-carbonitrile, 2-(hydroxymethyl)pyridine and DBU in DME. ES-MS m/e (%): 294 ($M+H^+$, 100).

Example 77
2-Amino-4-ethylamino-6-furan-2-yl-pyrimidine-5-carbonitrile

From 2-amino-4-furan-2-yl-6-methanesulfonyl-pyrimidine-5-carbonitrile and ethylamine in DME. EI-MS m/e (%): 229 ($M^+$, 100), 228 ($[M-H]^+$, 76), 214 ($[M-CH_3]^+$, 84), 201 (50), 44 (61).

Example 78
2-Amino-4-furan-2-yl-6-(2-piperidin-1-yl-ethylamino)-pyrimidine-5-carbonitrile From 2-amino-4-furan-2-yl-6-methanesulfonyl-pyrimidine-5-carbonitrile and 1,2-(aminoethyl)piperidine in DME. ES-MS m/e (%): 313 ($M+H^+$, 100).

Example 79
2-Amino-4-butylamino-6-furan-2-yl-pyrimidine-5-carbonitrile

From 2-amino-4-furan-2-yl-6-methanesulfonyl-pyrimidine-5-carbonitrile and butylamine in DME. ES-MS m/e (%): 258 ($M+H^+$, 100).

Example 80
2-Amino-4-(2-morpholin-4-yl-ethylamino)-6-phenyl-pyrimidine-5-carbonitrile From 2-amino-4-furan-2-yl-6-methanesulfonyl-pyrimidine-5-carbonitrile and 4-(2-aminoethyl)morpholine in DME. ES-MS m/e (%): 325 ($M+H^+$, 100).

Example 81
2-Amino-4-phenyl-6-piperidin-1-yl-pyrimidine-5-carbonitrile

From 2-amino-4-methanesulfonyl-6-phenyl-pyrimidine-5-carbonitrile and piperidine in DME. EI-MS m/e (%): 279 ($M^+$, 32), 278 ($[M-H]^+$, 100).

Example 82
2-Amino-4-morpholin-4-yl-6-phenyl-pyrimidine-5-carbonitrile

From 2-amino-4-methanesulfonyl-6-phenyl-pyrimidine-5-carbonitrile and morpholine in DME. EI-MS m/e (%): 281 ($M^+$, 38), 280 ($[M-H]^+$, 100).

Analogously to Example 19 there was obtained:

Example 83
2-Amino-4-phenethylsulfanyl-6-phenyl-pyrimidine-5-carbonitrile

From 2-amino-4-phenyl-6-thioxo-1,6-dihydro-pyrimidine-5-carbonitrile, phenethyl bromide and sodium ethylate in ethanol. ES-MS m/e (%): 333 ($M+H^+$, 100).

Analogously to Example 47 there was obtained:

Example 84
2-Amino-4-furan-2-yl-6-(4-methyl-piperazin-1-yl)-pyrimidine-5-carbonitrile From 2-amino-4-furan-2-yl-6-methanesulfonyl-pyrimidine-5-carbonitrile N-methylpiperazine in DME. ES-MS m/e (%): 2859 ($M+H^+$, 100), 228 (35).

Analogously to Example 19 there was obtained:

Example 85
2-Amino-4-phenyl-6-(3-phenyl-propylsulfanyl)-pyrimidine-5-carbonitrile From 2-amino-4-phenyl-6-thioxo-1,6-dihydro-pyrimidine-5-carbonitrile, 3-phenylpropyl bromide and sodium ethylate in ethanol. ES-MS m/e (%): 347 ($M+H^+$, 100).

Analogously to Example 47 there was obtained:

Example 86
2-Amino-4-[2-(4-hydroxy-phenyl)-ethylamino]-6-phenyl-pyrimidine-5-carbonitrile From 2-amino-4-methanesulfonyl-6-phenyl-pyrimidine-5-carbonitrile and tyramine in DME. ES-MS m/e (%): 332 ($M+H^+$, 100).

Example 87
2-Amino-4-phenoxy-6-phenyl--pyrimidine-5-carbonitrile

From 2-amino-4-chloro-6-phenyl-pyrimidine-5-carbonitrile, phenol and DBU in DME. EI-MS m/e (%): 288 ($M^+$, 100), 287 ($[M-H]^+$, 60).

Example 88
2-Amino-4-benzo[1,3]dioxol-5-yl-6-[2-(4-hydroxy-phenyl)-ethylamino]-pyrimidine-5-carbonitrile From 2-amino-4-benzo[1,3]dioxol-5-yl-6-methanesulfonyl-pyrimidine-5-carbonitrile and tyramine in DME. ES-MS m/e (%): 376 ($M+H^+$, 100).

Example 89
2-Amino-4-benzyloxy-6-phenyl-pyrimidine-5-carbonitrile

From 2-amino-4-chloro-6-phenyl-pyrimidine-5-carbonitrile, benzyl alcohol and DBU in DME. EI-MS m/e (%): 303 ($M+H^+$, 100).

Example 90
2-Amino-4-phenoxy-6-(3,4,5-trimethoxy-phenyl)-pyrimidine-5-carbonitrile From 2-amino-4-methanesulfonyl-6-(3,4,5-trimethoxy-phenyl)-pyrimidine-5-carbonitrile, phenol and DBU in DME. ES-MS m/e (%): 379 ($M+H^+$, 100).

Example 91
2-Amino-4-benzo[1,3]dioxol-5-yl-6-phenoxy-pyrimidine-5-carbonitrile From 2-amino-4-benzo[1,3]dioxol-5-yl-6-methanesulfonyl-pyrimidine-5-carbonitrile, phenol and DBU in DME. ES-MS m/e (%): 333 ($M+H^+$, 100).

Example 92
2-Amino-4-benzo[1,3]dioxol-5-yl-6-phenethylamino-pyrimidine-5-carbonitrile From 2-amino-4-benzo[1,3]dioxol-5-yl-6-methanesulfonyl-pyrimidine-5-carbonitrile and phenethylamine in DME. ES-MS m/e (%): 360 ($M+H^+$, 100).

Example 93
2-Amino-4-benzo[1,3]dioxol-5-yl-6-(3-phenylpropylamino)-pyrimidine-5-carbonitrile From 2-amino-4-benzo[1,3]dioxol-5-yl-6-methanesulfonyl-pyrimidine-5-carbonitrile and 3-phenylpropylamine in DME. ES-MS m/e (%): 374 (M+H$^+$, 100).

Example 94
2-Amino-6-furan-2-yl-pyrimidine-4,5-dicarbonitrile

To a stirred suspension of 218 mg (0.83 mmol) 2-amino-4-furan-2-yl-6-methanesulfonyl-pyrimidine-5-carbonitrile in 10 ml dichloromethane was added 193 mg (1.24 mmol) tetraethylammonium cyanide and stirring continued for 2 hours at room temperature. The reaction mixture was then concentrated in vacuo. Chromatography (ethyl acetate) afforded 17 mg (10%) 2-amino-6-furan-2-yl-pyrimidine-4,5-dicarbonitrile as a pale pink crystalline solid. EI-MS m/e (%): 211 (M$^+$, 100).

Analogously to Example 47 there was obtained:

Example 95
2-Amino-4-phenyl-6-phenylsulfanyl-pyrimidine-5-carbonitrile

From 2-amino-4-methanesulfonyl-6-phenyl-pyrimidine-5-carbonitrile, thiophenol and DBU in DME. EI-MS m/e (%): 304 (M$^+$, 76), 303 ([M—H]$^+$, 100).

Example 96
2-Amino-4-benzo[1,3]dioxol-5-yl-6-phenylsulfanyl-pyrimidine-5-carbonitrile From 2-amino-4-benzo[1,3]dioxol-5-yl-6-methanesulfonyl-pyrimidine-5-carbonitrile, thiophenol and DBU in DME. EI-MS m/e (%): 348 (M$^+$, 96), 347 ([M—H]$^+$, 100).

Analogously to Example 94 there was obtained:

Example 97
2-Amino-6-phenyl-pyrimidine-4,5-dicarbonitrile

From 2-amino-4-chloro-6-phenyl-pyrimidine-5-carbonitrile and tetraethylammonium cyanide in dichloromethane. EI-MS m/e (%): 221 (M$^+$, 1090), 220 ([M—H]$^+$, 40).

Analogously to Example 47 there were obtained:

Example 98
2-Amino-4-(2-methoxy-ethoxy)-6-phenyl-pyrimidine-5-carbonitrile

From 2-amino-4-chloro-6-phenyl-pyrimidine-5-carbonitrile, 2-methoxyethanol and DBU in DME. ES-MS m/e (%): 271 (M+H$^+$, 100).

Example 99
2-Amino-4-cyclohexyloxy-6-phenyl-pyrimidine-5-carbonitrile

From 2-amino-4-chloro-6-phenyl-pyrimidine-5-carbonitrile, cyclohexanol and DBU in DME. EI-MS m/e (%): 294 (M$^+$, 12), 213 ([M—C$_6$H$_9$]$^+$, 100), 212 ([M—C$_6$H$_{10}$]$^+$, 48), 170 (60).

Example 100
2-Amino-4-isopropoxy-6-phenyl-pyrimidine-5-carbonitrile

From 2-amino-4-chloro-6-phenyl-pyrimidine-5-carbonitrile, isopropanol and DBU in DME. EI-MS m/e (%): 254 (M$^+$, 41), 212 ([M—C$_3$H$_6$]$^+$, 55), 184 (35), 170 (100).

Example 101
2-Amino-4-benzo[1,3]dioxol-5-yl-6-(2-morpholin-4-yl-ethylamino)-pyrimidine-5-carbonitrile From 2-amino-4-benzo[1,3]dioxol-5-yl-6-methanesulfonyl-pyrimidine-5-carbonitrile and 4-(2-aminoethyl)morpholine in DME. ES-MS m/e (%): 369 (M+H$^+$, 100), 282 ([M+H—C$_4$H$_9$NO]$^+$, 75).

Example 102
2-Amino-4-(2-methoxy-ethoxy)-6-(3,4,5-trimethoxyphenyl)-pyrimidine-5-carbonitrile From 2-amino-4-methanesulfonyl-6-(3,4,5-trimethoxyphenyl)-pyrimidine-5-carbonitrile, 2-methoxyethanol and DBU in DME. EI-MS m/e (%): 360 (M$^+$, 100), 302 (36), 287 (28), 259 (32), 43 (42).

Example 103
2-Amino-4-benzo[1,3]dioxol-5-yl-6-(2-methoxy-ethoxy)-pyrimidine-5-carbonitrile From 2-amino-4-benzo[1,3]dioxol-5-yl-6-methanesulfonyl-pyrimidine-5-carbonitrile, 2-methoxyethanol and DBU in DME. EI-MS m/e (%): 314 (M$^+$, 54), 256 ([M—MeOCH=CH$_2$]$^+$, 100), 214 (59).

Example 104
2-Amino-4-phenethyloxy-6-phenyl-pyrimidine-5-carbonitrile

From 2-amino-4-chloro-6-phenyl-pyrimidine-5-carbonitrile, 2-phenylethanol and DBU in DME. EI-MS m/e (%): 316 (M$^+$, 4), 212 ([M—PhCH=CH$_2$]$^+$, 100), 184 (28), 170 (20), 104 ([PhCH=CH$_2$]$^+$, 84), 77 (20).

Example 105
2-Amino-4-phenyl-6-(pyridin-2-ylmethoxy)-pyrimidine-5-carbonitrile From 2-amino-4-chloro-6-phenyl-pyrimidine-5-carbonitrile, 2-(hydroxymethyl)pyridine and DBU in DME. EI-MS m/e (%): 303 (M$^+$, 52), 302 ([M—H]$^+$, 74), 286 (30), 108 (100), 92 (63), 65 (52).

Example 106
2-Amino-4-benzyloxy-6-(3,4,5-trimethoxy-phenyl)-pyrimidine-5-carbonitrile From 2-amino-4-methanesulfonyl-6-(3,4,5-trimethoxyphenyl)-pyrimidine-5-carbonitrile, benzyl alcohol and DBU in DME. EI-MS m/e (%): 392 (M$^+$, 40), 91 ([PhCH$_2$]$^+$, 100).

Example 107
2-Amino-4-benzo[1,3]dioxol-5-yl-6-benzyloxy-pyrimidine-5-carbonitrile From 2-amino-4-benzo[1,3]dioxol-5-yl-6-methanesulfonyl-pyrimidine-5-carbonitrile, benzyl alcohol and DBU in DME. EI-MS m/e (%): 346 (M$^+$, 32), 91 ([PhCH$_2$]$^+$, 100).

Example 108
2-Amino-4-benzo[1,3]dioxol-5-yl-6-ethoxy-pyrimidine-5-carbonitrile From 2-amino-4-benzo[1,3]dioxol-5-yl-6-methanesulfonyl-pyrimidine-5-carbonitrile, ethanol and DBU in DMB. EI-MS rn/e 2%) 284 (M$^+$, 100), 214 (32).

Example 109
2-Amino-4-benzylsulfanyl-6-(3,4,5-trimethoxy-phenyl)-pyrimidine-5-carbonitrile From 2-amino-4-methanesulfonyl-6-(3,4,5-trimethoxyphenyl)-pyrimidine-5-carbonitrile, benzyl mercaptan and DBU in DME. ES-MS m/e (%): 409 (M+H$^+$, 100).

Example 110
2-Amino-4-benzo[1,3]dioxol-5-yl-6-benzylsulfanyl-pyrimidine-5-carbonitrile From 2-amino-4-benzo[1,3]dioxol-5-yl-6-methanesulfonyl-pyrimidine-5-carbonitrile, benzyl mercaptan and DBU in DME. ES-MS m/e (%): 401 (M+K$^+$, 30), 385 (M+Na$^+$, 24), 363 (M+H$^+$, 100).

Example 111
2-Amino-4-propylamino-6-(3,4,5-trimethoxy-phenyl)-pyrimidine-5-carbonitrile From 2-amino-4-methanesulfonyl-6-(3,4,5-trimethoxy-phenyl)-pyrimidine-5-carbonitrile and propylamine in DME. ES-MS m/e (%): 382 (M+K$^+$, 10), 366 (M+Na$^+$, 20), 344 (M+H$^+$, 100).

Example 112
2-Amino-4-benzo[1,3]dioxol-5-yl-6-propylamino-pyrimidine-5-carbonitrile From 2-amino-4-benzo[1,3]dioxol-5-yl-6-methanesulfonyl-pyrimidine-5-carbonitrile and propylamine in DME. ES-MS m/e (%): 298 (M+H$^+$, 100).

Example 113
2-Amino-4-ethylsulfanyl-6-(3,4,5-trimethoxy-phenyl)-pyrimidine-5-carbonitrile From 2-amino-4-methanesulfonyl-6-(3,4,5-trimethoxy-phenyl)-pyrimidine-5-carbonitrile, ethyl mercaptan and DBU in DME. EI-MS m/e (%):46 (M$^+$, 100), 315 (52).

Example 114
2-Amino-4-benzo[1,3]dioxol-5-yl-6-ethylsulfanyl-pyrimidine-5-carbonitrile From 2-amino-4-benzo[1,3]dioxol-5-yl-6-methanesulfonyl-pyrimidine-5-carbonitrile, ethyl mercaptan and DBU in DME. EI-MS m/e (%): 300 (M$^+$, 74), 299 ([M—H]+, I100).

Example 115
2-Amino-4-cyclohexylamino-6-(3,4,5-trimethoxy-phenyl)-pyrimidine-5-carbonitrile From 2-amino-4-methanesulfonyl-6-(3,4,5-trimethoxy-phenyl)-pyrimidine-5-carbonitrile and cyclohexylamine in DME. ES-MS m/e (%): 384 (M+H$^+$, 100).

Example 116
2-Amino-4-benzo[1,3]dioxol-5-yl-6-cyclohexylamino-pyrimidine-5-carbonitrile From 2-amino-4-benzo[1,3]dioxol-5-yl-6-methanesulfonyl-pyrimidine-5-carbonitrile and cyclohexylamine in !)ME. ES-MS m/e (%): 338 (M+H$^+$, 100).

Example 117
2-Amino-4-cyclohexylamino-6-phenyl-pyrimidine-5-carbonitrile

From 2-amino-4-methanesulfonyl-6-phenyl-pyrimidine-5-carbonitrile and cyclohexylamine in DME. ES-MS m/e (%): 294 (M+H$^+$, 100).

Analogously to Example 30 there was obtained:

Example 118
2-Amino-4-isopropoxy-6-(3,4,5-trimethoxy-phenyl)-pyrimidine-5-carbonitrile From 2-amino-4-methylsulfanyl-6-(3,4,5-trimethoxy-phenyl)-pyrimidine-5-carbonitrile and sodium isopropoxide in isopropanol. ES-MS m/e (%): 367 (M+Na$^+$, 20), 345 (M+H$^+$, 78), 303 ([M+H—C$_3$H$_6$]$^+$, 100).

Example 119
3-Chloro-benzoic acid 4-[2-(2-amino-5-cyano-6-furan-2-yl-pyrimidin-4-ylamino)-ethyl]-phenyl ester To a cooled (0° C.) stirred suspension of 1.6 g (6.9 mmol) 2-amino-4-(2-furyl)-6-(methylthio)-5-pyrimidinecarbonitrile in 100 ml dichloromethane was added 3.6 g (20.7 mmol) m-chloroperbenzoic acid (70% purity) and stirring continued for 15 minutes at 0° C. The reaction mixture was then concentrated in vacuo and residue resuspended in 100 ml DME. To this stirred suspension were added 0.47 g (3.4 mmol) tyramine and 1.4 ml (10.3 mmol) DBU and the mixture heated at 100° C. for 1 hour. The reaction mixture was then concentrated in vacuo. Chromatography (ethyl acetate) followed by trituration in ether afforded 160 mg (5%) 3-chloro-benzoic acid 4-[2-(2-amino-5-cyano-6-furan-2-yl-pyrimidin-4-ylamino)-ethyl]-phenyl ester as a white crystalline solid. ES-MS m/e (%): 484 (M{$^{37}$Cl}+Na$^+$, 10), 482 (M{$^{35}$Cl}+Na$^+$, 25), 462 (M{$^{37}$Cl}+H$^+$, 35), 460 (M{$^{35}$Cl}+H$^+$, 100).

Analogously to Example 30 there was obtained:

Example 120
2-Amino-4-benzo[1,3]dioxol-5-yl-6-isopropoxy-pyrimidine-5-carbonitrile From 2-amino-4-benzo[1,3]dioxol-5-yl-6-methanesulfonyl-pyrimidine-5-carbonitrile and sodium isopropoxide in isopropanol. ES-MS m/e (%): 299 (M+H$^+$, 100).

Analogously to Example 47 there were obtained:

Example 121
2-Amino-4-ethoxy-6-(3,4,5-trimethoxy-phenyl)-pyrimidine-5-carbonitrile From 2-amino-4-methanesulfonyl-6-(3,4,5-trimethoxy-phenyl)-pyrimidine-5-carbonitrile, ethanol and DBU in DME. ES-MS m/e (%): 331 (M+H$^+$, 100).

Example 122
2-Amino-4-benzo[1,3]dioxol-5-yl-6-cyclohexyloxy-pyrimidine-5-carbonitrile From 2-amino-4-benzo[1,3]dioxol-5-yl-6-methanesulfonyl-pyrimidine-5-carbonitrile, cyclohexanol and DBU in DME. ES-MS m/e (%): 339 (M+H$^+$, 45), 257 (100).

Analogously to Example 30 there was obtained:

Example 123
2-Amino-4-cyclohexyloxy-6-(3,4,5-trimethoxy-phenyl)-pyrimidine-5-carbonitrile From 2-amino-4-methylsulfanyl-6-(3,4,5-trimethoxy-phenyl)-pyrimidine-5-carbonitrile and sodium cyclohexoxide in cyclohexanol. ES-MS m/e (%): 407 (M+Na$^+$, 15), 385 (M+H$^+$, 50), 303 ([M+H—C$_6$H$_{10}$]$^+$, 100).

Analogously to Example 47 there was obtained:

Example 124
2-Amino-4-{2-[4-(2-amino-5-cyano-6-furan-2-yl-pyrimidin-4-yloxy)-phenyl]-ethylamino}-6-furan-2-yl-pyrimidine-5-carbonitrile From 2-amino-4-furan-2-yl-6-methanesulfonyl-pyrimidine-5-carbonitrile, tyramine and DBU in DME. ES-MS m/e (%): 506 (M+H$^+$, 100).

Analogously to Example 19 there was obtained:

Example 125
2-Amino-4-(2-methylsulfanyl-ethylsulfanyl)-6-phenyl-pyrimidine-5-carbonitrile From 2-amino-4-phenyl-6-thioxo-1,6-dihydro-pyrimidine-5-carbonitrile, 2-chloroethyl methylsulfide and sodium ethylate in ethanol. EI-MS m/e (%): 302 (M$^+$, 2), 228 ([M—MeSCH=CH$_2$]$^+$, 100).

Example 126
5-Bromo-4-phenyl-pyrimidin-2-ylamine

Following the method of Ziegler and Clementon (U.S. Pat. No. 2,609,372), to a stirred suspension of 5.0 g (29.2 mmol) 2-amino-4-phenylpyrimidine and 1.46 g (14.6 mmol) $CaCO_3$ in 30 ml water at 50° C. was added dropwise 1.65 ml (32.2 mmol) bromine and stirring continued for 30 minutes. The reaction mixture was then made basic by addition of ammonium hydroxide solution and extracted three times with ethyl acetate. The combined organic phases were washed with saturated brine, dried over sodium sulfate, and concentrated in vacuo. Recrystallisation from ethanol afforded 3.27 g (45%) 5-bromo-4-phenyl-pyrimidin-2-ylamine as a green crystalline solid. EI-MS m/e (%): 251 ($M\{^{81}Br\}^+$, 64), 249 ($M\{^{79}Br\}^+$, 64), 170 ([M—Br]$^+$, 100).

Example 127
2-Amino-4-phenyl-6-vinyl-pyrimidine-5-carbonitrile

To a stirred solution of 515 mg (2.23 mmol) 2-amino-4-chloro-6-phenyl-pyrimidine-5-carbonitrile in 20 ml dioxane under argon at room temperature were added 0.65 ml (2.23 mmol) vinyltributylstannane, 258 mg (0.22 mmol) tetrakis (triphenylphosphine)palladium(O) and 4.5 ml (9.0 mmol) 2M aqueous sodium carbonate solution. The reaction mixture was heated at reflux for 16 h, then concentrated in vacuo. The residue was partitioned between ethyl acetate and water and the organic phase washed with brine, dried over sodium sulfate, and concentrated in vacuo. Flash chromatography (1/1 ethyl acetate/hexane) followed by trituration in ether afforded 40 mg (8%) 2-Amino-4-phenyl-6-vinyl-pyrimidine-5-carbonitrile as a yellow crystalline solid. EI-MS m/e (%): 222 (M$^+$, 85), 221 ([M—H]$^+$, 100).

In an analogous manner there was obtained:

Example 128
2-Amino-4,6-diphenyl-pyrimidine-5-carbonitrile

From 2-amino-4-chloro-6-phenyl-pyrimidine-5-carbonitrile, phenylboronic acid, tetrakis (triphenylphosphine)palladium(O) and sodium carbonate in dioxane/water. EI-MS m/e (%): 272 (M$^+$, 58), 271 ([M—H]$^+$, 100).

Example 129
2-Amino-4-ethyl-6-phenyl-pyrimidine-5-carbonitrile

A solution of 100 mg (0.45 mmol) 2-amino-4-phenyl-6-vinyl-pyrimidine-5-carbonitrile in 10 ml ethanol was stirred with a spatula end of 10% palladium on charcoal under 1 atm of hydrogen for 16 h at room temperature. After filtration to remove the catalyst, the reaction mixture was concentrated in vacuo and the residue triturated in ether to afford 35 mg (35%) 2-amino-4-ethyl-6-phenyl-pyrimidine-5-carbonitrile as a white crystalline solid. EI-MS m/e (%): 224 (M$^+$, 44), 223 ([M—H]$^+$, 100).

Analogously to Example 127 there was obtained:

Example 130
(E)-2-Amino-4-phenyl-6-styryl-pyrimidine-5-carbonitrile

From 2-amino-4-chloro-6-phenyl-pyrimidine-5-carbonitrile, (E)-styrylboronic acid, tetrakis (triphenylphosphine)palladium(O) and sodium carbonate in dioxane/water. EI-MIS m/e (%): 298 (M$^+$, 84), 297 ([M—H]$^+$, 100).

Example 131
2-Amino-4-phenyl-6-phenylethynyl-pyrimidine-5-carbonitrile

Following the method of Thorand and Krause (*J. Org Chem.* 1998, 63, 8551), to a stirred solution of 500 mg (2.17 mmol) 2-amino-4-chloro-6-phenyl-pyrimidine-5-carbonitrile in 8.5 ml dry degassed THF under argon at room temperature were added 300 mg (0.43 mmol) bis (triphenylphosphine)palladium(II) chloride, 14 mg (0.05 mmol) triphenylphosphine, 0.36 ml (3.28 mmol) phenylacetylene and 0.45 ml (3.23 mmol) triethylamine. Stirring was continued for 30 minutes then 4.0 mg (0.02 mmol) copper(I) iodide was added and the reaction mixture stirred for an additional 16 hours at room temperature. The reaction mixture was then concentrated in vacuo. Chromatography (1/2 ethyl acetate/hexane) afforded 350 mg (55%) 2-amino-4-phenyl-6-phenylethynyl-pyrimidine-5-carbonitrile as a light yellow crystalline solid. EI-MS m/e (%): 296 (M$^+$, 100), 270 (80).

Analogously to Example 47 there were obtained:

Example 132
2-Amino-4-furan-2-yl-6-(2-phenylamino-ethylamino)-pyrimidine-5-carbonitrile From 2-amino-4-furan-2-yl-6-methanesulfonyl-pyrimidine-5-carbonitrile and N-phenylethylenediamine in DME. ES-MS m/e (%): 321 (M+H$^+$, 100).

Example 133
2-Amino-4-furan-2-yl-6-(4-phenyl-piperazin-1-yl)-pyrimidine-5-carbonitrile From 2-amino-4-furan-2-yl-6-methanesulfonyl-pyrimidine-5-carbonitrile and 1-phenylpiperazine in DME. ES-MS m/e (%): 347 (M+H$^+$, 100).

Example 134
2-Amino-4-(4-benzoyl-piperazin-1-yl)-6-furan-2-yl-pyrimidine-5-carbonitrile From 2-amino-4-furan-2-yl-6-methanesulfonyl-pyrimidine-5-carbonitrile and phenyl-piperazin-1-ylmethanone in DME. ES-MS m/e (%): 397 (M+Na$^+$, 25), 375 (M+H$^+$, 100).

Example 135
2-Amino-4-chloro-6-furan-2-yl-pyrimidine-5-carbonitrile a) 2-Amino-4-furan-2-yl-6-oxo-1,6-dihydro-pyrimidine-5-carbonitrile To a stirred solution of 4.2 g (18.1 mmol) 2-amino-4-(2-furyl)-6-(methylthio)-pyrimidine-5-carbonitrile in 50 ml dioxane was added 50 ml (100 mmol) 2M sodium hydroxide solution and the mixture heated at reflux for 16 h. The reaction mixture was then concentrated in vacuo and the residue resuspended in 300 ml ethyl acetate and the mixture stirred for 30 minutes. The resulting crystals were collected by filtration and dried in vacuo. They were then dissolved in 150 ml water and the mixture neutralised with 1M hydrochloric acid. The resulting crystals were collected by filtration and washed with water to afford 3.3 g (90%) 2-amino-4-furan-2-yl-6-oxo-1,6-dihydro-pyrimidine-5-carbonitrile as an off-white crystalline solid. ES-MS m/e (%): 201 ([M—H]$^-$, 100).

b) 2-Amino-4-chloro-6-furan-2-yl-pyrimidine-5-carbonitrile

Following the method of Hull (*J. Chem. Soc.* 1957, 4845), a stirred suspension of 3.26 g (16.1 mmol) 2-amino-4-furan-2-yl-6-oxo-1,6-dihydro-pyrimidine-5-carbonitrile in 3.7 ml (40.3 mmol) phosphorus oxychloride was heated at reflux for 90 minutes. The reaction mixture was then cooled to room temperature, diluted with dichloromethane, and poured cautiously onto 100 ml rapidly stirred ice-water such that the temperature remained around 10° C. The phases were separated and the aqueous phase further extracted with dichloromethane. The combined organic phases were dried over sodium sulfate and concentrated in vacuo. Chromatography (ethyl acetate) afforded 0.16 g (4%) 2-amino-4-chloro-6-furan-2-yl-pyrimidine-5-carbonitrile as an orange crystalline solid. EI-MS m/e (%): 222 (M{$^{37}$Cl}$^+$, 34), 220 (M{$^{35}$Cl}$^+$, 100), 143 (30).

Examples 136 and 137
2-Amino-4-furan-2-yl-6-vinyl-pyrimidine-5-carbonitrile and 2-amino-4-ethyl-6-f ran-2-yl-pyrimidine-5-carbonitrile
a) Trifluoromethanesulfonic Acid 2-amino-5-cyano-6-furan-2-yl-pyrimidin-4-yl Ester To a stirred suspension of 0.5 g (2.47 mmol) 2-amino-4-furan-2-yl-6-oxo-1,6-dihydro-pyrimidine-5-carbonitrile in 10 ml dichloromethane was added 1.11 ml (4.95 mmol) 2,6-di-tert-butylpyridine and the mixture was ultrasonicated for 30 minutes. 0.41 ml (2.47 mmol) triflic anhydride was then added dropwise at 0° C. with stirring and stirring continued at room temperature for 16 hours. 3 g of kieselgel was added to the reaction mixture, which was then concentrated in vacuo. Chromatography (ethyl acetate) followed by trituration in ether/hexane afforded 0.25 g (30%) trifluoromethanesulfonic acid 2-amino-5-cyano-6-furan-2-yl-pyrimidin-4-yl ester as a light brown crystalline solid. EI-MS m/e (%): 334 (M$^+$, 100), 173 (62), 69 (50).
b) 2-Amino-4-furan-2-yl-6-vinyl-pyrimidine-5-carbonitrile and 2-amino-4-ethyl-6-furan-2-yl-pyrimidine-5-carbonitrile To a stirred solution of 250 mg (0.75 mmol) trifluoromethanesulfonic acid 2-amino-5-cyano-6-furan-2-yl-pyrimidin-4-yl ester in 15 ml dioxane under argon at room temperature were added 0.22 ml (0.75 mmol) vinyltributylstannane, 86 mg (0.07 mmol) tetrakis(triphenylphosphine)palladium(O) and 1.5 ml (3.0 mmol) 2M aqueous sodium carbonate solution. The reaction mixture was heated at reflux for 16 h, then concentrated in vacuo. The residue was partitioned between ethyl acetate and water and the organic phase washed with brine, dried over sodium sulfate, and concentrated in vacuo. Flash chromatography (1/1 ethyl acetate/hexane) followed by trituration in ether afforded 6 mg (4%) 2-amino-4-furan-2-yl-6-vinyl-pyrimidine-5-carbonitrile as a white crystalline solid. ES-MS m/e (%): 213 (M+H$^+$, 100). Also obtained (as a by-product) was 3 mg (2%) 2-amino-4-ethyl-6-furan-2-yl-pyrimidine-5-carbonitrile as a yellow crystalline solid. ES-MS m/e (%): 215 (M+H$^+$, 100).

Example 138
5-Bromo-4-furan-2-yl-6-methylsulfanyl-pyrimidin-2-ylamine
a) 1-Furan-2-yl-3,3-bis-methylsulfanyl-propenone Following the method of Rudorf and Augustin (Phosphorus and Sulfur 1981, 9, 329), a solution of 15.0 g (136 mmol) 2-acetylfuran in 80 ml dry DMSO was added dropwise to a stirred suspension of 10.9 g (272 mmol, 60% dispersion in mineral oil) sodium hydride in 80 ml DMSO under argon at room temperature. 8.2 ml (136 mmol) carbon disulfide was then added dropwise, with external water bath cooling, and stirring continued for 45 minutes, after which 17.0 ml (272 mmol) methyl iodide was added dropwise, with external water bath cooling, and stirring continued for a further 16 h. The reaction mixture was poured into 3 l ice-cold water, stirred for 10 minutes, and the resulting precipitate collected by filtration and dried in vacuo to afford 29.2 g (99%) 1-furan-2-yl-3,3-bis-methylsulfanyl-propenone none as a brown crystalline solid. ES-MS m/e (%): 215 (M+H$^+$, 100).
b) 4-Furan-2-yl-6-methylsulfanyl-pyrimidin-2-ylamine To a stirred suspension of 1.87 g (46.7 mmol, 60% dispersion in mineral oil) sodium hydride in 100 ml dry DMF at room temperature was added portionwise 10.1 g (56.0 mmol) guanidine carbonate and the mixture stirred for 30 minutes. A solution of 10.0 g (46.7 mmol) 1-furan-2-yl-3,3-bis-methylsulfanyl-propenone in 50 ml DMF was then added dropwise and the mixture heated at 100° C. for 16 hours. The reaction mixture was then poured into 1 l ice-cold water, stirred for 30 minutes, and the resulting precipitate collected by filtration and dried in vacuo to afford 7.4 g (77%) 4-furan-2-yl-6-methylsulfanyl-pyrimidin-2-ylamine as a sand-coloured solid. EI-MS m/e (%): 207 (M$^+$, 100), 206 ([M—H]$^+$, 35).
c) 5-Bromo-4-furan-2-yl-6-methylsulfanyl-pyrimidin-2-ylamine To a stirred solution of 197 mg (0.95 mmol) 4-furan-2-yl-6-methylsulfanyl-pyrimidin-2-ylamine in 15 ml acetic acid was added 178 mg (1.00 mmol) N-bromosuccinimide and stirring continued at room temperature for 48 h. The reaction mixture was then concentrated in vacuo and the residue partitioned between ether and water. The organic phase was dried over, sodium sulfate and concentrated in vacuo. Chromatography (ethyl acetate/hexane 1/2) followed by trituration in ether/hexane then afforded 93 mg (34%) 5-bromo-4-furan-2-yl-6-methylsulfanyl-pyrimidin-2-ylamine as a yellow crystalline solid. EI-MS m/e (%): 287 (M{$^{81}$Br}$^+$, 44), 285 (M{$^{79}$Br}$^+$, 42), 206 ([M—Br]$^+$, 100).

Analogously to Example 1 there was obtained:

Example 139
4-Furan-2-yl-5-iodo-pyrimidin-2-ylamine

From 2-acetylfuran and N,N-dimethylformamide dimethyl acetal in DMF. Then treatment with guanidine carbonate and sodium methylate in methanol. Then treatment with N-iodosuccinimide in acetic acid. EI-MS m/e (%): 287 (M$^+$, 100).

Analogously to Example 138 there was obtained:

Example 140
4-Furan-2-yl-5-iodo-6-methylsulfanyl-pyrimidin-2-ylamine

From 4-furan-2-yl-6-methylsulfanyl-pyrimidin-2-ylamine and N-iodosuccinimide in acetic acid. EI-MS m/e (%): 333 (M$^+$, 66), 206 ([M—I]$^+$, 100), 118 (44).

Example 141
2-Amino-4-furan-2-yl-6-methylsulfanyl-pyridine-3,5-dicarbonitrile
a) 2,6-Diamino-4-furan-2-yl-4H-thiopyran-3,5-dicarbonitrile Following an adaptation of the method of Elghandour et al. (Ind. J. Chem. 1997, B36, 79), to a stirred solution of 3.98 g (60.3 mmol) malonitrile, 6.04 g (60.3 mmol) cyanothioacetamide and 5.0 ml (60.3 mmol) furfural in 100 ml ethanol and 5 ml DMF at 0° C. was added dropwise 0.4 ml (3.0 mmol) triethylamine and stirring was continued at 0° C. for 2 hours. The resulting crystals were collected by filtration and washed with ice-cold ether to afford 10.4 g (71%) 2,6-diamino-4-furan-2-yl-4H-thiopyran-3,5-dicarbonitrile as a white crystalline solid. EI-MS m/e (%): 244 (M$^+$, 100), 211 ([M—SH]$^+$, 64), 60 (50).
b) 6-Amino-4-furan-2-yl-2-thioxo-1,2-dihydro-pyridine-3,5-dicarbonitrile To a stirred solution of 310 mg (1.27 mmol) 2,6-diamino-4-furan-2-yl-4H-thiopyran-3,5-dicarbonitrile in 20 ml ethanol was added 7.5 ml 25% ammonium hydroxide solution and the mixture was heated at reflux for 2 hours. The reaction mixture was then concentrated in vacuo and the residue triturated in ether to afford 170 mg (55%) 6-amino-4-furan-2-yl-2-thioxo-1,2-dihydro-pyridine-3,5-dicarbonitrile as a dark red crystalline solid. EI-MS m/e (%): 242 (M$^+$, 100).

c) 2-Amino-4-furan-2-yl-6-methylsulfanyl-pyridine-35-dicarbonitrile

To a stirred solution of 210 mg (0.87 mmol) 6-amino-4-furan-2-yl-2-thioxo-1,2-dihydro-pyridine-3,5-dicarbonitrile in 25 ml methanol were added 0.16 ml (0.87 mmol) sodium methylate solutiuon (5.4M in methanol) and 0.11 ml (1.73 mmol) methyl iodide and stirring continued for 90 minutes at room temperature. The reaction mixture was then poured onto 100 ml ice-water and the resulting crystals collected by filtration and dried in vacuo to afford 135 mg (61%) 2-amino-4-furan-2-yl-6-methylsulfanyl-pyridine-3,5-dicarbonitrile as a light brown crystalline solid. EI-MS m/e (%): 256 (M$^+$, 49), 255 ([M—H]$^+$, 100).

Example 142
2-Amino-4-furan-2-yl-pyrimidine-5-carboxylic Acid Ethyl Ester a) 3-Dimethylamino-2-(furan-2-carbonyl)-acrylic Acid Ethyl Ester Following the method of Menozzi et al. (*J. Heterocyclic Chem.* 1987, 24, 1669), a mixture of 5.3 g (29.1 mmol) ethyl beta-oxo-2-furanpropionate and 7.7 ml (57.8 mmol) N,N-dimethylformamide dimethyl acetal was stirred for 6.5 hours at room temperature. The reaction mixture was then concentrated in vacuo and the residue partitioned between ethyl acetate and water. The organic phase was dried with sodium sulfate and concentrated in vacuo. Chromatography (ethyl acetate) afforded 3.6 g (52%) 3-dimethylamino-2-(furan-2-carbonyl)-acrylic acid ethyl ester as a yellow oil. EI-MS m/e (%): 237 (M$^+$, 36), 163 ([M—EtOH—CO]$^+$, 100), 95 (86).

b) 2-Amino-4-furan-2-yl-pyrimidine-5-carboxylic Acid Ethyl Ester

Following the method of Sansebastiano et al. (*Il Farmaco* 1993, 48, 335), to a stirred solution of 2.44 g (10.3 mmol) 3-dimethylamino-2-(furan-2-carbonyl)-acrylic acid ethyl ester and 2.26 g (18.5 mmol) guanidine nitrate in 20 ml DMF was added 1.51 g (18.5 mmol) sodium acetate and the mixture heated at 90° C. for 36 h. The reaction mixture was then partitioned between ether and water. The phases were separated and the aqueous phase extracted twice more with ethyl acetate. The combined organic phases were dried over sodium sulfate and concentrated in vacuo. The residue was recrystallised from ether/ethyl acetate/hexane to afford 669 mg (28%) 2-amino-4-furan-2-yl-pyrimidine-5-carboxylic acid ethyl ester as a white crystalline solid. Chromatography (ethyl acetate/hexane 2/1) of the mother liquor afforded a further 150 mg (6%) product. ES-MS m/e (%): 234 (M+H$^+$, 100), 206 ([M—C$_2$H4]$^+$, 35), 188 ([M+H-EtOH]$^+$, 42).

Example 143
4-Furan-2-yl-6-methylsulfanyl-5-phenylethynyl-pyrimidin-2-ylamine Following the method of Thorand and Krause (*J. Org. Chem.* 1998, 63, 8551), to a stirred solution of 500 mg (1.50 mmol) 4-furan-2-yl-5-iodo-6-methylsulfanyl-pyrimidin-2-ylamine in 10 ml dry degassed THF under argon at room temperature were added 211 mg (0.30 mmol) bis(triphenylphosphine)palladium(II) chloride, 10 mg (0.04 mmol) triphenylphosphine, 0.25 ml (2.28 mmol) phenylacetylene and 0.31 ml (2.22 mmol) triethylamine. Stirring was continued for 30 minutes then 3.0 mg (0.02 mmol) copper(I) iodide was added and the reaction mixture stirred for an additional 72 hours at room temperature. The reaction mixture was then concentrated in vacuo. Chromatography (1/4-1/1 ethyl acetate/hexane) afforded 161 mg (35%) 4-furan-2-yl-6-methylsulfanyl-5-phenylethynyl-pyrimidin-2-ylamine as a yellow crystalline solid. EI-MS m/e (%): 307 (M$^+$, 100), 306 ([M—H]$^+$, 52), 230 (38).

Analogously to Example 47 there was obtained:

Example 144
2-Amino-4-furan-2-yl-6-[2-(4-methoxy-phenyl)-ethylamino]-pyrimidine-5-carbonitrile From 2-amino-4-furan-2-yl-6-methanesulfonyl-pyrimidine-5-carbonitrile and 2-(4-methoxyphenyl)ethylamine in DME. ES-MS m/e (%): 336 (M+H$^+$, 100).

Analogously to Example 1 there was obtained:

Example 145
5-Bromo-4-furan-2-yl-pyrimidin-2-ylamine

From 2-acetylfuran and N,N-dimethylformamide dimethyl acetal in DMF. Then treatment with guanidine carbonate and sodium methylate in methanol. Then treatment with N-bromosuccinimide in acetic acid. EI-MS m/e (%): 241 (M{$^{81}$Br}$^+$, 98), 239 (M{$^{81}$Br}$^+$, 100).

Analogously to Example 136 there was obtained:

Example 146
2-Amino-4-furan-2-yl-6-isopropenyl-pyrimidine-5-carbonitrile

From trifluoromethanesulfonic acid 2-amino-5-cyano-6-furan-2-yl-pyrimidin-4-yl ester, isopropenylboronic acid, tetrakis(triphenylphosphine)palladium(O) and sodium carbonate in dioxane/water. EI-MS m/e (%): 226 (M$^+$, 74), 225 ([M—H]$^+$, 100).

Analogously to Example 129 there was obtained:

Example 147
2-Amino-4-furan-2-yl-6-isopropyl-pyrimidine-5-carbonitrile

From 2-amino-4-furan-2-yl-6-isopropenyl-pyrimidine-5-carbonitrile, hydrogen and palladium on charcoal in THF. ES-MS m/e (%): 229 (M+H$^+$, 100).

Analogously to Example 136 there were obtained:

Example 148
2-Amino-4-furan-2-yl-6-phenyl-pyrimidine-5-carbonitrile

From trifluoromethanesulfonic acid 2-amino-5-cyano-6-furan-2-yl-pyrimidin-4-yl ester, phenylboronic acid, tetrakis(triphenylphosphine)palladium(O) and sodium carbonate in dioxane/water. ES-MS m/e (%): 263 (M+H$^+$, 100).

Example 149
(E)-2-Amino-4-furan-2-yl-6-styryl-pyrimidine-5-carbonitrile

From trifluoromethanesulfonic acid 2-amino-5-cyano-6-furan-2-yl-pyrimidin-4-yl ester, (E)-styrylboronic acid, tetrakis(triphenylphosphine)palladium(O) and sodium carbonate in dioxane/water. ES-MS m/e (%): 289 (M+H$^+$, 100).

Analogously to Example 129 there was obtained:

Example 150
2-Amino-4-furan-2-yl-6-phenethyl-pyrimidine-5-carbonitrile

From (E)-2-Amino-4-furan-2-yl-6-styryl-pyrimidine-5-carbonitrile, hydrogen and palladium on charcoal in THF. ES-MS m/e (%): 291 (M+H$^+$, 100).

Analogously to Example 131 there was obtained:

Example 151
2-Amino-4-furan-2-yl-6-phenylethynyl-pyrimidine-5-carbonitrile

From trifluoromethanesulfonic acid 2-amino-5-cyano-6-furan-2-yl-pyrimidin-4-yl ester, phenylacetylene, bis(triphenylphosphine)palladium(II) chloride, triphenylphosphine, triethylamine and copper (I) iodide in THF. EI-MS m/e (%): 286 (M$^+$, 100).

Example 152
(E)-3-(2-Amino-4-furan-2-yl-6-methylsulfanyl-pyrimidin-5-yl)-acrylic Acid Methyl Ester A stirred suspension of 457 mg (1,37 mmol) 4-furan-2-yl-5-iodo-6-methylsulfanyl-pyrimidin-2-ylamine, 0.25 ml (2.77 mmol) methyl acrylate, 96 mg (0.14 mmol) bis(triphenylphosphine)palladium(II) chloride and 0.67 g (2.06 mmol) cesium carbonate in 5 ml dioxane under argon in a sealed tube was heated at 100° C. for 16 h. After cooling to room temperature, the mixture was diluted with 50 ml ethyl acetate, filtered, and the filtrate was concentrated in vacuo. Flash chromatography (1/2-1/1 ethyl acetate/hexane) followed by trituration in ether/pentane afforded 194 mg (49%) (E)-3-(2-amino-4-furan-2-yl-6-methylsulfanyl-pyrimidin-5-yl)-acrylic acid methyl ester as an off-white crystalline solid. ES-MS m/e (%): 292 (M+H$^+$, 100).

In an analogous manner there was obtained:

Example 153
(E)-3-(2-Amino-4-furan-2-yl-pyrimidin-5-yl)-acrylic Acid Methyl Ester From 4-furan-2-yl-5-iodo-pyrimidin-2-ylamine, methyl acrylate, bis(triphenylphosphine)palladium(II) chloride and cesium carbonate in dioxane. EI-MS m/e (%): 245 (M$^+$, 54), 228 ([M—NH$_3$]$^+$, 100), 186 ([M—CO$_2$Me]$^+$, 56), 158 (52).

Example 154
(E)-3-(2-Amino-4-furan-2-yl-pyrimidin-5-yl)-acrylonitrile

From 4-furan-2-yl-5-iodo-pyrimidin-2-ylamine, acrylonitrile, bis(triphenyl-phosphine)palladium(II) chloride and cesium carbonate in dioxane. EI-MS m/e (%): 212 (M$^+$, 52), 195 ([M—NH$_3$]$^+$, 100), 184 (32), 158 (52).

Example 155
(E)-3-(2-Amino-4-furan-2-yl-6-methylsulfanyl-pyrimidin-5-yl)-acrylonitrile From 4-furan-2-yl-5-iodo-6-methylsulfanyl-pyrimidin-2-ylamine, acrylonitrile, bis(triphenylphosphine)palladium(II) chloride and cesium carbonate in dioxane. EI-MS m/e (%): 258 (M$^+$, 76), 241 ([M—NH$_3$]$^+$, 100), 150 (56), 114 (32).

Analogously to Example 1 there was obtained:

Example 156
5-Chloro-4-furan-2-yl-pyrimidin-2-ylamine

From 2-acetylfuran and N,N-dimethylformamide dimethyl acetal in DMF. Then treatment with guanidine carbonate and sodium methylate in methanol. Then treatment with N-chlorosuccinimide in acetic acid. EI-MS m/e (%): 197 (M{$^{37}$Cl}$^+$, 32), 195 (M{$^{35}$Cl}$^+$, 100).

Example 157
5-(3,5-Dichloro-phenyl)-4-furan-2-yl-6-methylsulfanyl-pyrimidin-2-yl-amine To a stirred solution of 500 mg (1.50 mmol) 4-furan-2-yl-5-iodo-6-methylsulfanyl-pyrimidin-2-ylamine in 20 ml dioxane under argon at room temperature were added 0.5 ml (1.50 mmol) 3,5-dichlorophenylboronic acid (50% solution in THF/water), 173 mg (0.15 mmol) tetrakis(triphenylphosphine)palladium(O) and 3.0 ml (6.0 mmol) 2M aqueous sodium carbonate solution. The reaction mixture was heated at reflux for 16 h, then cooled to room temperature, 1 g of kieselgel added, and the mixture concentrated in vacuo. Flash chromatography (1/1 ethyl acetate/hexane) followed trituration in ether/hexane afforded 328 mg (62%) 5-(3,5-dichloro-phenyl)-4-furan-2-yl-6-methylsulfanyl-pyrimidin-2-ylamine as a beige crystalline solid. ES-MS m/e (%):354 (M{$^{37}$Cl}+H$^+$, 60), 352 (M{$^{35}$Cl}+H$^+$, 100).

Analogously to Example 2 there was obtained:

Example 158
2-Amino-4-furan-2-yl-6-methylsulfanyl-pyrimidine-5-carboxylic Acid Ethyl Ester From ethyl beta-oxo-2-furanpropionate with sodium hydride, carbon disulphide and methyl iodide in DMSO. Then treatment with guanidine nitrate and triethylamine in DMF. EI-MS m/e (%): 279 (M$^+$, 100), 234 ([M—EtO]$^+$, 88), 233 ([M—EtOH]$^+$, 48), 206 (62).

Analogously to Example 138 there was obtained:

Example 159
5-Chloro-4-furan-2-yl-6-methylsulfanyl-pyrimidin-2-ylamine

From 4-furan-2-yl-6-methylsulfanyl-pyrimidin-2-ylamine and N-chlorosuccinimide in acetic acid. ES-MS m/e (%): 244 (M{$^{37}$Cl}+H$^+$, 40), 242 (M{$^{35}$Cl}+H$^+$, 100).

Example 160
2-Amino-4-furan-2-yl-6-methylsulfanyl-pyrimidine-5-carboxylic Acid Benzyl Ester To a stirred solution of 534 mg (1.60 mmol) 4-furan-2-yl-5-iodo-6-methylsulfanyl-pyrimidin-2-ylamine in 10 ml benzyl alcohol at room temperature were added 146 mg (0.16 mmol) tris(dibenzylideneacetone)dipalladium(O), 122 mg (0.40 mmol) triphenylarsine and 1.12 ml (8.00 mmol) triethylamine. Carbon monoxide was bubbled through the reaction mixture while it was heated at 110° C. for 16 hours. The reaction mixture was then concentrated in vacuo. Flash chromatography (1/2 ethyl acetate/hexane) afforded 83 mg (15%) 2-amino-4-furan-2-yl-6-methylsulfanyl-pyrimidine-5-carboxylic acid benzyl ester as a yellow gum. ES-MS m/e (%): 341 (M$^+$, 30), 250 ([M—PhCH$_2$]$^+$, 100), 207 (38), 91 (98).

Example 161
4-Furan-2-yl-6-methylsulfanyl-5-nitro-pyrimidin-2-ylamine
a) 2-Amino-6-chloro-5-nitro-3H-pyrimidin-4-one Following the method of O'Brien and Cheng (*J. Med. Chem.* 1966, 9, 573), to a stirred solution of 10.0 g (61.1 mmol) 2-amino-6-chloro-4-pyrimidinol monohydrate in 46 ml 98% sulfuric acid was added dropwise 9 ml 65% nitric acid at a rate such that the reaction temperature remainded around 40° C. After the addition was complete, stirring was continued for 1 hour at room temperature. The reaction mixture was then poured onto 150 ml ice-water and the resulting crystals were collected by filtration and washed sequentially with water, ethanol and ether to afford 12.6 g (99%) 2-amino-6-chloro-5-nitro-3H-pyrimidin-4-one as a light yellow crystalline solid. ES-MS m/e (%): 191 (M+H$^+$, 100).
b) 2-Amino-6-furan-2-yl-5-nitro-3H-pyrimidin-4-one To a stirred solution of 15.7 g (75.3 mmol) 2-amino-6-chloro-5-nitro-3H-pyrimidin-4-one in 300 ml dioxane and 100 ml water at room temperature were added 8.40 g (75.0 mmol) 2-furylboronic acid, 8.70 g (7.53 mmol) tetrakis(triphenylphosphine)palladium(O) and 150 ml (300 mmol) 2M aqueous sodium carbonate solution. The reaction mixture was heated at reflux for 7 h, then concentrated in vacuo. The residue was resuspended in acetone and the insoluble material collected by filtration. This solid material was then dissolved in 1.21 water and acidified to pH 4–5 with 25% hydrochloric acid. The resulting crystals were collected by filtration and washed with water. After drying in vacuo they were additionally washed with dichloromethane to afford 7.33 g (44%) 2-amino-6-furan-2-yl-5-nitro-3H-pyrimidin-4-one as a yellow crystalline solid. ES-MS m/e (%): 221 ([M—H]$^-$, 100).

c) Trifluoro-methanesulfonic Acid 2-amino-6-furan-2-yl-5-nitro-pyrimidin-4-yl Ester To a stirred suspension of 0.5 g (2.25 mmol) 2-amino-6-furan-2-yl-5-nitro-3H-pyrimidin-4-one in 5 ml dichloromethane was added 1.01 ml (4.50 mmol) 2,6-di-tert-butylpyridine and the mixture was ultrasonicated for 30 minutes. 0.37 ml (2.25 mmol) triflic anhydride was then added dropwise at 0° C. with stirring and stirring continued at room temperature for 16 hours. The reaction mixture was then partitioned between water and dichloromethane and the organic phase was dried over sodium sulfate and concentrated in vacuo. The residue was recrystallised from ether/hexane and the resulting crystals (2,6-di-tert-butylpyridinium triflate) were removed by filtration. The mother liquor was concentrated in vacuo to afford 0.67 g (84%) trifluoro-methanesulfonic acid 2-amino-6-furan-2-yl-5-nitro-pyrimidin-4-yl ester as a brown oil. ES-MS m/e (%): 353 ([M—H]$^-$, 100).

d) 4-Furan-2-yl-6-methylsulfanyl-5-nitro-pyrimidin-2-ylamine

A stirred solution of 335 mg (0.95 mmol) trifluoro-methanesulfonic acid 2-amino-6-furan-2-yl-5-nitro-pyrimidin-4-yl ester and 663 mg (9.46 mmol) sodium methanethiolate in 20 ml dry dioxane under argon was heated at reflux for one hour. The reaction mixture was then concentrated in vacuo. Flash chromatography (ethyl acetate) followed by recrystallisation from ether/hexane afforded 110 mg (46%) 4-furan-2-yl-6-methylsulfanyl-5-nitro-pyrimidin-2-ylamine as a yellow crystalline solid. EI-MS ni/e (%): 252 (M$^+$, 22), 235 (26), 223 (66), 207 (100), 178 (86), 161 (44), 134 (62), 94 (90).

Example 162
N-4-Benzyl-6-furan-2-yl-5-nitro-pyrimidine-2,4-diamine

To a stirred solution of 335 mg (0.95 mmol) trifluoro-methanesulfonic acid 2-amino-6-furan-2-yl-5-nitro-pyrimidin-4-yl ester in 20 ml dioxane was added 1.03 ml (9.46 mmol) benzylamine and the mixture heated at reflux for 1 hour. The reaction mixture was then concentrated in vacuo. Chromatography (ethyl acetate) followed by recrystallisation from ether/hexane afforded 230 mg (78%) N4-benzyl-6-furan-2-yl-5-nitro-pyrimidine-2,4-diamine as a yellow crystalline solid. ES-MS m/e (%): 312 (M+H$^+$, 100).

Example 163
N-4-Benzyl-5-bromo-6-furan-2-yl-pyrimidine-2,4-diamine a) 5-Bromo-4-furan-2-yl-6-methanesulfinyl-pyrimidin-2-ylamine To a stirred suspension of 350 mg (1.22 mmol) 5-bromo-4-furan-2-yl-6-methylsulfanyl-pyrimidin-2-ylamine in 30 ml dichloromethane was added 1.28 g (4.89 mmol) 3-phenyl-2-(phenylsulfonyl)oxaziridine and stirring continued for 16 hours at room temperature. The reaction mixture was then concentrated in vacuo and the residue recrystallised from hexane/dichloromethane to afford 225 mg (61%) 5-bromo-4-furan-2-yl-6-methanesulfinyl-pyrimidin-2-ylamine as a beige crystalline solid. EI-MS m/e (%): 303 (M{flBr}$^+$, 24), 301 (M{$^{79}$Br}$^+$24), 257(48), 255 (50), 198 (81), 196(84), 117(100).

b) N-4-Benzyl-5-bromo-6-furan-2-yl-pyrimidine-2,4-diamine

To a stirred suspension of 200 mg (0.66 mmol) 5-bromo-4-furan-2-yl-6-methanesulfinyl-pyrimidin-2-ylamine in 5 ml dioxane was added 0.16 ml (1.46 mmol) benzylamine and the mixture heated at 100° C. for 2 hour. The reaction mixture was then concentrated in vacuo. Chromatography (ethyl acetate) followed by trituration in ether/hexane afforded 162 mg (71%) N4-benzyl-5-bromo-6-furan-2-yl-pyrimidine-2,4-diamine as a white crystalline solid. EI-MS m/e (%): 346 (M{$^{81}$Br}$^+$, 50), 344 (M{$^{79}$Br} +51), 265 (46), 106 (100), 91 (61).

In an analogous manner there was obtained:

Example 164
N-4-Benzyl-5-chloro-6-furan-2-yl-pyrimidine-2,4-diamine

From 5-chloro-4-furan-2-yl-6-methanesulfinyl-pyrimidin-2-ylamine and benzylamine in DME. EI-MS m/e (%): 302 (M{$^{37}$Cl}$^+$, 20), 300 (M{$^{35}$Cl}$^+$, 80), 106 (100), 91 (44).

Example 165
5-Chloro-4-furan-2-yl-6-(pyridin-2-ylmethoxy)-pyrimidin-2-yl-amine From 5-chloro-4-furan-2-yl-6-methanesulfinyl-pyrimidin-2-yl-amine, 2-(hydroxymethyl)pyridine and DBU in DME. ES-MS m/e (%): 305 (M{$^{37}$Cl}+H$^+$, 45), 303 (M{$^{35}$Cl}+H$^+$, 100).

Example 166
4-[2-(2-Amino-5-chloro-6-furan-2-yl-pyrimidin-4-yl-amino)-ethyl]-phenol From 5-chloro-4-furan-2-yl-6-methanesulfinyl-pyrimidin-2-yl-amine and tyramine in DME. ES-MS m/e (%): 333 (M{$^{37}$Cl}+H$^+$, 40), 331 (M{$^{35}$C}+H$^+$, 100).

Example 167
4-[2-(2-Amino-5-chloro-6-furan-2-yl-pyrimidin-4-ylamino)-ethyl]-phenol From 5-bromo-4-furan-2-yl-6-methanesulfinyl-pyrimidin-2-yl-amine and tyramine in dioxane. ES-MS m/e (%:377 (M{$^{81}$Br}+H$^+$, 95), 375 ({$^9$Br}+H$^+$, 100).

Example 168
5-Bromo-4-furan-2-yl-6-(pyridin-2-ylmethoxy)-pyrimidin-2-yl-amine From 5-bromo-4-furan-2-yl-6-methanesulfinyl-pyrimidin-2-yl amine, 2-(hydroxymethyl)pyridine and DBU in dioxane. 349 (M{$^{81}$Br}+H$^+$, 98), 347 (M{$^{79}$Br}+H$^+$, 100).

Example 169
5-Bromo-4-(2-dimethylamino-ethoxy)-6-furan-2-yl-pyrimidin-2-yl-amine From 5-bromo-4-furan-2-yl-6-methanesulfinyl-pyrimidin-2-yl-amine, dimethylaminoethanol and DBU in dioxane. 329 (M{9Br}+H$^+$, 95), 327 (M{10Br}+H$^+$, 100).

Example 170
5-Bromo-6-furan-2-yl-N4-(2-phenylamino-ethyl)-pyrimidine-2,4-diamine From 5-bromo-4-furan-2-yl-6-methanesulfinyl-pyrimidin-2-yl-amine and N-phenylethylenediamine in dioxane. ES-MS m/e (%): 376 (M{$^{81}$Br}+H$^+$, 100), 374 (M{$^{79}$Br}+H$^+$, 95).

Example 171
5-Bromo-6-furan-2-yl-N4-[2-(4-methoxy-phenyl)-ethyl]-pyrimidine-2,4-diamine From 5-bromo-4-furan-2-yl-6-methanesulfinyl-pyrimidin-2-yl-amine and 2-(4-methoxyphenyl)ethylamine in dioxane. ES-MS m/e (%): 391 (M{$^{81}$Br}+H$^+$, 100), 389 (M{$^{79}$Br}+H$^+$, 99).

Example 172
5-Bromo-6-furan-2-yl-N4-(2-methoxy-ethyl)-pyrimidine-2,4-diamine From 5-bromo-4-furan-2-yl-6-methanesulfinyl-pyrimidin-2-yl-amine and 2-methoxyethylamine in dioxane. ES-MS m/e (%): 315 (M{$^{81}$Br}+H$^+$, 100), 313 (M{$^{79}$Br}+H+, 80).

Example 173
5-Bromo-6-furan-2-yl-N4-(2-morpholin-4-yl-ethyl)-pyrimidine-2,4-diamine From 5-bromo-4-furan-2-yl-6-methanesulfinyl-pyrimidin-2-yl-amine and 4-(2-aminoethyl)morpholine in dioxane. ES-MS m/e (%): 370 (M{$^{81}$Br}+H$^+$, 100), 368 (M{$^{79}$Br}+H$^+$, 97).

Example 174
5-Chloro-6-furan-2-yl-N4-(2-phenylamino-ethyl)-pyrimidine-2,4-diamine From 5-chloro-4-furan-2-yl-6-methanesulfinyl-pyrimidin-2-yl-amine and N-phenylethylenediamine in DME. ES-MS m/e (%): 332 (M{$^{37}$Cl}+H$^+$, 40), 330 (M{$^{35}$Cl}+H+, 100).

Analogously to Example 162 there were obtained:

Example 175
4-[2-(2-Amino-6-furan-2-yl-5-nitro-pyrimidin-4-ylamino)-ethyl]-phenol From trifluoro-methanesulfonic acid 2-amino-6-furan-2-yl-5-nitro-pyrimidin-4-yl ester and tyramine in DME. ES-MS m/e (%): 400 ([M+OAc]$^-$, 20), 340 ([M—H]$^-$, 100).

Example 176
6-Furan-2-yl-5-nitro-N4-(2-phenylamino-ethyl)-pyrimidine-2,4-diamine From trifluoro-methanesulfonic acid 2-amino-6-furan-2-yl-5-nitro-pyrimidin-4-yl ester and N-phenylethylenediamine in DME. ES-MS m/e (%): 363 (M+Na$^+$, 20), 341 (M+H$^+$, 100).

Example 177
5-Fluoro-4-furan-2-yl-6-methylsulfanyl-pyrimidin-2-yl-amine a) (RS)-2-Fluoro-3-furan-2-yl-3-oxo-propionic Acid Ethyl Ester Following the method of Banks et al. (*J. Chem. Soc., Chem. Commun.* 1994, 343), to a stirred solution of 10.0 g (54.9 mmol) ethyl beta-oxo-2-furanpropionate in 500 ml acetonitrile at room temperature was added 19.4 g (54.9 mmol) 1-chloromethyl-4-fluoro-1,4-diazonia-bicyclo[2.2.2] octane bis(tetrafluoroborate) and stirring continued for 90 hours at room temperature. The reaction mixture was concentrated in vacuo and the residue resuspended in ether and washed sequentially with water and with brine. The organic phase was then dried over sodium sulfate and concentrated in vacuo to afford 8.72 g (79%) (RS)-2-fluoro-3-furan-2-yl-3-oxo-propionic acid ethyl ester as a yellow oil which was used in the next step without further purification. EI-MS m/e (%): 200 (M$^+$, 8), 155 ([M—OEt]$^+$, 4), 95 (100).

b) 2-Amino-5-fluoro-6-furan-2-yl-3H-pyrimidin-4-one

Following the method of Skulnick and Wierenga (Patent WO 86/04583), a mixture of 8.72 g (43.6 mmol) (RS)-2-fluoro-3-furan-2-yl-3-oxo-propionic acid ethyl ester and 8.89 g (49.3 mmol) guanidine carbonate in 30 ml ethanol was heated at 100° C. for 16 hours. The reaction mixture was then cooled to 0° C. and diluted with 100 ml water. 1M hydrochloric acid was added dropwise until the mixture was ca pH 3, whereupon the resulting crystals were collected by filtration and washed sequentially with water and with ether to afford 6.11 g (72%) 2-amino-5-fluoro-6-furan-2-yl-3H-pyrimidin-4-one as a brown crystalline solid. EI-MS m/e (%): 95 (M$^+$, 100), 154 ([M—MeCN]$^+$, 24).

c) Trifluoromethanesulfonic Acid 2-amino-5-fluoro-6-furan-2-yl-pyrimidin-4-yl Ester To a stirred suspension of 0.5 g (2.58 mmol) 2-amino-5-fluoro-6-furan-2-yl-3H-pyrimidin-4-one in 5 ml dichloromethane was added 1.16 ml (5.17 mmol) 2,6-di-tert-butylpyridine and the mixture was ultrasonicated for 30 minutes. 0.42 ml (2.55 mmol) triflic anhydride was then added dropwise at 0° C. with stirring and stirring continued at room temperature for 16 hours. The reaction mixture was then partitioned between water and dichloromethane and the organic phase was dried over sodium sulfate and concentrated in vacuo. The residue was recrystallised from ether/hexane and the resulting crystals (2,6-di-tert-butylpyridinium triflate) were removed by filtration. The mother liquor was concentrated in vacuo to afford 0.84 g (99%) trifluoromethanesulfonic acid 2-amino-5-fluoro-6-furan-2-yl-pyrimidin-4-yl ester as a brown crystalline solid. ES-MS m/e (%): 326 ([M—H]$^-$, 100).

d) 5-Fluoro-4-furan-2-yl-6-methylsulfanyl-pyrimidin-2-ylamine

A stirred solution of 260 mg (0.80 mmol) trifluoromethanesulfonic acid 2-amino-5-fluoro-6-furan-2-yl-pyrimidin-4-yl ester and 560 mg (7.99 mmol) sodium methanethiolate in 10 ml dry DME under argon was heated at 50° C. for 2 hours. The reaction mixture was then concentrated in vacuo. Flash chromatography (ethyl acetate/hexane 1/2) followed by trituration in ether/hexane afforded 65 mg (36%) 5-fluoro-4-furan-2-yl-6-methylsulfanyl-pyrimidin-2-ylamine as a white crystalline solid. EI-MS m/e (%): 225 (M$^+$, 100), 180 (28).

Example 178
5-Fluoro-4-furan-2-yl-6-(pyridin-2-ylmethoxy)-pyrimidin-2-yl-amine To a stirred solution of 260 mg (0.80 mmol) trifluoromethanesulfonic acid 2-amino-5-fluoro-6-furan-2-yl-pyrimidin-4-yl ester in 15 ml DME were added 0.27 ml (2.80 mmol) 2-(hydroxymethyl)pyridine and 0.12 ml (0.80 mmol) DBU and the mixture heated at 50° C. for 2 hour. The reaction mixture was then concentrated in vacuo. Chromatography (ethyl acetate) followed by trituration in dichloromethane/ether/hexane afforded 22 mg (10%) 5-fluoro-4-furan-2-yl-6-(pyridin-2-ylmethoxy)-pyrimidin-2-ylamine as a white crystalline solid. EI-MS m/e (%): 286 (M$^+$, 100), 107 (52).

Analogously to Example 163 there were obtained:

Example 179
N-4-Benzyl-5-chloro-6-furan-2-yl-pyrimidine-2,4-diamine

From 4-furan-2-yl-5-iodo-6-methanesulfinyl-pyrimidin-2-yl-amine and 4-(2-aminoethyl)morpholine in dioxane. ES-MS m/e (%): 416 (M+H$^+$, 100).

Example 180
6-Furan-2-yl-5-iodo-N4-(2-methoxy-ethyl)-pyrimidine-2,4-diaminee From 4-furan-2-yl-5-iodo-6-methanesulfinyl-pyrimidin-2-yl-amine and 2-methoxyethylamine in dioxane. ES-MS m/e (%): 361 (M+H$^+$, 100).

Example 181
6-Furan-2-yl-5-iodo-N4-[2-(4-methoxy-phenyl)-ethyl]-pyrimidine-2,4-diamine From 4-furan-2-yl-5-iodo-6-methanesulfinyl-pyrimidin-2-yl-amine and 2-(4-methoxyphenyl)ethylamine in dioxane. ES-MS m/e (%): 437 (M+H$^+$, 100).

Example 182
N-4-Benzyl-6-furan-2-yl-5-iodo-pyrimidine-2,4-diamine

From 4-furan-2-yl-5-iodo-6-methanesulfinyl-pyrimidin-2-yl-amine and benzylamine in dioxane. ES-MS m/e (%): 393 (M+H$^+$, 100).

Example 183
6-Furan-2-yl-5-iodo-N4-(2-phenylamino-ethyl)-pyrimidine-2,4-diamine From 4-furan-2-yl-5-iodo-6-methanesulfinyl-pyrimidin-2-yl-amine and N-phenylethylenediamine in dioxane. ES-MS m/e (%): 422 (M+H$^+$, 100).

Example 184
4-[2-(2-Amino-6-furan-2-yl-5-iodo-pyrimidin-4-ylamino)-ethyl]-phenol From 4-furan-2-yl-5-iodo-6-methanesulfinyl-pyrimidin-2-y-lamine and tyramine in dioxane. ES-MS m/e (%): 423 (M+H$^+$, 100).

Example 185
4-Furan-2-yl-5-iodo-6-(pyridin-2-ylmethoxy)-pyrimidin-2-yl-amine From 4-furan-2-yl-5-iodo-6-methanesulfinyl-pyrimidin-2-yl-amine, 2-(hydroxymethyl)pyridine and DBU in dioxane. ES-MS m/e (%): 395 (M+H$^+$, 100).

Example 186
4-[(2-Dimethylamino-ethoxy)-6-furan-2-yl-5-iodo-pyrimidin-2-yl-amine From 4-furan-2-yl-5-iodo-6-methanesulfinyl-pyrimidin-2-yl-amine, dimethylaminoethanol and DBU in dioxane. ES-MS me (%): 375 (M+H$^+$, 100).

Analogously to Example 162 there were obtained:

Example 187
6-Furan-2-yl-N4-[2-(4-methoxy-phenyl)-ethyl]-5-nitro-pyrimidine-2,4-diamine From trifluoro-methanesulfonic acid 2-amino-6-furan-2-yl-5-nitro-pyrimidin-4-yl ester and 2-(4-methoxyphenyl)ethylamine in DME. ES-MS m/e (%): 356 (M+H$^+$, 100).

Example 188
6-Furan-2-yl-N4-(2-morpholin-4-yl-ethyl)-5-nitro-pyrimidine-2,4-diamine From trifluoro-methanesulfonic acid 2-amino-6-furan-2-yl-5-nitro-pyrimidin-4-yl ester and 4-(2-aminoethyl)morpholine in DME. ES-MS m/e (%): 335 (M+H$^+$, 100).

Analogously to Example 178 there were obtained:

Example 189
N-4-Benzyl-5-fluoro-6-furan-2-yl-pyrimidine-2,4-diamine

From trifluoromethanesulfonic acid 2-amino-5-fluoro-6-furan-2-yl-pyrimidin-4-yl ester and benzylamine in DME. ES-MS m/e (%): 285 (M+H$^+$, 100).

Example 190
4-[2-(2-Amino-5-fluoro-6-furan-2-yl-pyrimidin-4-ylamino)-ethyl]-phenol From trifluoromethanesulfonic acid 2-amino-5-fluoro-6-furan-2-yl-pyrimidin-4-yl ester and tyramine in DME. ES-MS m/e (%): 315 (M+H$^+$, 100).

Example 191
5-Fluoro-6-furan-2-yl-N4-(2-phenylamino-ethyl)-pyrimidine-2,4-diamine From trifluoromethanesulfonic acid 2-amino-5-fluoro-6-furan-2-yl-pyrimidin-4-yl ester and N-phenylethylenediamne in DME. ES-MS m/e (%): 314 (M+H$^+$, 100).

Analogously to Example 162 there was obtained:

Example 192
6-Furan-2-yl-N4-(2-methoxy-ethyl)-5-nitro-pyrimidine-2,4-diamine From trifluoro-methanesulfonic acid 2-amino-6-furan-2-yl-5-nitro-pyrimidin-4-yl ester and 2-methoxyethylamine in DME. ES-MS m/e (%): 280 (M+H$^+$, 100).

Analogously to Example 178 there were obtained:

Example 193
5-Fluoro-6-furan-2-Yl-N4-[2-(4-methoxy-phenyl)-ethyl]-pyrimidine-2,4-diamine From trifluoromethanesulfonic acid 2-amino-5-fluoro-6-furan-2-yl-pyrimidin-4-yl ester and 2-(4-methoxyphenyl)ethylamine in DME. ES-MS m/e (%): 329 (M+H$^+$, 100).

Example 194
5-Fluoro-6-furan-2-yl-N4-(2-methoxy-ethyl)-pyrimidine-2,4-diamine From trifluoromethanesulfonic acid 2-amino-5-fluoro-6-furan-2-yl-pyrimidin-4-yl ester and 2-methoxyethylamine in DME. ES-MS m/e (%): 253 (M+H$^+$, 100).

Analogously to Example 163 there were obtained:

Example 195
5-Chloro-6-furan-2-yl-N4-[2-(4-methoxy-phenyl)-ethyl]2-pyrimidine-2,4-diamine From 5-chloro-4-furan-2-yl-6-methanesulfinyl-pyrimidin-2-y-lamine and 2-(4-methoxyphenyl)ethylamine in DME. ES-MS m/e (%): 347 (M{$^{37}$Cl}+H$^+$, 21), 345 (M{$^{35}$Cl}+H$^+$, 100).

Example 196
5-Chloro-6-furan-2-yl-N4-(2-methoxy-ethyl)-pyrimidine-2,4-diamine From 5-chloro-4-furan-2-yl-6-methanesulfinyl-pyrimidin-2-yl-amine and 2-methoxyethylamine in DME. ES-MS m/e (%): 271 (M{$^{37}$Cl}+H$^+$, 43), 269 (M{$^{35}$Cl}+H$^+$, 100).

Example 197
5-Chloro-6-furan-2-yl-N4-(2-morpholin-4-yl-e hyl)-pyrimidine-2,4-diamine From 5-chloro-4-furan-2-yl-6-methanesulfinyl-pyrimidin-2-yl-amine and 4-(2-aminoethyl)morpholine in DME. ES-MS m/e (%): 326 (M{$^{37}$Cl}+H$^+$, 55), 324 (M{$^{35}$Cl}+H$^+$, 100).

Analogously to Example 162 there was obtained:

Example 198
4-(2-Dimethylamino-ethoxy)-6-furan-2-yl-5-nitro-pyrimidin-2-yl-amine From trifluoro-methanesulfonic acid 2-amino-6-furan-2-yl-5-nitro-pyrimidin-4-yl ester, 2-dimethylaminoethanol and DBU in DME. ES-MS m/e (%): 294 (M+H$^+$, 100).

Example 199
2-Amino-4-benzylamino-6-thiophen-2-yl-pyrimidine-5-carbonitrile a) 2-Amino-4-methanesulfinyl-6-thiophen-2-yl-pyrimidine-5-carbonitrile To a stirred suspension of 2.65 g (10.7 mmol) 2-amino-4-(methylthio)-6-(2-thienyl)-pyrimidine-5-carbonitrile in 200 ml dichloromethane was added 2.79 g (10.7 mmol) 3-phenyl-2-(phenylsulfonyl)oxaziridine and stirring continued for 16 hours at room temperature. The resulting crystals were collected by filtration and washed with 30 ml dichloromethane to afford 1.54 g (55%) 2-amino-4-methanesulfinyl-6-thiophen-2-yl-pyrimidine-5-carbonitrile as a white crystalline solid. EI-MS m/e (%): 264 (M$^+$, 20), 218 (32), 201 (20), 159 (100).

b) 2-Amino-4-benzylamino-6-thiophen-2-yl-pyrimidine-5-carbonitrile

To a stirred suspension of 150 mg (0.57 mmol) 2-amino-4-methanesulfinyl-6-thiophen-2-yl-pyrimidine-5-carbonitrile in 3 ml dioxane was added 0.16 ml (1.42 mmol) benzylamine and the mixture heated at 100° C. for 30 minutes. The reaction mixture was then concentrated in vacuo. Chromatography (ethyl acetate/hexane 1/3) followed by trituration in ether/hexane afforded 118 mg (68%) 2-amino-4-benzylamino-6-thiophen-2-yl-pyrimidine-5-carbonitrile as a light yellow crystalline solid. ES-MS m/e (%): 308 (M+H$^+$, 100).

In an analogous manner there were obtained:

Example 200
2-Amino-4-[2-(4-methoxy-phenyl)-ethylamino]-6-thiophen-2-yl-pyrimidine-5-carbonitrile From 2-amino-4-methanesulfinyl-6-thiophen-2-yl-pyrimidine-5-carbonitrile and 2-(4-methoxyphenyl)ethylamine in dioxane. ES-MS m/e (%): 352 (M+H$^+$, 100).

Example 201
2-Amino-4-(2-morpholin-4-yl-ethylamino)-6-thiophen-2-yl-pyrimidine-5-carbonitrile From 2-amino-4-methanesulfinyl-6-thiophen-2-yl-pyrimidine-5-carbonitrile and 4-(2-aminoethyl)morpholine in dioxane. ES-MS m/e (%): 331 (M+H$^+$, 100).

Example 202
2-Amino-4-(2-phenylamino-ethylamino)-6-thiophen-2-yl-pyrimidine-5-carbonitrile From 2-amino-4-methanesulfinyl-6-thiophen-2-yl-pyrimidine-5-carbonitrile and N-phenylethylenediamine in dioxane. ES-MS m/e (%): 337 (M+H$^+$, 100).

Example 203
2-Amino-4-[2-(4-hydroxy-phenyl)-ethylamino]-6-thiophen-2-1-pyrimidine-5-carbonitrile From 2-amino-4-methanesulfinyl-6-thiophen-2-yl-pyrimidine-5-carbonitrile and tyramine in dioxane. ES-MS m/e (%): 338 (M+H$^+$, 100).

Example 204
2-Amino-4-(2-methoxy-ethylamino)-6-thiophen-2-yl-pyrimidine-5-carbonitrile From 2-amino-4-methanesulfinyl-6-thiophen-2-yl-pyrimidine-5-carbonitrile and 2-methoxyethylamine in dioxane. ES-MS m/e (%): 276 (M+H$^+$, 100).

Example 205
2-Amino-4-(2-dimethylamino-ethoxy)-6-thiophen-2-yl-pyrimidine-5-carbonitrile hydrochloride The free base 2-amino-4-(2-dimethylamino-ethoxy)-6-thiophen-2-yl-pyrimidine-5-carbonitrile was obtained from 2-amino-4-methanesulfinyl-6-thiophen-2-yl-pyrimidine-5-carbonitrile, 2-dimethylaminoethanol and DBU in dioxane. The free base was then converted to the hydrochloride salt with 2N ethereal HCl in ether at room temperature and recrystallised from methanol/acetonitrile/ether. ES-MS m/e (%): 290 (M+H$^+$, 100).

Example 206
2-Amino-4-(pyridin-2-ylmethoxy)-6-thiophen-2-yl-pyrimidine-5-carbonitrile From 2-amino-4-methanesulfinyl-6-thiophen-2-yl-pyrimidine-5-carbonitrile, 2-(hydroxymethyl)pyridine and DBU in dioxane. EI-MS m/e (%): 309 (M$^+$, 53), 308 ([M—H]$^+$, 48), 292 ([M—NH$_3$]$^+$, 32), 108 (100), 92 (50), 65 (49).

Example 207
2-Amino-4-(3-methyl-furan-2-yl)-6-methylsulfanyl-pyrimidine-5-carbonitrile a) 3-(3-Methyl-furan-2-yl)-3-oxo-propionitrile Following the method of Turner and Jacks (J. Org. Chem. 1989, 54, 4229), to a stirred solution of 9.4 ml (179 mmol) acetonitrile in 250 ml dry THF under argon at −78° C. was added dropwise 78.9 ml (78.9 mmol) lithium bis (trimethylsilyl)amide solution (1M in THF) and stirring continued for 30 minutes, after which a solution of 5.0 g (35.7 mmol) methyl 3-methyl-2-furoate in 20 ml THF was added dropwise and stirring continued while the reaction mixture was allowed to warm slowly to −20° C. The reaction mixture was then cannulated into a rapidly stirred solution of 1M hydrochloric acid at 0° C. The mixtured was extracted twice with ether and the combined organic phases dried over sodium sulfate and concentrated in vacuo. Chromatography (ethyl acetate/hexane 1/4) afforded 4.43 g (83%) 3-(3-methyl-furan-2-yl)-3-oxo-propionitrile as a yellow crystalline solid. EI-MS m/e (%): 149 (M$^+$, 20), 109 ([M—CH$_2$CN]$^+$, 100).

b) 2-(3-Methyl-furan-2-carbonyl)-3,3-bis-methylsulfanyl-acrylonitrile

Following the method of Rudorf and Augustin (Phosphorus and Sulfur 1981, 9, 329), a solution of 4.4 g (29.5 mmol) 3-(3-methyl-furan-2-yl)-3-oxo-propionitrile in 30 ml dry DMSO was added dropwise to a stirred suspension of 2,4 g (59.0 mmol, 60% dispersion in mineral oil) sodium hydride in 20 ml DMSO under argon at room temperature. 1.8 ml (29.5 mmol) carbon disulfide was then added dropwise, with external water bath cooling, and stirring continued for 1 hour, after which 3.7 ml (59.0 mmol) methyl iodide was added dropwise, with external water bath cooling, and stirring continued for a further 16 h. The reaction mixture was then poured into 2 l ice-cold water, and the precipitate collected by filtration and dried in vacuo to afford 7.45 g (99%) 2-(3-methyl-furan-2-carbonyl)-3,3-bis-methylsulfanyl-acrylonitrile as a pale yellow crystalline solid. ES-MS m/e (%): 271 (M+NH$_4$+, 33), 254 (M+H$^+$, 100).

c) 2-Amino-4-(3-methyl-furan-2-yl)-6-methylsulfanyl-pyrimidine-5-carbonitrile 6.32 g (39.5 mmol) guanidine carbonate was added portionwise to a stirred suspension of 0.7 g (17.5 mmol, 60% dispersion in mineral oil) sodium hydride in 70 ml DMF under argon at room temperature and stirring continued at 40° C. for 30 minutes. A solution of 7.4 g (29.2 mmol) 2-(3-methyl-furan-2-carbonyl)-3,3-bis-methylsulfanyl-acrylonitrile in 15 ml DMF was then added dropwise and the reaction mixture heated at 100° C. for 30 minutes. The reaction mixture was then poured onto 2 l ice-water, and the precipitate collected by filtration and dried in vacuo to afford 6.12 g (85%) 2-amino-4-(3-methyl-furan-2-yl)-6-methylsulfanyl-pyrimidine-5-carbonitrile as a yellow solid. ES-MS m/e (%): 247 (M+H$^+$, 100).

Analogously to Example 163 there were obtained:

Example 208
5-Bromo-6-furan-2-yl-N4-(3-phenyl-propyl)-pyrimidine-2,4-diamine hydrochloride The free base 5-bromo-6-furan-2-yl-N4-(3-phenyl-propyl)-pyrimidine-2,4-diamine was obtained from 5-bromo-4-furan-2-yl-6-methanesulfinyl-pyrimidin-2-ylamine and 3-phenylpropylamine in dioxane. The free base was then converted to the hydrochloride salt with 2N ethereal HCl in acetone at room temperature and recrystallised from acetone/ether. ES-MS m/e (%): 375 (M{$^{81}$Br}+H$^+$, 100), 373 (M{$^{79}$Br}+H$^+$, 95).

Example 209

5-Bromo-6-furan-2-yl-N4-phenethyl-pyrimidine-2,4-diamine hydrochloride

The free base 5-bromo-6-furan-2-yl-N4-phenethyl-pyrimidine-2,4-diamine was obtained from 5-bromo-4-furan-2-yl-6-methanesulfinyl-pyrimidin-2-ylamine and 3-phenethylamine in dioxane. The free base was then converted to the hydrochloride salt with 2N ethereal HCl in acetone at room temperature and recrystallised from acetone/ether. ES-MS m/e (%): 361 (M{$^{81}$Br}+H$^+$, 99), 359 (M{$^{79}$Br}+H$^+$, 100).

Example 210

5-Bromo-N4-butyl-6-furan-2-yl-pyrimidine-2,4-diamine hydrochloride

The free base 5-bromo-N4-butyl-6-furan-2-yl-pyrimidine-2,4-diamine was obtained from 5-bromo-4-furan-2-yl-6-methanesulfinyl-pyrimidin-2-ylamine and butylamine in dioxane. The free base was then converted to the hydrochloride salt with 2 N ethereal HCl in acetone at room temperature and recrystallised from acetone/ether. ES-MS m/e (%): 313 (M{$^{81}$Br}+H$^+$, 80), 311 (M{$^{79}$Br}+H$^+$, 100).

Example 211

5-Bromo-6-furan-2-yl-N4-propyl-pyrimidine-2,4-diamine hydrochloride

The free base 5-bromo-6-furan-2-yl-N4-propyl-pyrimidine-2,4-diamine hydrochloride was obtained from 5-bromo-4-furan-2-yl-6-methanesulfinyl-pyrimidin-2-ylamine and propylamine in dioxane. The free base was then converted to the hydrochloride salt with 2N ethereal HCl in acetone at room temperature and recrystallised from acetone/ether. ES-MS m/e (%): 299 (M{$^{81}$Br}+H$^+$, 99), 297 (M{$^{79}$Br}+H$^+$, 100).

Analogously to Example 199 there were obtained:

Example 212

2-Amino-4-(3-methyl-furan-2-yl)-6-(pyridin-2-ylmethoxy)-pyrimidine-5-carbonitrile From 2-amino-4-(3-methyl-furan-2-yl)-6-methylsulfanyl-pyrimidine-5-carbonitrile, 2-(hydroxymethyl)pyridine and DBU in DME. ES-MS m/e (%): 308 (M+H$^+$, 100).

Example 213

2-Amino-4-benzylamino-6-(3-methyl-furan-2-yl)-pyrimidine-5-carbonitrile

From 2-amino-4-(3-methyl-furan-2-yl)-6-methylsulfanyl-pyrimidine-5-carbonitrile and benzylamine in DME. EI-MS m/e (%): 305 (M$^+$, 40), 304 ([M—H]$^+$, 100).

Analogously to Example 163 there were obtained:

Example 214

5-Bromo-6-furan-2-yl-N4-methyl-pyrimidine-2,4-diamine

From 5-bromo-4-furan-2-yl-6-methanesulfinyl-pyrimidin-2-yl-amine and methylamine in ethanol. ES-MS m/e (°/o): 271 (M{$^{81}$Br}+H$^+$, 95), 269 (M{$^{79}$Br}+H$^+$, 100).

Example 215

5-Bromo-N4-ethyl-6-furan-2-yl-pyrimidine-2,4-diamine

From 5-bromo-4-furan-2-yl-6-methanesulfinyl-pyrimidin-2-yl-amine and ethylamine in THF. ES-MS m/e (%): 285 (M{$^{81}$Br}+H$^+$, 100), 283 (M{$^{79}$Br}+H$^+$, 95).

Example 216

5-Bromo-4-furan-2-yl-6-phenylsulfanyl-pyrimidin-2-yl-amine

From 5-bromo-4-furan-2-yl-6-methanesulfinyl-pyrimidin-2-yl-amine, thiophenol and DBU in dioxane. EI-MS m/e (%): 349 (M{$^{81}$Br}$^+$, 40), 348 ([M{$^{81}$Br}-H]$^+$, 28), 347 (M{$^{79}$Br}$^+$, 39), 346 ([M{$^{79}$Br}-H]$^+$, 24), 268 ([M—Br]$^+$, 100), 175 (92).

Example 217

4-Benzylsulfanyl-5-bromo-6-furan-2-yl-pyrimidin-2-yl-amine

From 5-bromo-4-furan-2-yl-6-methanesulfinyl-pyrimidin-2-yl-amine, benzylmercaptan and DBU in dioxane. EI-MS m/e (%): 363 (M{$^{81}$Br}$^+$, 48), 361 (M{$^{79}$Br}$^+$, 46), 282 ([M—Br]$^+$, 68), 249 (35), 91 (100).

Example 218

5-Bromo-4-ethylsulfanyl-6-furan-2-yl-pyrimidin-2-yl-amine

From 5-bromo-4-furan-2-yl-6-methanesulfinyl-pyrimidin-2-yl-amine, ethanethiol and DBU in dioxane. EI-MS m/e (%): 301 (M{$^{81}$Br}$^+$, 28), 299 (M{$^{79}$Br}$^+$, 27), 220 ([M—Br]$^+$, 100), 160 (30), 118 (24).

Analogously to Example 199 there was obtained:

Example 219

2-Amino-4-furan-2-yl-6-(pyridin-3-ylmethoxy)-pyrimidine-5-carbonitrile

From 2-amino-4-furan-2-yl-6-methanesulfinyl-pyrimidine-5-carbonitrile, 3-(hydroxymethyl)pyridine and DBU in DME. EI-MS m/e (%): 293 (M$^+$, 54), 276 ([M—NH$_3$]$^+$, 36), 92 (100), 65 (44), 39 (23).

Example 220

2-Amino-6-benzylsulfanyl-4-furan-2-yl-pyridine-3,5-dicarbonitrile

To a stirred solution of 150 mg (0.55 mmol) 6-amino-4-furan-2-yl-2-thioxo-1,2-dihydro-pyridine-3,5-dicarbonitrile in 20 ml methanol were added 0.11 ml (0.55 mmol) sodium methylate solutiuon (5.4M in methanol) and 0.15 ml (1.10 mmol) benzyl bromide and stirring continued for 90 minutes at room temperature. The reaction mixture was then poured onto 100 ml ice-water and the mixture extracted three times with dichloromethane. The combined organic phases were dried over sodium sulfate and concentrated in vacuo to afford, after trituration in ether, 80 mg (44%) 2-amino-6-benzylsulfanyl-4-furan-2-yl-pyridine-3,5-dicarbonitrile as a light brown crystalline solid. EI-MS m/e (%): 332 (M$^+$, 46), 331 ([M—H]$^+$, 30), 299 (29), 91 (100).

Analogously to Example 199 there was obtained:

Example 221

2-Amino-4-furan-2-yl-6-(pyridin-4-ylmethoxy)-pyrimidine-5-carbonitrile

From 2-amino-4-furan-2-yl-6-methanesulfinyl-pyrimidine-5-carbonitrile, 4-(hydroxymethyl)pyridine and DBU in DME. EI-MS m/e (%): 293 (M$^+$, 100), 92 (40), 65 (39).

Analogously to Example 163 there were obtained:

Example 222
4-Benzyloxy-5-bromo-6-furan-2-yl-pyrimidin-2-yl-amine

From 5-bromo-4-furan-2-yl-6-methanesulfinyl-pyrimidin-2-ylamine, benzylalcohol and DBU in dioxane. ES-MS m/e (%): 348 (M{$^{81}$Br}+H$^+$, 96), 346 (M{$^{79}$Br}+H$^+$, 100).

Example 223
5-Bromo-4-furan-2-yl-6-phenethyloxy-pyrimidin-2-yl-amine

From 5-bromo-4-furan-2-yl-6-methanesulfinyl-pyrimidin-2-yl-amine, phenylethanol and DBU in dioxane. ES-MS m/e (%): 362 (M{$^{81}$Br}+H$^+$, 96), 360 (M{$^{79}$Br}+H$^+$, 100), 258 ([M{$^{81}$Br}+H-PhCH=CH$_2$]$^+$, 55), 256 ([M{$^{81}$Br}+H-PhCH=CH$_2$]$^+$, 52).

Example 224
5-Bromo-4-furan-2-yl-6-(2-methoxy-ethoxy)-pyrimidin-2-yl-amine

From 5-bromo-4-furan-2-yl-6-methanesulfinyl-pyrimidin-2-yl-amine, 2-methoxyethanol and DBU in dioxane. ES-MS m/e (%): 316 (M{$^{81}$Br}+H$^+$, 96), 314 (M{$^{79}$Br}+H$^+$, 100), 258 ([M{$^{81}$Br}+H-MeOCH=CH$_2$]$^+$, 70), 256 ([M{$^{81}$Br}+H-MeOCH=CH$_2$]$^+$, 75).

Example 225
5-Bromo-4-furan-2-yl-6-phenoxy-pyrimidin-2-yl-amine

From 5-bromo-4-furan-2-yl-6-methanesulfinyl-pyrimidin-2-yl-amine, phenol and DBU in dioxane. EI-MS m/e (%): 333 (M{$^{81}$Br}$^+$, 64), 331 (M{$^{79}$Br}$^+$, 68), 252 ([M—Br]$^+$, 100), 159 (98).

Example 226
5-Bromo-4-ethoxy-6-furan-2-yl-pyrimidin-2-ylamine

From 5-bromo-4-furan-2-yl-6-methanesulfinyl-pyrimidin-2-yl-amine, ethanol and DBU in dioxane. ES-MS m/e (%): 286 (M{$^{81}$Br}+H$^+$, 99), 284 (M{$^{79}$Br}+H$^+$, 100), 258 ([M{$^{81}$Br}+H—CH$_2$=CH$_2$]$^+$, 52), 256 ([M{$^{81}$Br}+H—CH$_2$=CH$_2$]$^+$, 50).

Example 227
5-Bromo-4-furan-2-yl-6-phenoxy-pyrimidin-2-yl-amine

From 5-bromo-4-furan-2-yl-6-methanesulfinyl-pyrimidin-2-yl-amine, cyclohexanol and DBU in dioxane. EI-MS m/e (%): 339 (M{$^{81}$Br}$^+$, 15), 337 (M{$^{79}$Br}$^+$, 16), 257 ([M—C$_6$H$_{10}$]$^+$, 97), 255 ([M—C$_6$H]$^+$, 100).

Example 228
5-Bromo-4-ethoxy-6-furan-2-yl-pyrimidin-2-yl-amine

From 5-bromo-4-furan-2-yl-6-methanesulfinyl-pyrimidin-2-yl-amine, isopropanol and DBU in dioxane. EI-MS m/e (%): 299 (M{$^{81}$Br}$^+$, 43), 297 (M{$^{79}$Br}$^+$, 45), 257 ([M—C$_6$H$_{10}$]$^+$, 98), 255 ([M—C$_6$H$_{10}$]$^+$, 100), 206 (32), 94 (44), 43 (52).

Example 229
5-Bromo-4-butoxy-6-furan-2-yl-pyrimidin-2-yl-amine

From 5-bromo-4-furan-2-yl-6-methanesulfinyl-pyrimidin-2-yl-amine, butanol and DBU in dioxane. ES-MS m/e (%): 314 (M{$^{81}$Br}+H$^+$, 100), 312 (M{$^{79}$Br}+H$^+$, 98), 258 ([M{$^{81}$Br}+H-EtCH=CH$_2$]$^+$, 92), 256 ([M{$^8$Br}+H-EtCH=CH$_2$]$^+$, 90).

Example 230
5-Bromo-4-furan-2-yl-6-(3-phenyl-propoxy)-pyrimidin-2-yl-amine

From 5-bromo-4-furan-2-yl-6-methanesulfinyl-pyrimidin-2-yl-amine, 3-phenyl-1-propanol and DBU in dioxane. ES-MS m/e (%): 376 (M{$^{81}$Br}+H$^+$, 98), 374 (M{$^{79}$Br}+H$^+$, 100), 258 ([M{$^{81}$Br}+H-BnCH=CH$_2$]$^+$, 55), 256 ([M{$^{81}$Br}+H-BnCH=CH$_2$]$^+$, 50).

Analogously to Example 199 there was obtained:

Example 231
2-Amino-4-furan-2-yl-6-(2-1-phenylamino-ethoxy)-pyrimidine-5-carbonitrile From 2-amino-4-furan-2-yl-6-methanesulfinyl-pyrimidine-5-carbonitrile, N-(2-hydroxyethyl)aniline and DBU in DME. ES-MS m/e (%): 322 (M+H$^+$, 100).

Example 232
2-Amino-4-(5-methyl-furan-2-yl)-6-methylsulfanyl-pyrimidine-5-carbonitrile a) 5-Methyl-2-furoic acid Following the method of Shapiro et al. (*Khim. Geterotsikl. Soedin.* 1982, 11, 1463), to a stirred solution of 80.3 g (2.00 mol) sodium hydroxide in 330 ml water at 0–5° C. was added dropwise 18 ml (0.35 mol) bromine. 25 ml (0.25 mol) 5-methyl-2-furfural was then added dropwise over 90 minutes and stirring continued for a further 45 minutes at 0–5° C. The reaction mixture was then extracted with ether and the phases separated. The aqueous phase was acidified to pH 1 with concentrated hydrochloric acid and the resulting precipitate collected by filtration and dried in vacuo to afford 19.1 g (60%) 5-methyl-2-furoic acid as a beige crystalline solid. $^1$H NMR δ (CDCl$_3$, 250 MHz): 8.00–6.60 (1H, v. br. s), 7.24 (1H, d, J=3.4 Hz), 6.17 (1H, d, J=3.4 Hz), 2,42 (3H, s).

b) Methyl 5-methyl-2-furoate

To a stirred solution of 25.0 g (198 mmol) 5-methyl-2-furoic acid in 160 ml THF and 100 ml DMF were added 110 g (793 mmol) potassium carbonate and 49 ml (787 mmol) methyl iodide and stirring continued for 18 hours at room temperature. The reaction mixture was then filtered and the filtrate concentrated in vacuo. The residue was then partitioned between ether and water, the phases separated, and the aqueous phase further extracted with dichloromethane. The combined organic phases were dried over sodium sulfate and concentrated in vacuo. Chromatography (hexane then ethyl acetate/hexane 1/9) afforded 27.8 g (100%) methyl 5-methyl-2-furoate as a yellow oil. EI-MS m/e (%): 140 (M$^+$, 44), 109 ([M—OMe]$^+$, 100).

c) 3-(5-Methyl-furan-2-yl)-3-oxo-propionitrile

Following the method of Turner and Jacks (*J. Org. Chem.* 1989, 54, 4229), to a stirred solution of 5.6 ml (107 mmol) acetonitrile in 20 ml dry THF under argon at –78° C. was added dropwise 47.0 ml (47.09 mmol) lithium bis(trimethylsilyl)amide solution (1M in THF) and stirring continued for 30 minutes, after which a solution of 3.0 g (21.4 mmol) methyl 5-methyl-2-furoate in 20 ml THF was added dropwise and stirring continued while the reaction mixture was allowed to warm slowly to –20° C. The reaction mixture was then cannulated into a rapidly stirred solution of 1M hydrochloric acid at 0° C. The mixtured was extracted twice with ether and the combined organic phases dried over sodium sulfate and concentrated in vacuo. Chromatography (ethyl acetatephexane 1/1) afforded 1.77 g (55%) 3-(5-methyl-furan-2-yl)-3-oxo-propionitrile as a yellow crystalline solid. EI-MS m/e (%): 149 (M$^+$, 24), 109 ([M—CH$_2$CN]$^+$, 100), 53 (30).

d) 2-(5-Methyl-furan-2-carbonyl)-3,3-bis-methylsulfanyl-acrylonitrile

Following the method of Rudorf and Augustin (*Phosphorus and Sulfur* 1981, 9, 329), a solution of 1.77 g (11.9 mmol) 3-(5-methyl-furan-2-yl)-3-oxo-propionitrile in 10 ml dry DMSO was added dropwise to a stirred suspension of 0.95 g (23.7 mmol, 60% dispersion in mineral oil) sodium hydride in 10 ml DMSO under argon at room temperature. 0.72 ml (11.9 mmol) carbon disulfide was then added dropwise, with external water bath cooling, and stirring continued for 1 hour, after which 1.48 ml (23.7 mmol) methyl iodide was added dropwise, with external water bath cooling, and stirring continued for a further 1 h. The reaction mixture was then poured into 300 ml ice-cold water, and the precipitate collected by filtration and dried in vacuo to afford 2.67 g (89%) 2-(5-methyl-furan-2-carbonyl)-3,3-bis-methylsulfanyl-acrylonitrile as a yellow crystalline solid. ES-MS m/e (%): 254 (M+H$^+$, 100).

e) 2-Amino-4-(5-methyl-furan-2-yl)-6-methylsulfanyl-pyrimidine-5-carbonitrile 2.22 g (12.3 mmol) guanidine carbonate was added portionwise to a stirred suspension of 0.41 g (10.3 mmol, 60% dispersion in mineral oil) sodium hydride in 20 ml DMF under argon at room temperature and stirring continued at 40° C. for 1 hour. A solution of 2.60 g (10.3 mmol) 2-(5-methyl-furan-2-carbonyl)-3,3-bis-methylsulfanyl-acrylonitrile in 10 ml DMF was then added dropwise and the reaction mixture heated at 100° C. for 1 hour. The reaction mixture was then poured onto 700 ml ice-water, and the precipitate collected by filtration, washed with water then hexane, and dried in vacuo to afford 2.38 g (94%) 2-amino-4-(5-methyl-furan-2-yl)-6-methylsulfanyl-pyrimidine-5-carbonitrile as a yellow solid. EI-MS m/e (%): 246 (M$^+$, 64), 245 ([M—H]$^+$, 100).

Analogously to Example 199 there were obtained:

Example 233

2-Amino-4-furan-2-yl-6-phenethylsulfanyl-pyrimidine-5-carbonitrile From 2-amino-4-furan-2-yl-6-methanesulfinyl-pyrimidine-5-carbonitrile, 2-phenylethanethiol and DBU in DME. ES-MS m/e (%): 345 (M+Na$^+$, 14), 323 (M+H$^+$, 100).

Example 234

2-Amino-4-furan-2-yl-6-(3-phenyl-propylsulfanl)-pyrimidine-5-carbonitrile

From 2-amino-4-furan-2-yl-6-methanesulfinyl-pyrimidine-5-carbonitrile, 3-phenylpropanethiol and DBU in DME. ES-MS m/e (%): 359 (M+Na$^+$, 39), 337 (M+H$^+$, 100).

Example 235

2-Amino-4-furan-2-yl-6-(2-phenoxy-ethylamino)-pyrimidine-5-carbonitrile

From 2-amino-4-furan-2-yl-6-methanesulfinyl-pyrimidine-5-carbonitrile and 2-phenoxyethylamine in DME. ES-MS m/e (%): 322 (M+H$^+$, 100).

Analogously to Example 220 there was obtained:

Example 236

2-Amino-4-furan-2-yl-6-phenethylsulfanyl-pyridine-3,5-dicarbonitrile

From 6-Amino-4-furan-2-yl-2-thioxo-1,2-dihydro-pyridine-3,5-dicarbonitrile, 2-phenylethyl bromide and sodium methylate in methanol. EI-MS m/e (%): 346 (M$^+$, 4), 242 ([M—PhCH=CH$_2$]$^+$, 100), 91 (16).

Analogously to Example 199 there was obtained:

Example 237

2-Amino-4-furan-2-yl-6-(6-methyl-pyridin-2-ylmethoxy)-pyrimidine-5-carbonitrile

From 2-amino-4-furan-2-yl-6-methanesulfinyl-pyrimidine-5-carbonitrile, 6-methyl-2-pyridinemethanol and DBU in DME. ES-MS m/e (%): 330 (M+Na$^+$, 10), 308 (M+H$^+$, 100).

Analogously to Example 162 there were obtained:

Example 238

6-Furan-2-yl-5-nitro-N4-(3-phenyl-propyl)-pyrimidine-2,4-diamine

From trifluoro-methanesulfonic acid 2-amino-6-furan-2-yl-5-nitro-pyrimidin-4-yl ester and 3-phenylpropylamine in DME. ES-MS m/e (%): 340 (M+H$^+$, 100).

Example 239

6-Furan-2-yl-5-nitro-N4-phenethyl-pyrimidine-2,4-diamine

From trifluoro-methanesulfonic acid 2-amino-6-furan-2-yl-5-nitro-pyrimidin-4-yl ester and phenethylarnine in DME. ES-MS m/e (%): 326 (M+H$^+$, 100).

Analogously to Example 163 there was obtained:

Example 240

5-Bromo-4-butylsulfanyl-6-furan-2-yl-pyrimidin-2-yl-amine

From 5-bromo-4-furan-2-yl-6-methanesulfinyl-pyrimidin-2-yl-amine, butanethiol and DBU in dioxane. EI-MS m/e (%): 329 (M{$^{81}$Br}$^+$, 29), 327 (M{$^{79}$Br}$^+$, 28), 287 ([M{$^{81}$Br}-C$_3$H$_6$]$^+$, 46), 285 ([M{$^{79}$Br}—C$_3$H$_6$]$^+$, 45), 273 ([M{$^{81}$Br}—C$_4$H$_8$]$^+$, 98), 271 ([M{$^{79}$Br}—C$_4$H$_8$]$^+$, 99), 248 ([M—Br]$^+$, 54), 206 (100), 192 (34), 117 (34).

Analogously to Example 199 there were obtained:

Example 241

2-Amino-4-furan-2-yl-6-(2-pyridin-2-yl-ethoxy)-pyrimidine-5-carbonitrile

From 2-amino-4-furan-2-yl-6-methanesulfinyl-pyrimidine-5-carbonitrile, 2-(2-hydroxyethyl)pyridine and DBU in DME. ES-MS m/e (%): 308 (M+H$^+$, 100).

Example 242

(RS)-2-Amino-4-furan-2-yl-6-(1-pyridin-2-yl-ethoxy)-pyrimidine-5-carbonitrile

From 2-amino-4-furan-2-yl-6-methanesulfinyl-pyrimidine-5-carbonitrile, (RS)-alpha-methyl-2-pyridinemethanol and DBU in DME. ES-MS m/e (%): 308 (M+H$^+$, 100).

Example 243

(RS)-2-Amino-4-furan-2-yl-6-(1-methyl-piperidin-3-yloxy)-pyrimidine-5-carbonitrile From 2-amino-4-furan-2-yl-6-methanesulfinyl-pyrimidine-5-carbonitrile, 3-hydroxy-1-methylpiperidine and DBU in DME. ES-MS m/e (%): 300 (M+H$^+$, 100).

Analogously to Example 162 there was obtained:

Example 244

4-Furan-2-yl-5-nitro-6-(4-phenyl-butoxy)-pyrimidin-2-ylamine

From trifluoro-methanesulfonic acid 2-amino-6-furan-2-yl-5-nitro-pyrimidin-4-yl ester, 4-phenyl-1-butanol and DBU in DME. ES-MS ni/e (%): 355 (M+H$^+$, 100).

Analogously to Example 199 there were obtained:

Example 245

2-Amino-4-benzylamino-6-(5-methyl-furan-2-yl)-pyrimidine-5-carbonitrile

From 2-amino-4-methanesulfinyl-6-(5-methyl-furan-2-yl)-pyrimidine-5-carbonitrile and benzylamine in DME. ES-MS m/e (%): 306 (M+H$^+$, 100).

Example 246
2-Amino-4-(5-methyl-furan-2-yl)-6-(6-methyl-pyridin-2-ylmethoxy)-pyrimidine-5-carbonitrile From 2-amino-4-methanesulfinyl-6-(5-methyl-furan-2-yl)-pyrimidine-5-carbonitrile, 6-methyl-2-pyridinemethanol and DBU in DME. ES-MS m/e (%): 322 (M+H$^+$, 100).

Example 247
2-Amino-4-(5-methyl-furan-2-yl)-6-(pyridin-2-ylmethoxy)-pyrimidine-5-carbonitrile From 2-amino-4-methanesulfinyl-6-(5-methyl-furan-2-yl)-pyrimidine-5-carbonitrile, 2-(hydroxymethyl)pyridine and DBU in DME. ES-MS m/e (%): 308 (M+H$^+$, 100).

Example 248
2-Amino-4-ethoxy-6-(5-methyl-furan-2-yl)-pyrimidine-5-carbonitrile From 2-amino-4-methanesulfinyl-6-(5-methyl-furan-2-yl)-pyrimidine-5-carbonitrile, ethanol and DBU in DME. ES-MS m/e (%): 245 (M+H$^+$, 100), 217 ([M+H—CH$_2$=CH$_2$]$^+$, 80).

Example 249
2-Amino-4-(5-methyl-furan-2-yl)-6-(2-phenylamino-ethylamino)-pyrimidine-5-carbonitrile From 2-amino-4-methanesulfinyl-6-(5-methyl-furan-2-yl)-pyrimidine-5-carbonitrile and phenylethylenediamine in DME. ES-MS m/e (%): 335 (M+H$^+$, 100), 242 ([M+H-PhNH$_2$]$^+$, 30).

Example 250
2-Amino-4-furan-2-yl-6-(tetahydro-pyran-4-yloxy)-pyrimidine-5-carbonitrile From 2-amino-4-furan-2-yl-6-methanesulfinyl-pyrimidine-5-carbonitrile, tetrahydro-2H-pyran-4-ol and DBU in DME. ES-MS m/e (%): 304 (M+NH$_4^+$, 23), 287 (M+H$^+$, 100), 203 ([M+H-C$_5$H$_8$O]$^+$, 30).

Example 251
2-Amino-4-furan-2-yl-6-(1-methyl-piperidin-4-yloxy)-pyrimidine-5-carbonitrile From 2-amino-4-furan-2-yl-6-methanesulfinyl-pyrimidine-5-carbonitrile, 4-hydroxy-1-methylpiperidine and DBU in DME. ES-MS m/e (%): 300 (M+H$^+$, 100).

Analogously to Example 163 there were obtained:

Example 252
5-Bromo-4-furan-2-yl-6-(2-molpholin-4-yl-ethoxy)-pyrimidin-2-ylamine From 5-bromo-4-furan-2-yl-6-methanesulfinyl-pyrimidin-2-ylamine, N-(2-hydroxyethyl)morpholine and DBU in dioxane. ES-MS m/e (%): 371 (M{$^{81}$Br}+H$^+$, 100), 369 (M{$^{79}$Br}+H$^+$, 93).

Example 253
6-Furan-2-yl-5-iodo-N4-(3-phenyl-propyl)-pyrimidine-2,4-diamine

From 4-furan-2-yl-5-iodo-6-methanesulfinyl-pyrimidin-2-yl-amine and 3-phenylpropylamine in THF. ES-MS m/e (%): 421 (M+H$^+$, 100).

Example 254
6-Furan-2-yl-5-iodo-N4-phenethyl-pyrimidine-2,4-diamine hydrochloride The free base 6-furan-2-yl-5-iodo-N4-phenethyl-pyrimidine-2,4-diamine was obtained from 4-furan-2-yl-5-iodo-6-methanesulfinyl-pyrimidin-2-yl-amine and phenethylamine in THF. The free base was then converted to the hydrochloride salt with 2 N ethereal HCl in ether at room temperature. ES-MS m/e (%): 407 (M+H$^+$, 100).

Example 255
N4-Butyl-6-furan-2-yl-5-iodo-pyrimidine-2,4-diamine

From 4-furan-2-yl-5-iodo-6-methanesulfinyl-pyrimidin-2-yl-amine and butylamine in THF. ES-MS m/e (%): 359 (M+H$^+$, 100).

Example 256
6-Furan-2-yl-5-iodo-N4-propyl-pyrimidine-2,4-diamine

From 4-furan-2-yl-5-iodo-6-methanesulfinyl-pyrimidin-2-yl-amine and propylamine in THF. ES-MS m/e (%): 345 (M+H$^+$, 100).

Example 257
6-Furan-2-yl-5-iodo-N4-methyl-pyrimidine-2,4-diamine

From 4-furan-2-yl-5-iodo-6-methanesulfinyl-pyrimidin-2-yl-amine and methylamine in THF/ethanol. ES-MS m/e (%): 317 (M+H$^+$, 100).

Example 258
N4-Ethyl-6-furan-2-yl-5-iodo-pyrimidine-2,4-diamine

From 4-furan-2-yl-5-iodo-6-methanesulfinyl-pyrimidin-2-yl-amine and ethylamine in THF. ES-MS m/e (%): 331 (M+H$^+$, 100).

Example 259
4-Benzyloxy-6-furan-2-yl-5-iodo-pyrimidin-2-yl-amine

From 4-furan-2-yl-5-iodo-6-methanesulfinyl-pyrimidin-2-yl-amine, benzyl alcohol and DBU in THF. ES-MS m/e (%): 394 (M+H$^+$, 100).

Example 260
4-Furan-2-yl-5-iodo-6-phenethyloxyy-pyrimidin-2-yl-amine

From 4-furan-2-yl-5-iodo-6-methanesulfinyl-pyrimidin-2-yl-amine, phenethyl alcohol and DBU in THF. ES-MS m/e (%): 408 (M+H$^+$, 100).

Example 261
4-Furan-2-yl-5-iodo-6-phenoxy-pyrimidin-2-ylamine

From 4-furan-2-yl-5-iodo-6-methanesulfinyl-pyrimidin-2-yl-amine, phenol and DBU in THF. ES-MS m/e (%): 380 (M+H$^+$, 100).

Example 262
4-Furan-2-yl-5-iodo-6-(2-methoxy-ethoxy)-pyrimidin-2-yl-amine

From 4-furan-2-yl-5-iodo-6-methanesulfinyl-pyrimidin-2-yl-amine, 2-methoxyethanol and DBU in THF. ES-MS m/e (%): 362 (M+H$^+$, 100).

Example 263
4-Ethoxy-6-furan-2-yl-5-iodo-pyrimidin-2-yl-amine

From 4-furan-2-yl-5-iodo-6-methanesulfinyl-pyrimidin-2-yl-amine, ethanol and DBU in THF. ES-MS m/e (%): 332 (M+H$^+$, 100).

Example 264
4-Cyclohexyloxy-6-furan-2-yl-5-iodo-pyrimidin-2-yl-amine

From 4-furan-2-yl-5-iodo-6-methanesulfinyl-pyrimidin-2-yl-amine, cyclohexanol and DBU in THF. ES-MS m/e (%): 386 (M+H$^+$, 100).

Example 265
4-Furan-2-yl-5-iodo-6-isopropoxy-pyrimidin-2-yl-amine

From 4-furan-2-yl-5-iodo-6-methanesulfinyl-pyrimidin-2-yl-amine, isopropanol and DBU in THF. ES-MS m/e (%): 346 (M+H$^+$, 100).

Example 266
4-Butoxy-6-furan-2-yl-5-iodo-pyrimidin-2-y-lamine

From 4-furan-2-yl-5-iodo-6-methanesulfinyl-pyrimidin-2-yl-amine, butanol and DBU in THF. ES-MS m/e (%): 360 (M+H$^+$, 100).

Example 267
4-Furan-2-yl-5-iodo-6-(3-phenyl-propoxy)-pyrimidin-2-yl-amine

From 4-furan-2-yl-5-iodo-6-methanesulfinyl-pyrimidin-2-yl-amine, 3-phenylpropanol and DBU in THF. ES-MS m/e (%): 422 (M+H$^+$, 100).

Example 268
4-Furan-2-yl-5-iodo-6-(2-morpholin-4-yl-ethoxy)-pyrimidin-2-yl-amine From 4-furan-2-yl-5-iodo-6-methanesulfinyl-pyrimidin-2-yl-amine, N-(2-hydroxyethyl)morpholine and DBU in THF. ES-MS m/e (%): 417 (M+H$^+$, 100).

Example 269
5-Bromo-4-furan-2-yl-6-phenethylsulfanyl-pyrimidin-2-yl-amine

From 5-bromo-4-furan-2-yl-6-methanesulfinyl-pyrimidin-2-ylamine, phenethylmercaptan and DBU in THF. ES-MS m/e (%): 378 (M{$^{81}$Br}+H$^+$, 100), 376 (M{$^{79}$Br}+H$^+$, 99).

Analogously to Example 162 there were obtained:

Example 270
N-4-Butyl-6-furan-2-yl-5-nitro-pyrimidine-2,4-diamine

From trifluoro-methanesulfonic acid 2-amino-6-furan-2-yl-5-nitro-pyrimidin-4-yl ester and butylamine in DME. ES-MS m/e (%): 278 (M+H$^+$, 100).

Example 271
4-Furan-2-yl-5-nitro-6-phenethyloxy-pyrimidin-2-yl-amine

From trifluoro-methanesulfonic acid 2-amino-6-furan-2-yl-5-nitro-pyrimidin-4-yl ester, phenethylalcohol and DBU in DME. ES-MS m/e (%): 327 (M+H$^+$, 100).

Example 272
4-Benzylsulfanyl-6-furan-2-yl-5-nitro-pyrimidin-2-yl-amine

From trifluoro-methanesulfonic acid 2-amino-6-furan-2-yl-5-nitro-pyrimidin-4-yl ester, benzylmercaptan and DBU in DME. ES-MS m/e (%): 329 (M+H$^+$, 100).

Analogously to Example 199 there were obtained:

Example 273
2-Amino-4-cyclohexyloxy-6-(5-methyl-furan-2-yl)-pyrimidine-5-carbonitrile From 2-amino-4-(5-methyl-furan-2-yl)-6-methylsulfanyl-pyrimidine-5-carbonitrile, cyclohexanol and DBU in DME. ES-MS m/e (%): 299 (M+H$^+$, 50), 217 (M+H—C$_6$H$_{10}$$^+$, 100).

Example 274
2-Amino-6-ethoxy-4-furan-2-yl-pyridine-3,5-dicarbonitrile
a) 2-Amino-4-furan-2-yl-6-methanesulfinyl-pyridine-3,5-dicarbonitrile To a stirred suspension of 680 mg (2.66 mmol) 2-amino-4-furan-2-yl-6-methylsulfanyl-pyridine-3,5-dicarbonitrile in 25 ml dichloromethane was added 1,39 g (5.32 mmol) 3!phenyl-2-(phenylsulfonyl)oxaziridine and stirring continued for 48 hours at room temperature. The resulting crystals were collected by filtration and washed with cold dichloromethane to afford 670 mg (93%) 2-amino-4-furan-2-yl-6-methanesulfinyl-pyridine-3,5-dicarbonitrile as a light brown crystalline solid. ES-MS m/e (%): 295 (M+Na+, 70), 273 (M+H$^+$, 100).

b) 2-Amino-6-ethoxy-4-furan-2-yl-pyridine-3,5-dicarbonitrile

To a stirred suspension of 300 mg (1.10 mmol) 2-amino-4-furan-2-yl-6-methanesulfinyl-pyridine-3,5-dicarbonitrile in 15 ml dry DME were added 0.23 ml (3.86 mmol) ethanol and 0.25 ml (1.65 mmol) DBU and stirring continued for 2 hours at room temperature. The reaction mixture was then concentrated in vacuo. Chromatography (ethyl acetate/hexane 1/4) followed by trituration in ether/hexane afforded 21 mg (8%) 2-amino-6-ethoxy-4-furan-2-yl-pyridine-3,5-dicarbonitrile as a light yellow crystalline solid. EI-MS m/e (%): 254 (M$^+$, 90), 226 (100), 198 (44), 143 (26).

In an analogous manner there were obtained:

Example 275
2-Amino-6-cyclohexyloxy-4-furan-2-yl-pyridine-3,5-dicarbonitrile From 2-amino-4-furan-2-yl-6-methanesulfinyl-pyridine-3,5-dicarbonitrile, cyclohexanol and DBU in DME. EI-MS m/e (%): 308 (M$^+$, 12), 226 ([M—C$_6$H$_{10}$]$^-$, 100).

Example 276
2-Amino-4-furan-2-yl-6-(pyridin-2-ylmethoxy)-pyridine-3,5-dicarbonitrile From 2-amino-4-furan-2-yl-6-methanesulfinyl-pyridine-3,5-dicarbonitrile, 2-(hydroxymethyl)pyridine and DBU in DME. EI-MS m/e (%): 317 (M$^+$, 66), 92 (100), 65 (55).

Analogously to Example 162 there was obtained:

Example 277
4-Butoxy-6-furan-2-yl-5-nitro-pyrimidin-2-yl-amine

From trifluoro-methanesulfonic acid 2-amino-6-furan-2-yl-5-nitro-pyrimidin-4-yl ester, butanol and DBU in DME. EI-MS m/e (%): 278 (M$^+$, 24), 249 ([M—C$_2$H$_5$]$^+$, 28), 193 (70), 177 (100), 150 (48), 108 (86), 94 (62), 70 (48), 69 (46), 43 (68), 41 (62), 29 (45).

Analogously to Example 199 there were obtained:

Example 278
2-Amino-4-furan-2-yl-6-(3-phenyl-allyloxy)-pyrimidine-5-carbonitrile From 2-amino-4-furan-2-yl-6-methanesulfinyl-pyrimidine-5-carbonitrile, (E)-cinnamyl alcohol and DBU in DME. ES-MS m/e (%): 319 (M+H$^+$, 100).

Example 279
(RS)-2-Amino-4-(5-methyl-furan-2-yl)-6-(1-pyridin-2-yl-ethoxy)-pyrimidine-5-carbonitrile From 2-amino-4-(5-methyl-furan-2-yl)-6-methylsulfanyl-pyrimidine-5-carbonitrile, (RS)-alpha-methyl-2-pyridinemethanol and DBU in DME. ES-MS m/e (%): 344 (M+Na$^+$, 20), 322 (M+H$^+$, 100).

Analogously to Example 163 there was obtained:

Example 280
5-Bromo-4-furan-2-yl-6-(3-phenyl-allyloxy)-pyrimidin-2-yl-amine

From 5-bromo-4-furan-2-yl-6-methanesulfinyl-pyrimidin-2-yl-amine, (E)-cinnamyl alcohol and DBU in dioxane. EI-MS m/e (%): 373 (M{$^{81}$Br}$^+$, 4), 371 (M{$^{79}$Br}$^+$, 4), 292 ([M—Br]$^+$, 8),202 (14), 117(100), 115 (38),91 (17).

Analogously to Example 162 there were obtained:

Example 281
6-Furan-2-yl-N4-methyl-5-nitro-pyrimidine-2,4-diamine

From trifluoromethanesulfonic acid 2-amino-6-furan-2-yl-5-nitro-pyrimidin-4-yl ester and methylamine in DME. ES-MS m/e(%): 236 (M+H$^+$, 100).

Example 282
N4-Ethyl-6-furan-2-yl-5-nitro-pyrimidine-2,4-diamine

From trifluoromethanesulfonic acid 2-amino-6-furan-2-yl-5-nitro-pyrimidin-4-yl ester and ethylamine in DME. ES-MS m/e (%): 250 (M+H$^+$, 100).

Analogously to Example 199 there was obtained:

Example 283
2-Amino-4-furan-2-yl-6-[(pyridin-2-ylmethyl)-amino]-pyrimidine-5-carbonitrile From 2-amino-4-furan-2-yl-6-methanesulfinyl-pyrimidine-5-carbonitrile and 2-(aminomethyl)pyridine in DME. ES-MS m/e (%): 293 (M+H$^+$, 100).

Example 284
2-Amino-4-furan-2-yl-6-(pyridin-2-ylmethylsulfanyl)-pyrimidine-5-carbonitrile a) 2-Amino-4-furan-2-yl-6-thioxo-1,6-dihydro-pyrimidine-5-carbonitrile To a stirred solution of 1.1 g (4.74 mmol) 2-amino-4-(2-furyl)-6-(methylthio)-pyrimidine-5-carbonitrile in 15 ml ethanol under argon was added 1.05 g (14.2 mmol) sodium thiolate and the mixture heated at reflux for 16 h. The reaction mixture was then cooled to room temperature, 20 ml water added, and the mixture made slightly acidic by dropwise addition of concentrated hydrochloric acid. The resulting crystals were collected by filtration, washed with water, and dried in vacuo to afford 0.90 g (87%) 2-amino-4-furan-2-yl-6-thioxo-1,6-dihydro-pyrimidine-5-carbonitrile as a yellow crystalline solid. ES-MS m/e (%): 217 ([M—H]$^-$, 100).

b) 2-Amino-4-furan-2-yl-6-(pyridin-2-ylmethylsulfanyl)-pyrimidine-5-carbonitrile To a stirred solution of 200 mg (0.92 mmol) 2-amino-4-furan-2-yl-6-thioxo-1,6-dihydro-pyrimidine-5-carbonitrile in 10 ml ethanol were added 0.69 (1.84 mmol) sodium ethylate solution (2.67M in ethanol) and 117 mg (0.92 mmol) 2-(chloromethyl)pyridine hydrochloride and stirring continued for 16 hours at room temperature. The reaction mixture was then concentrated in vacuo and the residue partitioned between dichloromethane and water. The organic phase was dried over sodium sulfate and concentrated in vacuo. The residue was triturated in ether to afford 205 mg (72%) 2-amino-4-furan-2-yl-6-(pyridin-2-ylmethylsulfanyl)-pyrimidine-5-carbonitrile as a white crystalline solid. ES-MS m/e (%): 310 (M+H$^+$, 100).

Analogously to Example 162 there were obtained:

Example 285
4-Cyclohexyloxy-6-furan-2-yl-5-nitro-pyrimidin-2-yl-amine

From trifluoromethanesulfonic acid 2-amino-6-furan-2-yl-5-nitro-pyrimidin-4-yl ester, cyclohexanol and DBU in DME. ES-MS m/e (%): 305 (M+H$^+$, 100), 223 ([M+H—C$_6$H$_{10}$]$^+$, 80).

Example 286
4-Benzyloxy-6-furan-2-yl-5-nitro-pyrimidin-2-yl-amine

From trifluoromethanesulfonic acid 2-amino-6-furan-2-yl-5-nitro-pyrimidin-4-yl ester, benzyl alcohol and DBU in DME. ES-MS m/e (%): 313 (M+H$^+$, 100).

Example 287
6-Furan-2-yl-5-nitro-N4-propyl-pyrimidine-2,4-diamine

From trifluoromethanesulfonic acid 2-amino-6-furan-2-yl-5-nitro-pyrimidin-4-yl ester and propylamine in DME. ES-MS m/e (%): 264 (M+H$^+$, 100).

Analogously to Example 199 there were obtained:

Example 288
2-Amino-4-furan-2-yl-6-(2-methyl-benzylamino)-pyrimidine-5-carbonitrile From 2-amino-4-furan-2-yl-6-methanesulfinyl-pyrimidine-5-carbonitrile and 2-methylbenzylamine in DME. ES-MS m/e (%:306 (M+H$^+$, 100).

Example 289
2-Amino-4-furan-2-yl-6-(3-methyl-benzylamino)-pyrimidine-5-carbonitrile From 2-amino-4-furan-2-yl-6-methanesulfinyl-pyrimidine-5-carbonitrile and 3-methylbenzylamine in DME. ES-MS m/e (%): 306 (M+H$^+$, 100).

Example 290
2-Amino-4-furan-2-yl-6-(4-methyl-benzylamino)-pyrimidine-5-carbonitrile From 2-amino-4-furan-2-yl-6-methanesulfinyl-pyrimidine-5-carbonitrile and 4-methylbenzylamine in DME. ES-MS m/e (%): 306 (M+H$^+$, 100).

Example 291
2-Amino-4-furan-2-yl-6-(3-methoxy-benzylamino)-pyrimidine-5-carbonitrile From 2-amino-4-furan-2-yl-6-methanesulfinyl-pyrimidine-5-carbonitrile and 3-methoxybenzylamine in DME. ES-MS m/e (%): 322 (M+H$^+$, 100).

Example 292
2-Amino-4-furan-2-yl-6-(4-methoxy-benzylamino)-pyrimidine-5-carbonitrile From 2-amino-4-furan-2-yl-6-methanesulfinyl-pyrimidine-5-carbonitrile and 4-methoxybenzylamine in DME. ES-MS m/e (%): 322 (M+H$^+$, 100).

Example 293
2-Amino-4-furan-2-yl-6-(2-methoxy-benzylamino)-pyrimidine-5-carbonitrile From 2-amino-4-furan-2-yl-6-methanesulfinyl-pyrimidine-5-carbonitrile and 2-methoxybenzylamine in DME. ES-MS m/e (%): 322 (M+H$^+$, 100).

Example 294
2-Amino-4-(2-benzylamino-ethylamino)-6-furan-2-yl-pyrimidine-5-carbonitrile From 2-amino-4-furan-2-yl-6-methanesulfinyl-pyrimidine-5-carbonitrile and benzylethylenediamine in DME. ES-MS m/e (%): 335 (M+H$^+$, 100), 228 ([M+H-BnNH$_2$]$^+$, 45).

Example 295
N-[2-(2-Amino-5-cyano-6-furan-2-yl-pyrimidin-4-ylamino)-ethyl]-4-chloro-benzenesulfonamide From 2-amino-4-furan-2-yl-6-methanesulfinyl-pyrimidine-5-carbonitrile, N-(2-aminoethyl)-p-chlorobenzenesulfonamide hydrochloride and DBU in DME. ES-MS m/e (%): 419 (M+H$^+$, 100).

Example 296
(RS)-2-Amino-4-furan-2-yl-6-[(1-methyl-1,2,3,4-tetrahydro-quinolin-2-ylmethyl)-amino]-pyrimidine-5-carbonitrile From 2-amino-4-furan-2-yl-6-methanesulfinyl-pyrimidine-5-carbonitrile, 2-(aminomethyl)-1,2,3,4- tetrahydro-1-methyl-quinoline hydrochloride and DBU in DME. ES-MS m/e (%): 361 (M+H+, 100).

Example 297
2-Amino-4-furan-2-yl-6-[(quinolin-2-ylmethyl)-amino]-pyrimidine-5-carbonitrile From 2-amino-4-furan-2-yl-6-methanesulfinyl-pyrimidine-5-carbonitrile, 2-aminomethyl-quinoline dihydrochloride and DBU in DME. ES-MS m/e (%): 343 (M+H+, 100).

Example 298
2-Amino-4-furan-2-yl-6-[(naphthalen-2-ylmethyl)-amino]-pyrimidine-5-carbonitrile From 2-amino-4-furan-2-yl-6-methanesulfinyl-pyrimidine-5-carbonitrile and C-Naphthalen-2-yl-methylamine in DME. ES-MS m/e (%): 342 (M+H+, 100).

Example 299
(RS)-2-Amino-4-furan-2-yl-6-[(1,2,3,4-tetrahydro-quinolin-2-ylmethyl)-amino]-pyrimidine-5-carbonitrile From 2-amino-4-furan-2-yl-6-methanesulfinyl-pyrimidine-5-carbonitrile, 2-(aminomethyl)-1,2,3,4-tetrahydroquinoline hydrochloride and DBU in DME. ES-MS m/e (%): 347 (M+H+, 100).

Example 300
N-[2-(2-Amino-5-cyano-6-furan-2-yl-pyrimidin-4-ylamino)-ethyl]-benzenesulfonamide From 2-amino-4-furan-2-yl-6-methanesulfinyl-pyrimidine-5-carbonitrile, N-(2-amino-ethyl)-benzenesulfonamide hydrochloride and DBU in DME. ES-MS m/e (%): 385 (M+H+, 100).

Example 301
2-Amino-4-furan-2-yl-6-(4-methanesulfonyl-benzylamino)-pyrimidine-5-carbonitrile From 2-amino-4-furan-2-yl-6-methanesulfinyl-pyrimidine-5-carbonitrile, 4-methanesulfonylbenzylamine hydrochloride and DBU in DME. ES-MS m/e (%): 370 (M+H+, 100).

Example 302
2-Amino-4-furan-2-yl-6-(2-phenylsulfanyl-ethylamino)-pyrimidine-5-carbonitrile From 2-amino-4-furan-2-yl-6-methanesulfinyl-pyrimidine-5-carbonitrile and 2-aminoethyl phenyl sulfide in DME. ES-MS m/e (%): 338 (M+H+, 100).

Example 303
2-Amino-4-furan-2-yl-6-(naphthalen-2-ylmethoxy)-pyrimidine-5-carbonitrile From 2-amino-4-furan-2-yl-6-methanesulfinyl-pyrimidine-5-carbonitrile, 2-naphthalenemethanol and DBU in DME. ES-MS m/e (%): 343 (M+H+, 100).

Example 304
2-Amino-4-(2-amino-benzylamino)-6-furan-2-yl-pyrimidine-5-carbonitrile From 2-amino-4-furan-2-yl-6-methanesulfinyl-pyrimidine-5-carbonitrile and 2-aminobenzylamine in DME. ES-MS m/e (%): 307 (M+H+, 100).

Example 305
2-Amino-4-(4-amino-benzylamino)-6-furan-2-yl-pyrimidine-5-carbonitrile From 2-amino-4-furan-2-yl-6-methanesulfinyl-pyrimidine-5-carbonitrile and 4-aminobenzylamine in DME. ES-MS m/e (%): 307 (M+H+, 100).

Example 306
2-Amino-4-(2-benzenesulfonyl-ethylamino)-6-furan-2-yl-pyrimidine-5-carbonitrile From 2-amino-4-furan-2-yl-6-methanesulfinyl-pyrimidine-5-carbonitrile, N-(2-amino-ethyl)-benzenesulfonamide hydrochloride and DBU in DME. ES-MS m/e (%): 370 (M+H+, 100).

Example 307
4-Furan-2-yl-5-methylsulfanylmethyl-pyrimidin-2-ylamine a) 1-Furan-2-yl-2-methyl-3,3-bis-methylsulfanyl-propenone Following the method of Rudorf and Augustin (*Phosphorus and Sulfur* 1981, 9, 329), a solution of 2.08 g (16.8 mmol) 1-(2-furyl)-1-propanone in 30 ml dry DMSO was added dropwise to a stirred suspension of 1,35 g (33.6 mmol, 60% dispersion in mineral oil) sodium hydride in 30 ml DMSO under argon at room temperature. 1.00 ml (16.8 mmol) carbon disulfide was then added dropwise, with external water bath cooling, and stirring continued for 1 hour, after which 2.09 ml (33.6 mmol) methyl iodide was added dropwise, with external water bath cooling, and stirring continued for a further 2 h. The reaction mixture was then poured into 11 ice-cold water, and the mixture extracted three times with ethyl acetate. The combined organic phases were washed three times with water, dried over sodium sulfate, and concentrated in vacuo. Chromatography (ethyl acetate/hexane 1/4) afforded 1.98 g (51%) 1-furan-2-yl-2-methyl-3,3-bis-methylsulfanyl-propenone as an orange oil. EI-MS m/e (%): 228 (M+, 21), 213 ([M—CH$_3$]+, 42), 211 ([M—OH]+, 41), 95 (100).

b) 4-Furan-2-yl-5-methylsulfanylmethyl-pyrimidin-2-ylamine 1.61 g (8.93 mmol) guanidine carbonate was added portionwise to a stirred suspension of 0.3 g (7.45 mmol, 60% dispersion in mineral oil) sodium hydride in 15 ml DMF under argon at room temperature and stirring continued at 40° C. for 30 minutes. A solution of 1.7 g (7.45 mmol) 1-furan-2-yl-2-methyl-3,3-bis-methylsulfanyl-propenone in 15 ml DMF was then added dropwise and the reaction mixture heated at 100° C. for 24 hours and at 120° C. for 4 hours. The reaction mixture was then poured onto 500 ml ice-water, and the mixture extracted three times with ethyl acetate. The combined organic phases were washed three times with water, dried over sodium sulfate, and concentrated in vacuo. The residue was triturated in dichloromethane/ethyl acetate/ether to afford 500 mg (30%) 4-furan-2-yl-5-methylsulfanylmethyl-pyrimidin-2-ylamine as a beige crystalline solid. ES-MS m/e (%): 222 (M+H+, 100).

Analogously to Example 199 there were obtained:

Example 308
2-Amino-4-[2-(3-amino-4-nitro-phenylamino)-ethylamino]-6-furan-2-yl-pyrimidine-5-carbonitrile From 2-amino-4-furan-2-yl-6-methanesulfinyl-pyrimidine-5-carbonitrile and N5-(2-amino-ethyl)-2-nitro-benzene-1,5-diamine in DME. ES-MS m/e (%): 403 (M+Na+, 50), 381 (M+H+, 100), 269 (46).

Example 309
2-Amino-4-[2-(5-chloro-pyridin-2-ylamino)-ethylamino]-6-furan-2-yl-pyrimidine-5-carbonitrile From 2-amino-4-furan-2-yl-6-methanesulfinyl-pyrimidine-5-carbonitrile, 2-[(2-aminoethyl)amino]-5-chloropyridine hydrochloride and DBU in DME. ES-MS m/e (%): 356 (M+H+, 100).

Example 310
2-Amino-4-[2-(2,6-dimethyl-phenylamino)-ethylamino]-6-furan-2-yl-pyrimidine-5-carbonitrile From 2-amino-4-furan-2-yl-6-methanesulfinyl-pyrimidine-5-carbonitrile and N-(2,6-xylyl)ethylenediamine in DME. ES-MS m/e (%): 349 (M+H$^+$, 100), 228 ([M+H—C$_8$H$_{11}$N]$^+$, 65).

Example 311
4-[(2-Amino-5-cyano-6-furan-2-yl-pyrimidin-4-ylamino)-methyl]-benzenesulfonamide From 2-amino-4-furan-2-yl-6-methanesulfinyl-pyrimidine-5-carbonitrile, 4-(aminoethyl)benzenesulfonamide hydrochloride and DBU in DME. ES-MS m/e (%): 369 ([M—H]$^-$, 100).

Example 312
2-Amino-4-(4-dimethylamino-benzylamino)-6-furan-2-yl-pyrimidine-5-carbonitrile From 2-amino-4-furan-2-yl-6-methanesulfinyl-pyrimidine-5-carbonitrile, 4-dimethylaminobenzylamine dihydrochloride and DBU in DME. ES-MS m/e (%): 335 (M+H$^+$, 100).

Example 313
2-Amino-4-furan-2—,yl-6-(2-pyridin-2-yl-ethylsulfanyl)-pyrimidine-5-carbonitrile From 2-amino-4-furan-2-yl-6-methanesulfinyl-pyrimidine-5-carbonitrile, 2-mercaptoethylpyridine and DBU in DME. ES-MS m/e (%): 324 (M+H$^+$, 100).

Example 314
4-Furan-2-yl-6-methylsulfanyl-5-vinyl-pyrimidin-2-yl-amine

To a stirred solution of 1.00 g (3.00 mmol) 4-furan-2-yl-5-iodo-6-methylsulfanyl-pyrimidin-2-yl-amine in 30 ml dioxane under argon at room temperature were added 0.96 ml (3.30 mmol) vinyltributylstannane, 347 mg (0.30 mmol) tetrakis(triphenylphosphine) palladium(O) and 6.0 ml (12.0 mmol) 2M aqueous sodium carbonate solution. The reaction mixture was heated at reflux for 16 h, then cooled to room temperature, 3 g of kieselgel added, and the mixture concentrated in vacuo. Flash chromatography (1/3 ethyl acetate/hexane) followed trituration in ether/hexane afforded 460mg (66%) 4-furan-2-yl-6-methylsulfanyl-5-vinyl-pyrimidin-2-ylamine as an orange crystalline solid. EI-MS m/e (%): 233 (M$^+$, 48), 218 ([M—CH$_3$]$^+$, 76), 216 ([M—NH$_3$]$^+$, 46), 125 (100).

Example 315
5-Ethyl-4-furan-2-yl-6-methylsulfanyl-pyrimidin-2-yl-amine

A solution of 200 mg (0.86 mmol) 4-furan-2-yl-6-methylsulfanyl-5-vinyl-pyrimidin-2-ylamine in 30 ml ethanol was stirred with a spatula end of 10% palladium on charcoal under 1 atm of hydrogen for 16 h at room temperature. After filtration to remove the catalyst, the reaction mixture was concentrated in vacuo and the residue triturated in ether/hexane to afford 60 mg (30%) 5-ethyl-4-furan-2-yl-6-methylsulfanyl-pyrimidin-2-ylamine as an off-white crystalline solid. ES-MS rn/e (%): 236 (M+H$^+$, 100).

Analogously to Example 199 there were obtained:

Example 316
2-Amino-4-furan-2-yl-6-[2-(5-nitro-pyridin-2-ylamino)-ethylamino]-pyrimidine-5-carbonitrile From 2-amino-4-furan-2-yl-6-methanesulfinyl-pyrimidine-5-carbonitrile and 2-(2-aminoethylamino)-5-nitropyridine in DME. ES-MS m/e (%): 389 (M+Na$^+$, 15), 367 (M+H$^+$, 100).

Example 317
2-Amino-4-[2-(3-cycano-pyridin-2-ylamino)-ethylamino]-6-furan-2-yl-pyrimidine-5-carbonitrile From 2-amino-4-furan-2-yl-6-methanesulfinyl-pyrimidine-5-carbonitrile, 2-(2-aminoethyl)aminonicotinonitrile hydro chloride and DBU in DME. ES-MS m/e (%): 369 (M+Na$^+$, 12), 347 (M+H$^+$, 100).

Example 318
2-Amino-4-[2-(4-chloro-phenylamino)-ethylamino]-6-furan-2-yl-pyrimidine-5-carbonitrile From 2-amino-4-furan-2-yl-6-methanesulfinyl-pyrimidine-5-carbonitrile, N-(p-chlorophenyl)ethylenediamine maleate and DBU in DME. ES-MS m/e (%): 357 (M{$^{37}$Cl}+H$^+$, 40), 355 (M{$^{35}$Cl}+H$^+$, 100).

Analogously to Example 163 there were obtained:

Example 319
5-Chloro-6-furan-2-yl-N4-phenethyl-pyrimidine-2,4-diamine

From 5-chloro-4-furan-2-yl-6-methanesulfinyl-pyrimidin-2-yl-amine and phenethylamine in dioxane. ES-MS m/e (%): 317 (M{$^{37}$Cl}+H$^+$, 30), 315 (M{$^{35}$Cl}+H$^+$, 100).

Example 320
5-Chloro-6-furan-2-yl-N4-(3-phenyl-propyl)-pyrimidine-2,4-diamine From 5-chloro-4-furan-2-yl-6-methanesulfinyl-pyrimidin-2-yl-amine and 3-phenylpropylamine in dioxane. ES-MS m/e (%): 331 (M{$^{37}$C }+H$^+$, 30), 329 (M{$^{35}$Cl}+H$^+$, 100).

Example 321
5-Chloro-4-furan-2-yl-6-(3-phenyl-propoxy)-pyrimidin-2-yl-amine

From 5-chloro-4-furan-2-yl-6-methanesulfinyl-pyrimidin-2-yl-amine, 3-phenyl-1-propanol and DBU in dioxane. ES-MS m/e (%): 332 (M{$^{37}$Cl}+H$^+$, 50), 330 (M{$^{35}$C,}+H$^+$, 100).

Example 322
5-Chloro-4-furan-2-yl-6-phenethyloxy-pyrimidin-2-yl-amine

From 5-chloro-4-furan-2-yl-6-methanesulfinyl-pyrimidin-2-yl-amine, phenethyl alcohol and DBU in dioxane. ES-MS m/e (%): 318 (M{$^{37}$Cl}+H$^+$, 33), 316 (M{$^{35}$Cl}+H$^+$, 100).

Example 323
4-Benzyloxy-5-chloro-6-furan-2-yl-pyrimidin-2-yl-amine

From 5-chloro-4-furan-2-yl-6-methanesulfinyl-pyrimidin-2-yl-amine, benzyl alcohol and DBU in dioxane. ES-MS m/e (%): 304 (M{$^{37}$Cl}+H$^+$, 30), 302 (M{$^{35}$Cl}+H$^+$, 100).

Example 324
4-Benzylsulfanyl-5-chloro-6-furan-2-yl-pyrimidin-2-yl-amine

From 5-chloro-4-furan-2-yl-6-methanesulfinyl-pyrimidin-2-yl-amine, benzyl mercaptan and DBU in dioxane. ES-MS m/e (%): 320 (M{$^{37}$Cl}+H$^+$, 45), 318 (M{$^{35}$Cl}+H$^+$, 100).

Analogously to Example 199 there was obtained:

Example 325
2-Amino-4-(4-bromo-benzylamino)-6-furan-2-yl-pyrimidine-5-carbonitrile From 2-amino-4-furan-2-yl-6-methanesulfinyl-pyrimidine-5-carbonitrile, 4-bromobenzylamine hydrochloride and DBU in DME. ES-MS m/e (%): 372 (M{$^{81}$Br}+H$^+$, 95), 370 (M{$^{79}$Br}+H$^+$, 100).

Example 326
2-Amino-4-furan-2-yl-6-(quinolin-2-yl-methoxy)-pyrimidine-5-carbonitrile To a stirred solution of 400 mg (1.98 mmol) 2-amino-4-furan-2-yl-6-oxo-1,6-dihydro-pyrimidine-5-carbonitrile in 15 ml DMF were added 1.93 g (5.94 mmol) cesium carbonate and 847 mg (3.96 mmol) 2-(chloromethyl)quinoline hydrochloride and stirring continued for 16 h ours at 100° C. The reaction mixture was then concentrated in vacuo and the residue partitioned between ethyl acetate and water. The organic phase was dried over sodium sulfate and concentrated in vacuo. The residue was triturated in ether/methanol to afford 110 mg (16%) 2-amino-4-furan-2-yl-6-(quinolin-2-ylmethoxy)-pyrimidine-5-carbonitrile as an orange crystalline solid. ES-MS m/e (%): 344 (M+H$^+$, 100).

Analogously to Example 199 there were obtained:

Example 327
(RS)-2-Amino-4-furan-2-yl-6-(1-methyl-2-phenylamino-ethylamino)-pyrimidine-5-carbonitrile From 2-amino-4-furan-2-yl-6-methanesulfinyl-pyrimidine-5-carbonitrile, 1-phenylamino-2-amino-propane hydrochloride and DBU in DME. ES-MS m/e (%): 335 (M+H$^+$, 100).

Example 328
2-Amino-4-(4-diethylaminomethyl-benzylamino)-6-furan-2-yl-pyrimidine-5-carbonitrile From 2-amino-4-furan-2-yl-6-methanesulfinyl-pyrimidine-5-carbonitrile, (4-aminomethyl-benzyl)-diethylamine and DBU in DME. ES-MS m/e (%): 377 (M+H$^+$, 100), 304 ([M+H-Et$_2$NH]$^+$, 40).

Example 329
4-[(2-Amino-5-cyano-6-furan-2-yl-pyrimidin-4-ylamino)-methyl]-N-isopropyl-benzamide From 2-amino-4-furan-2-yl-6-methanesulfinyl-pyrimidine-5-carbonitrile, p-aminomethyl-benzoic acid isopropylamide hydrochloride and DBU in DME. ES-MS m/e (%): 377 (M+H$^+$, 100).

Example 330
2-Amino-4-furan-2-yl-6-[2-(pyridin-2-ylamino)-ethylamino]-pyrimidine-5-carbonitrile From 2-amino-4-furan-2-yl-6-methanesulfinyl-pyrimidine-5-carbonitrile and N1-pyridin-2-yl-ethane-1,2-diamine in DME. ES-MS m/e (%): 322 (M+H$^+$, 100).

Example 331
(RS)-2-Amino-4-furan-2-yl-6-(1-naphthalen-2-yl-ethoxy)-pyrimidine-5-carbonitrile From 2-amino-4-furan-2-yl-6-methanesulfinyl-pyrimidine-5-carbonitrile, (RS)-1-(2-naphthyl)ethanol and DBU in DME. ES-MS m/e (%): 357 (M+H$^+$, 100).

Example 332
2-Amino-4-furan-2-yl-6-(2-isopropylamino-ethylamino)-pyrimidine-5-carbonitrile From 2-amino-4-furan-2-yl-6-methanesulfinyl-pyrimidine-5-carbonitrile and N-isopropylethylenediamine in DME. ES-MS m/e (%): 287 (M+H$^+$, 100), 228 ([M+H-iPrNH$_2$]$^+$, 40).

Example 333
2-Amino-4-furan-2-yl-6-[2-(naphthalen-1-ylamino)-ethylamino]-pyrimidine-5-carbonitrile From 2-amino-4-furan-2-yl-6-methanesulfinyl-pyrimidine-5-carbonitrile, N-(1-naphthyl)ethylendiamine dihydrochioride and DBU in DME. ES-MS m/e (%): 371 (M+H$^+$, 100).

Example 334
(S)-2-Amino-4-furan-2-yl-6-(1-naphthalen-2-yl-ethylamino)-pyrimidine-5-carbonitrile From 2-amino-4-furan-2-yl-6-methanesulfinyl-pyrimidine-5-carbonitrile, (S)-(–)-1-(2-naphthyl)ethylamine and DBU in DME. ES-MS m/e(%): 356 (M+H$^+$, 100).

Example 335
(R)-2-Amino-4-furan-2-yl-6-(1-naphthalen-2-yl-ethylamino)-pyrimidine-5-carbonitrile From 2-amino-4-furan-2-yl-6-methanesulfinyl-pyrimidine-5-carbonitrile, (R)-(–)-1-(2-naphthyl)ethylamine and DBU in DME. ES-MS m/e (%): 356 (M+H$^+$, 100).

Example 336
2-Amino-4-(3,4-dihydro-1H-isoquinolin-2-yl)-6-furan-2-yl-pyrimidine-5-carbonitrile From 2-amino-4-furan-2-yl-6-methanesulfinyl-pyrimidine-5-carbonitrile and 1,2,3,4-tetrahydroisoquinoline in DME. ES-MS m/e (%): 318 (M+H$^+$, 100).

Example 337
2-Amino-4-[(benzo [1,3]dioxol-5-ylmethyl)-amino]-6-furan-2-yl-pyrimidine-5-carbonitrile From 2-amino-4-furan-2-yl-6-methanesulfinyl-pyrimidine-5-carbonitrile and piperonylamine in DME. ES-MS m/e (%): 336 (M+H$^+$, 100).

Example 338
2-Amino-4-furan-2-yl-6-(4-trifluoromethoxy-benzylamino)-pyrimidine-5-carbonitrile From 2-amino-4-furan-2-yl-6-methanesulfinyl-pyrimidine-5-carbonitrile and 4-(trifluoromethoxy)benzylamine in DME. ES-MS m/e (%): 376 (M+H$^+$, 100).

Example 339
[2-(2-Amino-5-cyano-6-furan-2-yl-pyrimidin-4-ylamino)-ethyl]-carbamic Acid Benzyl Ester From 2-amino-4-furan-2-yl-6-methanesulfinyl-pyrimidine-5-carbonitrile, (2-amino-ethyl)-carbamic acid benzyl ester hydrochloride and DBU in DME. ES-MS m/e (%): 401 (M+Na$^+$, 20), 379 (M+H$^+$, 100).

Example 340
N4-Benzyl-6-furan-2-yl-5-methyl-pyrimidine-2,4-diamine a) (RS)-3-Furan-2-yl-2-methyl-3-oxo-propionic Acid Ethyl Ester To a stirred solution of 5.0 g (27.4 mmol) ethyl beta-oxo-2-furanpropionate in 15 ml dry THF under argon at –78° C. was added dropwise 27.4 ml (27.4 mmol, 1M solution in THF) lithium bis(trimethylsilyl)amide and stirring continued for 15 minutes at –78° C. 5.44 ml (87.4 mmol) methyl iodide was then added dropwise and stirring continued for 30 minutes at –78° C., 2.5 hours at 0° C. and 20 hours at room temperature. The reaction mixture was poured into 100 ml 1M hydrochloric acid at 0° C. and the phases separated. The aqueous phase was extracted twice with ether and the combined organic extracts washed with brine, dried over sodium sulfate, and concentrated in vacuo. Chromatography (ethyl acetate/hexane 1/3) afforded 4.42 g (82%) (RS)-3-furan-2-yl-2-methyl-3-oxo-propionic acid ethyl ester as a yellow oil. EI-MS m/e (%): 196 (M$^+$, 10), 168 ([M—C$_2$H$_4$]$^+$, 6), 151 ([M—OEt]$^+$, 7), 95 (100).

b) 2-Amino-6-furan-2-yl-5-methyl-3H-pyrimidin-4-one

Following the method of Rorig and Nicholson (U.S. Pat. No. 2,710,867), a mixture of 3.00 g (15.3 mmol) (RS)-3- furan-2-yl-2-methyl-3-oxo-propionic acid ethyl ester and 1,38 g (7.65 mmol) guanidine carbonate in 20 ml ethanol was heated at 100° C. for 16 hours. The reaction mixture was then cooled to 0° C., whereupon the resulting crystals were collected by filtration and washed sequentially with water and with ice-cold ethanol to afford 1.80 g (62%) 2-amino-6-furan-2-yl-5-methyl-3H-pyrimidin-4-one as a white crystalline solid. ES-MS m/e (%): 190 ([M—H]$^-$, 100).

c) Trifluoromethanesulfonic Acid 2-amino-6-furan-2-yl-5-methyl-pyrimidin-4-yl Ester To a stirred suspension of 1.5 g (7.85 mmol) 2-amino-6-furan-2-yl-5-methyl-3H-pyrimidin-4-one in 20 ml dichloromethane was added 3,52 ml (15.7 mmol) 2,6-di-tert-butylpyridine and the mixture was ultrasonicated for 30 minutes. 1.55 ml (9.42 mmol) triflic anhydride was then added dropwise at 0° C. with stirring and stirring continued at room temperature for 16 hours. Water was then added to the reaction mixture and the resulting crystals collected by filtration. The filtrate phases were separated and the organic phase concentrated in vacuo to ca 10 ml and cooled to 0° C. The resulting crystals were collected by filtration. The mother liquor was then concentrated in vacuo to ca 5 ml and recooled to 0° C. The resulting crystals were collected by filtration. All three batches of crystals were then combined and washed with a minimum quantity of ice-cold dichloromethane to afford 1.65 g (65%) trifluoromethanesulfonic acid 2-amino-6-furan-2-yl-5-methyl-pyrimidin-4-yl ester as a white crystalline solid. ES-MS m/e (%): 324 (M+H$^+$, 100).

d) N-4-Benzyl-6-furan-2-yl-5-methyl-pyrimidine-2,4-diamine

To a stirred solution of 250 mg (0.77 mmol) trifluoromethanesulfonic acid 2-amino-6-furan-2-yl-5-methyl-pyrimidin-4-yl ester in 10 ml DME in a pressure tube was added 0.63 ml (5.77 mmol) benzylamine and the mixture heated at 80° C. for 16 hours. The reaction mixture was then poured onto 80 ml water and cooled to 0° C. The resulting crystals were collected by filtration and washed sequentially with water, ether/hexane and a minimum quantity of ice-cold ether to afford 140 mg (65%) N4-benzyl-6-furan-2-yl-5-methyl-pyrimidine-2,4-diamine as a white crystalline solid. ES-MS m/e (%): 281 (M+H$^+$, 100).

In an analogous manner there was obtained:

Example 341
6-Furan-2-yl-5-methyl-N4-(2-phenylamino-ethyl)-pyrimidine-2,4-diamine From trifluoromethanesulfonic acid 2-amino-6-furan-2-yl-5-methyl-pyrimidin-4-yl ester and N-phenylethylenediamine in DME. ES-MS m/e (%): 310 (M+H$^+$, 100).

Example 342
4-Furan-2-yl-5-methyl-6-methylsulfanyl-pyrimidin-2-yl-amine

A stirred solution of 250 mg (0.77 mmol) trifluoromethanesulfonic acid 2-amino-6-furan-2-yl-5-methyl-pyrimidin-4-yl ester and 217 mg (3.09 mmol) sodium methanethiolate in 10 ml dry DME under argon was heated at 80° C. for 2 hours. The reaction mixture was then partitioned between ethyl acetate and water. The organic phase was washed with brine, dried over sodium sulfate, and concentrated in vacuo. The residue was triturated in ethyl acetate/ether and the crystals collected by filtration to afford 36 mg (24%) 2-amino-6-furan-2-yl-5-methyl-3H-pyrimidin-4-one as a yellow crystalline solid. The mother liquor was concentrated in vacuo and the residue triturated in ether/hexane and the crystals collected by filtration to afford 13 mg (8%) 4-furan-2-yl-5-methyl-6-methylsulfanyl-pyrimidin-2-ylamine as a yellow crystalline solid. EI-MS m/e (%): 221 (M$^+$, 76), 188 ([M—SH]$^+$, 100).

In an analogous manner there was obtained:

Example 343
4-Furan-2-yl-5-methyl-6-(pyridin-2-ylmethoxy)-pyrimidin-2-yl-amine From trifluoromethanesulfonic acid 2-amino-6-furan-2-yl-5-methyl-pyrimidin-4'-yl ester and 2-(hydroxymethyl)pyridine sodium alcoholate in DME. ES-MS m/e (%): 283 (M+H$^+$, 100).

Example 344
4-Chloro-6-furan-2-yl-5-methyl-pyrimidin-2-yl-amine

To a stirred solution of 250 mg (0.77 mmol) trifluoromethanesulfonic acid 2-amino-6-furan-2-yl-5-methyl-pyrimidin-4-yl ester in 10 ml DME was added 489 mg (2.12 mmol) 2-(aminomethyl)quinoline dihydrochloride and the mixture heated at 80° C. for 16 hours. The reaction mixture was then concentrated in vacuo. Chromatography (ethyl acetate/hexane 4/1) followed by trituration in ether/hexane afforded 80 mg (50%) 4-chloro-6-furan-2-yl-5-methyl-pyrimidin-2-ylamine as a white crystalline solid. ES-MS m/e (%): 212 (M{$^{37}$Cl}+H$^+$, 50), 210 (M{$^{35}$Cl}+H$^+$, 100).

Analogously to Example 199 there were obtained:

Example 345
2-Amino-4-furan-2-yl-6-(4-trifluoromethyl-benzylamino)-pyrimidine-5-carbonitrile From 2-amino-4-furan-2-yl-6-methanesulfinyl-pyrimidine-5-carbonitrile and 4-(trifluoromethyl)benzylamine in DME. ES-MS m/e (%): 360 (M+H$^+$, 100).

Example 346
2-Amino-4-furan-2-yl-6-(3-trifluoromethyl-benzylamino)-pyrimidine-5-carbonitrile From 2-amino-4-furan-2-yl-6-methanesulfinyl-pyrimidine-5-carbonitrile and 3-(trifluoromethyl)benzylamine in DME. ES-MS m/e (%): 360 (M+H$^+$, 100).

Example 347
2-Amino-4-(3,4-dimethyl-benzylamino)-6-furan-2-yl-pyrimidine-5-carbonitrile From 2-amino-4-furan-2-yl-6-methanesulfinyl-pyrimidine-5-carbonitrile and 3,4-dimethylbenzylamine in DME. ES-MS m/e (%): 320 (M+H$^+$, 100).

Example 348
2-Amino-4-furan-2-yl-6-[(4-methyl-pyridin-2-ylmethyl)-amino]-pyrimidine-5-carbonitrile From 2-amino-4-furan-2-yl-6-methanesulfinyl-pyrimidine-5-carbonitrile, C-(4-methyl-pyridin-2-yl)-methylamine dihydrochloride and DBU in DME. ES-MS m/e (%): 307 (M+H$^+$, 100).

Example 349
1-(2-Amino-4-furan-2-yl-6-methylsulfanyl-pyrimidin-5-yl)-ethanone a) 5-(1-Ethoxy-vinyl)-4-furan-2-yl-6-methylsulfanyl-pyrimidin-2-ylamine To a stirred solution of 1.12 g (3.37 mmol) 4-furan-2-yl-5-iodo-6-methylsulfanyl-pyrimidin-2-ylamine in 30 ml dioxane under argon at room temperature were added 1.25 ml (3.70 mmol) tributyl(1-ethoxyvinyl)tin, 236 mg (0.34 mmol) bis(triphenylphosphine) palladium(II) chloride and 2.19 g (6.74 mmol) cesium carbonate. The reaction mixture was heated at reflux for 16 h, then cooled to room temperature, 1 g of kieselgel added, and the mixture concentrated in vacuo. Flash chromatography (1/2 ethyl acetate/hexane) afforded 730 mg (78%) 5-(1-ethoxy-vinyl)-4-furan-2-yl-6-methylsulfanyl-pyrimidin-2-ylamine as an orange crystalline solid. ES-MS m/e (%): 278 (M+H+, 100).

b) 1-(2-Amino-4-furan-2-yl-6-methylsulfanyl-pyrimidin-5-yl)-ethanone

To a stirred solution of 670 mg (2,42 mmol) 5-(1-ethoxy-vinyl)-4-furan-2-yl-6-methylsulfanyl-pyrimidin-2-ylamine in 18 ml THF was added 2.00 ml (2.00 mmol) 1M hydrochloric acid and stirring continued for 43 hours at room temperature. The reaction mixture was partitioned between ethyl acetate and sodium bicarbonate solution and the layers separated. The organic phase was washed with brine, dried over sodium sulfate, and concentrated in vacuo. The residue was triturated in ethyl acetate/ether to afford 200 mg (33%) 1-(2-amino-4-furan-2-yl-6-methylsulfanyl-pyrimidin-5-yl)-ethanone as a light brown crystalline solid. EI-MS m/e (%): 249 (M+, 14), 234 (38), 221 (100), 206 (20), 43 (30).

Example 350
6-Amino-4-benzylamino-2-furan-2-yl-nicotinonitrile
a) (E or Z)-3-Amino-3-furan-2-yl-acrylonitrile Following the method of Gupta et al. (*Tetrahedron* 1990, 46, 3703) and Bullock and Gregory (*Can. J. Chem.* 1965, 43, 332), to a stirred solution of 0.53 ml (10.0 mmol) acetonitrile in 25 ml dry THF under argon at −78° C. was added 6.25 ml (10.0 mmol) n-butyllithium solution (1.6M in hexane) and stirring continued for 15 minutes. 0.87 ml (10.0 mmol) 2-furonitrile was then added dropwise and stirring continued for 45 minutes at −78° C. The reaction mixture was quenched at 0° C. with 3 ml water and then partitioned between ether and water. The organic phase was then washed with brine, dried over sodium sulfate, and concentrated in vacuo to afford 1.10 g (82%) (E or Z)-3-amino-3-furan-2-yl-acrylonitrile as a yellow crystalline solid which was stored in the refrigerator. EI-MS m/e (%): 134 (M+, 100).

b) (E or Z)-2-(Amino-furan-2-yl-methylene)-3-oxo-pentanedinitrile

Following a modification of the method of Kappe et al. (*Monatsh. Chem.* 1983, 114, 953) and Toledo et al. (*Chem. Mater.* 1994, 6, 1222), to a stirred solution 8.06 g (94.8 mmol) cyanoacetic acid in 70 ml dry dioxane under argon at room temperature were added 9.03 ml (94.8 mmol) acetic anhydride and 6.35 g (47.4 mmol) (E or Z)-3-amino-3-furan-2-yl-acrylonitrile and the reaction mixture heated at 100° C. for 90 minutes. The reaction mixture was then concentrated in vacuo and the residue resuspended in ether and washed sequentially with water and with brine. The organic phase was then dried over sodium sulfate and concentrated in vacuo to afford, after trituration in cold methanol, 3.16 g (33%) (E or Z)-2-(amino-furan-2-yl-methylene)-3-oxo-pentanedinitrile as a light brown crystalline solid. ES-MS m/e (%): 219 (M+NH$_4^+$, 100), 202 (M+H+, 42).

c) 6-Amino-2-furan-2-yl-4-oxo-1,4-dihydro-pyridine-3-carbonitrile

Following the method of Toledo et al. (*Chem. Mater.* 1994, 6, 1222), to a stirred solution 2.61 g (13.0 mmol) (E or Z)-2-(amino-furan-2-yl-methylene)-3-oxo-pentanedinitrile in 30 ml dry ethanol under argon at room temperature was added 4.86 ml (13.0 mmol) sodium ethylate solution (2.67M in ethanol) and the reaction mixture heated at 100° C. for 1 hour. The reaction mixture was then concentrated in vacuo and the residue dissolved in a minimum of water and acidified to pH 4.5 with glacial acetic acid. The resulting crystals were collected by filtration and washed sequentially with water and ether to afford 2,41 g (93%) 6-amino-2-furan-2-yl-4-oxo-1,4-dihydro-pyridine-3-carbonitrile as a white crystalline solid. ES-MS m/e (%): 200 ([M—H]−, 100).

d) Trifluoromethanesulfonic Acid 6-amino-3-cyano-2-furan-2-yl-pyridin-4-yl Ester To a stirred suspension of 2,41 g (12.0 mmol) 6-amino-2-furan-2-yl-4-oxo-1,4-dihydro-pyridine-3-carbonitrile in 25 ml dichloromethane at 0° C. were added 5.38 ml (24.0 mmol) 2,6-di-tert-butylpyridine and 2.00 ml (12.0 mmol) triflic anhydride and stirring continued at room temperature for 16 hours. The reaction mixture was then concentrated in vacuo. Chromatography (ethyl acetate/hexane 1/1) followed by trituration in ether/hexane afforded 2.05 g (51%) trifluoromethanesulfonic acid 6-amino-3-cyano-2-furan-2-yl-pyridin-4-yl ester as a white crystalline solid. ES-MS m/e (%): 351 (M+NH$_4^+$, 100), 334 (M+H+, 11).

e) 6-Amino-4-benzylamino-2-furan-2-yl-nicotinonitrile

To a stirred solution of 250 mg (0.75 mmol) trifluoromethanesulfonic acid 6-amino-3-cyano-2-furan-2-yl-pyridin-4-yl ester in 10 ml DME was added 0.82 ml (7.56 mmol) benzylamine and the mixture heated at 80° C. for 72 hours. The reaction mixture was then cooled to room temperature and partitioned between dichloromethane and water. The phases were separated and the organic phase dried over sodium sulfate and concentrated in vacuo. The residue was triturated in ether/hexane to afford 79 mg (38%) 6-amino-4-benzylamino-2-furan-2-yl-nicotinonitrile as a white crystalline solid. ES-MS m/e (%): 291 (M+H+, 100).

In an analogous manner there was obtained:

Example 351
6-Amino-2-furan-2-yl-4-(2-phenylamino-ethylamino)-nicotinonitrile

From trifluoromethanesulfonic acid 6-amino-3-cyano-2-furan-2-yl-pyridin-4-yl ester and N-phenylethylenediamine in DME. ES-MS m/e (%): 320 (M+H+, 100).

Analogously to Example 163 there were obtained:

Example 352
4-Furan-2-yl-5-iodo-6-(2-pyridin-2-yl-ethylsulfanyl)-pyrimidin-2-yl-amine From 4-furan-2-yl-5-iodo-6-methanesulfinyl-pyrimidin-2-yl-amine, 2-mercaptoethylpyridine and DBU in dioxane. ES-MS m/e (%): 425 (M+H+, 100).

Example 353
5-Bromo-4-furan-2-yl-6-(2-pyridin-2-yl-ethylsulfanyl)-pyrimidin-2-yl-amine From 5-bromo-4-furan-2-yl-6-methanesulfinyl-pyrimidin-2-yl-amine, 2-mercaptoethylpyridine and DBU in dioxane. ES-MS m/e (%): 379 (M{$^{81}$Br}+H+, 100), 377 (M{$^{79}$Br}+H+, 95).

Example 354
5-Chloro-4-furan-2-yl-6-(2-pyridin-2-yl-ethylsulfanyl)-pyrimidin-2-yl-amine From 5-chloro-4-furan-2-yl-6-methanesulfinyl-pyrimidin-2-yl-amine, 2-mercaptoethylpyridine and DBU in dioxane. ES-MS m/e (%): 335 (M{$^{37}$Cl}+H+, 30), 333 (M{$^{35}$Cl}+H+, 100).

Analogously to Example 326 there was obtained:

Example 355
6-Amino-2-furan-2-yl-4-(pyridin-2-yl-methoxy)-nicotinonitrile

From 6-amino-2-furan-2-yl-4-oxo-1,4-dihydro-pyridine-3-carbonitrile, 2-picolyl chloride hydrochloride and cesium carbonate in DMF. ES-MS m/e (%): 293 (M+H+, 100).

Analogously to Example 350 there were obtained:

Example 356
6-Amino-2-furan-2-yl-4-(2-pyridin-2-yl-ethylsulfanyl)-nicotinonitrile From trifluoromethanesulfonic acid 6-amino-3 l-cyano-2-furan-2-yl-pyridin-4-yl ester, 2-pyridylethylmercaptan and DBU in DME. ES-MS m/e (%): 23 (M+H$^+$, 100).

Example 357
6-Amino-2-furan-2-yl4-(4-(trifluoromethyl-benzlamino)-nicotinonitrile From trifluoromethanesulfonic acid 6-amino-3-cyano-2-furan-2-yl-pyridin-4-yl ester and 4-trfluoromethylbenzylamine in DME. ES-MS m/e (%): 359 (M+H$^+$, 100).

Example 358
2-Amino-4-(2-cyclohexylamino-ethylamino)-6-furan-2-yl-pyrimidine-5-carbonitrile A solution of 200 mg (0.53 mmol) [2-(2-amino-5-cyano-6-furan-2-yl-pyrimidin-4-ylamino)-ethyl]-carbamic acid benzyl ester and 0.055 ml (0.53 mmol) cyclohexanone in 10 ml dioxane and 5 ml ethanol was stirred with a spatula end of 10% palladium on charcoal under 1 atm of hydrogen for 4 h at room temperature. After filtration to remove the catalyst, the reaction mixture was concentrated in vacuo and the residue triturated in ether to afford 80 mg (46%) 2-amino-4-(2-cyclohexylamino-ethylamino)-6-furan-2-yl-pyrimidine-5-carbonitrile as a white crystalline solid. ES-MS m/e (%): 327 (M+H$^+$, 100), 228 ([M+H—C$_6$H$_{11}$NH$_2$]$^+$, 40).

Analogously to Example 199 there were obtained:

Example 359
2-Amino-4-(2-bromo-benzylamino)-6-furan-2-yl-pyrimidine-5-carbonitrile From 2-amino-4-furan-2-yl-6-methanesulfinyl-pyrimidine-5-carbonitrile and 2-bromobenzylamine in DME. ES-MS m/e (%): 372 (M{$^{81}$Br}+H$^+$, 95), 370 (M{$^{79}$Br}+H$^+$, 100).

Example 360
2-Amino-4-(2-chloro-benzylamino)-6-furan-2-yl-pyrimidine-5-carbonitrile From 2-amino-4-furan-2-yl-6-methanesulfinyl-pyrimidine-5-carbonitrile and 2-chlorobenzylamine in DME. ES-MS m/e (%): 328 (M{$^{37}$Cl}+H$^+$, 30), 326 (M{$^{35}$Cl}+H$^+$, 100).

Example 361
2-Amino-4-furan-2-yl-6-(3-methyl-pyridin-2-yl-methoxy)-pyrimidine-5-carbonitrile From 2-amino-4-furan-2-yl-6-methanesulfinyl-pyrimidine-5-carbonitrile, (3-methyl-pyridin-2-yl)methanol and DBU in DME. ES-MS m/e (%): 308 (M+H$^+$, 100).

Example 362
2-Amino-4-furan-2-yl-6-(5-methyl-pyridin-2-yl-methoxy)-pyrimidine-5-carbonitrile From 2-amino-4-furan-2-yl-6-methanesulfinyl-pyrimidine-5-carbonitrile, (5-methyl-pyridin-2-yl)methanol and DBU in DME. EI-MS m/e (%): 307 (M$^+$, 76), 290 (28), 278 (16), 122 (100), 106 (78), 79 (30), 77 (38).

Example 363
2-Amino-4-furan-2-yl-6-[(5-methyl-pyridin-2-yl-methyl)-amino]-pyrimidine-5-carbonitrile From 2-amino-4-furan-2-yl-6-methanesulfinyl-pyrimidine-5-carbonitrile, C-(5-methyl-pyridin-2-yl)-methylamine dihydrochloride and DBU in DME. ES-MS m/e (%): 307 (M+H$^+$, 100).

Analogously to Example 350 there was obtained:

Example 364
6-Amino-2-furan-2-yl-4-[(quinolin-2-ylmethyl)-amino]-nicotinonitrile From trifluoromethanesulfonic acid 6-amino-3-cyano-2-furan-2-yl-pyridin-4-yl ester and 2-(aminomethyl)quinoline in DME. ES-MS m/e (%): 342 (M+H$^+$, 100).

Example 365
5-Ethyl-4-furan-2-yl-6-(2-pyridin-2-yl-ethylsulfanyl)-pyrimidin-2-ylamine a) 5-Ethyl-4-furan-2-yl-6-methanesulfinyl-pyrimidin-2-ylamine To a stirred suspension of 350 mg (1.49 mmol) 5-ethyl-4-furan-2-yl-6-methylsulfanyl-pyrimidin-2-ylamine in 15 ml dichloromethane was added 780 mg (3.00 mmol) 3-phenyl-2-(phenylsulfonyl)oxaziridine and stirring continued for 16 hours at room temperature. The reaction mixture was then partitioned between dichloromethane and water and the phases separated. The organic phase was dried over sodium sulfate and concentrated in vacuo. Chromatography (ethyl acetate then methanol/ethyl acetate 1/5) afforded 170 mg (46%) 5-ethyl-4-furan-2-yl-6-methanesulfinyl-pyrimidin-2-ylamine as a yellow crystalline solid. ES-MS m/e (%): 252 (M+H$^+$, 100).

b) 5-Ethyl-4-furan-2-yl-6-(2-pyridin-2-yl-ethylsulfanyl)-pyrimidin-2-ylamine

To a stirred suspension of 100 mg (0.40 mmol) 5-ethyl-4-furan-2-yl-6-methanesulfinyl-pyrimidin-2-ylamine in 5 ml DME in a pressure tube were added 230 mg (1.65 mmol) 2-pyridylethyl mercaptan and 0.18 ml (1.19 mmol) DBU and the mixture heated at 90° C. for 16 hours. The reaction mixture was then concentrated in vacuo. Chromatography (ethyl acetate/hexane 1/1 then ethyl acetate) followed by trituration in ether afforded 25 mg (19%) 5-ethyl-4-furan-2-yl-6-(2-pyridin-2-yl-ethylsulfanyl)-pyrimidin-2-ylamine as a beige crystalline solid. ES-MS m/e (%): 327 (M+H$^+$, 100).

Analogously to Example 199 there were obtained:

Example 366
2-Amino-4-furan-2-yl-6-(isoguinolin-3-yl-methoxy)-pyrimidine-5-carbonitrile From 2-amino-4-furan-2-yl-6-methanesulfinyl-pyrimidine-5-carbonitrile, isoquinolin-3-yl-methanol and DBU in DME. ES-MS m/e (%): 344 (M+H$^+$, 100).

Example 367
2-Amino-4-furan-2-yl-6-[(isoguinolin-3-yl-methyl)-amino]-pyrimidine-5-carbonitrile From 2-amino-4-furan-2-yl-6-methanesulfinyl-pyrimidine-5-carbonitrile, C-isoquinolin-3-yl-methylamine dihydrochloride and DBU in DME. ES-MS rn/e (%): 343 (M+H$^+$, 100).

Example 368
2-Amino-4-furan-2-yl-6-[(3-methyl-pyridin-2-yl-methyl)-amino]-pyrimidine-5-carbonitrile From 2-amino-4-furan-2-yl-6-methanesulfinyl-pyrimidine-5-carbonitrile, C-(3-methyl-pyridin-2-yl)- methylamine dihydrochloride and DBU in DME. ES-MS m/e (%): 307 (M+H⁺, 100).

Example 369
2-Amino-4-phenyl-6-(2-pyridin-2-yl-ethylsulfanyl)-pyrimidine-5-carbonitrile From 2-amino-4-methanesulfinyl-6-phenyl-pyrimidine-5-carbonitrile, 2-mercaptoethylpyridine and DBU in DME. ES-MS m/e (%): 334 (M+H⁺, 100).

Example 370
2-Amino-4-(2-pyridin-2-yl-ethylsulfanyl-6-thiophen-2-yl)-pyrimidine-5-carbonitrile From 2-amino-4-methanesulfinyl-6-thiophen-2-yl-pyrimidine-5-carbonitrile, 2-mercaptoethylpyridine and DBU in DME. ES-MS m/e (%): 340 (M+H⁺, 100).

Analogously to Example 350 there was obtained:

Example 371
6-Amino-2-furan-2-yl-4-[(pyridin-2-yl-methyl)-amino]-nicotinonitrile From trifluoromethanesulfonic acid 6-amino-3-cyano-2-furan-2-yl-pyridin-4-yl ester and 2-picolylamine in DME. ES-MS m/e (%): 292 (M+H⁺, 100).

Example 372
2-Amino-4-(4-fluoro-phenyl)-6-methylsulfanyl-pyrimidine-5-carbonitrile a) 2,2-Dicyano-1-methylsulfanyl-vinyl-cyanamide sodium salt Following the method of Kristinsson and Kristiansen (European Patent EP 244 360), to a stirred solution of 39.0 g (267 mmol) N-cyanoimido-S,S-dimethyl-carbonate in 500 ml ethanol under argon at room temperature were added 17.6 g (267 mmol) malonitrile and 100 ml (267 mmol) sodium ethylate solution (2.67M in ethanol) and stirring continued for 14 hours at room temperature. The resulting crystals were collected by filtration to afford 24.0 g (48%) 2,2-dicyano-1-methylsulfanyl-vinyl-cyanamide sodium salt as a white crystalline solid. A further 23.0 g (46%) was obtained by concentration of the mother liquor followed by trituration in ether. ES-MS m/e (%): 163 (M⁻, 100).

b) 2-Amino-4-chloro-6-methylsulfanyl-pyrimidine-5-carbonitrile

Following a modification of the method of Kristinsson and Kristiansen (European Patent EP 244 360), 15.0 g (80.6 mmol) 2,2-dicyano-1-methylsulfanyl-vinyl-cyanamide sodium salt was suspended in 400 ml 4M ethereal hydrogen chloride at 0° C. and the mixture was stirred at room temperature for 48 hours. The mixture was then cooled to 0° C. and 200 ml ice-water added. The resulting crystals were collected by filtration and washed with water (ca 500 ml) until the washings were free of chloride ion, and finally with 100 ml cold ether, to afford 14.4 (89%) as a pale yellow crystalline solid. ES-MS m/e (%): 203 (M{³⁷Cl}+H⁺, 38), 201 (M{³⁵Cl}+H⁺, 100).

c) 2-Amino-4-(4-fluoro-phenyl)-6-methylsulfanyl-pyrimidine-5-carbonitrile

To a stirred suspension of 0.50 g (2,49 mmol) 2-amino-4-chloro-6-methylsulfanyl-pyrimidine-5-carbonitrile in 10 ml toluene under argon at room temperature were added 384 mg (2.74 mmol)p-fluorobenzeneboronic acid, 288 mg (0.25 mmol) tetrakis(triphenyl-phosphine)palladium(O) and 638 mg (4.98 mmol) anhydrous potassium carbonate. The reaction mixture was heated at reflux for 16 h, then cooled to room temperature and partitioned between ethyl acetate and water. The organic phase was washed with brine, dried over sodium sulfate, and concentrated in vacuo. Chromatography (1/1 ethyl acetate/hexane) followed trituration in ether/hexane afforded 350 mg (54%) 2-amino-4-(4-fluoro-phenyl)-6-methylsulfanyl-pyrimidine-5-carbonitrile as a yellow crystalline solid. EI-MS m/e (%): 260 (M⁺, 37), 259 ([M—H]⁺, 100).

Analogously to Example 199 there were obtained:

Example 373
2-Amino-4-furan-2-yl-6-(4-methyl-pyridin-2-yl-methoxy)-pyrimidine-5-carbonitrile From 2-amino-4-furan-2-yl-6-methanesulfinyl-pyrimidine-5-carbonitrile, (4-methyl-pyridin-2-yl)methanol and DBU in DME. ES-MS m/e (%): 308 (M+H⁺, 100).

Example 374
2-Amino-4-furan-2-yl-6-(4-vinyl-benzylamino)-pyrimidine-5-carbonitrile From 2-amino-4-furan-2-yl-6-methanesulfinyl-pyrimidine-5-carbonitrile, 4-vinylbenzylamine hydrochloride and DBU in DME. ES-MS m/e (%): 318 (M+H⁺, 100).

Example 375
2-Amino-4-(4-ethyl-benzylamino)-6-furan-2-yl-pyrimidine-5-carbonitrile A solution of 50 mF (0.16 mmol) 2-amino-4-furan-2-yl-6-(4-vinyl-benzylamino)-pyrimidine-5-carbonitrile in 10 ml ethanol was stirred with a spatula end of 10% palladium on charcoal under 1 atm of hydrogen for 16 h at room temperature. After filtration to remove the catalyst, the reaction mixture was concentrated in vacuo. Chromatography (ethyl acetate) followed by trituration in ether/hexane afforded 12 mg (24%) 2-amino-4-(4-ethyl-benzylamino)-6-furan-2-yl-pyrimidine-5-carbonitrile as a white crystalline solid. ES-MS m/e (%): 320 (M+H⁺, 100).

Analogously to Example 350 there were obtained:

Example 376
6-Amino-2-furan-2-yl-4-[(pyridin-2-yl-methyl)-amino]-nicotinonitrile From trifluoromethanesulfonic acid 6-amino-3-cyano-2-furan-2-yl-pyridin-4-yl ester and C-(3-methyl-pyridin-2-yl)-methylamine in DME. ES-MS m/e (%): 306 (M+H⁺, 100).

Example 377
6-Amino-2-furan-2-yl-4-[(5-methyl-pyridin-2-yl-methyl)-amino]-nicotinonitrile From trifluoromethanesulfonic acid 6-amino-3-cyano-2-furan-2-yl-pyridin-4-yl ester and C-(5-methyl-pyridin-2-yl)-methylamine in DME. ES-MS m/e (%): 328 (M+Na⁺, 30), 306 (M+H⁺, 100).

Example 378
2,6-Diamino-4-furan-2-yl-nicotinonitrile and 6-Amino-4-furan-2-yl-2-thioxo-1,2-dihydro-pyridine-3-carbonitrile Following the method of Elnagdi and Erian (Arch. Pharm. 1991, 324, 853–858), to a stirred solution of 5.00 g (37.3 mmol) (E or Z)-3-amino-3-furan-2-yl-acrylonitrile in 50 ml dioxane at room temperature was added 7.46 (74.5 mmol) 2-cyanothioacetamide and the reaction mixture heated at reflux for 72 hours. The reaction mixture was then concentrated in vacuo. Chromatography (ethyl acetate/hexane 1/1 then ethyl acetate) afforded 1.40 g (17%) 6-amino-4-furan-2-yl-2-thioxo-1,2-dihydro-pyridine-3-carbonitrile as an orange crystalline solid, ES-MS m/e (%): 218 (M+H⁺, 100), and 0.46 g (6%) 2,6-diamino-4-furan-2-yl-nicotinonitrile as an orange crystalline solid, ES-MS m/e (%): 201 (M+H⁺, 100).

Example 379
6-Amino-4-furan-2-yl-2-(2-pyridin-2-yl-ethylsulfanyl)-nicotinonitrile To a stirred solution of 100 mg (0.46 mmol) 6-amino-4-furan-2-yl-2-thioxo-1,2-dihydro-pyridine-3-carbonitrile in 3.4 ml ethanol were added 0.60 ml (1.60 mmol) sodium ethylate solution (2.67M in ethanol) and 368 mg (1,38 mmol) 2-(2-bromoethyl)pyridine hydrobromide and the reaction mixture heated at reflux for 1 hour. The reaction mixture was then concentrated in vacuo and the residue partitioned between dichloromethane and water. The organic phase was dried over sodium sulfate and concentrated in vacuo. The residue was triturated in ether to afford 112 mg (76%) 6-amino-4-furan-2-yl-2-(2-pyridin-2-yl-ethylsulfanyl)-nicotinonitrile as a white crystalline solid. ES-MS m/e (%): 323 (M+H$^+$, 100).

Example 380
6-Amino-4-furan-2-yl-2-methylsulfanyl-nicotinonitrile

To a stirred solution of 150 mg (0.69 mmol) 6-amino-4-furan-2-yl-2-thioxo-1,2-dihydro-pyridine-3-carbonitrile in 3 ml methanol were added 0.13 ml (0.69 mmol) sodium methylate solution (5.4M in ethanol) and 0.04 ml (0.69 mmol) methyl iodide and the reaction mixture stirred at room temperature for 30 minutes. The reaction mixture was then concentrated in vacuo and the residue partitioned between dichloromethane and water. The organic phase was dried over sodium sulfate and concentrated in vacuo. The residue was triturated in ether to afford 113 mg (71%) 6-amino-4-furan-2-yl-2-methylsulfanyl-nicotinonitrile as a brown crystalline solid. ES-MS m/e (%): 232 (M+H$^+$, 100).

Analogously to Example 199 there was obtained:

Example 381
2-Amino-4-furan-2-yl-6-(6-methyl-pyridin-3-yl-methoxy)-pyrimidine-5-carbonitrile From 2-amino-4-furan-2-yl-6-methanesulfinyl-pyrimidine-5-carbonitrile, (6-methyl-pyridin-3-yl)-methanol hydrochloride and DBU in DME. ES-MS m/e (%): 308 (M+H$^+$, 100).

Analogously to Example 372 there was obtained:

Example 382
2-Amino-4-(3-fluoro-phenyl)-6-methylsulfanyl-pyrimidine-5-carbonitrile From 2-amino-4-chloro-6-methylsulfanyl-pyrimidine-5-carbonitrile, m-fluorobenzeneboronic acid, tetrakis(triphenylphosphine)palladium(O) and potassium carbonate in toluene. EI-MS m/e (%): 260 (M$^+$, 40), 259 ([M—H]$^+$, 100).

Example 383
6-Amino-2-furan-2-yl-4-(3-methyl-pyridin-2-yl-methoxy)-nicotinonitrile To a stirred solution of 1.24 g (3.75 mmol) trifluoromethanesulfonic acid 6-amino-3-cyano-2-furan-2-yl-pyridin-4-yl ester in 5 ml DME was added 0.55 g (4.50 mmol) sodium (3-methyl-pyridin-2-yl)methylate and the mixture stirred at 100° C. for 1 hour. The reaction mixture was then cooled to room temperature and partitioned between dichloromethane and water. The phases were separated and the organic phase dried over sodium sulfate and concentrated in vacuo. Chromatography (ethyl acetate then methanol/ethyl acetate 1/20) followed by trituration in ether/hexane/ethyl acetate afforded 18 mg (2%) 6-amino-2-furan-2-y]-4-(3-methyl-pyridin-2-ylmethoxy)-nicotinonitrile as a white crystalline solid. ES-MS m/e (%): 329 (M+Na$^+$, 60), 307 (M+H$^+$, 100).

In an analogous manner there was obtained:

Example 384
6-Amino-2-furan-2-yl-4-(2-pyridin-2-yl-ethoxy)-nicotinonitrile

From trifluoromethanesulfonic acid 6-amino-3-cyano-2-furan-2-yl-pyridin-4-yl ester and sodium 2-(pyridin-2-yl)ethylate in DME. ES-MS m/e (%): 329 (M+Na+, 90), 307 (M+H$^+$, 100).

Analogously to Example 372 there was obtained:

Example 385
2-Amino-4-(2-fluoro-phenyl)-6-methylsulfanyl-pyrimidine-5-carbonitrile From 2-amino-4-chloro-6-methylsulfanyl-pyrimidine-5-carbonitrile, o-fluorobenzeneboronic acid, tetrakis(triphenylphosphine)palladium(O) and potassium carbonate in toluene. ES-MS m/e (%): 261 (M+H$^+$, 100).

Example 386
2-Allylsulfanyl-6-amino-4-furan-2-yl-pyridine-3,5-dicarbonitrile This compound is already known in the chemical literature.

Example 387
6-Methyl-5-nitro-N2,N4-diphenyl-pyrimidine-2,4-diamine

This compound is already known in the chemical literature.

Example 388
(4,6-Diphenyl-pyrimidin-2-yl)-(4-methoxy-phenyl)-amine

This compound is already known in the chemical literature.

Example 389
2-Amino-6-benzylsulfanyl-4-thiophen-2-yl-pyridine-3.5-dicarbonitrile This compound is already known in the chemical literature.

Example 390
2-Allylsulfanyl-6-amino-4-thiophen-2-yl-pyridine-3,5-dicarbonitrile This compound is already known in the chemical literature.

Example 391
2-Amino-6-methylsulfuranyl-4-thiophen-2-yl-pyridine-3,5-dicarbonitrile This compound is already known in the chemical literature.

Example 392
2-Amino-5-cyano-4-furan-2-yl-6-mercapto-thionicotinamide

This compound is already known in the chemical literature.

Example 393
2'-Amino-6'-ethoxy-[3,4']bipyridinyl-3',5'-dicarbonitrile

This compound is already known in the chemical literature.

Example 394
2-Amino-6-propoxy-[4,4']bipyridinyl-3,5-dicarbonitrile

This compound is already known in the chemical literature.

Example 395
2-Amino-6-furan-2-yl-5-methyl-pyrimidin-4-ol

The preparation of this compound has already been described in Example 340.

Example 396
4-Furan-2-yl-5-methyl-pyrimidin-2-yl-amine

This compound is already known in the chemical literature.

Example 397
2,4-Diamino-6-furan-2-yl-pyrimidine-5-carbonitrile

This compound is already known in the chemical literature.

Example 398
2-Amino-4-furan-2-yl-6-(4-isopropyl-benzylamino)-pyrimidine-5-carbonitrile a) 2-Amino-4-furan-2-yl-6-(4-isopropenyl-benzylamino)-pyrimidine-5-carbonitrile To a stirred suspension of 1.00 g (4.03 mmol) 2-amino-4-methanesulfinyl-6-thiophen-2-yl-pyrimidine-5-carbonitrile in 30 ml DME were added 1.48 g (8.06 mmol) 4-isopropenyl-benzylamine hydrochloride and 1.50 ml (10.1 mmol) DBU and stirring continued for 16 hours at room temperature. 100 ml water was then added and the resulting crystals collected by filtration to afford 200 mg (15%) 2-amino-4-furan-2-yl-6-(4-isopropenyl-benzylamino)-pyrimidine-5-carbonitrile as a white crystalline solid. ES-MS m/e (%): 332 (M+H$^+$, 100).

b) 2-Amino-4-furan-2-yl-6-(4-isopropyl-benzylamino)-pyrimidine-5-carbonitrile

A solution of 200 mg (0.60 mmol) 2-amino-4-furan-2-yl-6-(4-isopropenyl-benzylamino)-pyrimidine-5-carbonitrile in 15 ml ethanol and 15 ml dioxane was stirred with a spatula end of 10% palladium on charcoal under 1 atm of hydrogen for 16 h at room temperature. After filtration to remove the catalyst, the reaction mixture was concentrated in vacuo. HPLC afforded 2 mg (1%) 2-amino-4-furan-2-yl-6-(4-isopropyl-benzylamino)-pyrimidine-5-carbonitrile as a white crystalline solid. ES-MS m/e (%): 334 (M+H$^+$, 100).

Analogously to Example 199 there were obtained:

Example 399
2-Amino-4-furan-2-yl-6-[(pyridin-3-ylmethyl)-amino]-pyrimidine-5-carbonitrile From 2-amino-4-furan-2-yl-6-methanesulfinyl-pyrimidine-5-carbonitrile and 3-picolylamine in DME. ES-MS m/e (%): 293 (M+H$^+$, 100).

Example 400
2-Amino-4-[(3-chloro-5-trifluoromethyl-pyridin-2-yl-methyl)-amino]-6-furan-2-yl-pyrimidine-5-carbonitrile From 2-amino-4-furan-2-yl-6-methanesulfinyl-pyrimidine-5-carbonitrile, 2-aminomethyl-3-chloro-5-(trifluoromethyl) pyridine hydrochloride and DBU in DME. ES-MS m/e (%): 397 (M{$^{37}$Cl}+H$^+$, 30), 395 (M{$^{35}$Cl}+H$^+$, 100).

Example 401
2-Amino-4-(3,5-dimethyl-pyridin-2-ylmethoxy)-6-furan-2-yl-pyrimidine-5-carbonitrile From 2-amino-4-furan-2-yl-6-methanesulfinyl-pyrimidine-5-carbonitrile, (3,5-dimethylpyridin-2-yl)methanol and DBU in DME. ES-MS m/e (%): 322 (M+H$^+$, 100).

Example 402
2-Amino-4-[(3,5-dimethyl-pyridin-2-ylmethyl)-amino]-6-furan-2-yl-pyrimidine-5-carbonitrile From 2-amino-4-furan-2-yl-6-methanesulfinyl-pyrimidine-5-carbonitrile, C-(3,5-dimethyl-pyridin-2-yl)-methylamine dihydrochloride and DBU in DME. ES-MS m/e (%): 321 (M+H$^+$, 100).

Example 403
2-Amino-4-(3-fluoro-phenyl)-6-(2-pyridin-2-yl-ethylsulfanyl)-pyrimidine-5-carbonitrile From 2-amino-4-(3-fluoro-phenyl)-6-methanesulfinyl-pyrimidine-5-carbonitrile, 2-mercaptoethylpyridine and DBU in DME. ES-MS m/e (%): 352 (M+H$^+$, 100).

Example 404
2-Amino-4-(4-fluoro-phenyl)-6-(2-pyridin-2-yl-ethoxy)-pyrimidine-5-carbonitrile From 2-amino-4-(4-fluoro-phenyl)-6-methanesulfinyl-pyrimidine-5-carbonitrile, (2-pyridyl)ethanol and DBU in DME. ES-MS m/e (%): 336 (M+H$^+$, 100).

Example 405
2-Amino-4-(3-fluoro-phenyl)-6-(2-pyridin-2-yl-ethoxy)-pyrimidine-5-carbonitrile From 2-amino-4-(3-fluoro-phenyl)-6-methanesulfinyl-pyrimidine-5-carbonitrile, (2-pyridyl)ethanol and DBU in DME. ES-MS m/e (%): 336 (M+H$^+$, 100).

Example 406
2-Amino-4-(4-fluoro-phenyl)-6-(2-pyridin-2-yl-ethylsulfanyl)-pyrimidine-5-carbonitrile From 2-amino-4-(4-fluoro-phenyl)-6-methanesulfinyl-pyrimidine-5-carbonitrile, 2-mercaptoethylpyridine and DBU in DME. ES-MS m/e (%): 352 (M+H$^+$, 100).

Example 407
2-Amino-4-(2-fluoro-phenyl)-6-oxo-1,6-dihydro-pyrimidine-5-carbonitrile From 2-amino-4-(2-fluoro-phenyl)-6-methanesulfinyl-pyrimidine-5-carbonitrile and water in dichloromethane. ES-MS m/e (%): 231 (M+H$^+$, 100).

Example 408
2-Amino-4-(2-fluoro-phenyl)-6-(2-pyridin-2-yl-ethoxy)-pyrimidine-5-carbonitrile From 2-amino-4-(2-fluoro-phenyl)-6-methanesulfinyl-pyrimidine-5-carbonitrile, (2-pyridyl)ethanol and DBU in DME. ES-MS m/e (%): 336 (M+H$^+$, 100).

Example 409
2-Amino-4-(2-fluoro-phenyl)-6-(2-pyridin-2-yl-ethylsulfanyl)-pyrimidine-5-carbonitrile From 2-amino-4-(2-fluoro-phenyl)-6-methanesulfinyl-pyrimidine-5-carbonitrile, 2-mercaptoethylpyridine and DBU in DME. ES-MS m/e (%): 352 (M+H$^+$, 100).

Example 410
2-Amino-4-(2-fluoro-phenyl)-6-[(pyridin-2-yl-methyl)-amino]-pyrimidine-5-carbonitrile From 2-amino-4-(2-fluoro-phenyl)-6-methanesulfinyl-pyrimidine-5-carbonitrile and 2-picolylamine in DME. ES-MS m/e (%): 321 (M+H$^+$, 100).

Example 411
6-Amino-4-furan-2-yl-2-[(pyridin-2-yl-methyl)-amino]-nicotinonitrile a) 6-Amino-4-furan-2-yl-2-methanesulfinyl-nicotinonitrile To a stirred suspension of 600 mg (2.59 mmol) 6-amino-4-furan-2-yl-2-methylsulfanyl-nicotinonitrile in 10 ml dichloromethane was added 1,36 g (5.19 mmol) 3-phenyl-2-(phenylsulfonyl)oxaziridine and stirring continued for 16 hours at room temperature. The resulting crystals were collected by filtration and washed with dichloromethane to afford 500 mg (78%) 6-amino-4-furan-2-yl-2-methanesulfinyl-nicotinonitrile as a white crystalline solid.

EI-MS m/e (%): 247 (M⁺, 26), 230 (12), 201 (100), 184 (24), 172 (27), 156 (28), 129 (24), 102 (13).

b) 6-Amino-4-furan-2-yl-2-[(pyridin-2-yl-methyl)-amino]-nicotinonitrile

To a stirred suspension of 250 mg (1.01 mmol) 6-amino-4-furan-2-yl-2-methanesulfinyl-nicotinonitrile in 10 ml DME was added 0.41 ml (4.04 mmol) 2-picolylamine and the mixture heated at 100° C. for 16 hours. The reaction mixture was then cooled to room temperature and partitioned between water and dichloromethane. The organic phase was dried over sodium sulfate and concentrated in vacuo. Chromatography (ethyl acetate) followed by trituration in ether afforded 100 mg (34%) 6-amino-4-furan-2-yl-2-[(pyridin-2-ylmethyl)-amino]-nicotinonitrile as an off-white crystalline solid. ES-MS m/e (%): 292 (M+H⁺, 100).

Analogously to Example 199 there were obtained:

Example 412
2-Amino-4-(3-fluoro-phenyl)-6-[(pyridin-2-yl-methyl)-amino]-pyrimidine-5-carbonitrile From 2-amino-4-(3-fluoro-phenyl)-6-methanesulfinyl-pyrimidine-5-carbonitrile and 2-picolylamine in DME. ES-MS m/e (%): 321 (M+H⁺, 100).

Example 413
2-Amino-4-(4-fluoro-phenyl)-6-[(pyridin-2-yl-methyl)-amino]-pyrimidine-5-carbonitrile From 2-amino-4-(4-fluoro-phenyl)-6-methanesulfinyl-pyrimidine-5-carbonitrile and 2-picolylamine in DME. ES-MS m/e (%): 321 (M+H⁺, 100).

Example 414
2-Amino-4-(4-methyl-furan-2-yl)-6-methyl sulfanyl-pyrimidine-5-carbonitrile To a stirred suspension of 2.19 g (10.9 mmol) 2-amino-4-chloro-6-methylsulfanyl-pyrimidine-5-carbonitrile in 40 ml benzene at room temperature were added 2,40 g (12.0 mmol) 2-(4-methyl-furan-2-yl)-benzo[1,3,2]dioxaborole, 252mg (0.22 mmol) tetrakis(triphenylphosphine)palladium (O) and 11 ml (22.0 mmol) 2M aqueous sodium carbonate. The reaction mixture was heated at 90° C. for 16 h, then concentrated in vacuo. Chromatography (1/3 ethyl acetate/hexane then 1/1 ethyl acetate/hexane) afforded 1.26 g (47%) 2-amino-4-(4-methyl-furan-2-yl)-6-methylsulfanyl-pyrimidine-5-carbonitrile as a light yellow crystalline solid. EI-MS m/e (%): 246 (M⁺, 61), 245 ([M—H]⁺, 100).

Analogously to Example 199 there was obtained:

Example 415
2-Amino-4-[(3-chloro-5-trifluoromethyl-pyridin-2:1-methyl)-amino]-6-phenyl-pyrimidine-5-carbonitrile From 2-amino-4-methanesulfinyl-6-phenyl-pyrimidine-5-carbonitrile, 2-aminomethyl-3-chloro-5-(trifluoromethyl)pyridine hydrochloride and DBU in DME. ES-MS m/e (%): 407 (M{³⁷Cl}+H⁺, 30), 405 (M{³⁵Cl}+H⁺, 100).

Example 416
4-Furan-2-yl-6-(2-pyridin-2-yl-ethoxy)-pyrimidin-2-yl-amine a) 4-Furan-2-yl-6-methanesulfinyl-pyrimidin-2-ylamine To a stirred suspension of 3.00 g (14.5 mmol) 4-furan-2-yl-6-methylsulfanyl-pyrimidin-2-yl-amine in 150 ml dichloromethane was added 7.56 g (29.0 mmol) 3-phenyl-2-(phenylsulfonyl)oxaziridine and stirring continued for 16 hours at room temperature. The resulting crystals were collected by filtration and washed with dichloromethane to afford 2.92 g (90%) 4-furan-2-yl-6-methanesulfinyl-pyrimidin-2-ylamine as a white crystalline solid. EI-MS m/e (%): 223 (M⁺, 50), 177 (32), 160 (25), 148 (23), 118 (100), 90 (23), 63 (24).

b) 4-Furan-2-yl-6-(2-pyridin-2-yl-ethoxy)-pyrimidin-2-yl-amine

To a stirred suspension of 500 mg (2.24 mmol) 4-furan-2-yl-6-methanesulfinyl-pyrimidin-2-yl-amine in 20 ml DME was added 0.50 ml (4.48 mmol) 2-(2-hydroxyethyl)pyridine and 0.84 ml (5.60 mmol) DBU and the mixture heated at 100° C. for 72 hours. The reaction mixture was then cooled to room temperature and partitioned between water and dichloromethane. The organic phase was dried over sodium sulfate and concentrated in vacuo. Chromatography (ethyl acetate) followed by trituration in ether afforded 220 mg (35%) 4-furan-2-yl-6-(2-pyridin-2-yl-ethoxy)-pyrimidin-2-ylamine as a white crystalline solid. ES-MS m/e (%): 283 (M+H⁺, 100).

In an analogous manner there was obtained:

Example 417
4-Furan-2-yl-6-(2-pyridin-2-yl-ethylsulfanyl)-pyrimidin-2-yl-amine From 4-furan-2-yl-6-methanesulfinyl-pyrimidin-2-yl-amine, 2-mercaptoethylpyridine and DBU in DME. ES-MS m/e (%): 299 (M+H⁺, 100), 194 (98), 106 (70).

Analogously to Example 199 there were obtained:

Example 418
2-Amino-4-[(3-chloro-5-trifluoromethyl-pyridin-2-yl-methyl)-amino]-6-(5-methyl-furan-2-yl)-pyrimidine-5-carbonitrile From 2-amino-4-methanesulfinyl-6-(5-methyl-furan-2-yl)-pyrimidine-5-carbonitrile, 2-aminomethyl-3-chloro-5-(trifluoromethyl)pyridine hydrochloride and DBU in DME. ES-MS m/e (%): 411 (M{³⁷Cl}+H⁺, 45), 409 (M{³⁵Cl}+H⁺, 100).

Example 419
2-Amino-4-furan-2-yl-6-[(5-trifluoromethyl-pyridin-2-yl-methyl)-amino]-pyrimidine-5-carbonitrile From 2-amino-4-furan-2-yl-6-methanesulfinyl-pyrimidine-5-carbonitrile and C-(5-trifluoromethyl-pyridin-2-yl)-methylamine in DME. ES-MS m/e (%): 361 (M+H⁺, 100).

Analogously to Example 350 there were obtained:

Example 420
6-Amino-4-[(3-chloro-5-trifluoromethyl-pyridin-2-yl-methyl)-amino]-2-furan-2-yl-nicotinonitrile From trifluoromethanesulfonic acid 6-amino-3-cyano-2-furan-2-yl-pyridin-4-yl ester, 2-aminomethyl-3-chloro-5-(trifluoromethyl)pyridine hydrochloride and DBU in DME. ES-MS m/e (%): 396 (M{³⁷Cl}+H⁺, 40), 394 (M{³⁵C}+H⁺, 100).

Example 421
6-Amino-4-(4-amino-benzylamino)-2-furan-2-yl-nicotinonitrile

From trifluoromethanesulfonic acid 6-amino-3-cyano-2-furan-2-yl-pyridin-4-yl ester and 4-aminobenzylamine in DME. ES-MS m/e (%): 306 (M+H⁺, 100).

Analogously to Example 199 there were obtained:

Example 422
2-Amino-4-(4-methyl-furan-2-yl)-6-(2-pyridin-2-yl-ethylsulfanyl)-pyrimidine-5-carbonitrile From 2-amino-4-methanesulfinyl-6-(4-methyl-furan-2-yl)-pyrimidine-5-carbonitrile, 2-(2-pyridyl)ethylmercaptan and DBU in DME. ES-MS m/e (%): 338 (M+H⁺, 100).

Example 423
2-Amino-4-(4-methyl-furan-2-yl)-6-(2-pyridin-2-yl-ethoxy)-pyrimidine-5-carbonitrile From 2-amino-4-methanesulfinyl-6-(4-methyl-furan-2-yl)-pyrimidine-5-carbonitrile, 2-(2-hydroxyethyl)pyridine and DBU in DME. ES-MS m/e (%): 322 (M+H$^+$, 100).

Analogously to Example 207 there was obtained:

Example 424
2-Amino-4-isoxazol-5-yl-6-methylsulfanyl-pyrimidine-5-carbonitrile From isoxazole-5-carboxylic acid ethyl ester with acetonitrile and butyllithium in THF. Then treatment with sodium hydride, carbon disulphide and methyl iodide in DMSO. Then treatment with guanidine nitrate and triethylamine in DMF. EI-MS m/e (%): 233 (M$^+$, 45), 206 ([M—HCN]$^+$, 100), 151 (33).

Analogously to Example 199 there was obtained:

Example 425
2-Amino-4-[(3-chloro-5-trifluoromethyl-pyridin-2-yl-methyl)-amino]-6-(4-methyl-furan-2-yl)-pyrimidine-5-carbonitrile From 2-amino-4-methanesulfinyl-6-(4-methyl-furan-2-yl)-pyrimidine-5-carbonitrile and 2-aminomethyl-3-chloro-5-(trifluoromethyl)pyridine in DME. ES-MS m/e (%): 411 (M{$^{37}$Cl}+H$^+$, 35), 409 (M{$^{35}$Cl}+H$^+$, 100).

Example 426
2-Amino-4-(1-ethoxy-vinyl)-6-methylsulfanyl-pyrimidine-5-carbonitrile a) 2-Amino-4-bromo-6-methylsulfanyl-1,2-pyrimidine-5-carbonitrile To a stirred suspension of 1.00 g (5.37 mmol) 2,2-dicyano-1-methylsulfanyl-vinyl-cyanamide sodium salt in 10 ml acetic acid at 5° C. was added dropwise 10 ml hydrobromic acid solution (33% in acetic acid) and the mixture was stirred at room temperature for 30 minutes. The mixture was then poured onto 100 ml ice-water added. The resulting crystals were collected by filtration and washed with water (ca 500 ml) until the washings were free of bromide ion. Chromatography (ethyl acetate/hexane 1/4) afforded 1.09 g (83%) 2-amino-4-bromo-6-methylsulfanyl-pyrimidine-5-carbonitrile as a white crystalline solid. EI-MS m/e (%): 246 (M{$^{81}$Br}$^+$, 93), 244 (M{$^{79}$Br}$^+$, 94), 165 ([M—Br]$^+$, 100).

b) 2-Amino-4-(1-ethoxy-vinyl)-6-methylsulfanyl-pyrimidine-5-carbonitrile

To a stirred solution of 300 mg (1.22 mmol) 2-amino-4-bromo-6-methylsulfanyl-pyrimidine-5-carbonitrile in 10 ml dioxane under argon at room temperature were added 0.41 ml (1.22 mmol) (1-ethoxyvinyl)tributylstannane and 86 mg (0.12 mmol) bis(triphenyl-phosphine)palladium(II) chloride. The reaction mixture was heated at reflux for 16 h, then cooled to room temperature, 2 g of kieselgel added, and the mixture concentrated in vacuo. Flash chromatography (hexane then 1/1 ethyl acetate/hexane) followed by trituration in ether/hexane afforded 140 mg (48%) 2-amino-4-(1-ethoxy-vinyl)-6-methylsulfanyl-pyrimidine-5-carbonitrile as a white crystalline solid. EI-MS m/e (%): 236 (M$^+$, 17), 221 ([M—CH$_3$]$^+$, 61), 207 ([M—C$_2$H$_5$]$^+$, 32), 192 ([M—C$_3$H$_8$]$^+$, 100).

Example 427
2-Amino-4-methylsulfanyl-6:pyridin-2-yl-pyrimidine-5-carbonitrile To a stirred solution of 600 mg (2,45 mmol) 2-amino-4-bromo-6-methylsulfanyl-pyrimidine-5-carbonitrile in 12 ml dry DMF under argon at room temperature were added 1.08 g (2.94 mmol) 2-(tributylstannyl)pyridine, 86 mg (0.12 mmol) bis(triphenylphosphine) palladium(II) chloride and 195 mg (2,45 mmol) copper(II) oxide. The reaction mixture was heated at 100° C. for 16 h, then cooled to room temperature, 2 g of kieselgel added, and the mixture concentrated in vacuo. Flash chromatography (hexane then 1/8 ethyl acetate/hexane) followed by trituration in ether/hexane afforded 120 mg (20%) 2-amino-4-methylsulfanyl-6-pyridin-2-yl-pyrimidine-5-carbonitrile as an off-white crystalline solid. EI-MS m/e (%): 243 (M$^+$, 95), 242 ([M—H]$^+$, 100).

Example 428
2-Amino-4-(4,5-dihydro-furan-2-yl)-6-methylsulfanyl-pyrimidine-5-carbonitrile a) Tributyl-(4,5-dihydro-furan-2-yl)-stannane To a stirred solution of 0.35 ml (7.13 mmol) 2,3-dihydrofuran in 10 ml dry THF under argon at −78° C. was added 4.7 ml (7.2 mmol) tert-butyllithium solution (1.5M in pentane) and stirring continued for 5 minutes at −78° C. and 15 minutes at 0° C. The reaction mixture was then recooled to −78° C. and 1.92 ml (7.13 mmol) tributyltin chloride added dropwise and stirring continued for 16 hours at room temperature. The reaction mixture was partitioned between ether and water. The organic phase was then washed with brine, dried over sodium sulfate, and concentrated in vacuo to afford 2.37 g (93%) tributyl-(4,5-dihydro-furan-2-yl)-stannane as a yellow liquid which was used in the next step without further purification. EI-MS m/e (%): cluster at 303 ([M—C$_4$H$_9$]$^+$, 100).

b) 2-Amino-4-(4,5-dihydro-furan-2-yl)-6-methylsulfanyl-pyrimidine-5-carbonitrile To a stirred solution of 700 mg (2.86 mmol) 2-amino-4-bromo-6-methylsulfanyl-pyrimidine-5-carbonitrile in 25 ml dry dioxane under argon at room temperature were added 1.13 g (3.14 mmol) tributyl-(4,5-dihydro-furan-2-yl)-stannane and 281 mg (0.40 mmol) bis(triphenylphosphine) palladium(II) chloride. The reaction mixture was heated at 100° C. for 18 h, then cooled to room temperature and concentrated in vacuo. Flash chromatography (ethyl acetate/hexane 1/1) afforded 325 mg (49%) 2-amino-4-(4,5-dihydro-furan-2-yl)-6-methylsulfanyl-pyrimidine-5-carbonitrile as a yellow crystalline solid. ES-MS m/e (%): 257 (M+Na$^+$, 47), 235 (M+H$^+$, 100).

In an analogous manner there was obtained:

Example 429
2-Amino-4-(5,6-dihydro-4H-pyran-2-yl)-6-methylsulfanyl-pyrimidine-5-carbonitrile From 3,4-dihydro-2H-pyran, tert-butyllithium and tributyltin chloride in THF. Then treatment with 2-amino-4-bromo-6-methylsulfanyl-pyrimidine-5-carbonitrile and bis (triphenylphosphine)palladium(II) chloride in dioxane. ES-MS m/e (%): 271 (M+Na$^+$, 39), 249 (M+H$^+$, 100).

Analogously to Example 199 there was obtained:

Example 430
2-Amino-4-pyridin-2-yl-6-(2-pyridin-2-yl-ethylsulfanyl)-pyrimidine-5-carbonitrile From 2-amino-4-methanesulfinyl-6-pyridin-2-yl-pyrimidine-5-carbonitrile, 2-mercaptoethylpyridine and DBU in DME. ES-MS m/e (%): 335 (M+H$^+$, 100).

Example 431
2-Amino-4-(2-methoxy-phenyl)-6-methylsulfanyl-pyrimidine-5-carbonitrile To a stirred solution of 250 mg (1.02 mmol) 2-amino-4-bromo-6-methylsulfanyl-pyrimidine-5-carbonitrile in 10 ml toluene at room temperature were added 310 mg (2.04 mmol) 2-methoxybenzeneboronic acid, 118 mg (0.10 mmol)

tetrakis(triphenylphosphine) palladium(O) and 262 mg (2.04 mmol) potassium carbonate. The reaction mixture was heated at 100° C. for 16 h, then cooled to room temperature and partitioned between ethyl acetate and water. The phases were separated and the organic phase dried over sodium sulfate and concentrated in vacuo. Chromatography (ethyl acetate/hexane 1/4 then ethyl acetate/hexane 1/2) followed by trituration in hexane afforded 80 mg (29%) 2-amino-4-(2-methoxy-phenyl)-6-methylsulfanyl-pyrimidine-5-carbonitrile as a white crystalline solid. EI-MS m/e (%): 272 ($M^+$, 32), 257 ($[M—CH_3]^+$, 100), 241 (17).

Example 432
2-Amino-4-methylsulfanyl-6-pyrazol-1-yl-pyrimidine-5-carbonitrile To a stirred solution of 500 mg (7.34 mmol) pyrazole in 15 ml diglyme at room temperature under argon was added 0.90 ml (7.34 mmol) potassium hydride (35% dispersion in oil) and the reaction mixture heated at 60° C. for 2 hours. 1.50 g (6.12 mmol) 2-amino-4-bromo-6-methylsulfanyl-pyrimidine-5-carbonitrile was then added and the reaction mixture heated at 60° C. for 16 h, then cooled to room temperature, 2 g of kieselgel added, and the mixture concentrated in vacuo. Flash chromatography (ethyl acetate/hexane 1/3) afforded 390 mg (27%) 2-amino-4-methylsulfanyl-6-pyrazol-1-yl-pyrimidine-5-carbonitrile as a white crystalline solid. EI-MS m/e (%): 232 ($M^+$, 61), 231 ($[M—H]^+$, 100).

Example 433
2-Amino-4-(1-ethoxy-vinyl)-6-(2-pyridin-2-yl-ethylsulfanyl)-pyrimidine-5-carbonitrile To a stirred suspension of 200 mg (0.85 mmol) 2-amino-4-(1-ethoxy-vinyl)-6-methylsulfanyl-pyrimidine-5-carbonitrile in 16 ml dioxane was added 546 mg (3.38 mmol) sodium 2-pyridin-2-yl-ethanethiolate and the mixture heated at 100° C. for 1 hour. The reaction mixture was then concentrated in vacuo and the residue triturated in ether. The crystals were removed by filtration and the mother liquor concentrated in vacuo. The residue was then recrystallised from ethyl acetate/hexane and the crystals additionally purified by HPLC to afford 4.0 mg (1%) 2-amino-4-(1-ethoxy-vinyl)-6-(2-pyridin-2-yl-ethylsulfanyl)-pyrimidine-5-carbonitrile as an off-white crystalline solid. ES-MS m/e (%): 328 ($M+H^+$, 100).

Example 434
N-(5-Cyano-4-furan-2-yl-6-methylsulfanyl-pyrimidin-2-yl)-benzamide Following the method of Rudorf and Augustin (*J. Prakt. Chem.* 1978, 320, 576), a solution of 250 mg (1.04 mmol) 2-(furan-2-carbonyl)-3,3-bis-methylsulfanyl-acrylonitrile, 205 mg (1.25 mmol) N-(aminoiminomethyl)benzamide and 0.36 ml (2.61 mmol) triethylamine in 5 ml DMF was heated at reflux for 6 h. The reaction mixture was then cooled to room temperature and partitioned between ethyl acetate and water. The phases were separated and the organic phase dried over sodium sulfate and concentrated in vacuo. Chromatography (hexane then ethyl acetate/hexane 1/1) afforded 199 mg (57%) N-(5-cyano-4-furan-2-yl-6-methylsulfanyl-pyrimidin-2-yl)-benzamide as an off-white amorphous solid. ES-MS m/e (%): 359 ($M+Na^+$, 36), 337 ($M+H^+$, 100).

Analogously to Example 199 there were obtained:

Example 435
2-Amino-4-(2-methoxy-phenyl)-6-(2-pyridin-2-yl-ethylsulfanyl)-pyrimidine-5-carbonitrile From 2-amino-4-methanesulfinyl-6-(2-methoxy-phenyl)-pyrimidine-5-carbonitrile, 2-mercaptoethylpyridine and DBU in DME. ES-MS m/e (%): 364 ($M+H^+$, 100).

Example 436
2-Amino-4-(3,4-dimethyl-benylamino)-6-pyridin-2-yl-pyrimidine-5-carbonitrile From 2-amino-4-methanesulfinyl-6-pyridin-2-yl-pyrimidine-5-carbonitrile and 3,4-dimethylbenzylamine in DME. ES-MS m/e (%): 331 ($M+H^+$, 100).

Example 437
N-[5-Cyano-4-furan-2-yl-6-(2-pyridin-2-yl-ethylsulfanyl)-pyrimidin-2-yl]-benzamide From N-(5-cyano-4-furan-2-yl-6-methanesulfinyl-pyrimidin-2-yl)-benzamide, 2-pyridylethylmercaptan and DBU in DME. ES-MS m/e (%): 428 ($M+H^+$, 100).

Example 438
2-Amino-4-methylsulfanyl-6-pyridin-3-yl-pyrimidine-5-carbonitrile To a stirred suspension of 2,45 g (10.0 mmol) 2-amino-4-bromo-6-methylsulfanyl-pyrimidine-5-carbonitrile in 65 ml dioxane at room temperature were added 2.18 g (20.0 mmol) 3-pyridineboronic acid, 1.15 g (1.00 mmol) tetrakis (triphenylphosphine)palladium(O) and 20 ml (40.0 mmol) 2M aqueous sodium carbonate. The reaction mixture was heated at reflux for 48 h, then concentrated in vacuo. Chromatography (1/4 ethyl acetate/hexane) afforded 460 mg (20%) 2-amino-4-methylsulfanyl-6-pyridin-3-yl-pyrimidine-5-carbonitrile as a light yellow crystalline solid. EI-MS m/e (%): 243 ($M^+$, 100), 242 ($[M—H]^+$, 70).

Analogously to Example 199 there were obtained:

Example 439
2-Amino-4-pyridin-3-yl-6-(2-pyridin-2-yl-ethylsulfanyl)-pyrimidine-5-carbonitrile From 2-amino-4-methanesulfinyl-6-pyridin-3-yl-pyrimidine-5-carbonitrile, 2-pyridylethylmercaptan and DBU in DME. EI-MS m/e (%): 334 ($M^+$, 35), 333 ($[M—H]^+$, 100), 138 (52), 106 (33).

Example 440
2-Amino-4-benzylamino-6-pyridin-2-yl-pyrimidine-5-carbonitrile

From 2-amino-4-methanesulfinyl-6-pyridin-2-yl-pyrimidine-5-carbonitrile and benzylamine in DME. ES-MS m/e (%): 303 ($M+H^+$, 100).

Example 441
2-Amino-4-(2-phenylamino-ethylamino)-6-pyridin-2-yl-pyrimidine-5-carbonitrile From 2-amino-4-methanesulfinyl-6-pyridin-2-yl-pyrimidine-5-carbonitrile and N-phenylethylenediamine in DME. ES-MS m/e (%): 332 ($M+H^+$, 100).

Example 442
2-Amino-4-pyridin-2-yl 6-(4-trifluoromethyl-benzlamino)-pyrimidine-5-carbonitrile From 2-amino-4-methanesulfinyl-6-pyridin-2-yl-pyrimidine-5-carbonitrile and 4-trifluoromethylbenzylamine in DME. ES-MS m/e (%): 371 ($M+H^+$, 100).

Example 443
2-Amino-4-pyrazol-1-yl-6-(2-pyridin-2-yl-ethylsulfanyl)-pyrimidine-5-carbonitrile From 2-amino-4-methanesulfinyl-6-pyrazol-1-yl-pyrimidine-5-carbonitrile, 2-pyridylethylmercaptan and DBU in DME. ES-MS m/e (%): 324 ($M+H^+$, 100).

Example 444
2-Amino-4-(3,4-dimethyl-benzylamino)-6-pyrazol-1-yl-pyrimidine-5-carbonitrile From 2-amino-4-methanesulfinyl-6-pyrazol-1-yl-pyrimidine-5-carbonitrile and 3,4-dimethylbenzylamine in DME. ES-MS m/e (%): 320 (M+H$^+$, 100).

Example 445
2-Amino-4-pyridin-2-yl-6-(pyridin-2-yl-methoxy)-pyrimidine-5-carbonitrile From 2-amino-4-methanesulfinyl-6-pyridin-2-yl-pyrimidine-5-carbonitrile, 2-(hydroxymethyl)pyridine and DBU in DME. EI-MS m/e (%): 304 (M$^+$, 100), 275 (33), 197 (50), 92 (30), 65 (34).

Example 446
2-Amino-4-pyridin-2-yl-6-(2-pyridin-2-yl-ethoxy)-pyrimidine-5-carbonitrile From 2-amino-4-methanesulfinyl-6-pyridin-2-yl-pyrimidine-5-carbonitrile, 2-(2-hydroxyethyl)pyridine and DBU in DME. ES-MS m/e (%): 319 (M+H$^+$, 100).

Example 447
2-Amino-4-methylsulfanyl-6-oxazol-2-yl-pyrimidine-5-carbonitrile a) 2-Tributylstannanyl-oxazole To a stirred solution of 1.00 g (14.5 mmol) oxazole in 25 ml dry THF under argon at −78° C. was added 9.14 ml (14.6 mmol) n-butyllithium solution (1.6M in hexane) and stirring continued for 30 minutes at −78° C. 3.91 ml (14.5 mmol) tributyltin chloride was then added dropwise and stirring continued for 15 minutes at −78° C. and for 1 hour at room temperature. The reaction mixture was then concentrated in vacuo and the residue resuspended in 50 ml hexane. The insoluble lithium salts were removed by filtration and the filtrate was concentrated in vacuo to afford 4.90 g (95%) 2-tributylstannanyl-oxazole as a light yellow liquid which was used in the next step without further purification. $^1$H NMR 6 (CDCl$_3$, 250 MHz): 7.84 (1H, s), 7.18 (1H, s), 1.67–1.53 (6H, m), 1.42–1.29 (6H, m), 1.20 (6H, t, J=8 Hz), 0.89 (9H, t, J=7 Hz).

b) 2-Amino-4-methylsulfanal-6-oxazol-2-yl-pyrimidine-5-carbonitrile

To a stirred solution of 2.37 g (9.67 mmol) 2-amino-4-bromo-6-methylsulfanyl-pyrimidine-5-carbonitrile in 50 ml dry DMF under argon at room temperature were added 4.50 g (12.6 mmol) 2-tributylstannanyl-oxazole, 889 mg (0.97 mmol) tris(dibenzylidene-acetone)dipalladium(O), 1.48 g (4.84 mmol) triphenylarsine and 185 mg (0.97 mmol) copper(I) iodide. The reaction mixture was heated at 95° C. for 48 h, then cooled to room temperature and partitioned between ethyl acetate and water. The phases were separated and the organic phase dried over sodium sulfate and concentrated in vacuo. Flash chromatography (ethyl acetate/hexane 1/1 followed by ethyl acetate) afforded 182 mg (7%) 2-amino-4-methylsulfanyl-6-oxazol-2-yl-pyrimidine-5-carbonitrile as a yellow crystalline solid. ES-MS m/e (%): 234 (M+H$^+$, 100).

Analogously to Example 199 there were obtained:

Example 448
2-Amino-4-[(3-chloro-5-trifluoromethyl-pyridin-2-yl-methyl)-amino]-6-pyridin-2-yl-pyrimidine-5-carbonitrile From 2-amino-4-methanesulfinyl-6-pyridin-2-yl-pyrimidine-5-carbonitrile, 2-aminomethyl-3-chloro-6-(trifluoromethyl)pyridine hydrochloride and DBU in DME. ES-MS m/e (%): 408 (M{$^{37}$Cl}+H$^+$, 25), 406 (M{$^{35}$Cl}+H$^+$, 100).

Example 449
2-Amino-4-(3,5-dimethyl-pyridin-2-yl-methoxy)-6-pyridin-2-yl-pyrimidine-5-carbonitrile From 2-amino-4-methanesulfinyl-6-pyridin-2-yl-pyrimidine-5-carbonitrile, 3,5-dimethyl-2-pyridinemethanol and DBU in DME. EI-MS m/e (%): 332 (M$^+$, 100), 303 (34), 120 (31).

Example 450
2-Amino-4-benzylamino-6-pyrazol-1-yl-pyrimidine-5-carbonitrile

From 2-amino-4-methanesulfinyl-6-pyrazol-1-yl-pyrimidine-5-carbonitrile and benzylamine in DME. ES-MS m/e (%): 292 (M+H$^+$, 100).

Example 451
2-Amino-4-(2-phenylamino-ethylamino)-6-pyrazol-1-yl-pyrimidine-5-carbonitrile From 2-amino-4-methanesulfinyl-6-pyrazol-1-yl-pyrimidine-5-carbonitrile and N-phenylethylenediamine in DME. ES-MS m/e (%): 321 (M+H$^+$, 100).

Example 452
2-Amino-4-[(3-chloro-5-trifluoromethyl-pyridin-2-yl-methyl)-amino]-6-pyrazol-1-yl-pyrimidine-5-carbonitrile From 2-amino-4-methanesulfinyl-6-pyrazol-1-yl-pyrimidine-5-carbonitrile, 2-aminomethyl-3-chloro-6-(trifluoromethyl)pyridine hydrochloride and DBU in DME. ES-MS m/e (%): 397 (M{$^{37}$Cl}+H$^+$, 25), 395 (M{$^{35}$Cl}+H$^+$, 100).

Example 453
2-Amino-4-(3-methyl-pyridin-2-ylmethoxy)-6-pyridin-2-yl-pyrimidine-5-carbonitrile From 2-amino-4-methanesulfinyl-6-pyridin-2-yl-pyrimidine-5-carbonitrile, 3-methyl-2-pyridinemethanol and DBU in DME. ES-MS m/e (%): 319 (M+H$^+$, 100).

Example 454
2-Amino-4-(5-methyl-pyridin-2-ylmethoxy)-6-pyridin-2-yl-pyrimidine-5-carbonitrile From 2-amino-4-methanesulfinyl-6-pyridin-2-yl-pyrimidine-5-carbonitrile, 5-methyl-2-pyridinemethanol and DBU in DME. ES-MS m/e (%): 319 (M+H$^+$, 100).

Example 455
2-Amino-4-(4,5-dihydro-furan-2-yl)-6-(2-pyridin-2-yl-ethylsulfanyl)-pyrimidine-5-carbonitrile a) 2-Amino-4,6-dichloro-pyrimidine-5-carbaldehyde Following the method of Bell et al. (*J. Heterocyclic Chem.* 1983, 20, 41), to 97.0 ml (1.06 mol) phosphorus oxychloride in a 2-necked flask cooled to 5° C. was added dropwise with stirring 32.5 ml (0.42 mol) DMF. The mixture was allowed to warm to room temperature and then 25.0 g (0.20 mol) 2-amino-4,6-dihydroxy-pyrimidine was added in small portions over 30 minutes. The reaction mixture was then heated at 100° C. for 4.5 hours before being poured cautiously onto water cooled to 10° C. and left standing at room temperature overnight. The resulting crystals were collected by filtration, and extracted with 4×450 ml hot ethyl acetate. The combined organic extracts were concentrated in vacuo and the residue triturated in 50 ml ethyl acetate to afford 22.5 g (60%) 2-amino-4,6-dichloro-pyrimidine-5-carbaldehyde as an orange crystalline solid. EI-MS m/e (%): 195 (M{$^{37}$Cl, $^{37}$Cl}$^+$, 5), 194 ([M{$^{37}$Cl, $^{37}$Cl}-H]$^+$, 12), 193 (M{$^{37}$Cl, $^{35}$Cl }$^+$, 29), 192 ([M{$^{37}$Cl, $^{35}$Cl }-H]$^+$, 70), 191 (M{$^{35}$Cl, $^{35}$Cl}$^+$, 40), 190 ([M{$^{35}$Cl, $^{35}$Cl}-H]$^+$, 100).

b) 2-Amino-4,6-dichloro-pyrimidine-5-carbaldehyde Oxime

Following the method of Bell et al. (*J. Heterocyclic Chem.* 1983, 20, 41), to a solution of 29.6 g (154 mmol) 2-amino- 4,6-dichloro-pyrimidine-5-carbaldehyde in 31 acetic acid in a 2-necked flask at room temperature was added dropwise with stirring a solution of 11.8 g (170 mmol) hydroxylamine hydrochloride in 2.31 ethanol. Stirring was continued for 3 h at room temperature during which time crystallisation occurred. The crystals were collected by filtration to afford 26.8 g (84%) 2-amino-4,6-dichloro-pyrimidine-5-carbaldehyde oxime as a light yellow crystalline solid. ES-MS m/e (%): 209 ([M{$^{37}$Cl, $^{37}$Cl}-H]$^-$, 20), 207 ([M{$^{37}$Cl, $^{35}$Cl}-H]$^-$, 55), 205 ([M{$^{35}$Cl, $^{35}$Cl}-H]$^-$, 100).

c) 2-Amino-4-chloro-6-oxo-1,6-dihydro-pyrimidine-5-carbonitrile

Following the method of Bell et al. (*J. Heterocyclic Chem.* 1983, 20, 41), hydrogen chloride gas was bubbled for 2 minutes though a solution of 6.00 g (29.0 mmol) 2-amino-4,6-dichloro-pyrimidine-5-carbaldehyde oxime in 800 ml acetic acid at 115° C. The mixture was then stirred at 115° C. for 16 hours before being cooled to room temperature. The resulting crystals were removed by filtration, and the filtrate concentrated in vacuo. The residue was triturated in 100 ml ether to afford 4.60 g (93%) 2-amino-4-chloro-6-oxo-1,6-dihydro-pyrimidine-5-carbonitrile as a light yellow crystalline solid. EI-MS m/e (%): 172 (M{$^{37}$Cl}$^+$, 23), 170 (M{$^{35}$Cl}$^+$, 71), 129 (53), 43 (100).

d) 2-Amino-6-oxo-4-(2-pyridin-2-yl-ethylsulfanyl)-1,6-dihydro-pyrimidine-5-carbonitrile To a stirred suspension of 500 mg (2.93 mmol) 2-amino-4-chloro-6-oxo-1,6-dihydro-pyrimidine-5-carbonitrile in 10 ml DME were added 0.61 g (4.40 mmol) 2-mercaptoethylpyridine and 1.10 ml (7.33 mmol) DBU and the mixture stirred at room temperature for 1 hour. The reaction mixture was then partitioned between water and ethyl acetate and the organic phase was dried over sodium sulfate and concentrated in vacuo. Chromatography (dichloromethane then methanol/dichloromethane 5/95) followed by trituration in ether/methanol afforded 310 mg (39%) 2-amino-6-oxo-4-(2-pyridin-2-yl-ethylsulfanyl)-1,6-dihydro-pyrimidine-5-carbonitrile as a white crystalline solid. ES-MS m/e (%): 274 (M+H$^+$, 100).

e) Trifluoromethanesulfonic Acid 2-amino-5-cyano-6-(2-pyridin-2-yl-ethylsulfanyl)-pyrimidin-4-yl Ester To a stirred suspension of 300 mg (1.10 mmol) 2-amino-6-oxo-4-(2-pyridin-2-yl-ethylsulfanyl)-1,6-dihydro-pyrimidine-5-carbonitrile in 10 ml dichloromethane was added 0.49 ml (2.20 mmol) 2,6-di-tert-butylpyridine and the mixture was ultrasonicated for 30 minutes. 0.18 ml (1.10 mmol) triflic anhydride was then added dropwise at 0° C. and stirring continued at room temperature for 16 hours. The reaction mixture was then diluted with 5 ml methanol, 2 g kieselgel was added, and the mixture was concentrated in vacuo. Chromatography (ethyl acetate) afforded 290 mg (65%) trifluoromethanesulfonic acid 2-amino-5-cyano-6-(2-pyridin-2-yl-ethylsulfanyl)-pyrimidin-4-yl ester as a light yellow crystalline solid. ES-MS m/e (%): 406 (M+H$^+$, 100).

f) 2-Amino-4-(4,5-dihydro-furan-2-yl)-6-(2-pyridin-2-yl-ethylsulfanyl)-pyrimidine-5-carbonitrile To a stirred solution of 290 mg (0.72 mmol) trifluoromethanesulfonic acid 2-amino-5-cyano-6-(2-pyridin-2-yl-ethylsulfanyl)-pyrimidin-4-yl ester in 10 ml dioxane and 2 ml DMF under argon at room temperature were added 283 mg (0.79 mmol) tributyl-(4,5-dihydro-furan-2-yl)-stannane and 50 mg (0.07 mmol) bis(triphenylphosphine)palladium (II) chloride. The reaction mixture was heated at 100° C. for 1 h, then cooled to room temperature and partitioned between water and ethyl acetate. The organic phase was dried over sodium sulfate and concentrated in vacuo. Flash chromatography (ethyl acetate then 5/95 methanol/ethyl acetate) followed by trituration in ether afforded 20 mg (9%) 2-amino-4-(4,5-dihydro-furan-2-yl)-6-(2-pyridin-2-yl-ethylsulfanyl)-pyrimidine-5-carbonitrile as a light brown crystalline solid. ES-MS m/e (%): 348 (M+Na$^+$, 30), 326 (M+H$^+$, 100).

Analogously to Example 199 there were obtained:

Example 456

2-Amino-4-pyrazol-1-yl-6-(pyridin-2-yl-methoxy)-pyrimidine-5-carbonitrile

From 2-amino-4-methanesulfinyl-6-pyrazol-1-yl-pyrimidine-5-carbonitrile, 2-(hydroxymethyl)pyridine and DBU in DME. ES-MS m/e (%): 294 (M+H$^+$, 100).

Example 457

2-Amino-4-(3,4-dimethyl-benzylamino)-6-pyridin-3-yl-pyrimidine-5-carbonitrile

From 2-amino-4-methanesulfinyl-6-pyridin-3-yl-pyrimidine-5-carbonitrile and 3,4-dimethylbenzylamine in DME. ES-MS m/e (%): 331 (M+H$^+$, 100).

Example 458

2-Amino-4-pyrazol-1-yl-6-(2-pyridin-2-yl-ethoxy)-pyrimidine-5-carbonitrile

From 2-amino-4-methanesulfinyl-6-pyrazol-1-yl-pyrimidine-5-carbonitrile, 2-(2-hydroxyethyl)pyridine and DBU in DME. ES-MS me/(%) 308 (M+H$^+$, 100)

Example 459

2-Amino-4-pyrazol-1-yl-6-(4-trifluoromethyl-benzylamino)-pyrimidine-5-carbonitrile From 2-amino-4-methanesulfinyl-6-pyrazol-1-yl-pyrimidine-5-carbonitrile and 4-trifluoromethylbenzylamine in DME. ES-MS m/e (%): 360 (M+H$^+$, 100).

Example 460

1-Amino-4-benzylamino-6-(2-methoxy-phenyl)-pyrimidine-5-carbonitrile

From 2-amino-4-methanesulfinyl-6-(2-methoxy-phenyl)-pyrimidine-5-carbonitrile and benzylamine in DME. ES-MS m/e (%): 332 (M+H$^+$, 100).

Example 461

2-Amino-4-(4,5-dihydro-furan-2-yl)-6-(3,4-dimethyl-benzylamino)-pyrimidine-5-carbonitrile a) 2-Amino-4-(4,5-dihydro-furan-2-yl)-6-oxo-1,6-dihydro-pyrimidine-5-carbonitrile To a stirred solution of 200 mg (1.17 mmol) 2-amino-4-chloro-6-oxo-1,6-dihydro-pyrimidine-5-carbonitrile in 10 ml dioxane under argon at room temperature were added 463 mg (1.29 mmol) tributyl-(4,5-dihydro-furan-2-yl)-stannane and 82 mg (0.12 mmol) bis(triphenylphosphine)palladium (II) chloride. The reaction mixture was heated at 100° C. for 16 h, then cooled to room temperature and concentrated in vacuo. Flash chromatography (ethyl acetate/hexane 1/1 then ethyl acetate then 5/95 methanol/ethyl acetate) afforded 65 mg (27%) 2-amino-4-(4,5-dihydro-furan-2-yl)-6-oxo-1,6-dihydro-pyrimidine-5-carbonitrile as a light yellow crystalline solid. ES-MS m/e (%): 205 (M+H$^+$, 100).

b) Trifluoromethanesulfonic Acid 2-amino-5-cyano-6-(4,5-dihydro-furan-2-yl)-pyrimidin-4-yl Ester To a stirred suspension of 300 mg (1.47 mmol) 2-amino-4-(4,5-dihydro-furan-2-yl)-6-oxo-1,6-dihydro-pyrimidine-5-carbonitrile in 10 ml dichloromethane was added 1,32 ml (5.88 mmol) 2,6-di-tert-butylpyridine and the mixture was ultrasonicated for 10 minutes. 0.24 ml (1.47 mmol) triflic anhydride was then added dropwise at 0° C. and stirring continued at 0° C. for 1.5 hours. 3 g kieselgel was then added and the mixture was concentrated in vacuo. Chromatography (ethyl acetate) afforded 40 mg (8%) trifluoromethanesulfonic acid 2-amino-5-cyano-6-(4,5-dihydro-furan-2-yl)-pyrimidin-4-yl ester as an off-white crystalline solid. ES-MS m/e (%): 337 (M+H$^+$, 100).

c) 2-Amino-4-(4,5-dihydro-furan-2-yl)-6-(3,4-dimethyl-benzylamino)-pyrimidine-5-carbonitrile To a stirred suspension of 250 mg (0.74 mmol) trifluoromethanesulfonic acid 2-amino-5-cyano-6-(4,5-dihydro-furan-2-yl)-pyrimidin-4-yl ester in 10 ml DME was added 0.20 g (1.49 mmol) 3,4-dimethylbenzylamine and the mixture stirred at room temperature for 1 hour. The reaction mixture was then partitioned between water and ethyl acetate and the organic phase was dried over sodium sulfate and concentrated in vacuo. Chromatography (ethyl acetate) followed by triturated in ether/hexane afforded 35 mg (15%) 2-amino-4-(4,5-dihydro-furan-2-yl)-6-(3,4-dimethyl-benzylamino)-pyrimidine-5-carbonitrile as a white crystalline solid. ES-MS m/e (%): 322 (M+H$^+$, 100).

In an analogous manner there were obtained:

Example 462
2-Amino-4-(4,5-dihydro-furan-2-yl)-6-(4-trifluoromethyl-benzylamino)-pyrimidine-5-carbonitrile From trifluoromethanesulfonic acid 2-amino-5-cyano-6-(4,5-dihydro-furan-2-yl)-pyrimidin-4-yl ester and 4-trifluoromethylbenzylamine in DME. ES-MS m/e (%): 362 (M+H$^+$, 100).

Example 463
2-Amino-4-(4,5-dihydro-furan-2-yl)-6-(2-phenylamino-ethylamino)-pyrimidine-5-carbonitrile From trifluoromethanesulfonic acid 2-amino-5-cyano-6-(4,5-dihydro-furan-2-yl)-pyrimidin-4-yl ester and N-phenylethylenediamine in DME. ES-MS m/e (%): 323 (M+H$^+$, 100).

Example 464
2-Amino-4-(4,5-dihydro-furan-2-yl)-6-[(4-methyl-pyridin-2-ylmethyl)-amino]-pyrimidine-5-carbonitrile From trifluoromethanesulfonic acid 2-amino-5-cyano-6-(4,5-dihydro-furan-2-yl)-pyrimidin-4-yl ester, C-(4-methyl-pyridin-2-yl)-methylamine dihydrochioride and DBU in DME. ES-MS m/e (%): 309 (M+H$^+$, 100).

Analogously to Example 199 there were obtained:

Example 465
2-Amino-4-(5-methyl-furan-2-yl)-6-(3-methyl-pyridin-2-ylmethoxy)-pyrimidine-5-carbonitrile From 2-amino-4-methanesulfinyl-6-(5-methyl-furan-2-yl)-pyrimidine-5-carbonitrile, 3-methyl-2-pyridinemethanol and DBU in DME. ES-MS m/e (%): 322 (M+H$^+$, 100).

Example 466
2-Amino-4-(3,5-dimethyl-pyridin-2-ylmethoxy)-6-(5-methyl-furan-2-yl)-pyrimidine-5'-carbonitrile From 2-amino-4-methanesulfinyl-6-(5-methyl-furan-2-yl)-pyrimidine-5-carbonitrile, 3,5-dimethyl-2-pyridinemethanol and DBU in DME. ES-MS m/e (%): 336 (M+H$^+$, 100).

Example 467
2-Amino-4-methylsulfanyl-6-(5-methylsulfanyl-furan-2-yl)-pyrimidine-5-carbonitrile a) 3-(5-Bromo-furan-2-yl)-3-oxo-propionitrile To 1.95 g (48.8 mmol, 60% dispersion in mineral oil) sodium hydride in a 2-necked flask fitted with a reflux condenser was added dropwise 30 ml THF and the mixture was then heated to reflux. A solution of 6.4 ml (122 mmol) acetonitrile and 5.00 g (24.4 mmol) 5-bromo-furan-2-carboxylic acid methyl ester in 20 ml dry THF was added dropwise and the reaction mixture heated at reflux for 5 hours. The reaction mixture was then cannulated into a rapidly stirred solution of 1M hydrochloric acid at 0° C. The mixture was extracted twice with ethyl acetate and the combined organic phases dried over sodium sulfate and concentrated in vacuo. Chromatography (ethyl acetate/hexane 2/3) afforded 3.90 g (75%) 3-(5-bromo-furan-2-yl)-3-oxo-propionitrile as a yellow crystalline solid. EI-MS m/e (%): 215 (M{$^{81}$Br}$^+$, 27), 213 (M{$^{79}$Br}$^+$, 28), 175 ([M{$^{81}$Br}—CH$_2$CN]$^+$, 100), 173 ([M{$^{79}$Br}—CH$_2$CN]$^+$, 100), 38 (59).

b) 2-(5-Bromo-furan-2-carbonyl)-3,3-bis-methylsulfanyl-acrylonitrile

Following the method of Rudorf and Augustin (*Phosphorus and Sulfur* 1981, 9, 329), a solution of 3.02 g (14.1 mmol) 3-(5-bromo-furan-2-yl)-3-oxo-propionitrile in 25 ml dry DMSO was added dropwise to a stirred suspension of 1.13 g (28.3 mmol, 60% dispersion in mineral oil) sodium hydride in 25 ml DMSO under argon at room temperature. 0.85 ml (14.1 mmol) carbon disulfide was then added dropwise, with external water bath cooling, and stirring continued for 2 hour, after which 1.8 ml (28.3 mmol) methyl iodide was added dropwise, with external water bath cooling, and stirring continued for a further 16 h. The reaction mixture was then poured into 1 l ice-cold water, and the precipitate collected by filtration, washed with hexane, and dried in vacuo to afford 2.91 g (65%) 2-(5-bromo-furan-2-carbonyl)-3,3-bis-methylsulfanyl-acrylonitrile as a yellow crystalline solid. EI-MS m/e (%): 319 (M{$^{81}$Br}$^+$, 10), 317 (M{$^{79}$Br}$^+$, 10), 304 ([M{$^{81}$Br}-CH$_3$]$^+$, 30), 302 ([M{$^{79}$Br}-CH$_3$]$^+$, 45), 238 ([M—Br]$^+$, 100), 223 (26), 210 (38), 195 (29), 175 (76), 173 (79), 95 (39), 38 (36).

c) 2-Amino-4-methylsulfanyl-6-(5-methylsulfanyl-furan-2-vyl)-pyrimidine-5-carbonitrile 1.97 g (10.9 mmol) guanidine carbonate was added portionwise to a stirred suspension of 0.36 g (9.11 mmol, 60% dispersion in mineral oil) sodium hydride in 20 ml DMF under argon at room temperature and stirring continued at 40° C. for 30 minutes. A solution of 2.90 g (9.11 mmol) 2-(5-bromo-furan-2-carbonyl)-3,3-bis-methylsulfanyl-acrylonitrile in 10 ml DMF was then added dropwise and the reaction mixture heated at 100° C. for 30 minutes. The reaction mixture was then poured onto 700 ml ice-water, and the precipitate collected by filtration, washed with hexane, and dried in vacuo. Chromatography (ethyl acetate/hexane 1/1) followed by trituration in ether afforded 1.01 g (40%) 2-amino-4-methylsulfanyl-6-(5-methylsulfanyl-furan-2-yl)-pyrimidine-5-carbonitrile as a light yellow solid. ES-MS m/e (%): 279 (M+H$^+$, 100).

Analogously to Example 199 there were obtained:

Example 468
2-Amino-4-(2-methoxy-phenyl)-6-(2-pyridin-2-yl-ethoxy)-pyrimidine-5-carbonitrile From 2-amino-4-methanesulfinyl-6-(2-methoxy-phenyl)-pyrimidine-5-carbonitrile, 2-(2-hydroxyethyl)pyridine and DBU in DME. ES-MS m/e (%): 348 (M+H$^+$, 100).

Example 469
2-Amino-4-(2-methoxy-phenyl)-6-(pyridin-2-yl-methoxy)-pyrimidine-5-carbonitrile From 2-amino-4-methanesulfinyl-6-(2-methoxy-phenyl)-pyrimidine-5-carbonitrile, 2-(hydroxymethyl)pyridine and DBU in DME. ES-MS m/e (%): 334 (M+H$^+$, 100).

Example 470
2-Amino-4-benzofuran-2-yl-6-methylsulfanyl-pyrimidine-5-carbonitrile To a stirred suspension of 1.21 g (4.94 mmol) 2-amino-4-bromo-6-methylsulfanyl-pyrimidine-5-carbonitrile in 35 ml toluene at room temperature were added 1,60 g (9.88 mmol) benzo[b]furan-2-boronic acid, 0.57 g (0.49 mmol) tetrakis(triphenylphosphine) palladium(O) and 1.27 g (9.88 mmol) potassium carbonate. The reaction mixture was heated at 100° C. for 16 h, then concentrated in vacuo. Chromatography (2/3 ethyl acetate/hexane) afforded 178 mg (13%) 2-amino-4-benzofuran-2-yl-6-methylsulfanyl-pyrimidine-5-carbonitrile as a yellow crystalline solid. ES-MS m/e (%): 283 (M+H$^+$, 100).

Example 471
2-Amino-4-(5-bromo-furan-2-yl)-6-methylsulfanyl-1,2-pyrimidine-5-carbonitrile To a stirred solution of 1.96 g (8.46 mmol) 2-amino-4-furan-2-yl-6-methylsulfanyl-pyrimidine-5-carbonitrile in 8 ml DMF was added dropwise a solution of 1.58 g (8.88 mmol) N-bromosuccinimide in 7 ml DMF and stirring continued at room temperature for 1 hour. The reaction mixture was then poured into 500 ml ice-water and the resulting precipitate collected by filtration and washed with water and then ether to afford 2.50 g (95%) 2-amino-4-(5-bromo-furan-2-yl)-6-methylsulfanyl-pyrimidine-5-carbonitrile as a light brown crystalline solid. ES-MS m/e (%): 311 ([M{$^{81}$Br}-H]$^-$, 100), 309 ([M{$^{79}$Br}-H]$^-$, 95).

Example 472
2-Amino-4-(5-methoxy-furan-2-yl)-6-methylsulfanyl-pyrimidine-5-carbonitrile To a stirred solution of 493 mg (1.58 mmol) 2-amino-4-(5-bromo-furan-2-yl)-6-methylsulfanyl-pyrimidine-5-carbonitrile in 10 ml DME was added 2.1 ml (11,3 mmol) sodium methylate solution (5.4M in methanol) and the mixture heated at 50° C. for 1 h. The reaction mixture was then poured into 100 ml ice-water and the resulting precipitate collected by filtration and washed with water. Chromatography (ethyl acetate/hexane 1/1) afforded 363 mg (87%) 2-amino-4-(5-methoxy-furan-2-yl)-6-methylsulfanyl-pyrimidine-5-carbonitrile as a light yellow crystalline solid. EI-MS m/e (%): 262 (M$^+$, 100).

Analogously to Example 199 there were obtained:

Example 473
2-Amino-4-benzofuran-2-yl-6-(2-pyridin-2-yl-ethylsulfanyl)-pyrimidine-5-carbonitrile From 2-amino-4-benzofuran-2-yl-6-methanesulfinyl-pyrimidine-5-carbonitrile, 2-mercaptoethylpyridine and DBU in DME. ES-MS m/e (%:374 (M+H$^+$, 100).

Example 474
2-Amino-4-(3-methyl-pyridin-2-ylmethoxy)-6-pyrazol-1-yl-pyrimidine-5-carbonitrile From 2-amino-4-methanesulfinyl-6-pyrazol-1-yl-pyrimidine-5-carbonitrile, 3-methyl-2-pyridinemethanol and DBU in DME. ES-MS m/e (%): 308 (M+H$^+$, 100).

Example 475
5-(2-Amino-5-cyano-6-methylsulfanyl-pyrimidin-4-yl)-furan-2-carboxylic Acid Ethyl Ester To a stirred solution of 1.17 g (3.74 mmol) 2-amino-4-(5-bromo-furan-2-yl)-6-methylsulfanyl-pyrimidine-5-carbonitrile in 15 ml DMF at room temperature were added 343 mg (0.37 mmol) tris(dibenzylideneacetone)dipalladium (O) and 287 mg (0.94 mmol) triphenylarsine. Carbon monoxide was bubbled through the reaction mixture for 10 min, then 2.61 ml (18.7 mmol) triethylamine and 10.9 ml (187 mmol) ethanol were added. The reaction mixture was then heated at 90° C. for 16 hours under a carbon monoxide atmosphere (balloon). The reaction mixture was then concentrated in vacuo. Flash chromatography (1/1 ethyl acetate/hexane then ethyl acetate) afforded 70 mg (6%) 5-(2-amino-5-cyano-6-methylsulfanyl-pyrimidin-4-yl)-furan-2-carboxylic acid ethyl ester as a yellow crystalline solid. EI-MS m/e (%): 304 (M$^+$, 95), 303 ([M—H]$^+$, 100), 275 (32), 259 (93), 231 (72), 202 (32).

Example 476
2-Amino-4-(5-chloro-furan-2-yl)-6-methylsulfanyl-pyrimidine-5-carbonitrile To a stirred solution of 2.03 g (8.73 mmol) 2-amino-4-furan-2-yl-6-methylsulfanyl-pyrimidine-5-carbonitrile in 12 ml DMF was added 1.22 g (9.16 mmol) N-chlorosuccinimide and stirring continued at 50° C. for 2 hours. The reaction mixture was then poured into 500 ml ice-water and the resulting precipitate collected by filtration and washed with water and then ether to afford 2.19 g (94%) 2-amino-4-(5-chloro-furan-2-yl)-6-methylsulfanyl-pyrimidine-5-carbonitrile as a light brown crystalline solid. EI-MS m/e (%): 268 (M{$^{37}$Cl}$^+$, 22), 267 ([M{$^{37}$Cl}-H]$^+$, 42), 266 (M{$^{35}$Cl}$^+$, 64), 265 ([M{$^{35}$Cl}-H]$^+$, 100), 231 ([M—Cl]$^+$, 37).

Analogously to Example 326 there was obtained:

Example 477
2-Amino-4-(4,5-dihydro-furan-2-yl)-6-(pyridin-2-yl-methoxy)-pyrimidine-5-carbonitrile From 2-amino-4-(4,5-dihydro-furan-2-yl)-6-oxo-1,6-dihydro-pyrimidine-5-carbonitrile, 2-picolyl chloride hydrochloride and caesium carbonate in DMF. ES-MS m/e (%): 296 (M+H$^+$, 100).

Analogously to Example 476 there was obtained:

Example 478
2-Amino-4-(5-chloro-furan-2-yl)-6-(2-pyridin-2-yl-ethylsulfanyl-pyrimidine-5-carbonitrile From 2-amino-4-furan-2-yl-6-(2-pyridin-2-yl-ethylsulfanyl)-pyrimidine-5-carbonitrile and N-chlorosuccinimide in DMF. ES-MS m/e (%): 360 (M{$^{37}$Cl}+H$^+$, 45), 358 (M{$^{35}$Cl}+H$^+$, 100).

Example 479
2-Amino-4-chloro-6-(3-methyl-pyridin-2-yl-methoxy)-pyrimidine-5-carbonitrile a) 2-Amino-4-chloro-6-methanesulfinyl-pyrimidine-5-carbonitrile To a stirred suspension of 2.00 g (9.97 mmol) 2-amino-4-chloro-6-methylsulfanyl-pyrimidine-5-carbonitrile in 6 ml dichloromethane and 20 ml DMF was added 5.21 g (19.9 mmol) 3-phenyl-2-(phenylsulfonyl)oxaziridine and stirring continued for 16 hours at room temperature. The reaction mixture was then concentrated in vacuo and the residue recrystallised from ether/dichloromethane to afford 1.50 g (69%) 2-amino-4-chloro-6-methanesulfinyl-pyrimidine-5-carbonitrile as a white crystalline solid. ES-MS m/e (%): 239 (M+Na$^+$, 45), 234 (M+NH$_4^+$, 55), 217 (M+H$^+$, 100).

b) 2-Amino-4-chloro-6-(3-methyl-pyridin-2-yl-methoxy)-pyrimidine-5-carbonitrile

To a stirred suspension of 50 mg (0.23 mmol) 2-amino-4-chloro-6-methanesulfinyl-pyrimidine-5-carbonitrile in 1 ml DME were added 28 mg (0.23 mmol) 3-methyl-2-pyridinemethanol and 5211 (0.35 mmol) DBU and stirring continued for 30 min at room temperature. 5 ml water was then added and the resulting crystals collected by filtration and washed with ether to afford 22 mg (35%) 2-amino-4-chloro-6-(3-methyl-pyridin-2-ylmethoxy)-pyrimidine-5- carbonitrile as a white crystalline solid. ES-MS m/e (%): 278 (M{$^{37}$Cl}+H$^+$, 35), 276 (M{$^{35}$Cl}+H$^+$, 100).

Analogously to Example 199 there were obtained:

Example 480
2-Amino-4-(5-methyl-pyridin-2-yl-methoxy)-6-pyrazol-1-yl-pyrimidine-5-carbonitrile From 2-amino-4-methanesulfinyl-6-pyrazol-1-yl-pyrimidine-5-carbonitrile, 5-methyl-2-pyridinemethanol and DBU in DME. ES-MS m/e (%): 308 (M+H$^+$, 100).

Example 481
2-Amino-4-(3,5-dimethyl-pyridin-2-yl-methoxy)-6-pyrazol-1-yl-pyrimidine-5-carbonitrile From 2-amino-4-methanesulfinyl-6-pyrazol-1-yl-pyrimidine-5-carbonitrile, 3,5-dimethyl-2-pyridinemethanol and DBU in DME. ES-MS m/e (%): 322 (M+H$^+$, 100).

Example 482
2-Amino-4,6-bis-(2-pyridin-2-yl-ethylsulfanyl)-pyrimidine-5-carbonitrile To a stirred suspension of 500 mg (2.31 mmol) 2-amino-4-chloro-6-methanesulfinyl-pyrimidine-5-carbonitrile in 10 ml DME were added 482 mg (3.46 mmol) 2-mercaptoethylpyridine and 0.88 ml (5.77 mmol) DBU and stirring continued for 1 hour at room temperature. 50 ml water was then added and the resulting crystals collected by filtration and washed with ethyl acetate to afford 300 mg (33%) 2-amino-4,6-bis-(2-pyridin-2-yl-ethylsulfanyl)-pyrimidine-5-carbonitrile as a white crystalline solid. ES-MS m/e (%): 395 (M+H$^+$, 100).

Analogously to Example 471 there was obtained:

Example 483
2-Amino-4-(5-bromo-furan-2-yl)-6-(2-pyridin-2-yl-ethylsulfanyl)-pyrimidine-5-carbonitrile From 2-amino-4-furan-2-yl-6-(3-methyl-pyridin-2-ylmethoxy)-pyrimidine-5-carbonitrile and N-chlorosuccinimide in DMF. ES-MS m/e (%): 404 (M{$^{81}$Br}+H$^+$, 98), 402 (M{$^{79}$Br}+H$^+$, 100).

Example 484
2-Amino-4-chloro-6-(2-pyridin-2-yl-ethylsulfanyl)-pyrimidine-5-carbonitrile To a stirred suspension of 1.00 g (4.62 mmol) 2-amino-4-chloro-6-methanesulfinyl-pyrimidine-5-carbonitrile in 10 ml DME were added 642 mg (4.62 mmol) 2-mercaptoethylpyridine and 1.05 ml (6.92 mmol) DBU and stirring continued for 1 hour at room temperature. 50 ml water was then added and the resulting crystals collected by filtration and washed with ether. Chromatography (ethyl acetate/hexane 111 then ethyl acetate) followed by trituration in ether afforded 300 mg (22%) 2-amino-4-chloro-6-(2-pyridin-2-yl-ethylsulfanyl)-pyrimidine-5-carbonitrile as a white crystalline solid. ES-MS m/e (%): 294 (M{$^{37}$Cl}+H$^+$, 30), 292 (M{$^{35}$Cl}+H$^+$, 100).

Example 485
2-Amino-4-[5-(1-ethoxy-vinyl)-furan-2-yl]-6-methylsulfanyl-pyrimidine-5-carbonitrile To a stirred solution of 492 mg (1.58 mmol) 2-amino-4-(5-bromo-furan-2-yl)-6-methylsulfanyl-pyrimidine-5-carbonitrile in 15 ml dioxane under argon at room temperature were added 0.59 ml (1.74 mmol) (I-ethoxyvinyl) tributylstannane and 111 mg (0.16 mmol) bis(triphenylphosphine)palladium(II) chloride. The reaction mixture was heated at 100° C. for 18 h, then cooled to room temperature, 2 g of kieselgel added, and the mixture concentrated in vacuo. Flash chromatography (1/2 ethyl acetate/hexane then 1/1 ethyl acetate/hexane then ethyl acetate) followed by trituration in ether afforded 304 mg (64%) 2-amino-4-[5-(1-ethoxy-vinyl)-furan-2-yl]-6-methylsulfanyl-pyrimidine-5-carbonitrile as an off-white crystalline solid. EI-MS m/e (%): 302 (M$^+$, 88), 273 ([M—C$_2$H$_5$]$^+$, 100), 243 (43), 231 (52).

Example 486
2-Amino-4-methylsulfanyl-6-(pyridin-2-yl-methoxy)-pyrimidine-5-carbonitrile To a stirred suspension of 1.00 g (4.08 mmol) 2-amino-4-bromo-6-methylsulfanyl-pyrimidine-5-carbonitrile in 10 ml DME were added 0.33 ml (4.08 mmol) 2-(hydroxymethyl)pyridine and 0.62 ml (4.08 mmol) DBU and stirring continued for 16 hours at room temperature. 50 ml water was then added and the resulting crystals collected by filtration. Chromatography (ethyl acetate) followed by trituration in ether afforded 180 mg (16%) 2-amino-4-methylsulfanyl-6-(pyridin-2-ylmethoxy)-pyrimidine-5-carbonitrile as a light yellow crystalline solid. EI-MS m/e (%): 273 (M$^+$, 100), 258 (89), 108 (63), 92 (95), 65 (70), 39 (36).

In an analogous manner there was obtained:

Example 487
2-Amino-4-benzyloxy-6-methylsulfanyl-pyrimidine-5-carbonitrile

From 2-amino-4-bromo-6-methylsulfanyl-pyrimidine-5-carbonitrile, benzyl alcohol and DBU in DME. ES-MS m/e (%): 273 (M+H$^+$, 100).

Analogously to Example 484 there were obtained:

Example 488
2-Amino-4-benzyloxy-6-chloro-pyrimidine-5-carbonitrile

From 2-amino-4-chloro-6-methanesulfinyl-pyrimidine-5-carbonitrile, benzyl alcohol and DBU in DME. EI-MS m/e (%): 262 (M{$^{37}$Cl}$^+$, 22), 260 (M{$^{35}$Cl}+,60), 91 (100).

Example 489
2-Amino-4-chloro-6-(pyridin-2-yl-methoxy)-pyrimidine-5-carbonitrile From 2-amino-4-chloro-6-methanesulfinyl-pyrimidine-5-carbonitrile, 2-(hydroxymethyl)pyridine and DBU in DME. EI-MS m/e (%): 261 (M$^+$, 75), 184 (46), 108 (95), 92 (100), 65 (70), 39 (45).

Example 490
2-Amino-4-phenoxy-6-(pyridin-2-yl-methoxy)-pyrimidine-5-carbonitrile a) 2-Amino-4-methylsulfanyl-6-phenoxy-pyrimidine-5-carbonitrile To a stirred suspension of 500 mg (2.04 mmol) 2-amino-4-bromo-6-methylsulfanyl-pyrimidine-5-carbonitrile in 5 ml DME were added 192 mg (2.04 mmol) phenol and 0.31 ml (2.04 mmol) DBU and stirring continued for 16 hours at room temperature. 15 ml water was then added and the resulting crystals collected by filtration and triturated in hexane to afforded 400 mg (76%) 2-amino-4-methylsulfanyl-6-phenoxy-pyrimidine-5-carbonitrile as a light yellow crystalline solid. EI-MS m/e (%): 258 (M$^+$, 100).

b) 2-Amino-4-methanesulfinyl-6-phenoxy-pyrimidine-5-carbonitrile

To a stirred suspension of 950 mg (3.68 mmol) 2-amino-4-methylsulfanyl-6-phenoxy-pyrimidine-5-carbonitrile in 20 ml dichloromethane was added 3.84 g (14.7 mmol) 3-phenyl-2-(phenylsulfonyl)oxaziridine and stirring continued for 24 hours at room temperature. The reaction mixture was then concentrated in vacuo and the residue resuspended in ether/hexane and filtered to afford 270 mg (27%) 2-amino-4-methanesulfinyl-6-phenoxy-pyrimidine-5-carbonitrile as a light yellow crystalline solid. ES-MS m/e (%): 275 (M+H$^+$, 100).

c) 2-Amino-4-phenoxy-6-(pyridin-2-yl-methoxy)-pyrimidine-5-carbonitrile

To a stirred suspension of 270 mg (0.98 mmol) 2-amino-4-methanesulfinyl-6-phenoxy-pyrimidine-5-carbonitrile in 10 ml DME were added 0.33 ml (3.45 mmol) 2-(hydroxymethyl) pyridine and 0.22 ml (1.48 mmol) DBU and stirring continued for 1 hour at room temperature. 50 ml water was then added and the resulting crystals collected by filtration and washed with ether to afford 40 mg (13%) 2-amino-4-phenoxy-6-(pyridin-2-ylmethoxy)-pyrimidine-5-carbonitrile as a white crystalline solid. ES-MS m/e (%): 320 (M+H$^+$, 100).

Example 491

2-Amino-4,6-bis-(pyridin-2-yl-methoxy)-pyrimidine-5-carbonitrile

To a stirred suspension of 130 mg (0.50 mmol) 2-amino-4-chloro-6-(pyridin-2-ylmethoxy)-pyrimidine-5-carbonitrile in 10 ml DME were added 0.17 ml (1.74 mmol) 2-(hydroxymethyl)pyridine and 0.11 ml (0.75 mmol) DBU and stirring continued for 1 hour at room temperature. 50 ml water was then added and the resulting crystals collected by filtration and washed with ether to afford 80 mg (48%) 2-amino-4,6-bis-(pyridin-2-ylmethoxy)-pyrimidine-5-carbonitrile as a white crystalline solid. ES-MS m/e (%): 357 (M+Na$^+$, 40), 335 (M+H$^+$, 100).

Analogously to Example 199 there were obtained:

Example 492

2-Amino-4-[(isoquinolin-3-yl-methyl)-amino]-6-pyrazol-1-yl-pyrimidine-5-carbonitrile From 2-amino-4-methanesulfinyl-6-pyrazol-1-yl-pyrimidine-5-carbonitrile, C-isoquinolin-3-yl-methylamine dihydrochloride and DBU in DME. ES-MS m/e (%): 343 (M+H$^+$, 100).

Example 493

2-Amino-4-[(4-methyl-pyridin-2-yl-methyl)-amino]-6-pyrazol-1-yl-pyrimidine-5-carbonitrile From 2-amino-4-methanesulfinyl-6-pyrazol-1-yl-pyrimidine-5-carbonitrile, C-(4-methyl-pyridin-2-yl)-methylamine dihydrochloride and DBU in DME. ES-MS m/e (%): 307 (M+H$^+$, 100).

Example 494

2-Amino-4-[(3,5-dimethyl-pyridin-2-yl-methyl)-amino]-6-pyrazol-1-yl-pyrimidine-5-carbonitrile From 2-amino-4-methanesulfinyl-6-pyrazol-1-yl-pyrimidine-5-carbonitrile, C-(3,5-dimethyl-pyridin-2-yl)-methylamine dihydrochloride and DBU in DME. ES-MS m/e (%): 321 (M+H$^+$, 100).

Analogously to Example 491 there was obtained:

Example 495

2-Amino-4-benzyloxy-6-(pyridin-2-yl-methoxy)-pyrimidine-5-carbonitrile

From 2-amino-4-chloro-6-(pyridin-2-ylmethoxy)-pyrimidine-5-carbonitrile, benzyl alcohol and DBU in DME. ES-MS m/e (%): 356 (MNa$^+$, 50), 334 (M+H$^+$, 100).

Example 496

2-Amino-4-(5-bromomethyl-furan-2-yl)-6-methylsulfanyl-pyrimidine-5-carbonitrile

To a stirred suspension of 500 mg (2.03 mmol) 2-amino-4-(5-methyl-furan-2-yl)-6-methylsulfanyl-pyrimidine-5-carbonitrile in 20 ml carbon tetrachloride under argon were added 397 mg (2.23 mmol) N-bromosuccinimide and a small spatula end of benzoyl peroxide. Stirring was continued for 8 hours while the reaction mixture was irradiated with a 500 W halogen lamp. The reaction mixture was then concentrated in vacuo. Chromatography (1/1 ethyl acetate/hexane) followed by trituration in ether afforded 250 mg (38%) 2-amino-4-(5-bromomethyl-furan-2-yl)-6-methylsulfanyl-pyrimidine-5-carbonitrile as a yellow crystalline solid. EI-MS m/e (%): 326 (M{$^{81}$Br}$^+$, 5), 325 ([M{$^{81}$Br}-H]$^+$, 6), 324 (M{$^{79}$Br}$^+$, 5), 324 ([M{$^{79}$Br}-H]$^+$, 6), 245 ([M—Br]$^+$, 100).

Example 497

2-Amino-4-(3-methyl-pyrazol-1-yl)-6-methylsulfanyl-pyrimidine-5-carbonitrile

To a stirred solution of 2.05 g (8.36 mmol) 2-amino-4-bromo-6-methylsulfanyl-pyrimidine-5-carbonitrile in 15 ml NMP were added 3.00 g (9.20 mmol) cesium carbonate and 0.74 ml (9.20 mmol) 3-methyl-pyrazole and the mixture heated at 70° C. for 16 h. The reaction mixture was then poured into 400 ml ice-water and the resulting precipitate collected by filtration. Chromatography (ethyl acetate/hexane 1/1 then 2/1) afforded 230 mg (11%) 2-amino-4-(3-methyl-pyrazol-1-yl)-6-methylsulfanyl-pyrimidine-5-carbonitrile as a white crystalline solid. ES-MS m/e (%): 247 (M+H$^+$, 100).

In an analogous manner there was obtained:

Example 498

2-Amino-4-(4-methyl-pyrazol-1-yl)-6-methylsulfanyl-pyrimidine-5-carbonitrile

From 2-amino-4-bromo-6-methylsulfanyl-pyrimidine-5-carbonitrile, 4-methyl-pyrazole and cesium carbonate in NMP. EI-MS m/e (%): 246 (M$^+$, 85), 245 ([M—H]$^+$, 100).

Analogously to Example 199 there were obtained:

Example 499

2-Amino-4-pyrazol-1-yl-6-(pyridin-3-yl-methoxy)-pyrimidine-5-carbonitrile

From 2-amino-4-methanesulfinyl-6-pyrazol-1-yl-pyrimidine-5-carbonitrile, 3-pyridinemethanol and DBU in DME. EI-MS m/e (%): 293 (M$^+$, 100), 92 (60), 65 (29), 39 (24).

Example 500

2-Amino-4-pyrazol-1-yl-6-[(quinolin-2-yl-methyl)-amino]-pyrimidine-5-carbonitrile From 2-amino-4-methanesulfinyl-6-pyrazol-1-yl-pyrimidine-5-carbonitrile, C-quinolin-2-yl-methylamine hydrochloride and DBU in DME. ES-MS m/e (%): 343 (M+H$^+$, 100).

Example 501

2-Amino-4-(isoquinolin-3-yl-methoxy)-6-pyrazol-1-yl-pyrimidine-5-carbonitrile

From 2-amino-4-methanesulfinyl-6-pyrazol-1-yl-pyrimidine-5-carbonitrile, isoquinolin-3-yl-methanol and DBU in DME. ES-MS m/e (%): 366 (M+Na$^+$, 60), 344 (M+H$^+$, 100).

Example 502

2-Amino-4-(naphthalen-2-yl-methoxy)-6-pyrazol-1-yl-pyrimidine-5-carbonitrile

From 2-amino-4-methanesulfinyl-6-pyrazol-1-yl-pyrimidine-5-carbonitrile, 2-naphthalenemethanol and DBU in DME. ES-MS m/e (%): 365 (M+Na$^+$, 100), 343 (M+H$^+$, 40).

Example 503
2-Amino-4-(5-hydroxymethyl-furan-2-yl)-6-methylsulfanyl-pyrimidine-5-carbonitrile To a stirred suspension of 100 mg (0.31 mmol) 2-amino-4-(5-bromomethyl-furan-2-yl)-6-methylsulfanyl-pyrimidine-5-carbonitrile in 5 ml water and 5 ml acetone was added 104 mg (0.61 mmol) silver nitrate and stirring continued for 16 h at room temperature in the dark. The reaction mixture was then concentrated in vacuo and the residue partitioned between ethyl acetate and water. The combined organic phases were dried over sodium sulfate and concentrated in vacuo. Chromatography (1/1 ethyl acetate/hexane then acetone) afforded 28 mg (35%) 2-amino-4-(5-hydroxymethyl-furan-2-yl)-6-methylsulfanyl-pyrimidine-5-carbonitrile e as an orange crystalline solid. EI-MS m/e (%): 262 ($M^+$, 100), 261 ($[M—H]^+$, 90).

Analogously to Example 497 there was obtained:

Example 504
2-Amino-4-(4-iodo-pyrazol-1-yl)-6-methylsulfanyl-pyrimidine-5-carbonitrile From 2-amino-4-bromo-6-methylsulfanyl-pyrimidine-5-carbonitrile, 4-iodopyrazole and cesium carbonate in NMP. EI-MS m/e (%): 359 ($M+H^+$, 100).

Analogously to Example 199 there were obtained:

Example 505
2-Amino-4-(4-methyl-pyrazol-1-yl)-6-(2-pyridin-2-yl-ethylsulfanyl)-pyrimidine-5-carbonitrile From 2-amino-4-methanesulfinyl-6-(4-methyl-pyrazol-1-yl)-pyrimidine-5-carbonitrile, 2-mercaptoethylpyridine and DBU in DME. ES-MS m/e (%): 338 ($M+H^+$, 100).

Example 506
2-Amino-4-(2-methyl-benzylamino)-6-pyrazol-1-yl-pyrimidine-5-carbonitrile From 2-amino-4-methanesulfinyl-6-pyrazol-1-yl-pyrimidine-5-carbonitrile, 2-methyl-benzylamine and DBU in DME. ES-MS m/e (%): 328 ($M+Na^+$, 35), 306 ($M+H^+$, 100).

Example 507
2-Amino-4-(3-methyl-pyrazol-1-yl)-6-(2-pyridin-2-yl-ethylsulfanyl)-pyrimidine-5-carbonitrile From 2-amino-4-methanesulfinyl-6-(3-methyl-pyrazol-1-yl)-pyrimidine-5-carbonitrile, 2-mercaptoethylpyridine and DBU in DME. ES-MS m/e (%): 338 ($M+H^+$, 100).

Analogously to Example 497 there was obtained:

Example 508
2-Amino-4-(3,5-dimethyl-pyrazol-1-yl)-6-methylsulfanyl-pyrimidine-5-carbonitrile From 2-amino-4-bromo-6-methylsulfanyl-pyrimidine-5-carbonitrile, 3,5-dimethylpyrazole and cesium carbonate in NMP. EI-MS m/e (%): 259 ($[M—H]^-$, 100).

Example 509
2-Amino-4-(5-methoxymethyl-furan-2-yl)-6-methylsulfanyl-pyrimidine-5-carbonitrile a) 3-(5-Methoxymethyl-furan-2-yl)-3-oxo-propionitrile Following the method of Turner and Jacks (*J. Org Chem.* 1989, 54, 4229), to a stirred solution of 11.4 ml (216 mmol) acetonitrile in 50 ml dry THF under argon at −78° C. was added dropwise 95.0 ml (95.0 mmol) lithium bis(trimethylsilyl)amide solution (1 M in THF) and stirring continued for 30 minutes, after which a solution of 7.34 g (43.1 mmol) 5-methoxymethyl-furan-2-carboxylic acid methyl ester in 20 ml THF was added dropwise and stirring continued while the reaction mixture was allowed to warm slowly to −20° C. over 2 hours. The reaction mixture was then cannulated into a rapidly stirred solution of 1M hydrochloric acid at 0° C. The mixtured was extracted twice with ether and the combined organic phases dried over sodium sulfate and concentrated in vacuo. Chromatography (ethyl acetate) afforded 7.73 g (99%) 3-(5-methoxymethyl-furan-2-yl)-3-oxo-propionitrile as an orange crystalline solid. EI-MS m/e (%): 179 ($M^+$, 23), 148 ($[M—OCH_3]^+$, 40), 147 ($[M—CH_3OH]^+$, 44), 139 ($[M—CH_2CN]^+$, 45), 111 ($[M—COCH_2CN]^+$, 100).

b) 2-(5-Methoxymethyl-furan-2-carbonyl)-3,3-bis-methylsulfanyl-acrylonitrile

Following the method of Rudorf and Augustin (*Phosphorus and Sulfur* 1981, 9, 329), a solution of 1.00 g (5.58 mmol) 3-(5-methoxymethyl-furan-2-yl)-3-oxo-propionitrile in 15 ml dry DMSO was added dropwise to a stirred suspension of 487 mg (11.2 mmol, 60% dispersion in mineral oil) sodium hydride in 15 ml DMSO under argon at room temperature. 0.34 ml (5.58 mmol) carbon disulfide was then added dropwise, with external water bath cooling, and stirring continued for 2 hour, after which 0.70 ml (11.2 mmol) methyl iodide was added dropwise, with external water bath cooling, and stirring continued for a further 16 h. The reaction mixture was then poured into 200 ml ice-cold water, and the precipitate collected by filtration, washed with hexane, and dried in vacuo to afford 1.12 g (71%) 2-(5-methoxymethyl-furan-2-carbonyl)-3,3-bis-methylsulfanyl-acrylonitrile as a brown crystalline solid. EI-MS m/e (%): 283 ($M^+$, 7), 282 ($[M—H]^+$, 6), 268 ($[M—CH_3]^+$, 50), 266 ($[M—OH]^+$, 35), 252 ($[M—OCH_3]^+$, 21), 238 ($[M—CH_2OCH_3]^+$, 100), 139 (61).

c) 2-Amino-4-(5-methoxymethyl-furan-2-yl)-6-methylsulfanyl-pyrimidine-5-carbonitrile Following the method of Rudorf and Augustin (*J. Prakt. Chem.* 1978, 320, 576), a solution of 1.00 g (3,53 mmol) 2-(5-methoxymethyl-furan-2-carbonyl)-3,3-bis-methylsulfanyl-acrylonitrile, 0.52 g (4.23 mmol) guanidine nitrate and 1.23 ml (8.83 mmol) triethylamine in 20 ml DMF was heated at reflux for 3 h. The reaction mixture was then cooled to room temperature and poured onto 300 ml water, and the precipitate collected by filtration, washed with hexane, and dried in vacuo to afford, after trituration in ether, 502 mg (52%) 2-amino-4-(5-methoxymethyl-furan-2-yl)-6-methylsulfanyl-pyrimidine-5-carbonitrile as a light yellow crystalline solid. EI-MS m/e (%): 276 ($M^+$, 85), 274 ($[M—H]^+$, 23), 261 ($[M—CH_3]^+$, 20), 245 ($[M—OCH_3]^+$, 100), 111 (30).

Example 510
2-Amino-4-(5-cyano-furan-2-yl)-6-methylsulfanyl-pyrimidine-5-carbonitrile a) 5-Cyanoacetyl-furan-2-carbonitrile To 1,67 g (41.7 mmol, 60% dispersion in mineral oil) sodium hydride in a 2-necked flask fitted with a reflux condenser was added dropwise 150 ml THF and the mixture was then heated to reflux. A solution of 1.0 ml (208 mmol) acetonitrile and 6.30 g (41.7 mmol) 5-cyano-furan-2-carboxylic acid methyl ester in 100 ml dry THF was added dropwise and the reaction mixture heated at reflux for 4 hours. The reaction mixture was then cannulated into a rapidly stirred solution of 1M hydrochloric acid at 0° C. The mixture was extracted three times with ethyl acetate and the combined organic phases dried over sodium sulfate and concentrated in vacuo. Chromatography (ethyl acetate/hexane 1/1) afforded 2.90 g (43%) 5-cyanoacetyl-furan-2-carbonitrile as an orange oil. EI-MS m/e (%): 160 ($M^+$, 19), 120 ($[M—CH_2CN]^+$, 100).

b) 5-(2-Cyano-3,3-bis-methylsulfanyl-acryloyl)-furan-2-carbonitrile

Following the method of Rudorf and Augustin (*Phosphorus and Sulfur* 1981, 9, 329), a solution of 2.90 g (18.1 mmol) 5-cyanoacetyl-furan-2-carbonitrile in 10 ml dry DMSO was added dropwise to a stirred suspension of 1.45 g (36.2 mmol, 60% dispersion in mineral oil) sodium hydride in 10 ml DMSO under argon at room temperature. 1.09 ml (18.1 mmol) carbon disulfide was then added dropwise, with external water bath cooling, and stirring continued for 2 hour, after which 2.26 ml (36.2 mmol) methyl iodide was added dropwise, with external water bath cooling, and stirring continued for a further 16 h. The reaction mixture was then poured into 1 l ice-cold water, and the precipitate collected by filtration, washed with hexane, and dried in vacuo to afford 3,50 g (73%) 5-(2-cyano-3,3-bis-methylsulfanyl-acryloyl)-furan-2-carbonitrile as a green crystalline solid. EI-MS m/e (%): 264 ($M^+$, 25), 263 ([M—H]$^+$, 30), 249 ([M—$CH_3$]$^+$, 40), 195 (37), 120 (100).

c) 2-Amino-4-(5-cyano-furan-2-yl)-6-methylsulfanyl-pyrimidine-5-carbonitrile

Following the method of Rudorf and Augustin (*J. Prakt. Chem.* 1978, 320, 576), a solution of 300 mg (1.13 mmol) 5-(2-cyano-3,3-bis-methylsulfanyl-acryloyl)-furan-2-carbonitrile, 166 mg (1,36 mmol) guanidine nitrate and 0.40 ml (2.84 mmol) triethylamine in 5 ml DMF was heated at reflux for 1 h. The reaction mixture was then cooled to room temperature and poured onto 250 ml water, extracted three times with ethyl acetate, and the combined organic phases dried over sodium sulfate and concentrated in vacuo. Chromatography (ethyl acetate) afforded 120 mg (41%) 2-amino-4-(5-cyano-furan-2-yl)-6-methylsulfanyl-pyrimidine-5-carbonitrile as a light yellow crystalline solid. ES-MS m/e (%): 256 ([M—H]$^-$, 100).

Analogously to Example 471 there were obtained:

Example 511
2-Amino-4-(5-bromo-furan-2-yl)-6-(5-methyl-pyridin-2-ylmethoxy)-pyrimidine-5-carbonitrile From 2-amino-4-furan-2-yl-6-(5-methyl-pyridin-2-ylmethoxy)-pyrimidine-5-carbonitrile and N-bromosuccinimide in DMF. ES-MS m/e (%): 388 (M{$^{81}$Br}+H$^+$, 100), 386 (M{$^{79}$Br}+H$^+$, 98).

Example 512
2-Amino-4-(2-bromo-benzylamino)-6-(5-bromo-furan-2-yl)-pyrimidine-5-carbonitrile From 2-amino-4-(2-bromo-benzylamino)-6-furan-2-yl-pyrimidine-5-carbonitrile and N-bromosuccinimide in DMF. ES-MS m/e (%): 451 (M{$^{81}$Br}+H$^+$, 100), 449 (M{$^{79}$Br}+H$^+$, 95).

Example 513
2-Amino-4-(5-bromo-furan-2-yl)-6-(3-methyl-pyridin-2-ylmethoxy)-pyrimidine-5-carbonitrile From 2-amino-4-furan-2-yl-6-(3-methyl-pyridin-2-ylmethoxy)-pyrimidine-5-carbonitrile and N-bromosuccinimide in DMF. ES-MS m/e (%): 388 (M{$^{81}$Br}+H$^+$, 100), 386 (M{$^{79}$Br}+H$^+$, 90).

Analogously to Example 199 there were obtained:

Example 514
2-Amino-4-(5-methoxymethyl-furan-2-yl)-6-(2-pyridin-2-yl-ethylsulfanyl)-pyrimidine-5-carbonitrile From 2-amino-4-methanesulfinyl-6-(5-methoxymethyl-furan-2-yl)-pyrimidine-5-carbonitrile, 2-mercaptoethylpyridine and DBU in DME. ES-MS m/e (%): 368 (M+H$^+$, 100).

Example 515
2-Amino-4-(2-chloro-benzylamino)-6-pyrazol-1-yl-pyrimidine-5-carbonitrile From 2-amino-4-methanesulfinyl-6-pyrazol-1-yl-pyrimidine-5-carbonitrile, 2-chlorobenzylamine and DBU in DME. EI-MS m/e (%): 327 (M{$^{37}$Cl}$^+$, 10), 325 (M{$^{35}$Cl}$^+$, 35), 290 ([M—Cl]$^+$, 100).

Analogously to Example 471 there were obtained:

Example 516
2-Amino-4-(5-bromo-furan-2-yl)-6-(2-pyridin-2-yl-ethoxy)-pyrimidine-5-carbonitrile From 2-amino-4-furan-2-yl-6-(2-pyridin-2-yl-ethoxy)-pyrimidine-5-carbonitrile and N-bromosuccinimide in DMF. ES-MS m/e (%): 388 (M{$^{81}$Br}+H$^+$, 100), 386 (M{$^{79}$Br}+H$^+$, 95).

Example 517
2-Amino-4-(5-bromo-furan-2-yl)-6-[(35-dimethyl-pyridin-2-ylmethyl)-amino]-pyrimidine-5-carbonitrile From 2-amino-4-[(3,5-dimethyl-pyridin-2-ylmethyl)-amino]-6-furan-2-yl-pyrimidine-5-carbonitrile and N-bromosuccinimide in DMF. ES-MS m/e (%): 401 (M{$^{81}$Br}+H$^+$, 100), 399 (M{$^{79}$Br}+H$^+$, 90).

Analogously to Example 510 there was obtained:

Example 518
2-Amino-4-(4-bromo-furan-2-yl)-6-methylsulfanyl-pyrimidine-5-carbonitrile From 4-bromo-furan-2-carboxylic acid methyl ester with sodium hydride and acetonitrile in THF. Then treatment with sodium hydride, carbon disulphide and methyl iodide in DMSO. Then treatment with guanidine nitrate and triethylamine in DMF. ES-MS m/e (%): 313 (M{$^{81}$Br}+H$^+$, 65), 311 (M{$^{79}$Br}+H$^+$, 100).

Analogously to Example 471 there was obtained:

Example 519
2-Amino-4-(5-bromo-furan-2-yl)-6-[(5-methyl-pyridin-2-ylmethyl)-amino]-pyrimidine-5-carbonitrile From 2-amino-4-furan-2-yl-6-[(5-methyl-pyridin-2-ylmethyl)-amino]-pyrimidine-5-carbonitrile and N-bromosuccinimide in DMF. ES-MS m/e (%): 387 (M{$^{81}$Br}+H$^+$, 100), 385 (M{$^{79}$Br}+H$^+$, 85).

Analogously to Example 199 there were obtained:

Example 520
2-Amino-4-(5-cyano-furan-2-yl)-6-(2-pyridin-2-yl-ethylsulfanyl)-pyrimidine-5-carbonitrile From 2-amino-4-(5-cyano-furan-2-yl)-6-methanesulfinyl-pyrimidine-5-carbonitrile, 2-mercaptoethylpyridine and DBU in DME. ES-MS m/e (%): 347 ([M—H]$^-$, 100).

Example 521
2-Amino-4-(4-bromo-furan-2-yl)-6-(2-pyridin-2-yl-ethylsulfanyl)-pyrimidine-5-carbonitrile From 2-amino-4-(4-bromo-furan-2-yl)-6-methanesulfinyl-pyrimidine-5-carbonitrile, 2-mercaptoethylpyridine and DBU in DME. ES-MS m/e (%): 404 (M{$^{81}$Br}+H$^+$, 85), 402 (M{$^{79}$Br}+H$^+$, 100).

Example 522
N-Benzoyl-N-[5-cyano-4-furan-2-yl-6-(2-pyridin-2-yl-ethylsulfanyl)-pyrimidin-2-yl]-benzamide To a stirred solution of 200 mg (0.62 mmol) 2-amino-4-furan-2-yl-6-(2-pyridin-2-yl-ethylsulfanyl)-pyrimidine-5-carbonitrile and 8 mg (0.06 mmol) 4-dimethylaminopyridine in 2 ml pyridine was added dropwise 0.73 ml (6.18 mmol) benzoyl bromide and the reaction mixture stirred at 50° C. for 3 hours. The reaction mixture was then cooled to room temperature and partitioned between water and ethyl acetate. The combined organic phases were dried with sodium sulfate and concentrated in vacuo. Chromatography (1/2 ethyl acetate/hexane then 1/1 ethyl acetate/hexane then ethyl acetate) followed by trituration in ether afforded 100 mg (30%) N-benzoyl-N-[5-cyano-4-furan-2-yl-6-(2-pyridin-2-yl-ethylsulfanyl)-pyrimidin-2-yl]-benzamide as a white crystalline solid. ES-MS m/e (%): 532 (M+H$^+$, 68).

Example 523
2-Amino-4-methylsulfanyl-6-pyrazin-2-yl-pyrimidine-5-carbonitrile To a stirred solution of 1.11 g (4.52 mmol) 2-amino-4-bromo-6-methylsulfanyl-pyrimidine-5-carbonitrile in 10 ml dry DMF under argon at room temperature were added 2.00 g (5.42 mmol) 2-(tri-n-butylstannanyl)pyrazine, 190 mg (0.27 mmol) bis(triphenylphosphine)palladium(II) chloride and 431 mg (5.42 mmol) copper(II) oxide. The reaction mixture was heated at reflux for 18 h, then cooled to room temperature and concentrated in vacuo. Flash chromatography (ethyl acetate/hexane 1/1 then ethyl acetate) afforded 344 mg (31%) 2-amino-4-methylsulfanyl-6-pyrazin-2-yl-pyrimidine-5-carbonitrile as an off-white crystalline solid. EI-MS m/e (%): 244 (M$^+$, 100), 243 ([M—H]$^+$, 40), 190 (55).

Example 524
2-Amino-4-(5-cyanomethyl-f ran-2-yl)-6-(2-pyridin-2:yl-ethylsulfanyl)-pyrimidine-5-carbonitrile To a stirred solution of 0.2 ml (3.72 mmol) acetonitrile in 25 ml dry THF under argon at −78° C. was added dropwise 3.3 ml (1,65 mmol) potassium bis(trimethylsilyl)amide solution (0.5M in toluene) and stirring continued for 1 hour. The solution was then transferred dropwise via cannula to a solution of 300 mg (0.75 mmol) 2-amino-4-(5-bromo-furan-2-yl)-6-(2-pyridin-2-yl-ethylsulfanyl)-pyrimidine-5-carbonitrile in 25 ml THF at −78° C. and stirring continued for 5 h at −78° C. and 1 h at −40° C. The reaction mixture was then quenched by addition of saturated aqueous ammonium chloride solution. The mixtured was extracted twice with ethyl acetate and the combined organic phases dried over sodium sulfate and concentrated in vacuo. Chromatography (ethyl acetate/hexane 4/1 then ethyl acetate) afforded 22 mg (8%) 2-amino-4-(5-cyanomethyl-furan-2-yl)-6-(2-pyridin-2-yl-ethylsulfanyl)-pyrimidine-5-carbonitrile as a brown crystalline solid. ES-MS m/e (%): 385 (M+Na$^+$, 45), 363 (M+H$^+$, 100).

Analogously to Example 476 there was obtained:

Example 525
2-Amino-4-(5-chloro-furan-2-yl)-6-(2-pyridin-2-yl-ethoxy)-pyrimidine-5-carbonitrile From 2-amino-4-furan-2-yl-6-(2-pyridin-2-yl-ethoxy)-pyrimidine-5-carbonitrile and N-chlorosuccinimide in DMF. ES-MS m/e (%): 344 (M{$^{37}$C }+H$^+$, 30), 342 (M{$^{35}$Cl}+H$^+$, 100).

Example 526
2-Amino-4-(5-chloro-furan-2-yl)-6-(3,5-dimethyl-pyridin-2-ylmethoxy)-pyrimidine-5-carbonitrile From 2-amino-4-(3,5-dimethyl-pyridin-2-ylmethoxy)-6-furan-2-yl-pyrimidine-5-carbonitrile and N-chlorosuccinimide in DMF. ES-MS m/e (%): 358 (M{$^{37}$Cl}+H$^+$, 30), 356 (M{$^{35}$Cl}+H$^+$, 100).

Analogously to Example 497 there were obtained:

Example 527
2-Amino-4-(4-chloro-pyrazol-1-yl)-6-methylsulfanyl-pyrimidine-5-carbonitrile From 2-amino-4-bromo-6-methylsulfanyl-pyrimidine-5-carbonitrile, 4-chloropyrazole and cesium carbonate in NMP. EI-MS m/e (%): 269 (M{$^{37}$Cl}+H$^+$, 30). 267 (M{$^{35}$Cl}+H$^+$, 100).

Example 528
2-Amino-4-(4-bromo-pyrazol-1-yl)-6-methylsulfanyl-pyrimidine-5-carbonitrile From 2-amino-4-bromo-6-methylsulfanyl-pyrimidine-5-carbonitrile, 4-bromopyrazole and cesium carbonate in NMP. EI-MS m/e (%): 313 (M{$^{81}$Br}+H$^+$, 95). 311 (M{$^{79}$Br}+H$^+$, 100).

Analogously to Example 510 there was obtained:

Example 529
2-Amino-4-(4-cyano-furan-2-yl)-6-methylsulfanyl-pyrimidine-5-carbonitrile From 4-cyano-furan-2-carboxylic acid methyl ester with sodium hydride and acetonitrile in THF. Then treatment with sodium hydride, carbon disulphide and methyl iodide in DMSO. Then treatment with guanidine nitrate and triethylamine in DMF. EI-MS m/e (%): 257 (M$^+$, 35), 256 ([M—H]$^+$, 100).

Analogously to Example 476 there were obtained:

Example 530
2-Amino-4-(5-chloro-furan-2-yl)-6-(3-methyl-pyridin-2-yl-methoxy)-pyrimidine-5-carbonitrile From 2-amino-4-furan-2-yl-6-(3-methyl-pyridin-2-ylmethoxy)-pyrimidine-5-carbonitrile and N-chlorosuccinimide in DMF. ES-MS m/e (%): 344 (M{$^{37}$Cl}+H$^+$, 35), 342 (M{$^{35}$Cl}+H$^+$, 100).

Example 531
2-Amino-4-(5-chloro-furan-2-yl)-6-(5-methyl-pyridin-2-yl-methoxy)-pyrimidine-5-carbonitrile From 2-amino-4-furan-2-yl-6-(5-methyl-pyridin-2-ylmethoxy)-pyrimidine-5-carbonitrile and N-chlorosuccinimide in DMF. ES-MS m/e (%): 344 (M{$^{37}$Cl}+H$^+$, 35), 342 (M{$^{35}$Cl}+H$^+$, 100).

Analogously to Example 199 there were obtained:

Example 532
2-Amino-4-(4-bromo-furan-2-yl)-6-(5-methyl-pyridin-2-yl-methoxy)-pyrimidine-5-carbonitrile From 2-amino-4-(4-bromo-furan-2-yl)-6-methanesulfinyl-pyrimidine-5-carbonitrile, 5-methyl-2-pyridinemethanol and DBU in DME. ES-MS m/e (%): 388 (M{$^{81}$Br}+H$^+$, 100), 386 (M{$^{79}$Br}+H$^+$, 95).

Example 533
2-Amino-4-(4-bromo-furan-2-yl)-6-(3,5-dimethyl-pyridin-2-yl-methoxy)-pyrimidine-5-carbonitrile From 2-amino-4-(4-bromo-furan-2-yl)-6-methanesulfinyl-pyrimidine-5-carbonitrile, 3,5-dimethyl-2-pyridinemethanol and DBU in DME. ES-MS m/e (%): 402 (M{$^{81}$Br}+H$^+$, 100), 400 (M{$^{79}$Br}+H$^+$, 95).

Example 534
2-Amino-4-(4-bromo-furan-2-yl)-6-(3-methyl-pyridin-2-yl-methoxy)-pyrimidine-5-carbonitrile From 2-amino-4-(4-bromo-furan-2-yl)-6-methanesulfinyl-pyrimidine-5-carbonitrile, 3-methyl-2-pyridinemethanol and DBU in DME. ES-MS m/e (%): 388 (M{$^{81}$Br}+H$^+$, 100), 386 (M{$^{79}$Br}+H$^+$, 80).

Example 535
2-Amino-4-(4-cyano-furan-2-yl)-6-(2-pyridin-2-yl-ethylsulfanyl)-pyrimidine-5-carbonitrile From 2-amino-4-(4-cyano-furan-2-yl)-6-methanesulfinyl-pyrimidine-5-carbonitrile, 2-mercaptoethylpyridine and DBU in DME. EI-MS m/e (%): 348 ($M^+$, 90), 347 ([M—H]$^+$, 65), 138 (100), 106 (70).

Analogously to Example 509 there was obtained:

Example 536
2-2Amino-4-(5-difluoromethyl-furan-2-yl)-6-methylsulfanyl-pyrimidine-5-carbonitrile From 5-difluoromethyl-furan-2-carboxylic acid methyl ester with lithium bis(trimethylsilyl)amide and acetonitrile in THF. Then treatment with sodium hydride, carbon disulphide and methyl iodide in DMSO. Then treatment with guanidine nitrate and triethylamine in DMF. EI-MS m/e (%): 282 ($M^+$, 50), 281 ([M—H]$^+$, 100).

Analogously to Example 434 there was obtained:

Example 537
N-(5-Cyano-4-furan-2-yl-6-methylsulfanyl-pyrimidin-2-yl)-4-{[(2-methoxy-ethyl)-methyl-amino]-methyl}-benzamide From 2-(furan-2-carbonyl)-3,3-bis-methylsulfanyl-acrylonitrile, N-(4-{[(2-methoxy-ethyl)-methyl-amino]-methyl}-benzoyl)-guanidine and triethylamine in DMF. ES-MS m/e (%): 438 (M+H$^+$, 100).

Analogously to Ex/ample 199 there were obtained:

Example 538
2-Amino-4-(5-difluoromethyl-furan-2-yl)-6-(2-pyridin-2-yl-ethylsulfanyl)-pyrimidine-5-carbonitrile From 2-amino-4-(5-difluoromethyl-furan-2-yl)-6-methanesulfinyl-pyrimidine-5-carbonitrile, 2-mercaptoethylpyridine and DBU in DME. ES-MS m/e (%): 374 (M+H$^+$, 100).

Example 539
Dimethyl-carbamic Acid 6-(2-amino-5-cyano-6-furan-2-yl-pyrimidin-4-yloxymethyl)-pyridin-3-yl Ester From 2-amino-4-furan-2-yl-6-methanesulfinyl-pyrimidine-5-carbonitrile, dimethyl-carbamic acid 6-hydroxymethyl-pyridin-3-yl ester and DBU in DME. ES-MS m/e (%): 403 (M+Na$^+$, 45), 381 (M+H$^+$, 100).

Example 540
2-Amino-4-(4-bromo-furan-2-yl)-6-[(5-methyl-pyridin-2-yl-methyl)-amino]-pyrimidine-5-carbonitrile From 2-amino-4-(4-bromo-furan-2-yl)-6-methanesulfinyl-pyrimidine-5-carbonitrile, C-(5-methyl-pyridin-2-yl)-methylamine dihydrochloride and DBU in DME. 387 (M{$^{81}$Br}+H$^+$, 100), 385 (M{$^{79}$Br}+H$^+$, 95).

Analogously to Example 509 there was obtained:

Example 541
2-Amino-4-(5-fluoromethyl-furan-2-yl)-6-methylsulfanyl-pyrimidine-5-carbonitrile From 5-fluoromethyl-furan-2-carboxylic acid ethyl ester with lithium bis(trimethylsilyl)amide and acetonitrile in THF. Then treatment with sodium hydride, carbon disulphide and methyl iodide in DMSO. Then treatment with guanidine nitrate and triethylamine in DMF. ES-MS m/e (%): 263 ([M—H]$^-$, 100).

What is claimed is:

1. A method of treatment of a disease state caused by malfunction of the adenosine receptor system comprising administering to a patient in need of such treatment, an effective amount of a composition for treating said disease state, said composition containing a compound that binds to an adenosine receptor and a pharmaceutically acceptable carrier, said compound having the formula:

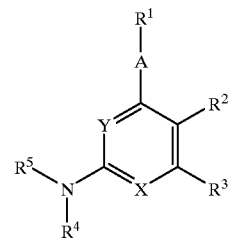

I wherein
A is selected from the group consisting of a bond, —S—, —N(R)—, —(CH$_2$)$_2$—, —CH=CH—, —C≡C— or —O—;

X and Y each are independently selected from the group consisting of —N= and =N—;

R$^1$ is selected from the group consisting of hydrogen, lower alkyl, lower alkenyl, lower alkynyl, halogen, cyano, cycloalkyl, —(CH$_2$)$_n$—C(O)O-lower alkyl,
—(CH$_2$)$_n$—C(O)O-lower alkyl-phenyl,
—(CH$_2$)$_n$—NH—C(O)O-lower alkyl-phenyl,
—(CH$_2$)$_n$—O-lower alkyl,
—(CH$_2$)$_n$—O-phenyl,
—(CH$_2$)$_n$—NH-phenyl,
—(CH$_2$)$_n$-phenyl,
—(CH$_2$)$_n$-phenyl substituted by 1 or 2 substituents selected from the group consisting of hydroxy, lower alkoxy, lower alkyl, CF$_3$-lower alkenyl, halogen, CF$_3$, OCF$_3$, amino, —(CH$_2$)$_n$—N-di-lower alkyl, —C(O)NH-lower alkyl, and —S(O)$_2$-lower alkyl,
—(CH$_2$)$_n$-morpholinyl,
—(CH$_2$)$_n$-amino,
—(CH$_2$)$_n$-amino substituted by lower alkyl or benzyl,
—(CH$_2$)$_n$-piperidin-1-yl or —(CH$_2$)$_n$-piperidin-3-yl,
—(CH$_2$)$_n$-piperidin-1-yl or —(CH$_2$)$_n$-piperidin-3-yl, said —(CH$_2$)-piperidin 1-yl or -3-yl being substituted by lower alkyl,
—(CH$_2$)$_n$-pyridin-2-yl, —(CH$_2$)$_n$-pyridin-3-yl, —(CH$_2$)$_n$-pyridin-4-yl,
—(CH$_2$)$_n$-pyridin-2-yl, —(CH$_2$)$_n$-pyridin-3-yl or —(CH$_2$)$_n$-pyridin-4-yl, said —(CH$_2$)-pyridin-2-yl, -3-yl or -4-yl, being substituted by 1 or 2 substituents selected from the group consisting of lower alkyl, hydroxy, nitro, cyano, halogen and CF$_3$,
—OC(O)N(R)$_2$,
—(CH$_2$)$_n$—NH—pyridin-2-yl,
—(CH$_2$)$_n$—NH—pyridin-2-yl, substituted by lower alkyl or halogen,
—(CH$_2$)$_n$-piperazin-4-yl,
—(CH$_2$)$_n$-piperazin-4-yl, substituted by lower alkyl, phenyl or carbonyl-phenyl,
—(CH$_2$)$_n$-phenyl—OC(O)-phenyl,
—(CH$_2$)$_n$-phenyl—OC(O)-phenyl substituted by halogen or the group

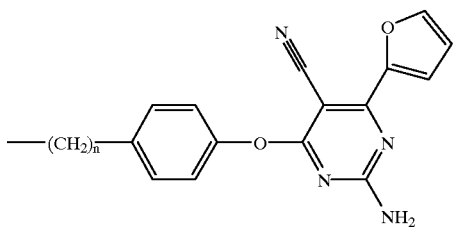

—(CH$_2$)$_n$-S-phenyl or —(CH$_2$)$_n$—S(O)$_2$-phenyl,
—(CH$_2$)$_n$—S-lower alkyl,
(CH$_2$)$_n$(CH=CH)$_m$-phenyl,
(CH$_2$)$_n$(CH≡CH)$_m$-phenyl,
—(CH$_2$)$_n$—NH-cycloalkyl,
—(CH$_2$)$_n$—NH-phenyl,
—(CH$_2$)$_n$—NH-phenyl, substituted by amino or nitro,
—(CH$_2$)$_n$-tetrahydro-pyran-4-yl,
—(CH$_2$)$_n$-quinolin-2-yl,
—(CH$_2$)$_n$-naphthyl or —(CH$_2$)$_n$—NH-naphthyl,
—(CH$_2$)$_n$-3,4-dihydro-1H-isoquinolin-2-yl,
—(CH$_2$)$_n$-benzo[1,3]dioxolyl,
—(CH$_2$)$_n$—NH—S(O)$_2$-phenyl,
—(CH$_2$)$_n$—NH—S(O)$_2$-phenyl substituted by halogen,
—(CH$_2$)$_n$-1,2,3,4-tetrahydro-quinolin-2-yl,
—(CH$_2$)$_n$-1,2,3,4-tetrahydro-quinolin-2-yl, substituted by lower alkyl, and
—(CH$_2$)$_n$-furanyl;
R$^2$ is selected from the group consisting of hydrogen, halogen, cyano, nitro, lower alkyl, lower alkenyl, —C(O)—lower alkyl, —C(O)O-lower alkyl, —C(O)O-lower alkyl-phenyl, lower alkynyl-phenyl, lower alkenyl—C(O)O-lower alkyl, lower alkenyl-cyano or phenyl, C(O)O-lower alkyl, —C(O)O-lower alkyl-phenyl, lower alkynyl-phenyl, lower alkenyl-C(O)O-lower alkyl, lower alkenyl-cyano or phenyl, substituted by halogen;
R$^3$ is selected from the group consisting of lower alkyl, phenyl, phenyl substituted by lower alkyl, lower alkoxy, or halogen,
thien-2yl or fur-2yl,
thien-2yl or fur-2yl, substituted by a substituent selected from the group consisting of lower alkyl, S-lower alkyl, halogen, lower alkoxy, —C(O)O-lower alkyl, —C(=CH$_2$)—O-lower alkyl, —(CH$_2$)$_n$-halogen, —(CH$_2$)$_n$—OH, —(CH$_2$)$_n$-lower alkoxy, cyano, CHF$_2$ and CH$_2$F,
2,3-dihydro-benzo[1,4]dioxin-6-yl,
benzo[1.3]dioxol-5-yl,
isoxazol-5-yl, pyridin-2-yl, pyridin-3-yl,
—C(=CH$_2$)O-lower alkyl,
4,5-dihydrofuran-2-yl,
5,6-dihydro-4H-pyran-2-yl,
oxazol-2-yl,
benzofuranyl,
pyrazin-2-yl,
—O—(CH$_2$)$_n$-phenyl,
—O—(CH$_2$)$_n$-pyridyl,
—O—(CH$_2$)$_n$-pyridyl substituted by lower alkyl,
—S—(CH$_2$)$_n$-pyridyl,
pyrazol-1-yl, and
pyrazol-1-yl substituted by lower alkyl or halogen;
R$^4$ and R$^5$ are independently from each other selected from the group consisting of hydrogen, —CO—(CH$_2$)$_n$-phenyl, optionally substituted by halogen or —CH$_2$N(R)(CH$_2$)$_n$-lower alkyl,
phenyl, phenyl substituted by lower alkoxy and —C(O)-phenyl;
R is selected from the group consisting of hydrogen or lower alkyl; and
A and R$^2$ may be together with the two carbon atoms

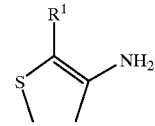

and wherein
n is 0,1,2,3 or 4;
m is 1 or 2;
or a pharmaceutically acceptable salt thereof.

2. A method of treatment of diseases responsive to Adenosine A$_{2A}$ receptor antagonists comprising administering a therapeutically effective amount of

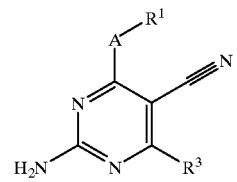

II wherein A is selected from the group consisting of a bond, —S—, —N(R)—, —(CH$_2$)$_2$—, —CH=CH—, —C≡C— or —O—;
R$^1$ is selected from the group consisting of hydrogen, lower alkyl, lower alkenyl, lower alkynyl, halogen, cyano, cycloalkyl,
—(CH$_2$)$_n$—C(O)O-lower alkyl,
—(CH$_2$)$_n$—C(O)O-lower alkyl-phenyl,
—(CH$_2$)$_n$—NH—C(O)O-lower alkyl-phenyl,
—(CH$_2$)$_n$—O-lower alkyl,
—(CH$_2$)$_n$—O-phenyl,
—(CH$_2$)$_n$—NH-phenyl,
—(CH$_2$)$_n$-phenyl,
—(CH$_2$)$_n$-phenyl substituted by 1 or 2 substituents selected from the group consisting of hydroxy, lower alkoxy, lower alkyl, CF$_3$—lower alkenyl, halogen, CF$_3$, OCF$_3$, amino, —(CH$_2$)$_n$—N-di-lower alkyl, —C(O)NH-lower alkyl and —S(O)$_2$—lower alkyl,
—(CH$_2$)$_n$-morpholinyl,
—(CH$_2$)$_n$-amino,
—(CH$_2$)$_n$-amino substituted by lower alkyl or benzyl,
—(CH$_2$)$_n$-piperidin-1-yl or —(CH$_2$)$_n$-piperidin-3-yl,
—(CH$_2$)$_n$-piperidin-1-yl or —(CH$_2$)$_n$-piperidin-3-yl, said —(CH$_2$)$_n$-piperidin-1-yl or -3-yl being substituted by lower alkyl,
—(CH$_2$)$_n$-pyridin-2-yl, —(CH$_2$)$_n$-pyridin-3-yl, —(CH$_2$)$_n$-pyridin-4-yl,
—(CH$_2$)$_n$-pyridin-2-yl, —(CH$_2$)$_n$-pyridin-3-yl or —(CH$_2$)$_n$-pyridin-4-yl, said pyridin-2-yl, -3-yl or -4-yl being substituted by 1 or 2 substituents, selected from the group consisting of lower alkyl, hydroxy, nitro, cyano, halogen, CF$_3$ and —OC(O)N(R)$_2$,
—(CH$_2$)$_n$—NH-pyridin-2-yl,
—(CH$_2$)$_n$—NH-pyridin-2-yl, substituted by a substituent selected from lower alkyl and halogen,
—(CH$_2$)$_n$-piperazin-4-yl, —(CH$_2$)$_n$-piperazin-4-yl, substituted by a substitutuent selected from lower alkyl, phenyl and carbonyl-phenyl,
—(CH$_2$)$_n$-phenyl—OC(O)-phenyl,
—(CH$_2$)$_n$-phenyl—OC(O)-phenyl substituted by halogen,
the group

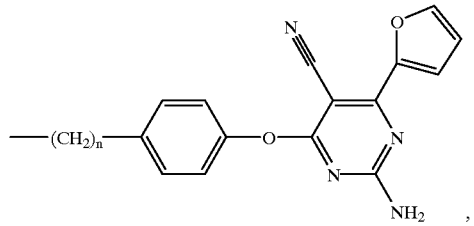

—(CH$_2$)$_n$—S-phenyl or —(CH$_2$)$_n$—S(O)$_2$-phenyl,
—(CH$_2$)$_n$—S-lower alkyl,
—(CH$_2$)$_n$(CH═CH)$_m$-phenyl,
—(CH$_2$)$_n$(CH≡CH)$_m$-phenyl,
—(CH$_2$)$_n$—NH-cycloalkyl,
—(CH$_2$)$_n$—NH-phenyl,
—(CH$_2$)$_n$—NH-phenyl, substituted by amino or nitro,
—(CH$_2$)$_n$-tetrahydro-pyran-4-yl,
—(CH$_2$)$_n$-quinolin-2-yl,
—(CH$_2$)$_n$-naphthyl or —(CH$_2$)$_n$—NH-naphthyl,
—(CH$_2$)$_n$-3,4-dihydro-1H-isoquinolin-2-yl,
—(CH$_2$)$_n$-benzo[1,3]dioxolyl,
—(CH$_2$)$_n$—NH—S(O)$_2$-phenyl,
—(CH$_2$)$_n$—NH—S(O)$_2$-phenyl substituted by halogen,
—(CH$_2$)$_n$-1,2,3,4-tetrahydro-quinolin-2-yl,
—(CH$_2$)$_n$-1,2,3,4-tetrahydro-quinolin-2-yl, substituted by lower alkyl and
—(CH$_2$)$_n$-furanyl; and
R$^3$ is selected from the group consisting of lower alkyl, phenyl, phenyl substituted by a substitutent selected from the group consisting of lower alkyl, lower alkoxy and halogen,
thien-2yl or fur-2yl,
thien-2yl or fur-2yl, substituted by lower alkyl, S-lower alkyl, halogen, lower alkoxy, —C(O)O-lower alkyl, —C(═CH$_2$)—O-lower alkyl, —(CH$_2$)$_n$-halogen, —(CH$_2$)$_n$—OH, —(CH$_2$)$_n$-lower alkoxy, cyano, CHF$_2$ and CH$_2$F,
2,3-dihydro-benzo[1.4]dioxin-6-yl,
benzo[1.3]dioxol-5-yl,
isoxazol-5-yl, pyridin-2-yl, pyridin-3-yl,
—C(═CH$_2$)O-lower alkyl,
4,5-dihydrofuran-2-yl,
5,6-dihydro-4H-pyran-2-yl,
oxazol-2-yl,
benzofuranyl,
pyrazin-2-yl,
—O—(CH$_2$)$_n$-phenyl,
—O—(CH$_2$)$_n$-pyridyl,
—O—(CH$_2$)$_n$-pyridyl substituted by lower alkyl,
—S—(CH$_2$)$_n$-pyridyl,
pyrazol-1-yl, and
pyrazol-1-yl substituted by lower alkyl or halogen; and
R is selected from the group consisting of hydrogen and lower alkyl;
or a pharmaceutically acceptable salt thereof.

3. The method of treatment of claim 1 wherein said compound has the structure of formula IV

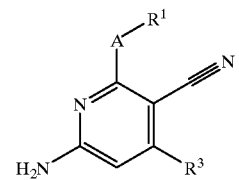

wherein A, R$^1$ and R$^3$ are as defined in claim 1.

4. The method of treatment of claim 1 using compounds of formula I wherein the disease state being treated includes Alzheimer's disease, Parkinson's disease, neuroprotection, schizophrenia, anxiety, pain, respiration deficits, depression, asthma, allergic responses, hypoxia, ischaemia, seizure, substance abuse, sedation, said compounds serving as muscle relaxants, antipsychotics, antiepileptics, anticonvulsants and cardiaprotective agents.

5. The method of treatment of claim 1 wherein said treatment is based upon A$_{2A}$ receptor antagonistic activity for the control or treatment of certain depressive disorders, neuroprotection and Parkinson's disease.

6. A method of treatment of diseases responsive to Adenosine A$_{2A}$ receptor antagonists

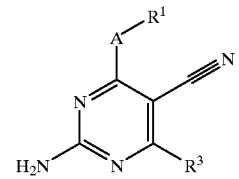

wherein A is —N(R);
R$^1$ is selected from the group consisting of hydrogen, lower alkyl, lower alkenyl, lower alkynyl, halogen, cyano, cycloalkyl,
—(CH$_2$)$_n$—C(O)O-lower alkyl,
—(CH$_2$)$_n$—C(O)O-lower alkyl-phenyl,
—(CH$_2$)$_n$—NH—C(O)O-lower alkyl-phenyl,
—(CH$_2$)$_n$—O-lower alkyl,
—(CH$_2$)$_n$—O-phenyl,
—(CH$_2$)$_n$—NH-phenyl,
—(CH$_2$)$_n$-phenyl,
—(CH$_2$)$_n$-phenyl substituted by 1 or 2 substituents selected from the group consisting of hydroxy, lower alkoxy, lower alkyl, CF$_3$-lower alkenyl, halogen, CF$_3$, OCF$_3$, amino, —(CH$_2$)$_n$—N-di-lower alkyl, —C(O)NH-lower alkyl and —S(O)$_2$-lower alkyl,
—(CH$_2$)$_n$-morpholinyl,
—(CH$_2$)$_n$-amino,
—(CH$_2$)$_n$-amino substituted by lower alkyl or benzyl,
—(CH$_2$)$_n$-piperidin-1-yl or —(CH$_2$)$_n$-piperidin-3-yl,
—(CH$_2$)$_n$-piperidin-1-yl or —(CH$_2$)$_n$-piperidin-3-yl, said —(CH$_2$)$_n$-piperidin-1-yl or -3-yl being substituted by lower alkyl,
—(CH$_2$)$_n$-pyridin-2-yl, —(CH$_2$)$_n$-pyridin-3-yl, —(CH$_2$)$_n$-pyridin-4-yl,
—(CH$_2$)$_n$-pyridin-2-yl, —(CH$_2$)$_n$-pyridin-3-yl or —(CH$_2$)$_n$-pyridin-4-yl, said pyridin-2-yl, -3-yl or -4-yl being substituted by 1 or 2 substituents, selected from the group consisting of lower alkyl, hydroxy, nitro, cyano, halogen, CF$_3$ and —OC(O)N(R)$_2$, —(CH$_2$)$_n$—NH-pyridin-2-yl,
—(CH$_2$)$_n$—NH-pyridin-2-yl, substituted by a substituent selected from lower alkyl and halogen,
—(CH$_2$)$_n$-piperazin-4-yl,
—(CH$_2$)$_n$-piperazin-4-yl, substituted by a substitutuent selected from lower alkyl, phenyl and carbonyl-phenyl,
—(CH$_2$)$_n$-phenyl—OC(O)-phenyl,
—(CH$_2$)$_n$-phenyl—OC(O)-phenyl substituted by halogen,
the group

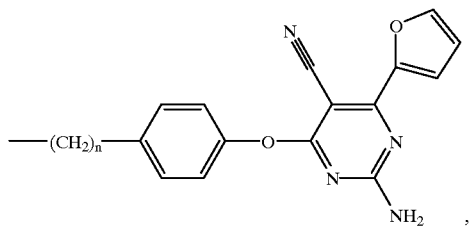

—(CH$_2$)$_n$—S-phenyl or —(CH$_2$)$_n$—S(O)$_2$-phenyl,
—(CH$_2$)$_n$—S-lower alkyl,
—(CH$_2$)$_n$(CH═CH)$_m$-phenyl,
(CH$_2$)$_n$(CH≡CH)$_m$-phenyl,
—(CH$_2$)$_n$—NH-cycloalkyl,
—(CH$_2$)$_n$—NH-phenyl,
—(CH$_2$)$_n$—NH-phenyl, substituted by amino or nitro,
—(CH$_2$)$_n$-tetrahydro-pyran-4-yl,
—(CH$_2$)$_n$-naphthyl or —(CH$_2$)$_n$—NH-naphthyl,
—(CH$_2$)$_n$-3,4-dihydro-1H-isoquinolin-2-yl,
—(CH$_2$)$_n$-benzo[1,3]dioxolyl,
—(CH$_2$)$_n$—NH—S(O)$_2$-phenyl,
—(CH$_2$)$_n$—NH—S(O)$_2$-phenyl substituted by halogen,
—(CH$_2$)$_n$-1,2,3,4-tetrahydro-quinolin-2-yl,
—(CH$_2$)$_n$-1,2,3,4-tetrahydro-quinolin-2-yl, substituted by lower alkyl and
—(CH$_2$)$_n$-furanyl; and
R$^3$ is selected from the group consisting of lower alkyl, phenyl, phenyl substituted by a substituent selected from the group consisting of lower alkyl, lower alkoxy and halogen,
thien-2yl or fur-2yl,
thien-2yl or fur-2yl, substituted by lower alkyl, S-lower alkyl, halogen, lower alkoxy, —C(O)O-lower alkyl, —C(═CH$_2$)—O-lower alkyl, —(CH$_2$)$_n$-halogen, —(CH$_2$)$_n$—OH, —(CH$_2$)$_n$-lower alkoxy, cyano, CHF$_2$ and CH$_2$F,
2,3-dihydro-benzo[1.4]dioxin-6-yl,
benzo[1.3]dioxol-5-yl,
isoxazol-5-yl, pyridin-2-yl, pyridin-3-yl,
—C(═CH$_2$)O-lower alkyl,
4,5-dihydrofuran-2-yl,
5,6-dihydro-4H-pyran-2-yl,
oxazol-2-yl,
benzofuranyl,
pyrazin-2-yl,
—O—(CH$_2$)$_n$-phenyl,
—O—(CH$_2$)$_n$-pyridyl,
—O—(CH$_2$)$_n$-pyridyl substituted by lower alkyl,
—S—(CH$_2$)$_n$-pyridyl,
pyrazol-1-yl, and
pyrazol-1-yl substituted by lower alkyl or halogen; and R is selected from the group consisting of hydrogen and lower alkyl;
or a pharmaceutically acceptable salt thereof.

7. A method of treatment of Parkinson's Disease, hypertension and ischemia comprising administering to a patient in need of such treatment, a therapeutically effective amount of a compound of formula

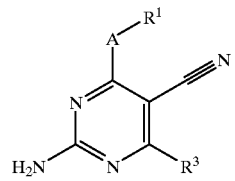

II wherein A is —NH—;
R$^1$ is selected from the group consisting of hydrogen, lower alkyl, lower alkenyl, lower alkynyl, halogen, cyano, cycloalkyl,
—(CH$_2$)$_n$—C(O)O-lower alkyl,
—(CH$_2$)$_n$—C(O)O-lower alkyl-phenyl,
—(CH$_2$)$_n$—NH—C(O)O-lower alkyl-phenyl,
—(CH$_2$)$_n$—O-lower alkyl,
—(CH$_2$)$_n$—O-phenyl,
—(CH$_2$)$_n$—NH-phenyl,
—(CH$_2$)$_n$-phenyl,
—(CH$_2$)$_n$-phenyl substituted by 1 or 2 substituents selected from the group consisting of hydroxy, lower alkoxy, lower alkyl, CF$_3$-lower alkenyl, halogen, CF$_3$, OCF$_3$, amino, —(CH$_2$)$_n$—N-di-lower alkyl, —C(O)NH-lower alkyl and —S(O)$_2$-lower alkyl,
—(CH$_2$)$_n$-morpholinyl,
—(CH$_2$)$_n$-amino,
—(CH$_2$)$_n$-amino substituted by lower alkyl or benzyl,
—(CH$_2$)$_n$-piperidin-1-yl or —(CH$_2$)$_n$-piperidin-3-yl,
—(CH$_2$)$_n$-piperidin-1-yl or —(CH$_2$)$_n$-piperidin-3-yl, said —(CH$_2$)$_n$-piperidin-1-yl or -3-yl being substituted lower alkyl,
—(CH$_2$)$_n$-pyridin-2-yl, —(CH$_2$)$_n$-pyridin-3-yl, —(CH$_2$)$_n$-pyridin-4-yl,
—(CH$_2$)$_n$-pyridin-2-yl, —(CH$_2$)$_n$-pyridin-3-yl or —(CH$_2$)$_n$-pyridin-4-yl, said pyridin-2-yl, -3-yl-or -4-yl being substituted by 1 or 2 substituents, selected from the group consisting of lower alkyl, hydroxy, nitro, cyano, halogen, CF$_3$ and —OC(O)N (R)$_2$,
—(CH$_2$)—NH—pyridin-2-yl,
—(CH$_2$)$_n$—NH—pyridin-2-yl, substituted by a substitutuent selected from lower alkyl and halogen,
—(CH$_2$)$_n$-piperazin-4-yl,
—(CH$_2$)$_n$-piperazin-4-yl, substituted by a substitutuent selected from lower alkyl, phenyl and carbonyl-phenyl,
—(CH$_2$)$_n$-phenyl—OC(O)-phenyl,
—(CH$_2$)$_n$-phenyl—OC(O)-phenyl substituted by a substituent selected from the group consisting of halogen and the group

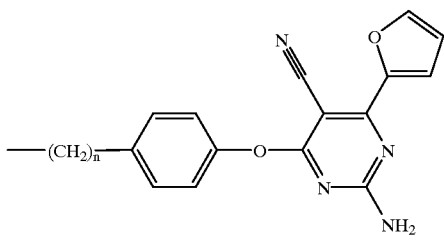

—(CH₂)ₙ—S-phenyl or —(CH₂)ₙ—S(O)₂-phenyl,
—(CH₂)ₙ—S-lower alkyl,
—(CH₂)ₙ(CH=CH)ₘ-phenyl,
—(CH₂)ₙ(CH≡CH)ₘ-phenyl,
—(CH₂)ₙ—NH-cycloalkyl,
—(CH₂)ₙ—NH-phenyl,
—(CH₂)ₙ—NH-phenyl, substituted by amino or nitro,
—(CH₂)ₙ-tetrahydro-pyran-4-yl,
—(CH₂)ₙ-quinolin-2-yl,
—(CH₂)ₙ-naphthyl or —(CH₂)ₙ—NH-naphthyl,
—(CH₂)ₙ-3,4-dihydro-1H-isoquinolin-2-yl,
—(CH₂)ₙ-benzo[1,3]dioxolyl,
—(CH₂)ₙ—NH—S(O)₂-phenyl,
—(CH₂)ₙ—NH—S(O)₂-phenyl substituted by halogen,
—(CH₂)ₙ-1,2,3,4-tetrahydro-quinolin-2-yl,
—(CH₂)ₙ-1,2,3,4-tetrahydro-quinolin-2-yl, substituted by lower alkyl and
—(CH₂)ₙ-furanyl; and R³ is selected from the group consisting of lower alkyl, phenyl, phenyl substituted by a substitutent selected from the group consisting of lower alkyl, lower alkoxy and halogen,
thien-2yl or fur-2yl,
thien-2yl or fur-2yl, substituted by a substituent selected from the group consisting of lower alkyl, S-lower alkyl, halogen, lower alkoxy, —C(O)O-lower alkyl, —C(=CH₂)—O-lower alkyl, —(CH₂)ₙ-halogen, —(CH₂)ₙ—OH, —(CH₂)ₙ-lower alkoxy, cyano, CHF₂ and CH₂F,
2,3-dihydro-benzo[1.4]dioxin-6-yl,
benzo[1.3]dioxol-5-yl,
isoxazol-5-yl, pyridin-2-yl, pyridin-3-yl,
—C(=CH₂)O-lower alkyl,
4,5-dihydrofuran-2-yl,
5,6-dihydro-4H-pyran-2-yl,
oxazol-2-yl,
benzofuranyl,
pyrazin-2-yl,
—O—(CH₂)ₙ-phenyl,
—O—(CH₂)ₙ-pyridyl,
—O—(CH₂)ₙ-pyridyl substituted by lower alkyl,
—S—(CH₂)ₙ-pyridyl,
pyrazol-1-yl, and
pyrazol-1-yl substituted by lower alkyl or halogen;
or a pharmaceutically acceptable salt thereof.

8. The method of treatment in accordance with claim 7, wherein the compound is selected from the group consisting of 2-Amino-4-benzylamino-6-furan-2-yl-pyrimidine-5-carbonitrile,
2-amino-4-furan-2-yl-6-(3-phenyl-propylamino)-pyrimidine-5-carbonitrile,
2-amino-4-furan-2-yl-6-[2-(4-hydroxy-phenyl)-ethylamino]-pyrimidine-5-carbonitrile,
2-amino-4-furan-2-yl-6-(2-phenylamino-ethylamino)-pyrimidine-5-carbonitrile,
2-amino-4-furan-2-yl-6-[2-(4-methoxy-phenyl)-ethylamino]-pyrimidine-5-carbonitrile,
2-amino-4-furan-2-yl-6-(2-phenylamino-ethoxy)-pyrimidine-5-carbonitrile,
2-amino-4-furan-2-yl-6-(2-phenoxy-ethylamino)-pyrimidine-5-carbonitrile,
2-amino-4-benzylamino-6-(5-methyl-furan-2-yl)-pyrimidine-5-carbonitrile,
6-furan-2-yl-5-nitro-N4-(3-phenyl-propyl)-pyrimidine-2,4-diamine,
2-amino-4-furan-2-yl-6-(2-methyl-benzylamino)-pyrimidine-5-carbonitrile,
2-amino-4-furan-2-yl-6-(3-methyl-benzylamino)-pyrimidine-5-carbonitrile,
2-amino-4-furan-2-yl-6-(4-methyl-benzylamino)-pyrimidine-5-carbonitrile,
2-amino-4-furan-2-yl-6 (3-methoxy-benzylamino)-pyrimidine-5-carbonitrile,
2-amino-4-furan-2-yl-6-(2-methoxy-benzylamino)-pyrimidine-5-carbonitrile,
2-amino-4-furan-2-yl-6-[(quinolin-2-yl-methyl)-amino]-pyrimidine-5-carbonitrile,
2-amino-4-furan-2-yl-6-[(naphthalen-2-yl-methyl)-amino]-pyrimidine-5-carbonitrile,
(RS)-2-amino-4-furan-2-yl-6-[(1,2,3,4-tetrahydro-quinolin-2-yl-methyl)-amino]-pyrimidine-5-carbonitrile,
2-amino-4-furan-2-yl-6-(2-phenylsulfanyl-ethylamino)-pyrimidine-5-carbonitrile
2-amino-4-(2-amino-benzylamino)-6-furan-2-yl-pyrimidine-5-carbonitrile,
2-amino-4-(4-amino-benzylamino)-6-furan-2-yl-pyrimidine-5-carbonitrile,
2-amino-4-(4-dimethylamino-benzylamino)-6-furan-2-yl-pyrimidine-5-carbonitrile,
2-amino-4-[2-(4-chloro-phenylamino)-ethylamino]-6-furan-2-yl-pyrimidine-5-carbonitrile,
2-amino-4-(4-bromo-benzylamino)-6-furan-2-yl-pyrimidine-5-carbonitrile,
2-amino-4-furan-2-yl-6-[2-(pyridin-2-ylamino)-ethylamino]-pyrimidine-5-carbonitrile,
2-amino-4-[(benzo[1,3]dioxol-5-yl-methyl)-amino]-6-furan-2-yl-pyrimidine-5-carbonitrile,
2-amino-4-furan-2-yl-6-(4-trifluoromethyl-benzylamino)-pyrimidine-5-carbonitrile,
2-amino-4-furan-2-yl-6-(3-trifluoromethyl-benzylamino)-pyrimidine-5-carbonitrile,
2-amino-4-(3,4-dimethyl-benzylamino)-6-furan-2-yl-pyrimidine-5-carbonitrile,
2-amino-4-furan-2-yl-6-[(4-methyl-pyridin-2-yl-methyl)-amino]-pyrimidine-5-carbonitrile,
2-amino-4-(2-bromo-benzylamino)-6-furan-2-yl-pyrimidine-5-carbonitrile,
2-amino-4-(2-chloro-benzylamino)-6-furan-2-yl-pyrimidine-5-carbonitrile,
2-amino-4-furan-2-yl-6-[(5-methyl-pyridin-2-yl-methyl)-amino]-pyrimidine-5-carbonitrile,
2-amino-4-furan-2-yl-6-[(isoquinolin-3-yl-methyl)-amino]-pyrimidine-5-carbonitrile,
2-amino-4-furan-2-yl-6-[(3-methyl-pyridin-2-yl-methyl)-amino]-pyrimidine-5-carbonitrile, 2-amino-4-furan-2-yl-6-(4-vinyl-benzylamino)-pyrimidine-5-carbonitrile, 2-amino-4-(4-ethyl-benzylamino)-6-furan-2-yl-pyrimidine-5-carbonitrile, 2-amino-4-[(3-chloro-5-trifluoromethyl-pyridin-2-yl-methyl)-amino]-6-furan-2-yl-pyrimidine-5-carbonitrile, 2-amino-4-[(3,5-dimethyl-pyridin-2-yl-methyl)-amino]-6-furan-2-yl-pyrimidine-5-carbonitrile, 2-amino-4-(4,5-dihydro-furan-2-yl)-6-[(4-methyl-pyridin-2-yl-methyl)-amino]-pyrimidine-5-carbonitrile and 2-amino-4-(2-bromo-benzylamino)-6-(5-bromo-furan-2-yl)-pyrimidine-5-carbonitrile.

9. The method of treatment of claim 2 wherein A is —O—.

10. The method of treatment in accordance with claim 9, wherein the compound is selected from the group consisting of 2-amino-4-ethoxy-6-furan-2-yl-pyrimidine-5-carbonitrile, 2-amino-4-benzyloxy-6-furan-2-yl-pyrimidine-5-carbonitrile, 2-amino-4-furan-2-yl-6-phenethyloxy-pyrimidine-5-carbonitrile, 2-amino-4-furan-2-yl-6-(3-phenyl-propoxy)-pyrimidine-5-carbonitrile, 2-amino-4-cyclohexyloxy-6-furan-2-yl-pyrimidine-5-carbonitrile, 2-amino-4-furan-2-yl-6-isopropoxy-pyrimidine-5-carbonitrile, 2-amino-4-furan-2-yl-6-(pyridin-2-yl-methoxy)-pyrimidine-5-carbonitrile, 2-amino-4-phenethyloxy-6-phenyl-pyrimidine-5-carbonitrile, 2-amino-4-phenyl-6-(pyridin-2-yl-methoxy)-pyrimidine-5-carbonitrile, 2-amino-4-(pyridin-2-yl-methoxy)-6-thiophen-2-yl-pyrimidine-5-carbonitrile, 2-amino-4-furan-2-yl-6-(pyridin-3-yl-methoxy)-pyrimidine-5-carbonitrile, 2-amino-4-furan-2-yl-6-(6-methyl-pyridin-2-yl-methoxy)-pyrimidine-5-carbonitrile, 2-amino-4-furan-2-yl-6-(2-pyridin-2-yl-ethoxy)-pyrimidine-5-carbonitrile, 2-amino-4-(5-methyl-furan-2-yl)-6-(6-methyl-pyridin-2-yl-methoxy)-pyrimidine-5-carbonitrile, 2-amino-4-(5-methyl-furan-2-yl)-6-(pyridin-2-yl-methoxy)-pyrimidine-5-carbonitrile, 2-amino-4-furan-2-yl-6-(3-phenyl-allyloxy)-pyrimidine-5-carbonitrile, 2-amino-4-furan-2-yl-6-(naphthalen-2-yl-methoxy)-pyrimidine-5-carbonitrile, 2-amino-4-furan-2-yl-6-(3-methyl-pyridin-2-yl-methoxy)-pyrimidine-5-carbonitrile, 2-amino-4-furan-2-yl-6-(5-methyl-pyridin-2-yl-methoxy)-pyrimidine-5-carbonitrile, 2-amino-4-furan-2-yl-6-(isoquinolin-3-yl-methoxy)-pyrimidine-5-carbonitrile, 2-amino-4-furan-2-yl-6-(4-methyl-pyridin-2-yl-methoxy)-pyrimidine-5-carbonitrile, 2-amino-4-furan-2-yl-6-(6-methyl-pyridin-3-yl-methoxy)-pyrimidine-5-carbonitrile, 2-amino-4-(3,5-dimethyl-pyridin-2-yl-methoxy)-6-furan-2-yl-pyrimidine-5-carbonitrile, 2-amino-4-(3-fluoro-phenyl)-6-(2-pyridin-2-yl-ethoxy)-pyrimidine-5-carbonitrile, 2-amino-4-(4-methyl-furan-2-yl)-6-(2-pyridin-2-yl-ethoxy)-pyrimidine-5-carbonitrile, 2-amino-4-(5-methyl-furan-2-yl)-6-(3-methyl-pyridin-2-yl-methoxy)-pyrimidine-5-carbonitrile, 2-amino-4-(3,5-dimethyl-pyridin-2-ylmethoxy)-6-(5-methyl-furan-2-yl)-pyrimidine-5-carbonitrile, 2-amino-4-(5-bromo-furan-2-yl)-6-(5-methyl-pyridin-2-yl-methoxy)-pyrimidine-5-carbonitrile, 2-amino-4-(5-bromo-furan-2-yl)-6-(3-methyl-pyridin-2-yl-methoxy)pyrimidine-5-carbonitrile, 2-amino-4-(5-bromo-furan-2-yl)-6-(2-pyridin-2-yl-ethoxy)-pyrimidine-5-carbonitrile, 2-amino-4-(5-chloro-furan-2-yl)-6-(2-pyridin-2-yl-ethoxy)-pyrimidine-5-carbonitrile, 2-amino-4-(5-chloro-furan-2-yl)-6-(3,5-dimethyl-pyridin-2-yl-methoxy)-pyrimidine-5-carbonitrile, 2-amino-4-(5-chloro-furan-2-yl)-6-(3-methyl-pyridin-2-yl-methoxy)-pyrimidine-5-carbonitrile, 2-amino-4-(5-chloro-furan-2-yl)-6-(5-methyl-pyridin-2-yl-methoxy)-pyrimidine-5-carbonitrile, 2-amino-4-(4-bromo-furan-2-yl)-6-(5-methyl-pyridin-2-yl-methoxy)pyrimidine-5-carbonitrile, 2-amino-4-(4-bromo-furan-2-yl)-6-(3,5-dimethyl-pyridin-2-yl-methoxy)-pyrimidine-5-carbonitrile and 2-amino-4-(4-bromo-furan-2-yl)-6-(3-methyl-pyridin-2-yl-methoxy)pyrimidine-5-carbonitrile;

or a pharmaceutically acceptable salt thereof.

11. The method of treatment of claim 2, wherein A is —S—.

12. The method of treatment of claim 11, wherein the compound is selected from the group consisting of 2-Amino-4-(2,3-dihydro-benzo[1,4]dioxin-6-yl)-6-methylsulfanyl-pyrimidine-5-carbonitrile, 2-amino-4-benzylsulfanyl-6-furan-2-yl-pyrimidine-5-carbonitrile, 2-amino-4-butylsulfanyl-6-furan-2-yl-pyrimidine-5-carbonitrile, 2-amino-4-ethylsulfanyl-6-furan-2-yl-pyrimidine-5-carbonitrile, 2-amino-4-phenyl-6-(3-phenyl-propylsulfanyl)-pyrimidine-5-carbonitrile, 2-amino-4-furan-2-yl-6-phenethylsulfanyl-pyrimidine-5-carbonitrile, 2-amino-4-furan-2-yl-6-(3-phenyl-propylsulfanyl)-pyrimidine-5-carbonitrile, 2-amino-4-furan-2-yl-6-(pyridin-2-yl-methylsulfanyl)-pyrimidine-5-carbonitrile, 2-amino-4-furan-2-yl-6-(2-pyridin-2-yl-ethylsulfanyl)-pyrimidine-5-carbonitrile, 2-amino-4-(2-pyridin-2-yl-ethylsulfanyl)-6-thiophen-2-yl-pyrimidine-5-carbonitrile, 2-amino-4-(4-methyl-furan-2-yl)-6-(2-pyridin-2-yl-ethylsulfanyl)-pyrimidine-5-carbonitrile, 2-amino-4-(5-chloro-furan-2-yl)-6-(2-pyridin-2-yl-ethylsulfanyl)-pyrimidine-5-carbonitrile, 2-amino-4-(5-bromo-furan-2-yl)-6-(2-pyridin-2-yl-ethylsulfanyl)-pyrimidine-5-carbonitrile, 2-amino-4-(4-bromo-furan-2-yl)-6-(2-pyridin-2-yl-ethylsulfanyl)-pyrimidine-5-carbonitrile, 2-amino-4-(5-cyanomethyl-furan-2-yl)-6-(2-pyridin-2-yl-ethylsulfanyl)-pyrimidine-5-carbonitrile, 2-amino-4-(4-cyano-furan-2-yl)-6-(2-pyridin-2-yl-ethylsulfanyl)-pyrimidine-5-carbonitrile and 2-amino-4-(5-difluoromethyl-furan-2-yl)-6-(2-pyridin-2-yl-ethylsulfanyl)-pyrimidine-5-carbonitrile;

or a pharmaceutically acceptable salt thereof.

13. The method of treatment of claim 2, wherein A is a bond.

14. The method of treatment of claim 13, wherein the compound is selected from the group consisting of 2-Amino-4-furan-2-yl-6-piperidin-1-yl-pyrimidine-5-carbonitrile, 2-amino-6-furan-2-yl-pyrimidine-4,5-dicarbonitrile, 2-amino-4-furan-2-yl-6-phenyl-pyrimidine-5-carbonitrile, (E)-2-amino-4-furan-2-yl-6-styryl-pyrimidine-5-carbonitrile and 2-amino-4-(3,4-dihydro-1H-isoquinolin-2-yl)-6-furan-2-yl-pyrimidine-5-carbonitrile;

or a pharmaceutically acceptable salt thereof.

15. The method of treatment of claim 1 for compounds of formula I as defined in claim 1, wherein X and Y are nitrogen, A is —O—, —NH— or —S—, $R^2$ is halogen or nitro and the other substituents are as defined in claim 1.

16. The method of treatment in accordance with claim 15, wherein the compound is selected from the group consisting of 5-Bromo-4-furan-2-yl-6-(pyridin-2-yl-methoxy)-pyrimidin-2-yl-amine, 5-bromo-6-furan-2-yl-N4-(3-phenyl-propyl)-pyrimidine-2,4-diamine, 5-bromo-4-furan-2-yl-6-(3-phenyl-propoxy)-pyrimidin-2-yl-amine, 4-furan-2-yl-5-iodo-6-(3-phenyl-propoxy)-pyrimidin-2-yl-amine, 5-bromo-4-furan-2-yl-6-phenethylsulfanyl-pyrimidin-2-yl-amine, 5-bromo-4-furan-2-yl-6-(3-phenyl-allyloxy)-pyrimidin-2-y-amine, 4-benzyloxy-6-furan-2-yl-5-nitro-pyrimidin-2-yl-amine, 5-chloro-6-furan-2-yl-N4-(3-phenyl-propyl)-pyrimidine-2,4-diamine, 5-chloro-4-furan-2-yl-6-(3-phenyl-propoxy)-pyrimidin-2-yl-amine, 5-chloro-4-furan-2-yl-6-phenethyloxy-pyrimidin-2-yl-amine, 4-benzylsulfanyl-5-chloro-6-furan-2-yl-pyrimidin-2-yl-amine, 4-furan-2-yl-5-iodo-6-(2-pyridin-2-yl-ethylsulfanyl)-pyrimidin-2-yl-amine, 5-bromo-4-furan-2-yl-6-(2-pyridin-2-yl-ethylsulfanyl)-pyrimidin-2-yl-amine and 5-chloro-4-furan-2-yl-6-(2-pyridin-2-yl-ethylsulfanyl)-pyrimidin-2-yl-amine;

or a pharmaceutically acceptable salt thereof.

17. The method of treatment of claim 1 for compounds of formula I, wherein X and Y are nitrogen, A is —S—, $R^2$ is cyano and R is —C(O)-phenyl, and the other substituents are as defined in claim 1.

18. The method of treatment of claim 17, wherein the compound is

N-[5-Cyano-4-furan-2-yl-6-(2-pyridin-2-yl-ethylsulfanyl)-pyrimidin-2-yl]-benzamide.

19. A compound selected from the group consisting of 2-amino-4-ethoxy-6-furan-2-yl-pyrimidine-5-carbonitrile, 2-amino-4-benzyloxy-6-furan-2-yl-pyrimidine-5-carbonitrile, 2-amino-4-furan-2-yl-6-phenethyloxy-pyrimidine-5-carbonitrile, 2-amino-4-furan-2-yl-6-(3-phenyl-propoxy)-pyrimidine-5-carbonitrile, 2-amino-4-cyclohexyloxy-6-furan-2-yl-pyrimidine-5-carbonitrile, 2-amino-4-furan-2-yl-6-isopropoxy-pyrimidine-5-carbonitrile, 2-amino-4-furan-2-yl-6-(pyridin-2-yl-methoxy)-pyrimidine-5-carbonitrile, 2-amino-4-phenethyloxy-6-phenyl-pyrimidine-5-carbonitrile, 2-amino-4-phenyl-6-(pyridin-2-yl-methoxy)-pyrimidine-5-carbonitrile, 2-amino-4-(pyridin-2-ylmethoxy)-6-thiophen-2-yl-pyrimidine-5-carbonitrile, 2-amino-4-furan-2-yl-6-(pyridin-3-yl-methoxy)-pyrimidine-5-carbonitrile, 2-amino-4-furan-2-yl-6-(6-methyl-pyridin-2-yl-methoxy)-pyrimidine-5-carbonitrile, 2-amino-4-furan-2-yl-6-(2-pyridin-2-yl-ethoxy)-pyrimidine-5-carbonitrile, 2-amino-4-(5-methyl-furan-2-yl)-6-(6-methyl-pyridin-2-yl-methoxy)-pyrimidine-5-carbonitrile, 2-amino-4-(5-methyl-furan-2-yl)-6-(pyridin-2-yl-methoxy)-pyrimidine-5-carbonitrile, 2-amino-4-furan-2-yl-6-(3-phenyl-allyloxy)-pyrimidine-5-carbonitrile, 2-amino-4-furan-2-yl-6-(naphthalen-2-yl-methoxy)-pyrimidine-5-carbonitrile, 2-amino-4-furan-2-yl-6-(3-methyl-pyridin-2-yl-methoxy)-pyrimidine-5-carbonitrile, 2-amino-4-furan-2-yl-6-(5-methyl-pyridin-2-yl-methoxy)-pyrimidine-5-carbonitrile, 2-amino-4-furan-2-yl-6-(isoquinolin-3-yl-methoxy)-pyrimidine-5-carbonitrile, 2-amino-4-furan-2-yl-6-(4-methyl-pyridin-2-yl-methoxy)-pyrimidine-5-carbonitrile, 2-amino-4-furan-2-yl-6-(6-methyl-pyridin-3-yl-methoxy)-pyrimidine-5-carbonitrile, 2-amino-4-(3,5-dimethyl-pyridin-2-yl-methoxy)-6-furan-2-yl-pyrimidine-5-carbonitrile, 2-amino-4-(3-fluoro-phenyl)-6-(2-pyridin-2-yl-ethoxy)-pyrimidine-5-carbonitrile, 2-amino-4-(4-methyl-furan-2-yl)-6-(2-pyridin-2-yl-ethoxy)-pyrimidine-5-carbonitrile, 2-amino-4-(5-methyl-furan-2-yl)-6-(3-methyl-pyridin-2-yl-methoxy)-pyrimidine-5-carbonitrile, 2-amino-4-(3,5-dimethyl-pyridin-2-ylmethoxy)-6-(5-methyl-furan-2-yl)-pyrimidine-5-carbonitrile, 2-amino-4-(5-bromo-furan-2-yl)-6-(5-methyl-pyridin-2-yl-methoxy)-pyrimidine-5carbonitrile, 2-amino-4-(5-bromo-furan-2-yl)-6-(3-methyl-pyridin-2-yl-methoxy)-pyrimidine-5-carbonitrile, 2-amino-4-(5-bromo-furan-2-yl)-6-(2-pyridin-2-yl-ethoxy)-pyrimidine-5-carbonitrile, 2-amino-4-(5-chloro-furan-2-yl)-6-(2-pyridin-2-yl-ethoxy)-pyrimidine-5-carbonitrile, 2-amino-4-(5-chloro-furan-2-yl)-6-(3,5-dimethyl-pyridin-2-yl-methoxy)-pyrimidine-5-carbonitrile, 2-amino-4-(5-chloro-furan-2-yl)-6-(3-methyl-pyridin-2-yl-methoxy)-pyrimidine-5-carbonitrile, 2-amino-4-(5-chloro-furan-2-yl)-6-(5-methyl-pyridin-2-yl-methoxy)-pyrimidine-5-carbonitrile, 2-amino-4-(4-bromo-furan-2-yl)-6-(5-methyl-pyridin-2-yl-methoxy)-pyrimidine-5-carbonitrile, 2-amino-4-(4-bromo-furan-2-yl)-6-(3,5-dimethyl-pyridin-2-yl-methoxy)-pyrimidine-5-carbonitrile and 2-amino-4-(4-bromo-furan-2-yl)-6-(3-methyl-pyridin-2-yl-methoxy)-pyrimidine-5-carbonitrile;

or a pharmaceutically acceptable salt thereof.

20. A compound selected from the group consisting of

2-Amino-4-(2,3-dihydro-benzo[1,4]dioxin-6-yl)-6-methylsulfanyl-pyrimidine-5-carbonitrile 2-amino-4-benzylsulfanyl-6-furan-2-yl-pyrimidine-5-carbonitrile, 2-amino-4-butylsulfanyl-6-furan-2-yl-pyrimidine-5-carbonitrile, 2-amino-4-ethylsulfanyl-6-furan-2-yl-pyrimidine-5-carbonitrile, 2-amino-4-phenyl-6-(3-phenyl-propylsulfanyl)-pyrimidine-5-carbonitrile, 2-amino-4-furan-2-yl-6-phenethylsulfanyl-pyrimidine-5-carbonitrile, 2-amino-4-furan-2-yl-6-(3-phenyl-propylsulfanyl)-pyrimidine-5-carbonitrile, 2-amino-4-furan-2-yl-6-(pyridin-2-yl-methylsulfanyl)-pyrimidine-5-carbonitrile, 2-amino-4-furan-2-yl-6-(2-pyridin-2-yl-ethylsulfanyl)-pyrimidine-5-carbonitrile, 2-amino-4-(2-pyridin-2-yl-ethylsulfanyl)-6-thiophen-2-yl-pyrimidine-5-carbonitrile, 2-amino-4-(4-methyl-furan-2-yl)-6-(2-pyridin-2-yl-ethylsulfanyl)-pyrimidine-5-carbonitrile, 2-amino-4-(5-chloro-furan-2-yl)-6-(2-pyridin-2-yl-ethylsulfanyl)-pyrimidine-5-carbonitrile, 2-amino-4-(5-bromo-furan-2-yl)-6-(2-pyridin-2-yl-ethylsulfanyl)-pyrimidine-5-carbonitrile, 2-amino-4-(4-bromo-furan-2-yl)-6-(2-pyridin-2-yl-ethylsulfanyl)-pyrimidine-5-carbonitrile, 2-amino-4-(5-cyanomethyl-furan-2-yl)-6-(2-pyridin-2-yl-ethylsulfanyl)-pyrimidine-5-carbonitrile, 2-amino-4-(4-cyano-furan-2-yl)-6-(2-pyridin-2-yl-ethylsulfanyl)-pyrimidine-5-carbonitrile and 2-amino-4-(5-difluoromethyl-furan-2-yl)-6-(2-pyridin-2-yl-ethylsulfanyl)-pyrimidine-5-carbonitrile, or a pharmaceutically acceptable salt thereof.

21. A compound selected from the group consisting of

2-Amino-4-furan-2-yl-6-piperidin-1-yl-pyrimidine-5-carbonitrile, 2-amino-6-furan-2-yl-pyrimidine-4,5-dicarbonitrile, 2-amino-4-furan-2-yl-6-phenyl-pyrimidine-5-carbonitrile, (E)-2-amino-4-furan-2-yl-6-styryl-pyrimidine-5-carbonitrile and 2-amino-4-(3,4-dihydro-1H-isoquinolin-2-yl)-6-furan-2-yl-pyrimidine-5-carbonitrile;

or a pharmaceutically acceptable salt thereof.

22. A compound selected from the group consisting of:

5-Bromo-4-furan-2-yl-6-(pyridin-2-yl-methoxy)-pyrimidin-2-yl-amine, 5-bromo-6-furan-2-yl-N4-(3-phenyl-propyl)-pyrimidine-2,4-diamine, 5-bromo-4-furan-2-yl-6-(3-phenyl-propoxy)-pyrimidin-2-yl-amine, 4-furan-2-yl-5-iodo-6-(3-phenyl-propoxy)-pyrimidin-2-yl-amine, 5-bromo-4-furan-2-yl-6-phenethylsulfanyl-pyrimidin-2-yl-amine, 5-bromo-4-furan-2-yl-6-(3-phenyl-allyloxy)-pyrimidin-2-yl-amine, 4-benzyloxy-6-furan-2-yl-5-nitro-pyrimidin-2-yl-amine, 5-chloro-6-furan-2-yl-N4-(3-phenyl-propyl)-pyrimidine-2,4-diamine, 5-chloro-4-furan-2-yl-6-(3-phenyl-propoxy)-pyrimidin-2-yl-amine, 5-chloro-4-furan-2-yl-6-phenethyloxy-pyrimidin-2-yl-amine, 4-benzylsulfanyl-5-chloro-6-furan-2-yl-pyrimidin-2-yl-amine, 4-furan-2-yl-5-iodo-6-(2-pyridin-2-yl-ethylsulfanyl)-pyrimidin-2-yl-amine, 5-bromo-4-furan-2-yl-6-(2-pyridin-2-yl-ethylsulfanyl)-pyrimidin-2-yl-amine and 5-chloro-4-furan-2-yl-6-(2-pyridin-2-yl-ethylsulfanyl)-pyrimidin-2-yl-amine;

or a pharmaceutically acceptable salt thereof.

23. A compound N-[5-Cyano-4-furan-2-yl-6-(2-pyridin-2-yl-ethylsulfanyl)-pyrimidin-2-yl]-benzamide.

* * * * *

UNITED STATES PATENT AND TRADEMARK OFFICE
CERTIFICATE OF CORRECTION

PATENT NO. : 6,586,441 B2
APPLICATION NO. : 09/788956
DATED : July 1, 2003
INVENTOR(S) : Edilio Maurizio Borroni et al.

It is certified that error appears in the above-identified patent and that said Letters Patent is hereby corrected as shown below:

TITLE PAGE:

- The Assginee information reads: "Hoffman-La Roche Inc., Nutley, NJ (US)" the Assignee information should read -- Hoffmann-La Roche Inc., Nutley, NJ (US) ---.

IN THE CLAIMS:

- Claim 7, Column 188, line 55: " -(CH$_2$)-NH-pyridin-2-yl," should read -- -(CH$_2$)$_n$-NH-pyridin-2-yl, --.
- Claim 14, Column 193, line 17: "carboriitrile," should read -- carbonitrile --.
- Claim 19, Column 194, line 61: "-5carbonitrile," should read -- -5-carbonitrile --.

UNITED STATES PATENT AND TRADEMARK OFFICE
CERTIFICATE OF CORRECTION

PATENT NO. : 6,586,441 B2
APPLICATION NO. : 09/788956
DATED : July 1, 2003
INVENTOR(S) : Edilio Maurizio Borroni et al.

It is certified that error appears in the above-identified patent and that said Letters Patent is hereby corrected as shown below:

IN THE CLAIMS: (cont'd)

- Claim 24 should be added:
"24. The compound of claim 1 having the structure of formula I further comprising A being selected from the group consisting of -O-, -NH-, -S-; $R^2$ being selected from the group consisting of halogen and nitro; and wherein $R^1$ is selected from the group consisting of $-(CH_2)_n$-phenyl substituted by lower alkoxy, lower alkyl, lower alkenyl, or halogen, or $-(CH_2)_n$-pyridin-2-yl substituted by lower alkyl; wherein $R^3$ is selected from the group consisting of fur-2-yl and halogen substituted fur-2-yl; and wherein $R^4$ and $R^5$ are independently from each other selected from the group consisting of hydrogen, $-CO-(CH_2)_n$-phenyl optionally substituted by halogen or $-CH_2N®$ $(CH_2)_n$-loweralkyl, phenyl, phenyl substituted by lower alkoxy, or $-C(O)$-phenyl; wherein R is selected from the group consisting of hydrogen or lower alkyl; and the pharmaceutically acceptable salts thereof."

Signed and Sealed this

Seventeenth Day of October, 2006

JON W. DUDAS
*Director of the United States Patent and Trademark Office*